(12) United States Patent
Steeneck et al.

(10) Patent No.: US 8,946,446 B2
(45) Date of Patent: Feb. 3, 2015

(54) PYRROLO SULFONAMIDE COMPOUNDS FOR MODULATION OF ORPHAN NUCLEAR RECEPTOR RAR-RELATED ORPHAN RECEPTOR-γ (ROR-γ, NR1F3) ACTIVITY AND FOR THE TREATMENT OF CHRONIC INFLAMMATORY AND AUTOIMMUNE DISEASES

(75) Inventors: Christoph Steeneck, Dossenheim (DE); Olaf Kinzel, Heidelberg (DE); Christian Gege, Ehingen (DE); Gerald Kleymann, Bad Salzuflen (DE); Thomas Hoffmann, Viernheim (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 0 days.

(21) Appl. No.: 14/110,702

(22) PCT Filed: Apr. 13, 2012

(86) PCT No.: PCT/EP2012/001621
§ 371 (c)(1),
(2), (4) Date: Dec. 23, 2013

(87) PCT Pub. No.: WO2012/139775
PCT Pub. Date: Oct. 18, 2012

(65) Prior Publication Data
US 2014/0142082 A1 May 22, 2014

Related U.S. Application Data

(60) Provisional application No. 61/475,406, filed on Apr. 14, 2011.

(30) Foreign Application Priority Data

Apr. 14, 2011 (EP) ..................................... 11003169

(51) Int. Cl.
| | | |
|---|---|---|
| C07D 209/02 | (2006.01) | |
| C07D 207/00 | (2006.01) | |
| C07D 215/00 | (2006.01) | |
| C07D 401/00 | (2006.01) | |
| C07D 413/00 | (2006.01) | |
| A61K 31/44 | (2006.01) | |
| A61K 31/535 | (2006.01) | |
| A61K 31/397 | (2006.01) | |
| A61K 31/445 | (2006.01) | |
| A61K 31/40 | (2006.01) | |
| C07D 209/30 | (2006.01) | |
| C07D 207/36 | (2006.01) | |
| C07D 401/04 | (2006.01) | |
| C07D 403/04 | (2006.01) | |
| C07D 403/10 | (2006.01) | |

(52) U.S. Cl.
CPC ............ *C07D 209/30* (2013.01); *C07D 207/36* (2013.01); *C07D 401/04* (2013.01); *C07D 403/04* (2013.01); *C07D 403/10* (2013.01)
USPC ........... 548/519; 548/556; 548/466; 546/208; 546/158; 544/141; 514/306; 514/230.8; 514/210.2; 514/326; 514/424

(58) Field of Classification Search
None
See application file for complete search history.

(56) References Cited

U.S. PATENT DOCUMENTS

| | | |
|---|---|---|
| 6,331,637 B1 | 12/2001 | Chan et al. |
| 6,458,805 B2 | 10/2002 | Blok et al. |
| 7,186,716 B2 | 3/2007 | Wei et al. |
| 2005/0043364 A1 | 2/2005 | Kennedy et al. |

FOREIGN PATENT DOCUMENTS

| | | |
|---|---|---|
| CN | 1769284 A | 5/2006 |
| WO | WO 03/002567 A1 | 1/2003 |
| WO | 2006/087543 A1 | 8/2006 |
| WO | 2008/154271 A1 | 12/2008 |
| WO | 2010/049144 A2 | 5/2010 |
| WO | 2011/107248 A1 | 9/2011 |
| WO | 2011/112263 A1 | 9/2011 |

(Continued)

OTHER PUBLICATIONS

André et al., *EMBO J.* 17(4): 3867-3877, 1998.
(Continued)

*Primary Examiner* — Nyeemah A Grazier
(74) *Attorney, Agent, or Firm* — Seed IP Law Group PLLC

(57) ABSTRACT

The invention provides modulators for the orphan nuclear receptor RORγ and methods for treating RORγ mediated diseases by administrating these novel RORγ modulators to a human or a mammal in need thereof. Specifically, the present invention provides pyrrolo sulfonamide compounds of Formula (1) and the enantiomers, diastereomers, tautomers, solvates and pharmaceutically acceptable salts thereof.

(1)

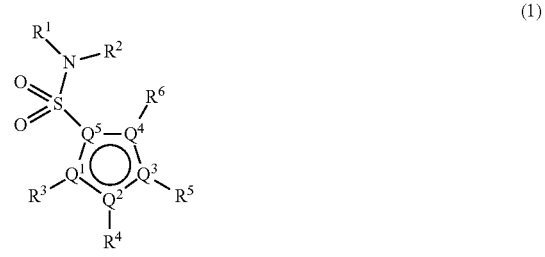

16 Claims, No Drawings

(56) References Cited

FOREIGN PATENT DOCUMENTS

| | | |
|---|---|---|
| WO | 2011/112264 A1 | 9/2011 |
| WO | 2011/115892 A1 | 9/2011 |
| WO | 2012/027965 A1 | 3/2012 |
| WO | 2012/028100 A1 | 3/2012 |

OTHER PUBLICATIONS

André et al., *Gene 216*: 277-283, 1998.
Awasthi et al., *Int. Immnol. 21*(5): 489-498, 2009.
Becker-André et al., *Biochem. Biophys. Res. Commun. 194*(3): 1371-1379, 1993.
Crome et al., *Clin. Exp. Immunol. 159*: 109-119, 2009.
Dyer et al., *Analytical Biochemistry 282*: 158-161, 2000.
Eberl et al., *Immunol. Rev. 195*: 81-90, 2003.
Eberl et al., *Science 305*: 248-251, 2004.
Evans, *Science 240*: 889-895, 1988.
Fukuda et al., *Tetrahedron 64*: 328-338, 2008.
Giguère et al., *Genomics 28*: 596-598, 1995.
Giuliano et al., *Gazzetta Chimica Italiana 116*: 589-593, 1986.
Gu et al., *Eur. J. Immunol. 38*: 1807-1813, 2008.
Hamilton et al., *Nature 379*: 736-739, 1996.
Handy et al., *J. Org. Chem. 69*: 2362-2366, 2004.
Harrisson et al., *Organic Letters 11*(16): 3586-3589, 2009.
He et al., *Immunity 9*: 797-806, 1998.
He et al., *J. Immunol. 164*: 5668-5674, 2000.
Houck et al., *Mol. Genet. Metab. 83*: 184-187, 2004.
Ivanov et al., *Cell 126*: 1121-1133, 2006.
Janosik et al., *Tetrahedron 62*: 1699-1707, 2006.
Kallen et al., *Structure 10*: 1697-1707, 2002.
Lau et al., *J. Biol. Chem. 283*(26): 18411-18421, 2008.
Magnus et al., *J. Am. Chem. Soc. 109*: 2706-2711, 1987.
Mangelsdorf et al., *Cell 83*: 835-839, 1995.
McKenna et al., *Endocrine Rev. 20*(3): 321-344, 1999.
Missbach et al., *J. Biol. Chem. 271*(23): 13515-13522, 1996.
Moranta et al., *J. Chem. Soc. Perkin Trans. 1*: 3285-3291, 1998.
Ptaszek et al., *Tetrahedron 63*: 3826-3839, 2007.
Setsune et al., *J. Am. Chem. Soc. 130*: 2404-2405, 2008.
Stehlin-Gaon et al., *Nat. Struct. Biol. 10*(10): 820-825, 2003.
Sun et al., *Science 288*: 2369-2373, 2000.
Tesmer et al., *Immunol. Rev. 223*: 87-113, 2008.
Tilley et al., *J. Immunol. 178*: 3208-3218, 2007.
Vanacker et al., *Mol.Endrocrinol. 13*: 764-773, 1999.
Villey et al., *Eur. J. Immunol. 29*: 4072-4080, 1999.
Wang et al., *J. Biol. Chem. 285*(7): 5013-5025, 2010.
Wiesenberg et al., *Nucleic Acid Res. 23*(3): 327-333, 1995.
Wilson et al., *Mol. Cell. Biol. 13*(9): 5794-5804, 1993.
Xue et al., *Bioorg. Med. Chem. 15*: 2156-2166, 2007.
Zarrinmayeh et al., *Bioorg. Med. Chem. Lett. 16*: 5203-5206, 2006.
Zhou et al., *Curr. Opin. Immunol. 21*(2): 146-152, 2009.
Basarab et al., "Design of *Helicobacter pylori* glutamate racemase inhibitors as selective antibacterial agents: A novel pro-drug approach to increase exposure," *Bioorganic & Medicinal Chemistry Letters 18*: 4716-4722, 2008.
Kumar et al., "The Benzenesulfoamide T0901317 [*N*-(2,2,2-Trifluoroethyl)-*N*-[4[2,2,2- trifluoro-1-hydroxy-1-(trifluoromethyl) ethyl]phenyl]-benzenesulfonamide] Is a Novel Retinoic Acid Receptor-Related Orphan Receptor-α/γ Inverse Agonist," *Mol. Pharmacol. 77*(2): 228-236, 2010.

PYRROLO SULFONAMIDE COMPOUNDS FOR MODULATION OF ORPHAN NUCLEAR RECEPTOR RAR-RELATED ORPHAN RECEPTOR-γ (ROR-γ, NR1F3) ACTIVITY AND FOR THE TREATMENT OF CHRONIC INFLAMMATORY AND AUTOIMMUNE DISEASES

CROSS-REFERENCE TO RELATED APPLICATIONS

This application is a U.S. National Phase Application of International Application No. PCT/EP2012/001621, filed Apr. 13, 2012, which claims priority to European Patent Application No. EP 11003169.7, filed Apr. 14, 2011, and U.S. Provisional Patent Application No. 61/475,406, filed Apr. 14, 2011. These applications are incorporated herein by reference in their entireties.

FIELD OF INVENTION

The invention provides pyrrolo sulphonamide compounds as modulators for the orphan nuclear receptor RORγ and methods for treating RORγ mediated chronic inflammatory and autoimmune diseases by administrating these novel RORγ modulators to a human or a mammal in need thereof.

The retinoid-receptor related orphan receptors consist of three family members, namely RORα (Beckerandre et al., Biochem. Biophys. Res. Commun. 1993, 194:1371), RORβ (Andre et al., Gene 1998, 516:277) and RORγ (He et al., Immunity 1998, 9:797) and constitute the NR1F (ROR/RZR) subgroup of the nuclear receptor superfamily (Mangelsdorf et al., Cell 1995, 83:835).

The nuclear receptor superfamily shares common modular structural domains consisting of a hypervariable N-terminal domain, a conserved DNA binding domain (DBD), a hinge region, and a conserved ligand-binding domain (LBD). The DBD targets the receptor to specific DNA sequences (nuclear hormone response elements or NREs), and the LBD functions in the recognition of endogenous or exogenous chemical ligands. A constitutive transcriptional activation domain is found at the N-terminus (AF1) and a ligand regulated transcriptional activation domain is embedded within the C-terminal LBD of typical NRs. The nuclear receptors can exist in a transcriptional activating or repressing state when bound to their target NREs. The basic mechanism of gene activation involves ligand dependent exchange of co-regulatory proteins, namely co-activators and co-repressors (McKenna et al., Endocrine Rev. 1999, 20:321). A NR in the repressing state is bound to its DNA recognition element and is associated with co-repressor proteins that recruit histone-deacetylases (HDACs). In the presence of an agonist, co-repressors are exchanged for coactivators that recruit transcription factors, which contribute to assembling of a chromatin-remodelling complex, which relieves transcriptional repression and stimulates transcriptional initiation via histone acetylation. The AF-2 domain of the LBD acts as a ligand dependant molecular switch presenting interaction surfaces for co-repressor or co-activator proteins and providing with a conserved mechanism for gene activation or repression that is shared by the members of the nuclear receptor superfamily.

The members of the NR1F family of nuclear receptors (such as RORγ) have been considered to be constitutively active transcription factors in the absence of known ligands, which is similar to the estrogen-related receptor alpha (Vanacker et al., Mol. Endocrinol. 1999, 13:764). Most recently, 7-oxygenated oxysterols were identified to be high affinity ligands for RORα and RORγ (Wang et al., J. Biol. Chem. 2010, 285:5013). 7-Hydroxycholesterol is a key metabolite during the conversion of cholesterol into bile acids, but to date it is not clear whether it is a true endogenous ligand for the RORs. In any case it can be expected that inverse agonists of RORγ should reduce the transcriptional activity of RORγ and influence the biological pathways controlled by RORγ.

The RORs are expressed as isoforms arising from differential splicing or alternative transcriptional start sites. So far, isoforms have been described that differ only in their N-terminal domain (A/B-domain). In humans, four different RORα isoforms have been identified (RORα 1-4) while only two isoforms are known for both RORβ (1 and 2) and RORγ (1 and 2) (Andre et al., Gene 1998, 216:277; Villey et al., Eur. J. Immunol. 1999, 29:4072). RORγ is used herein as a term describing both, RORγ 1 and/or RORγ 2.

The ROR isoforms show different tissue expression patterns and regulate different target genes and physiological pathways. For example, the RORγ 2 (also called RORγ t) is highly restricted to $CD4^+CD8^+$ thymocytes and to interleukin-17 (IL-17) producing T cells while other tissues express RORγ 1 (Eberl et al., Science 2004, 305:248, Zhou and Littmann, Curr. Opin. Immunol. 2009, 21:146).

RORs exhibit a structural architecture that is typical of nuclear receptors. RORs contain four major functional domains: an amino-terminal (A/B) domain, a DNA-binding domain (DBD), a hinge domain, and a ligand-binding domain (LBD) (Evans et al., Science 1988, 240:889). The DBD consists of two highly conserved zinc finger motifs involved in the recognition of ROR response elements (ROREs) which consist of the consensus motif AGGTCA preceded by an AT-rich sequence (Andre et al., Gene 1998, 216:277) which is similar to that of the nuclear receptors Rev-ErbAα and Rev-Erbβ (NR1D1 and D2, respectively) (Giguere et al., Genomics 1995, 28:596). These recognition elements do also show high similarity to those identified for the estrogen related receptors and in particular ERRα (ERRs, NR3B1, -2, -3) (Vanacker et al., Mol. Endocrinol. 1999, 13:764), steroidogenic factor 1 (SF-1, NR5A) and NGFI-B (NR4A1, -2, -3) (Wilson et al., Mol. Cell. Biol. 1993, 13:5794).

RORα is highly expressed in different brain regions and most highly in cerebellum and thalamus. RORα knock-out mice show ataxia with strong cerebellar atrophy, highly similar to the symptoms displayed in the so-called staggerer mutant mouse ($ROR\alpha^{sg/sg}$). This mouse carries mutations in RORα that results in a truncated RORα which does not contain a LBD (Hamilton et al., Nature 1996, 379:736).

Analysis of $ROR\alpha^{sg/sg}$ staggerer-mice have revealed a strong impact on lipid metabolism beyond the CNS defects, namely significant decreases in serum and liver triglyceride, reduced serum HDL cholesterol levels and reduced adiposity. SREBP1c and the cholesterol transporters ABCA1 and ABCG1 are reduced in livers of staggerer mice and CHIP analysis suggest that RORα is directly recruited to and regulates the SREBP1c promoter. In addition, PGC1a, PGC1β, lipin1 and P2-adrenergic receptor were found to be increased in tissues such as liver or white and brown adipose tissue, which may help to explain the observed resistance to diet-induced obesity in staggerer mice (Lau et al., J. Biol. Chem. 2008, 283:18411).

RORβ expression is mainly restricted to the brain and most abundantly found in the retina. RORβ knock-out mice display a duck-like gait and retinal degeneration which leads to blindness (Andre et al., EMBO J. 1998, 17:3867). The molecular mechanisms behind this retinal degeneration are still poorly understood.

RORγ (particularly RORγ 2) null-mutant mice lack lymph nodes and Peyer's patches (Eberl and Littmann, *Immunol. Rev.* 2003, 195:81) and lymphatic tissue inducer (LTi) cells are completely absent from spleen mesentery and intestine. In addition, the size of the thymus and the number of thymocytes is greatly reduced in RORγ null mice (Sun et al., *Science* 2000, 288:2369) due to a reduction in double-positive CD4$^+$CD8$^+$ and single positive CD4$^-$CD8$^+$ or CD4$^+$CD8$^-$ cells suggesting a very important role of RORγ 2 in thymocyte development.

Thymocyte development follows a complex program involving coordinated cycles of proliferation, differentiation, cell death and gene recombination in cell populations dedicated by their microenvironment. Pluripotent lymphocyte progenitors migrating from fetal liver or adult bone marrow to the thymus are being committed to the T-cell lineage. They develop through a series of steps from CD4$^-$CD8$^-$ double negative cells to CD4$^+$CD8$^+$cells and those with low affinity towards self-MHC peptides are eliminated by negative selection. These develop further into CD4$^-$CD8$^+$(killer) or CD4$^+$CD8$^-$(helper) T-cell lineages. RORγ 2 is not expressed in double negative and little expressed in immature single negative thymocytes (He et al., *J. Immunol.* 2000, 164:5668), while highly upregulated in double-positive thymocytes and downregulated during differentiation in single-positive thymocytes. RORγ deficiency results in increased apoptosis in CD4$^+$CD8$^+$ cells and the number of peripheral blood thymocytes is decreased by 6-fold (10-fold CD4$^+$and 3-fold CD8$^+$ thymocytes).

Recent experiments in a model of ovalbumin (OVA)-induced inflammation in mice, as a model for allergic airway disease, demonstrated a severe impairment of the development of the allergic phenotype in the RORγ KO mice with decreased numbers of CD4$^+$cells and lower Th2 cytokine/chemokine protein and mRNA expression in the lungs after challenge with OVA (Tilley et al., *J. Immunol.* 2007, 178:3208). IFN-γ and IL-10 production were increased in splenocytes following re-stimulation with the OVA antigen compared to wt splenocytes suggesting a shift towards a Th1 type immune response on cost of a reduction of Th2 type response. This suggests that down-modulation of RORγ transcriptional activity with a ligand could result in a similar shift of the immune response towards a Th1 type response, which could be beneficial in the treatment of certain pulmonary diseases like asthma or allergic inflammatory conditions.

T-helper cells were previously considered to consist of Th1 and Th2 cells. However, a new class of Th cells, the Th17 cells, which produce IL-17, were also identified as a unique class of T-cells that are considered to be pro-inflammatory. They are recognized as key players in autoimmune and inflammatory diseases since IL-17 expression has been associated with many inflammatory diseases such as rheumatoid arthritis, systemic lupus erythematosus (SLE) and allograft rejection. (Tesmer et al., *Immunol. Rev.* 2008, 223:87).

RORγ2 is exclusively expressed in cells of the immune system and has been identified as a master regulator of Th17 cell differentiation. Expression of RORγ 2 is induced by TGF-beta or IL-6 and overexpression of RORγ2 results in increased Th17 cell lineage and IL-17 expression. RORγ 2 KO mice show very little Th17 cells in the intestinal lamina propria and demonstrate an attenuated response to challenges that usually lead to autoimmune disease (Ivanov et al., *Cell* 2006, 126:1121).

Inhibition of IL-17 production via inhibition of Th17 cell development may also be advantageous in atopic dermatitis and psoriasis where IL-17 is deeply involved. Interestingly, recent evidence was presented that IL-10 suppresses the expression of IL-17 secreted by both, macrophages and T-cells. In addition, the expression of the Th17 transcription factor RORγ 2 was suppressed (Gu et al., *Eur. J. Immunol.* 2008, 38:1807). Moreover, IL-10 deficient mice provide a good model for inflammatory bowel disease (IBD) where a shift towards a Th1 type inflammatory response is frequently observed. Oral IL-10 delivery poses a potential treatment option for IBD.

The proinflammatory actions of IL-17 producing Th17 cells are counteracted by another T-helper cell type, so-called regulatory T-cells or Tregs. Naïve T cells are differentiated into Tregs upon stimulation by TGFβ. This results in upregulation of the transcriptional modulator FoxP3 resulting in CD4$^+$FoxP3$^+$Tregs. In case the naïve T-cells are co-stimulated by IL-6, FoxP3 expression is suppressed and RORγ t expression is induced. These CD4$^+$FoxP3$^-$RORγ t+T-helper cells then differentiate into IL-17 producing Th17 cells. (reviewed in Awasthi and Kuchroo, *Int. Immunol.* 2009, 21:489, and Zhou and Littmann, *Curr. Opin. Immunol.* 2009, 21:146). Several lines of evidence suggest that these Th17 cells are responsible for the etiology of a whole range of autoimmune diseases such as multiple sclerosis, rheumatoid arthritis, ankylosing spondylitis, psoriasis, Crohn's disease and other types of inflammatory bowel disease, lupus erythematosus and asthma. The severity of disease seems to correlate with the presence of IL-17$^+$ Th17 cells and it is believed that interception of RORγt by a small molecule inverse agonist or antagonist should result in a reduction of these IL-17$^+$Th17 cells ultimately leading to alleviation of disease symptoms and outcome (Crome et al., *Clin. Exp. Immunol.* 2010, 159:109).

Ligands for the RORs:

It was reported that cholesterol and its sulfated derivatives might function as RORα ligands and in particular cholesterol-sulfate could restore transcriptional activity of RORα in cholesterol-depleted cells (Kallen et al., *Structure* 2002, 10:1697). Previously, melatonin (Missbach et al., *J. Biol. Chem.* 1998, 271:13515) and thiazolidinediones were suggested to bind to RORα (Wiesenberg et al., *Nucleic Acid Res.* 1995, 23:327). However, none of these have been shown to be functional ligands of RORα or of any other of the RORs. Certain retinoids including all-trans retinoid acid have been demonstrated to bind to RORβ and function as partial antagonists for RORβ but not RORα (Stehlin-Gaon et al., *Nat. Struct Biol.* 2003, 10:820).

Recently, 7-oxygenated sterols such as 7-hydroxy-cholesterol and 7-keto-cholesterol were identified as highly potent modulators of RORγ activity (Wang et al., *J. Biol. Chem.* 2010, 285:5013) in in vitro assays. The same group of investigators also found that a known LXR agonist, T0901317 ([N-(2,2,2-trifluoroethyl)-N-[4-[2,2,2-trifluoro-1-hydroxy-1-(trifluoromethyl)ethyl]phenyl]-benzenesulfonamide]) acts as a RORγ inverse agonist at submicromolar potency (Kumar et al., *Mol. Pharmacol.* 2010, 77:228). In neither case, however, in vivo data were obtained that demonstrate a beneficial impact of these RORγ modulating compounds. In case of the 7-oxysterols their endogenous presence as metabolites naturally produced by the body itself as well as their rapid turnover and their biological activities on many cellular proteins prevent a meaningful animal study that allows drawing conclusions on the role of RORγ. In case of the T0901317 its polypharmacodynamic properties, acting on at least six different nuclear receptors (LXRα/β, FXR, PXR, RORα/γ) prevents its usefulness as a drug candidate for the development in an autoimmune disease application (Houck et al., *Mol. Genet. Metab.* 2004, 83:184; Xue et al., *Bioorg. Med. Chem.* 2007, 15:2156).

US2005/0043364 describes pyrrolo sulfonamide compounds as 3-hydroxy-3-methylglutaryl-coenzyme A reductase inhibitors for the treatment of e.g. hyperlipidemia or hypercholesterolemia. As shown exemplarily in Formula (A), all of the examples in US2005/0043364 bear a hydroxylated alkyl as pyrrolo N-substituent.

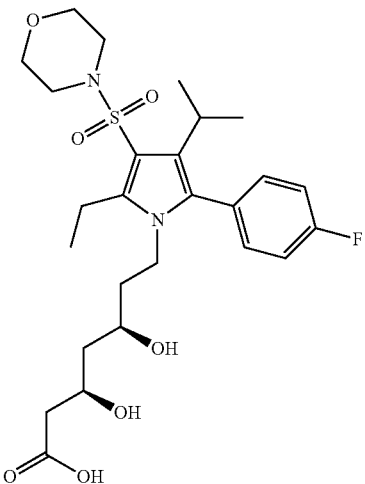

(A)

WO2003/002567 and *Bioorg. Med. Chem. Lett.* 2008, 18:4716 describe glutamate racemate inhibitors as antibacterial agents of general Formula (B), which can be substituted at R' with a pyrrole moiety. Structure (B') shows a representative example.

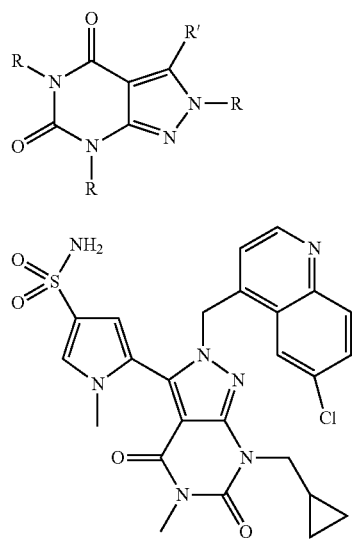

(B)

(B')

U.S. Pat. No. 6,458,805 claims in a very broad range sulfonamides of general Structure (C),

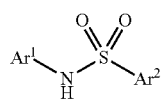

(C)

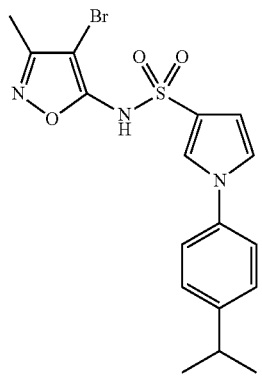

(C')

wherein Ar¹ is limited to a "five or six membered aromatic or heteroaromatic ring" or a "bicyclic or tricyclic carbon or heterocyclic ring" and Ar² is selected from a broad range of heterocycles including pyrrole. The only example in this patent wherein Ar² is a substituted pyrrole is Compound C'.

In the similar U.S. Pat. No. 6,331,637 with general Structure (C), Ar¹ is broadly defined to be "a substituted or unsubstituted group, having from 1 to 30 carbon atoms, selected from the group consisting of alkyl, alkenyl and alkynyl groups, which are straight or branched chains or have cyclic portions; aryl groups; and fused bicyclic or tricylic rings". However no other 3-sulfonamide-pyrrole is shown except Compound C'.

U.S. Pat. No. 7,186,716 claims pyrroles, which are optionally substituted with $SO_2N(R)R'$ but have to be substituted with the bicyclic pyridopyrazole as shown in Formula D.

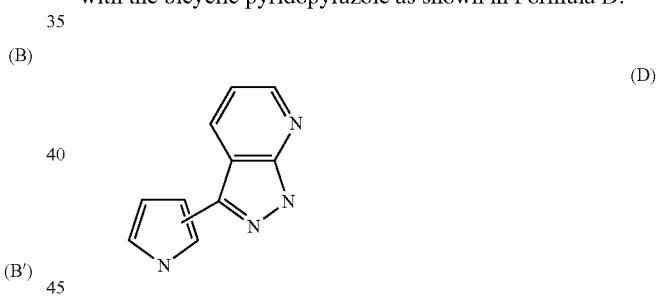

(D)

Modulators of the RORγ receptor were recently disclosed in WO2011/107248, WO2011/112263, WO2011/112264, WO2011/115892, WO2012/027965 and WO2012/028100 which are based upon other structural classes.

SUMMARY OF THE INVENTION

It is therefore the object of the present invention to provide compounds, which bind to the orphan nuclear receptors RORγ1 and/or RORγ2 and, thus, to open new methods for treating diseases associated with the modulation of RORγ, such as autoimmune diseases, inflammatory skin diseases or multiple sclerosis.

This object is solved by the surprising discovery of small molecule ligands for the human RORγ.

Thus, the present invention provides pyrrolo sulfonamides compounds as RORγ modulators, which can be used for treating or preventing a disease or disorder associated with the inactivation or activation of the RORγ receptor.

The present invention relates to a RORγ modulator which are based on a pyrrolo sulphonamide scaffold for use in the treatment or prophylaxis of a disease or disorder associated with the inhibition or activation of RORγ.

When treating the disease or disorder associated with the modulation of the RORγ receptor, the activity of said receptor is preferably reduced.

Preferably, the disease or disorder is selected from the group consisting of autoimmune diseases. Autoimmune diseases comprise a group of diseases with a similar etiology of an overshooting immune response against endogenous targets resulting in chronic inflammation and physical disabilities or other severe symptoms. Autoimmune diseases comprise e.g. rheumatoid arthritis, ankylosing spondylitis, lupus erythematosus, psoriasis, atopic eczema, inflammatory bowel diseases such as Crohn's disease, asthma, multiple sclerosis, type 1 diabetes and amyotrophic lateral sclerosis.

The present invention provides novel compounds to be used in the treatment of diseases or disorders associated with the inactivation or activation of the RORγ receptor.

DETAILED DESCRIPTION OF THE INVENTION

Specifically, the present invention provides compounds of Formula (1)

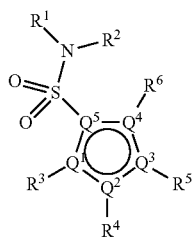

the possible enantiomers, diastereomers and tautomers and pharmaceutically acceptable salts thereof,
wherein
one of $Q^1$ to $Q^5$ is a nitrogen atom and the remaining radicals are carbon atoms;
$R^1$ is selected from the group consisting of H, $C_{1-10}$alkyl, $C_{1-10}$alkenyl, $C_{1-10}$ alkynyl, $C_{0-6}$ alkylene-$C_{3-10}$ cycloalkyl, $C_{0-6}$ alkylene-$C_{3-10}$ heterocycloalkyl, $C_{0-6}$ alkylene-5-membered heteroaromatic ring system containing 1, 2, or 3 heteroatoms independently selected from the group consisting of N, O and S
  wherein alkyl, alkylene, alkenyl, alkynyl, cycloalkyl, heterocycloalkyl and the 5-membered heteroaromatic ring system are unsubstituted or substituted with 1 to 6 substituents independently selected from the group consisting of OH, oxo, CN, O—$C_{1-6}$ alkyl, O-halo-$C_{1-6}$ alkyl, $C_{1-6}$ alkyl, halo-$C_{1-6}$ alkyl, halogen, COOR$^{10}$, CON(R$^{10}$)$_2$, SO$_2$R$^{10}$, SO$_2$N(R$^{10}$)$_2$, NR$^{10}$COR$^{10}$, NR$^{10}$SO$_2$R$^{10}$ and N(R$^{10}$)$_2$;
$R^2$ is selected from the group consisting of H, $C_{1-6}$ alkyl and halo-$C_{1-6}$ alkyl,
or $R^1$ and $R^2$ when taken together with the nitrogen to which they are attached complete a 3- to 8-membered ring containing carbon atoms and optionally containing an additional heteroatom selected from O, S, SO, SO$_2$ or NR$^{10}$, wherein the ring is unsubstituted or substituted with one to four substitutents independently selected from halogen, oxo or $C_{1-6}$-alkyl;

$R^3$ is H, $C_{1-6}$ alkyl, halo-$C_{1-6}$alkyl, CN or halogen
  wherein alkyl is unsubstituted or substituted with 1 to 3 substituents independently selected from the group consisting of O—$C_{1-6}$ alkyl, O-halo-$C_{1-6}$alkyl, oxo and OH;
$R^4$ is SO$_2$—(CR$^8$R$^8$)$_y$R$^7$ or (CR$^8$R$^8$)$_x$—R$^{11}$;
$R^5$ is pyridinone, a 6-10 membered mono- or bicyclic aryl or a 5-14 membered mono-, bi- or tricyclic heteroaryl containing 1 to 4 heteroatoms independently selected from the group consisting of N, O and S
  wherein pyridinone, aryl and heteroaryl are unsubstituted or substituted with 1 to 5 substituents independently selected from halogen, CN, $C_{1-6}$alkyl, $C_{1-6}$alkenyl, $C_{1-6}$ alkynyl, halo-$C_{1-6}$ alkyl, OH, O—$C_{1-6}$alkyl, O-halo-$C_{1-6}$ alkyl, $C_{3-10}$ cycloalkyl, O—$C_{3-10}$ cycloalkyl, COOR$^9$, C(O)R$^9$, C(O)N(R$^9$)$_2$, SO$_2$—N(R$^9$)$_2$, SO$_2$—R$^9$, $C_{3-10}$ heterocycloalkyl, phenyl, 5-6 membered heteroaryl containing 1 to 4 heteroatoms independently selected from N, O and S
    wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, =N—OH, =N—O—($C_{1-6}$alkyl), N(R$^9$)$_2$, O—$C_{1-6}$ alkyl; COOH, CON(R$^9$)$_2$, CN, NR$^9$—COR$^{10}$, $C_{3-10}$ cycloalkyl, $C_{3-10}$ heterocycloalkyl, 6-10 membered mono- or bicyclic aryl
    or wherein two adjacent substituents may complete a 3- to 8-membered saturated or partially unsaturated ring containing carbon atoms and optionally containing 1 to 3 heteroatoms selected from O, S, SO, SO$_2$ or NR$^{10}$, wherein the ring is unsubstituted or substituted with one to four substituents independently selected from halogen, oxo, =N—OH, =N—O—($C_{1-6}$alkyl), OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl;
$R^6$ is H, $C_{1-6}$alkyl, halo-$C_{1-6}$ alkyl or halogen;
$R^7$ is $C_{1-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl
  wherein cycloalkyl, heterocycloalkyl, aryl and heteroaryl are unsubstituted or substituted with 1 to 3 substituents independently selected from the group consisting of halogen, OH, O—$C_{1-6}$ alkyl, O-halo-$C_{1-6}$ alkyl, $C_{1-6}$alkyl, halo-$C_{1-6}$ alkyl and NH$_2$
  and wherein alkyl is unsubstituted or substituted with 1 to 3 substituents independently selected from the group consisting of halogen, OH, O—$C_{1-6}$ alkyl, O-halo-$C_{1-6}$ alkyl and NH$_2$;
$R^8$ is independently H, $C_{1-4}$ alkyl, O—$C_{1-4}$ alkyl, halo-$C_{1-4}$ alkyl or halogen;
$R^9$ is independently selected from H, $C_{1-6}$alkyl, $C_{3-10}$ cycloalkyl, $C_{3-10}$ heterocycloalkyl, phenyl, 5-6 membered heteroaryl containing 1 to 4 heteroatoms independently selected from N, O and S
  wherein alkyl, cycloalkyl and heterocycloalkyl is unsubstituted or substituted with 1 to 3 substituents selected from the group consisting of OH, O—$C_{1-6}$ alkyl, O-halo-$C_{1-6}$alkyl, phenyl, heteroaryl, halogen, NH$_2$, NH($C_{1-6}$alkyl), N($C_{1-6}$alkyl)$_2$, $C_{3-10}$ heterocycloalkyl and $C_{3-10}$ cycloalkyl
    wherein cycloalkyl and heterocycloalkyl is unsubstituted or substituted with 1 to 3 substituents independently selected from the group consisting of $C_{1-6}$ alkyl, halo-$C_{1-6}$ alkyl, OH, O—$C_{1-6}$ alkyl, O-halo-$C_{1-6}$alkyl, phenyl, heteroaryl, halogen, NH$_2$, NH($C_{1-6}$alkyl), N($C_{1-6}$alkyl)$_2$ and $C_{3-10}$ cycloalkyl
  wherein phenyl and heteroaryl are unsubstituted or substituted with 1 to 3 substituents independently selected from the group consisting of OH, O—$C_{1-6}$ alkyl, O-halo-$C_{1-6}$ alkyl, halogen, $C_{1-6}$ alkyl, halo-$C_{1-6}$ alkyl, $NH_2$, $NH(C_{1-6}alkyl)$, $N(C_{1-6}alkyl)_2$ and $C_{3-10}$ cycloalkyl;

$R^{10}$ is independently selected from H, $C_{1-6}$ alkyl, halo-$C_{1-6}$ alkyl and $C_{3-10}$ cycloalkyl;

$R^{11}$ is $C_{2-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl wherein alkyl, cycloalkyl, heterocycloalkyl, aryl and heteroaryl is unsubstituted or substituted with 1 to 3 substituents independently selected from the group consisting of halogen, OH, oxo, O—$C_{1-6}$alkyl, O-halo-$C_{1-6}$ alkyl, $C_{1-6}$ alkyl, halo-$C_{1-6}$ alkyl and $NH_2$;

x is 1, 2 or 3;

and y is 0, 1, or 2;

with the proviso that for $R^5$ the 5-14 membered mono-, bi- or tricyclic heteroaryl containing ring is not

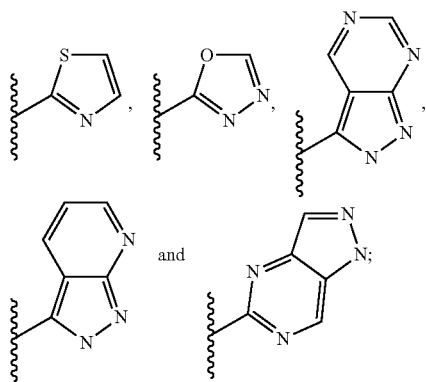

and with the proviso that $(CR^8R^8)_x$—$R^{11}$ is not

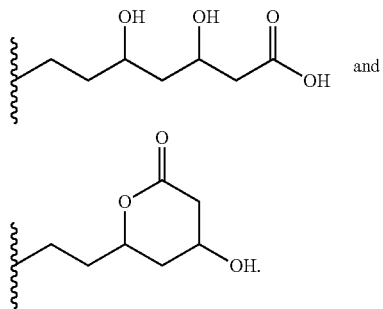

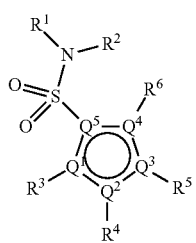

In an embodiment the present invention provides compounds of Formula (1)

the possible enantiomers, diastereomers and tautomers and pharmaceutically acceptable salts thereof, wherein one of $Q^1$ to $Q^5$ is a nitrogen atom and the remaining radicals are carbon atoms;

$R^1$ is selected from the group consisting of H, $C_{1-10}$ alkyl, $C_{1-10}$ alkenyl, $C_{1-10}$ alkynyl, $C_{0-6}$ alkylene-$C_{3-10}$ cycloalkyl, $C_{0-6}$ alkylene-$C_{3-10}$ heterocycloalkyl, $C_{0-6}$ alkylene-5-membered heteroaromatic ring system containing 1, 2, or 3 heteroatoms independently selected from the group consisting of N, O and S wherein alkyl, alkylene, alkenyl, alkynyl, cycloalkyl, heterocycloalkyl and the 5-membered heteroaromatic ring system are unsubstituted or substituted with 1 to 6 substituents independently selected from the group consisting of OH, oxo, CN, O—$C_{1-6}$ alkyl, O-halo-$C_{1-6}$alkyl, $C_{1-6}$ alkyl, halogen, $COOR^{10}$, $CON(R^{10})_2$, $SO_2R^{10}$, $SO_2N(R^{10})_2$, $NR^{10}COR^{10}$, $NR^{10}SO_2R^{10}$ and $N(R^{10})_2$;

$R^2$ is selected from the group consisting of H, $C_{1-6}$ alkyl and halo-$C_{1-6}$ alkyl, or $R^1$ and $R^2$ when taken together with the nitrogen to which they are attached complete a 3- to 8-membered ring containing carbon atoms and optionally containing an additional heteroatom selected from O, S, SO, $SO_2$ or $NR^{10}$, wherein the ring is unsubstituted or substituted with one to four substitutents independently selected from halogen, oxo or $C_{1-6}$-alkyl;

$R^3$ is H, $C_{1-6}$ alkyl, halo-$C_{1-6}$alkyl or halogen wherein alkyl is unsubstituted or substituted with 1 to 3 substituents independently selected from the group consisting of O—$C_{1-6}$alkyl, O-halo-$C_{1-6}$ alkyl and OH;

$R^4$ is $SO_2$—$(CR^8R^8)_y R^7$ or $(CR^8R^8)_x$—$R^{11}$;

$R^5$ is a 6-10 membered mono- or bicyclic aryl or a 5-14 membered mono-, bi- or tricyclic heteroaryl containing 1 to 4 heteroatoms independently selected from the group consisting of N, O and S wherein aryl and heteroaryl are unsubstituted or substituted with 1 to 5 substituents independently selected from halogen, CN, $C_{1-6}$alkyl, $C_{1-6}$alkenyl, $C_{1-6}$alkynyl, halo-$C_{1-6}$ alkyl, OH, O—$C_{1-6}$alkyl, O-halo-$C_{1-6}$alkyl, O—$C_{3-10}$cycloalkyl, $COOR^9$, $C(O)R^9$, $C(O)N(R^9)_2$, $SO_2$—$N(R^9)_2$, $SO_2$—$R^9$, $C_{3-10}$ heterocycloalkyl, phenyl, 5-6 membered heteroaryl containing 1 to 4 heteroatoms independently selected from N, O and S wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, $N(R^9)_2$, O—$C_{1-6}$ alkyl; COOH, $CON(R^9)_2$, CN, $NR^9$—$COR^{10}$, 3-10 membered cycloalkyl, 3-10 membered mono- or bicyclic heterocycloalkyl, 6-10 membered mono- or bicyclic aryl or wherein two substituents may complete a 3- to 8-membered saturated or partially unsaturated ring containing carbon atoms and optionally containing 1 to 3 heteroatoms selected from O, S, SO, $SO_2$ or $NR^{10}$, wherein the ring is unsubstituted or substituted with one to four substituents independently selected from halogen, oxo, OH, O—$C_{1-6}$-alkyl, $C_{1-6}$-alkyl, $C_{1-6}$-cycloalkyl and halo-$C_{1-6}$-alkyl;

$R^6$ is H, $C_{1-6}$ alkyl, halo-$C_{1-6}$ alkyl or halogen;

$R^7$ is $C_{1-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl wherein cycloalkyl, heterocycloalkyl, aryl and heteroaryl are unsubstituted or substituted with 1 to 3 substituents independently selected from the group consisting of halogen, OH, O—$C_{1-6}$ alkyl, O-halo-$C_{1-6}$ alkyl, $C_{1-6}$ alkyl, halo-$C_{1-6}$ alkyl and $NH_2$ and wherein alkyl is unsubstituted or substituted with 1 to 3 substituents independently selected from the group consisting of halogen, OH, O—$C_{1-6}$ alkyl, O-halo-$C_{1-6}$ alkyl and $NH_2$;

$R^8$ is independently H, $C_{1-4}$ alkyl, halo-$C_{1-4}$ alkyl or halogen;

$R^9$ is independently selected from H, $C_{1-6}$alkyl, $C_{3-10}$ cycloalkyl, $C_{3-10}$ heterocycloalkyl, phenyl, 5-6 membered heteroaryl containing 1 to 4 heteroatoms independently selected from N, O and S wherein alkyl, cycloalkyl and heterocycloalkyl is unsubstituted or substituted with 1 to 3 substituents independently selected from the group consisting of OH, O—$C_{1-6}$alkyl, O-halo-$C_{1-6}$alkyl, phenyl, halogen, $NH_2$, $NH(C_{1-6}$ alkyl), $N(C_{1-6}$alkyl$)_2$, $C_{3-10}$ cycloalkyl wherein phenyl and heteroaryl are unsubstituted or substituted with 1 to 3 substituents independently selected from the group consisting of OH, O—$C_{1-6}$ alkyl, O-halo-$C_{1-6}$ alkyl, halogen, $C_{1-6}$alkyl, halo-$C_{1-6}$ alkyl, $NH_2$, $NH(C_{1-6}$alkyl), $N(C_{1-6}$alkyl$)_2$ and $C_{3-10}$ cycloalkyl;

$R^{10}$ is independently selected from H, $C_{1-6}$ alkyl, halo-$C_{1-6}$ alkyl and $C_{3-10}$ cycloalkyl;

$R^{11}$ is $C_{2-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl wherein alkyl, cycloalkyl, heterocycloalkyl, aryl and heteroaryl is unsubstituted or substituted with 1 to 3 substituents independently selected from the group consisting of halogen, OH, oxo, O—$C_{1-6}$alkyl, O-halo-$C_{1-6}$alkyl, $C_{1-6}$alkyl, halo-$C_{1-6}$alkyl and $NH_2$;

x is 1, 2 or 3;

and y is 0, 1, or 2;

with the proviso that for $R^5$ the 5-14 membered mono-, bi- or tricyclic heteroaryl containing ring is not

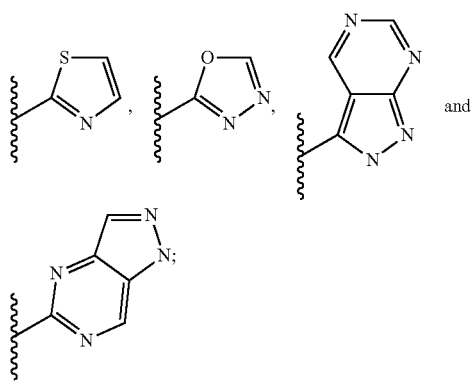

and with the proviso that $(CR^8R^8)_x$—$R^{11}$ is not

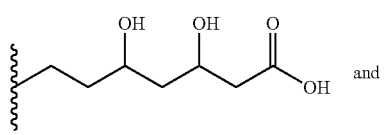

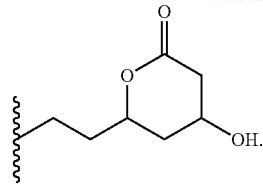

In a preferred embodiment in combination with any of the embodiments mentioned above or below, one of the radicals $Q^1$, $Q^2$ and $Q^3$ represents a nitrogen atom and the remaining radicals are carbon atoms. In an even more preferred embodiment in combination with any of the embodiments mentioned above or below, $Q^2$ is a nitrogen atom and the remaining radicals are carbon atoms.

In a further preferred embodiment in combination with any of the embodiments mentioned above or below, $R^1$ is H, $C_{1-10}$ alkyl, $C_{3-10}$ cycloalkyl or $C_{3-10}$ heterocycloalkyl, wherein alkyl, cycloalkyl and heterocycloalkyl are unsubstituted or substituted with 1 to 3 substituents independently selected from the group consisting of OH, oxo, CN, O—$C_{1-6}$ alkyl, O-halo-$C_{1-6}$ alkyl, $C_{1-6}$ alkyl, halogen, $COOR^{10}$, $CON(R^{10})_2$, $SO_2R^{10}$, $SO_2N(R^{10})_2$, $NR^{10}COR^{10}$, $NR^{10}SO_2R^{10}$ and $N(R^{10})_2$.

In a preferred embodiment in combination with any of the embodiments mentioned above or below, $R^2$ is H, $C_{1-6}$ alkyl or halo-$C_{1-6}$ alkyl.

In an even more preferred embodiment in combination with any of the embodiments mentioned above or below, $R^2$ is H.

In another preferred embodiment in combination with any of the embodiments mentioned above or below, $R^1$ is selected from the group consisting of H, $C_{1-10}$ alkyl, $C_{3-10}$ cycloalkyl and $C_{3-10}$ heterocycloalkyl wherein alkyl, cycloalkyl and heterocycloalkyl are unsubstituted or substituted with 1 to 3 substituents independently selected from the group consisting of OH, oxo, CN, O—$C_{1-6}$ alkyl, O-halo-$C_{1-6}$ alkyl, $C_{1-6}$ alkyl, halogen, $COOR^{10}$, $CON(R^{10})_2$, $SO_2R^{10}$, $SO_2N(R^{10})_2$, $NR^{10}COR^{10}$, $NR^{10}SO_2R^{10}$ and $N(R^{10})_2$;

$R^2$ is selected from the group consisting of H, $C_{1-6}$ alkyl and halo-$C_{1-6}$ alkyl, or $R^1$ and $R^2$ when taken together with the nitrogen to which they are attached complete a 3- to 8-membered ring containing carbon atoms and optionally containing an additional heteroatom selected from O, S, SO, $SO_2$ or $NR^{10}$, wherein the ring is unsubstituted or substituted with one to four substitutents independently selected from halogen, oxo or $C_{1-6}$-alkyl.

In a further preferred embodiment in combination with any of the embodiments mentioned above or below, $NR^1R^2$ is selected from

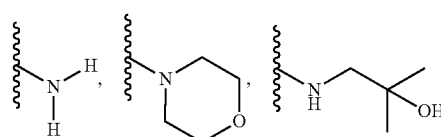

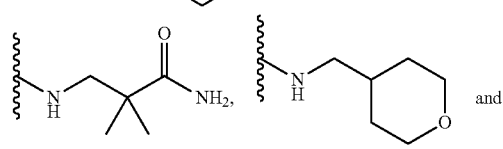

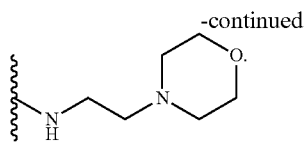

In a further preferred embodiment in combination with any of the embodiments mentioned above or below, $R^1$ and $R^2$ are hydrogen.

In another preferred embodiment in combination with any of the embodiments mentioned above or below, $R^4$ is $CH_2$—$R^{11}$; and $R^{11}$ is $C_{4-8}$cycloalkyl, wherein cycloalkyl is unsubstituted or substituted with 1 to 3 substituents independently selected from the group consisting of halogen, OH, oxo, O—$C_{1-6}$alkyl, O-halo-$C_{1-6}$ alkyl, $C_{1-6}$ alkyl, and halo-$C_{1-6}$ alkyl.

In an even more preferred embodiment in combination with any of the embodiments mentioned above or below, $R^4$ is

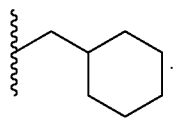

In a preferred embodiment in combination with any of the embodiments mentioned above or below, $R^5$ is a 6-10 membered mono- or bicyclic aryl or a 5-10 membered mono- or bicyclic heteroaryl containing 1 to 4 heteroatoms independently selected from the group consisting of N, O and S wherein aryl and heteroaryl is unsubstituted or substituted with 1 to 5 substituents independently selected from halogen, CN, $C_{1-6}$alkyl, $C_{1-6}$alkenyl, $C_{1-6}$ alkynyl, halo-$C_{1-6}$ alkyl, OH, O—$C_{1-6}$ alkyl, O-halo-$C_{1-6}$ alkyl, $C_{3-10}$ cycloalkyl, O—$C_{3-10}$ cycloalkyl, $COOR^9$, $C(O)R^9$, $C(O)N(R^9)_2$, $SO_2$—$N(R^9)_2$, $SO_2$—$R^9$, $C_{3-10}$ heterocycloalkyl, phenyl, 5-6 membered heteroaryl containing 1 to 4 heteroatoms independently selected from N, O and S wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, $N(R^9)_2$, O—$C_{1-6}$ alkyl; COOH, $CON(R^9)_2$, CN, $NR^9$—$COR^{10}$, $C_{3-10}$ cycloalkyl, $C_{3-10}$ heterocycloalkyl, 6-10 membered mono- or bicyclic aryl and wherein two adjacent substituents complete a 3- to 8-membered saturated or partially saturated ring containing carbon atoms and optionally containing 1 to 3 heteroatoms selected from O, S, SO, $SO_2$ or $NR^{10}$, wherein the ring is unsubstituted or substituted with one to four substitutents independently selected from halogen, oxo, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

In another preferred embodiment in combination with any of the embodiments mentioned above or below, $R^5$ is selected from

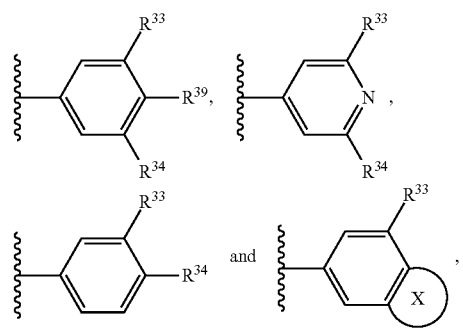

wherein $R^{33}$ is selected from $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, $C_{3-10}$-cycloalkyl, $C(O)N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{34}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{37})_2$, $S(O_2)N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{37}$ is independently selected from H, $C_{1-6}$-alkyl, halo-$C_{1-6}$-alkyl, $C_{1-6}$-cycloalkyl, wherein cycloalkyl is unsubstituted or substituted with 1 to 3 substituents independently selected from F, $C_{1-3}$-alkyl and fluoro-$C_{1-3}$-alkyl, and wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, oxo, $C_{1-4}$-alkyl and halo-$C_{1-4}$-alkyl;

$R^{38}$ is selected from H, $C_{1-3}$-alkyl and fluoro-$C_{1-3}$-alkyl;

$R^{39}$ is independently selected from H, F, OH, $C_{1-6}$-alkyl, halo-$C_{1-6}$-alkyl, O—$C_{1-6}$-alkyl and $C_{1-6}$-cycloalkyl;

X is an annelated saturated heterocycle selected from the group consisting of

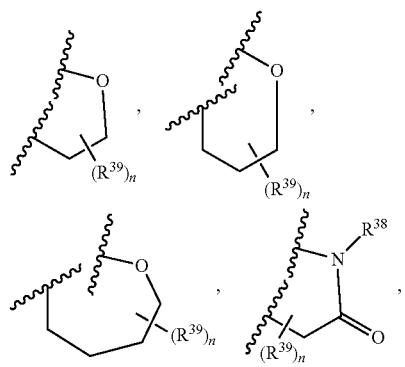

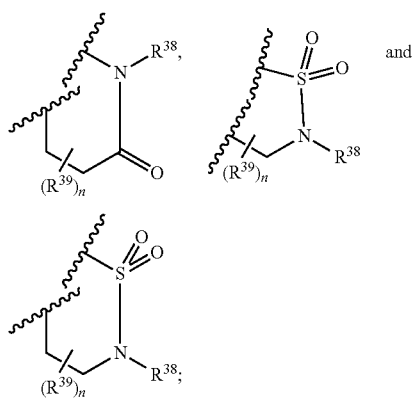
n is selected from 1 to 4.
In a preferred embodiment in combination with any of the embodiments mentioned above or below, $R^5$ is selected from
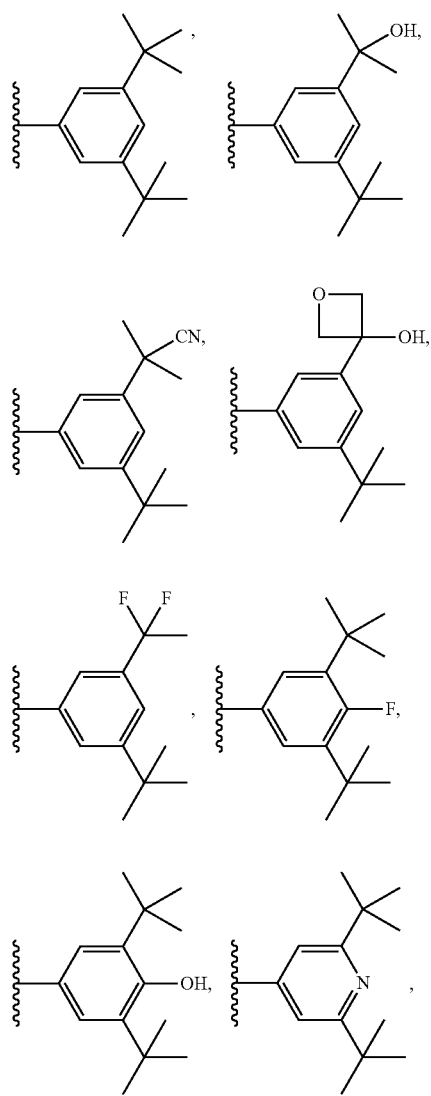
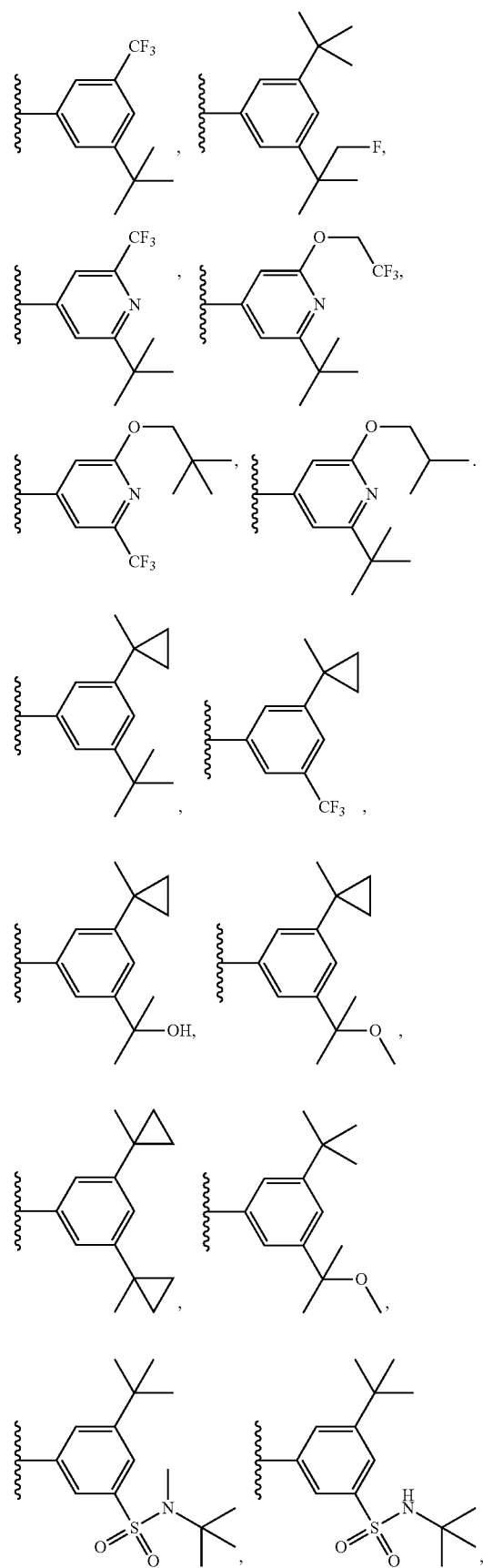

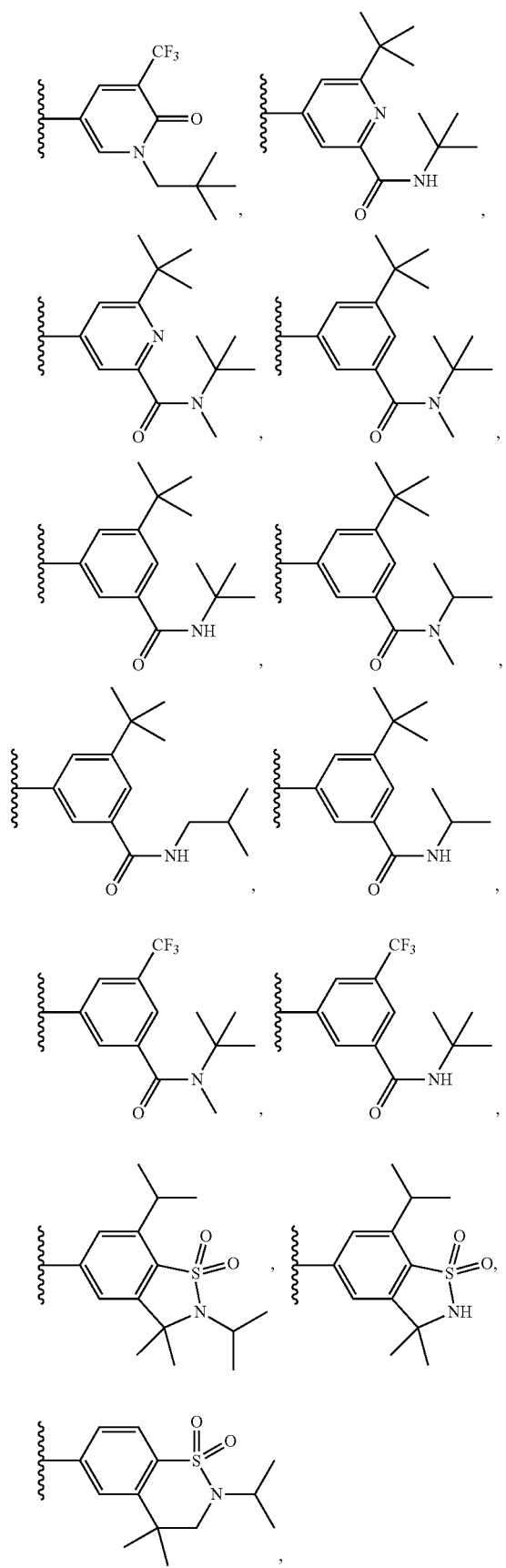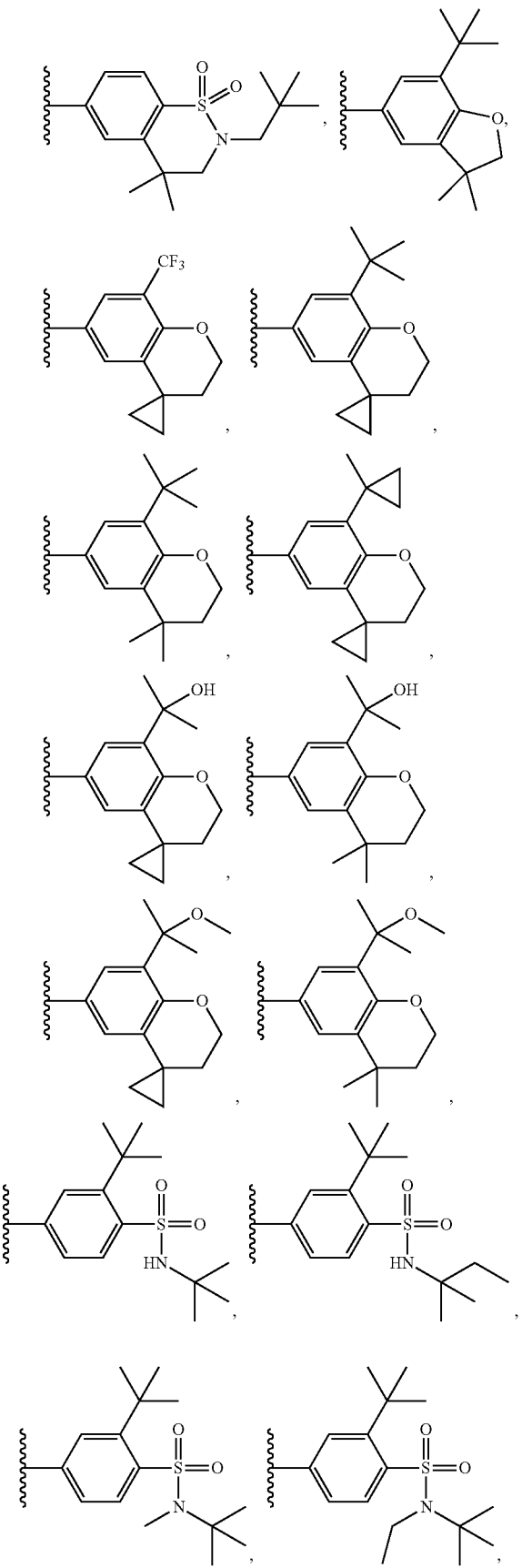

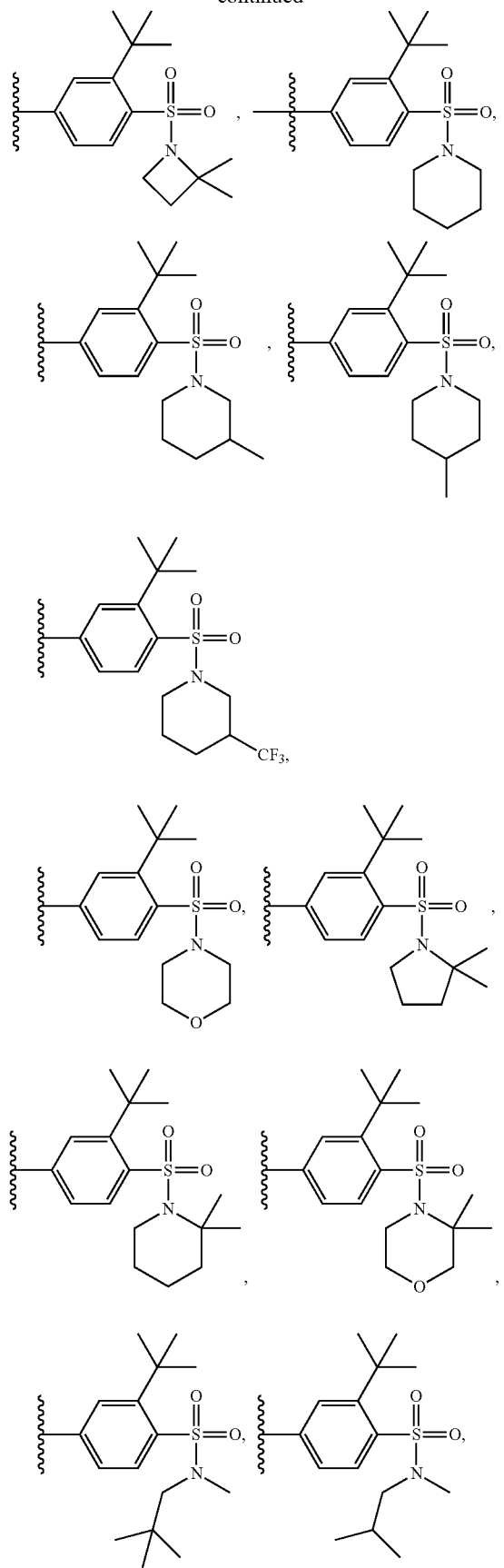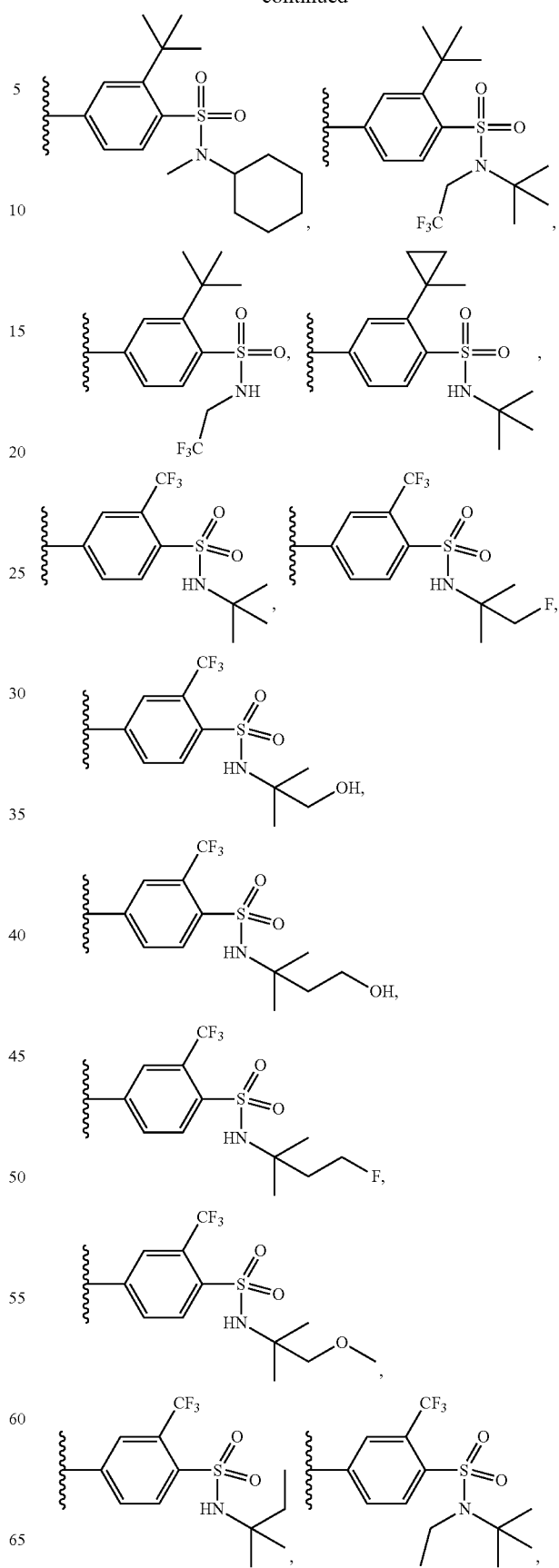

-continued
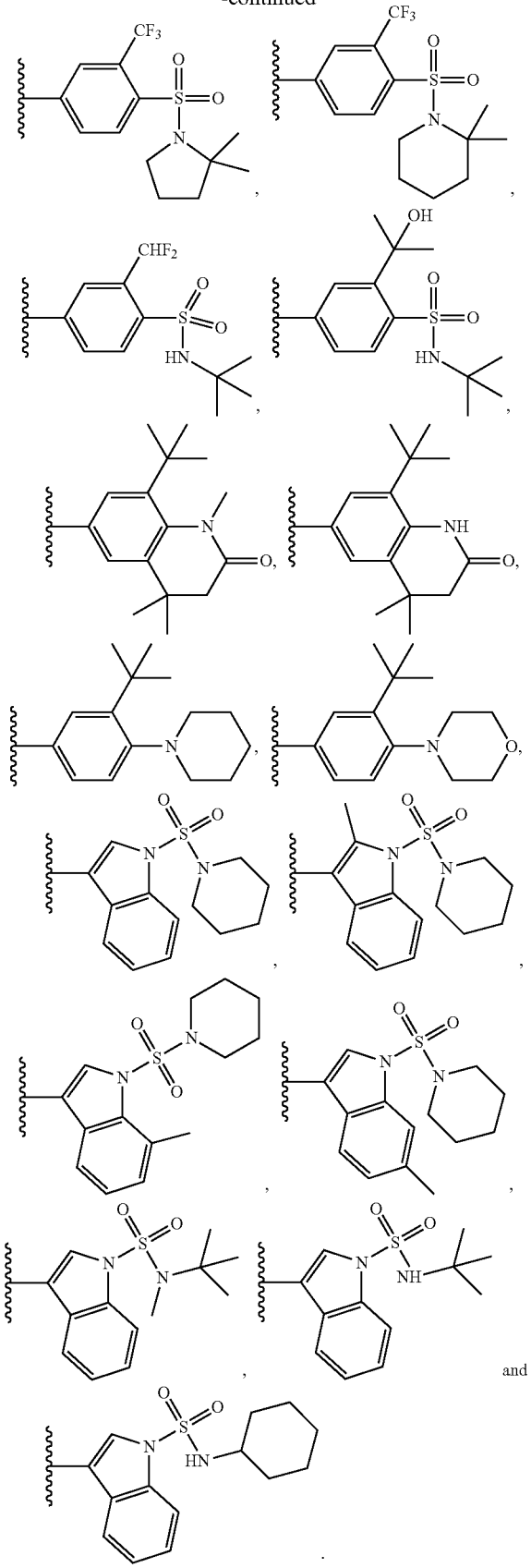
More preferably $R^5$ is
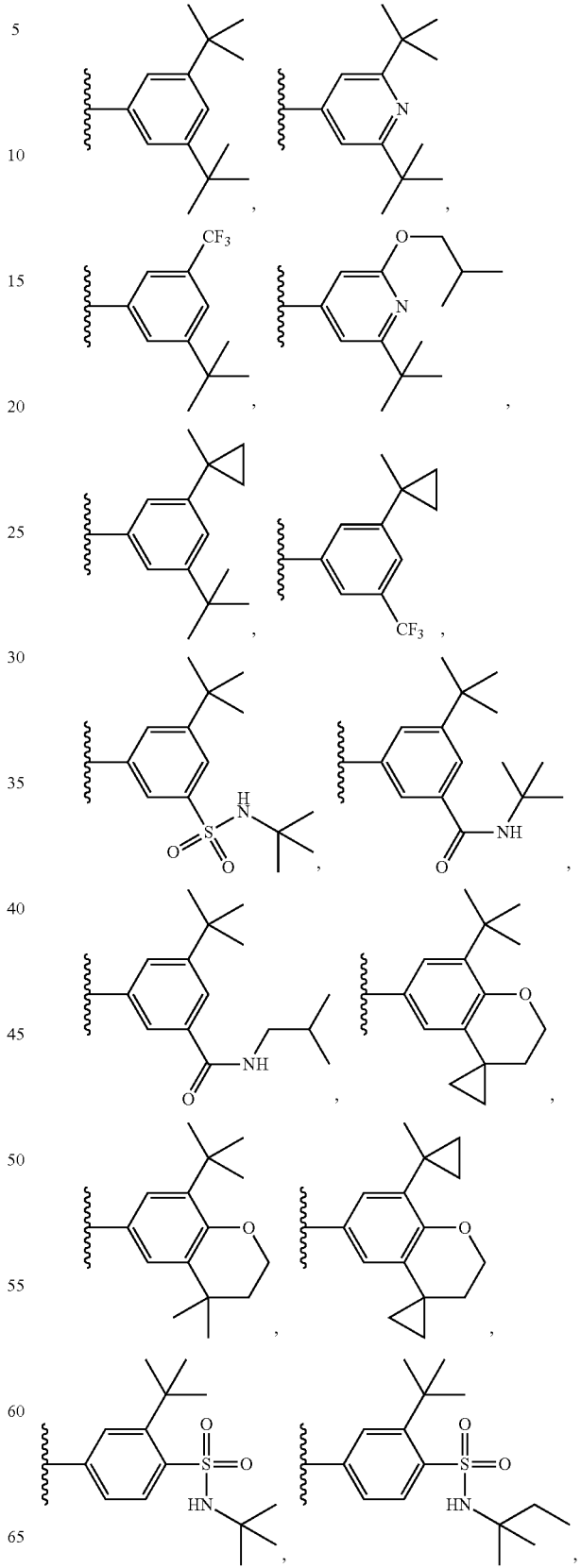

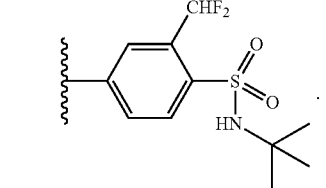

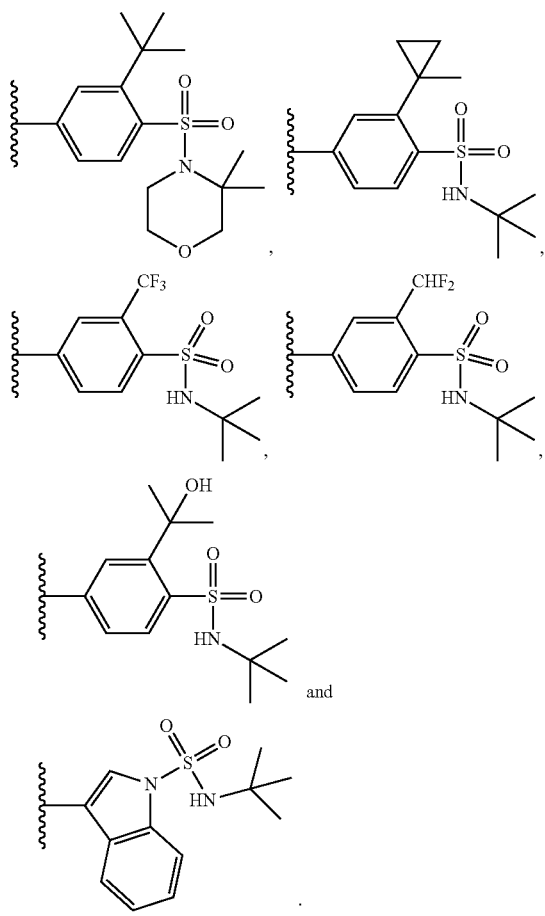

Most preferably R⁵ is

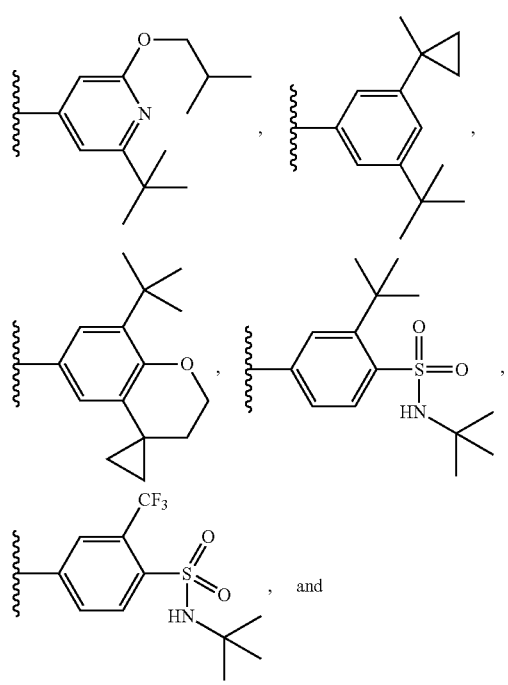

and

In another preferred embodiment in combination with any of the above or below embodiments, $R^3$ is selected from H, $C_{1-3}$ alkyl, fluoro and chloro.

In an even more preferred embodiment in combination with any of the embodiments mentioned above or below, $R^3$ is methyl and $R^6$ is H.

In a preferred embodiment in combination with any of the embodiments mentioned above or below, $R^4$ represents $(CR^8R^8)_x—R^{11}$, wherein $R^8$ is independently H, $C_{1-4}$alkyl or halo-$C_{14}$ alkyl and $R^{11}$ is $C_{3-10}$ cycloalkyl or $C_{3-10}$ heterocycloalkyl wherein cycloalkyl and heterocycloalkyl are unsubstituted or substituted as defined above. More preferably, cycloalkyl and heterocycloalkyl are unsubstituted or substituted with 1 to 3 substituents independently selected from the group consisting of halogen, OH, oxo, O—$C_{1-6}$ alkyl, O-halo-$C_{1-6}$ alkyl, $C_{1-6}$ alkyl and halo-$C_{1-6}$alkyl. It is further preferred that x is 1 or 2.

In a preferred embodiment in combination with any of the embodiments mentioned above or below, $R^5$ is a 6-10 membered mono- or bicyclic aryl or a 5-10 membered mono- or bicyclic heteroaryl containing 1 to 4 heteroatoms independently selected from the group consisting of N, O and S wherein aryl and heteroaryl is unsubstituted or substituted with 1 to 5 substituents independently selected from halogen, CN, $C_{1-6}$ alkyl, $C_{1-6}$ alkenyl, $C_{1-6}$ alkynyl, halo-$C_{1-6}$ alkyl, OH, O—$C_{1-6}$ alkyl, O-halo-$C_{1-6}$ alkyl, O—$C_{3-10}$ cycloalkyl, COOR⁹, C(O)R⁹, C(O)N(R⁹)₂, SO₂—N(R⁹)₂, SO₂—R⁹, $C_{3-10}$ heterocycloalkyl, phenyl, 5-6 membered heteroaryl containing 1 to 4 heteroatoms independently selected from N, O and S wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, N(R⁹)₂, O—$C_{1-6}$ alkyl; COOH, CON(R⁹)₂, CN, NR⁹—COR¹⁰, 3-10 membered cycloalkyl, 3-10 membered mono- or bicyclic heterocycloalkyl, 6-10 membered mono- or bicyclic aryl and wherein two substituents complete a 3- to 8-membered saturated or partially saturated ring containing carbon atoms and optionally containing 1 to 3 heteroatoms selected from O, S, SO, SO₂ or NR¹⁰, wherein the ring is unsubstituted or substituted with one to four substitutents independently selected from halogen, oxo, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

In a more preferred embodiment in combination with any of the embodiments mentioned above or below, $R^5$ is

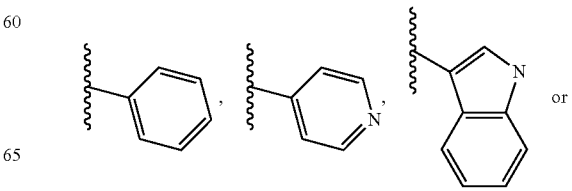

or

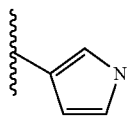

wherein aryl and heteroaryl are unsubstituted or substituted with 1 to 5 substituents independently selected from halogen, CN, $C_{1-6}$ alkyl, $C_{1-6}$ alkenyl, $C_{1-6}$ alkynyl, halo-$C_{1-6}$ alkyl, OH, O—$C_{1-6}$alkyl, O-halo-$C_{1-6}$alkyl, O—$C_{3-10}$cycloalkyl, COOR$^9$, C(O)R$^9$, C(O)N(R$^9$)$_2$, SO$_2$—N(R$^9$)$_2$, SO$_2$—R$^9$, heterocycloalkyl, phenyl, 5-6 membered heteroaryl containing 1 to 4 heteroatoms independently selected from N, O and S wherein alkyl, alkenyl, alkynyl, cycloalkyl, heterocycloalkyl, phenyl and heteroaryl is unsubstituted or substituted by 1 to 3 substituents independently selected from the group consisting of halogen, OH, oxo, N(R$^9$)$_2$, O—$C_{1-6}$ alkyl; COOH, CON(R$^9$)$_2$, CN, NR$^9$—COR$^{10}$, 3-10 membered cycloalkyl, 3-10 membered mono- or bicyclic heterocycloalkyl, 6-10 membered mono- or bicyclic aryl and wherein two substituents complete a 3- to 8-membered saturated or partially saturated ring containing carbon atoms and optionally containing 1 to 3 heteroatoms selected from O, S, SO, SO$_2$ or NR$^{10}$, wherein the ring is unsubstituted or substituted with one to four substituents independently selected from halogen, oxo, OH, O—$C_{1-6}$-alkyl, O-halo-$C_{1-6}$-alkyl, $C_{1-6}$-alkyl, $C_{3-6}$-cycloalkyl and halo-$C_{1-6}$-alkyl.

In a further preferred embodiment in combination with any of the embodiments mentioned above or below, R$^6$ is hydrogen.

The present invention provides in a preferred embodiment the following compounds:

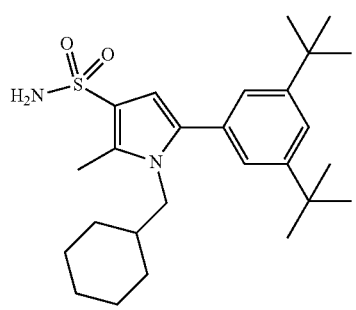

,

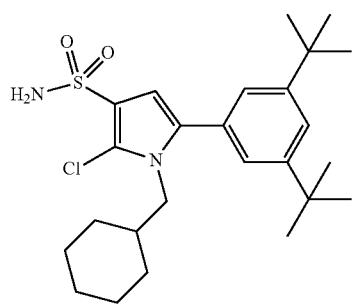

,

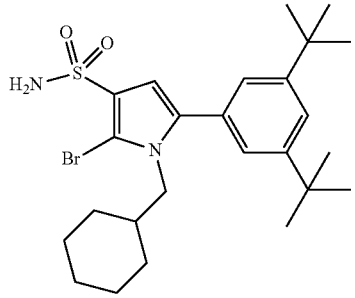

,

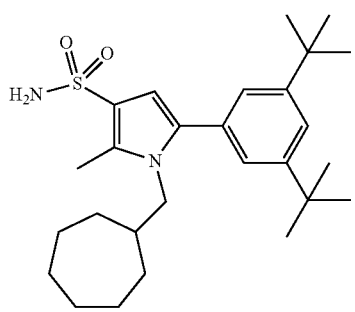

,

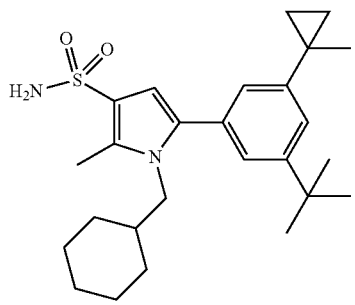

,

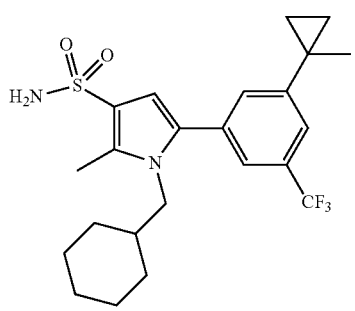

,

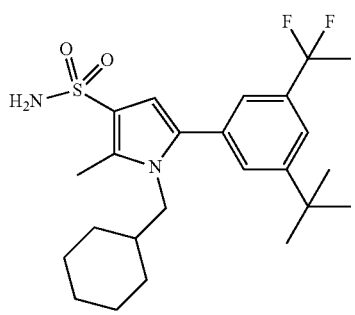

,

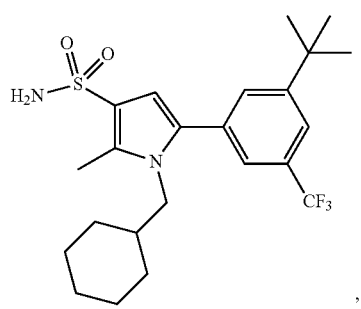
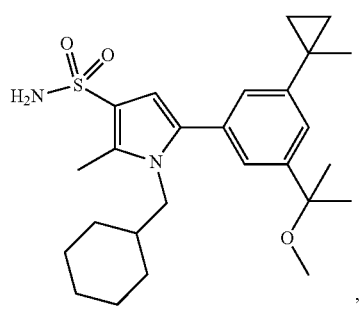
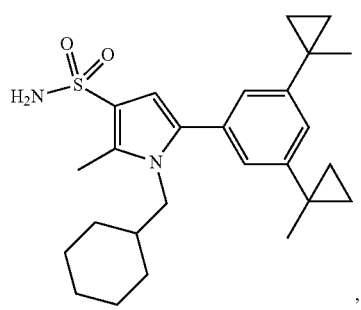
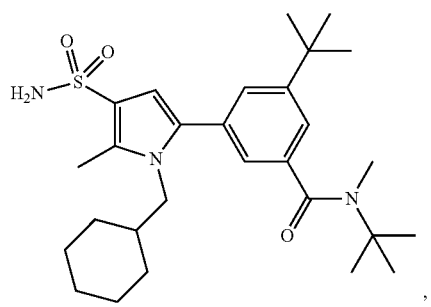
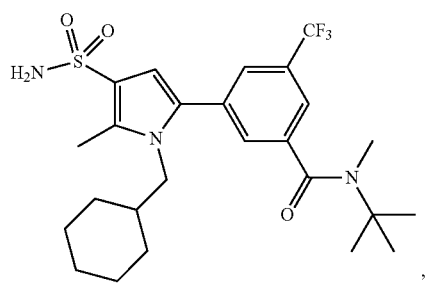
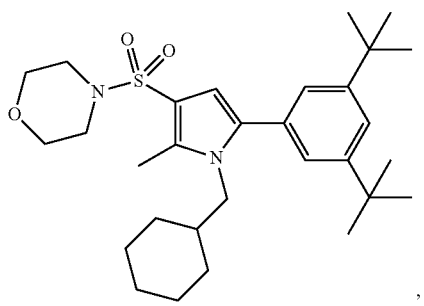
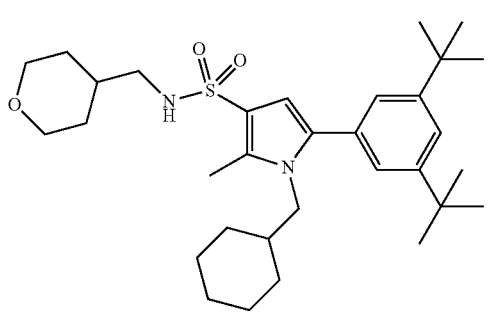
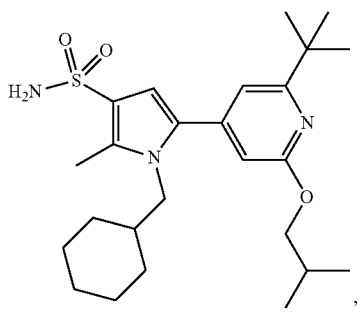
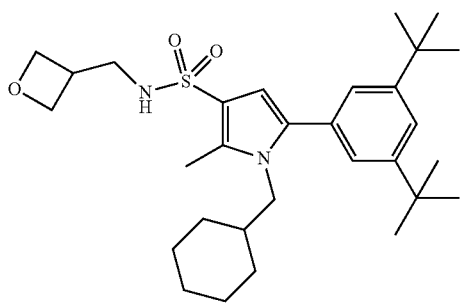
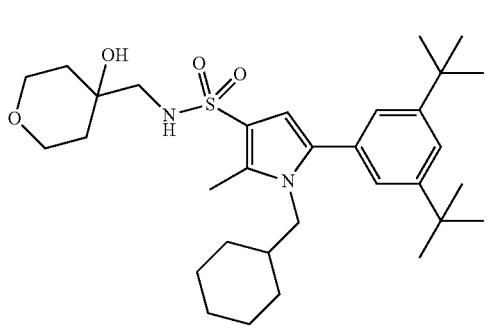

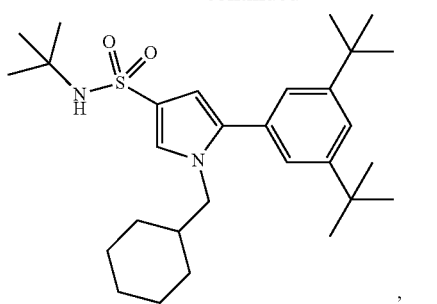
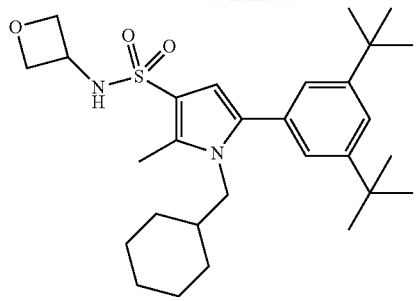
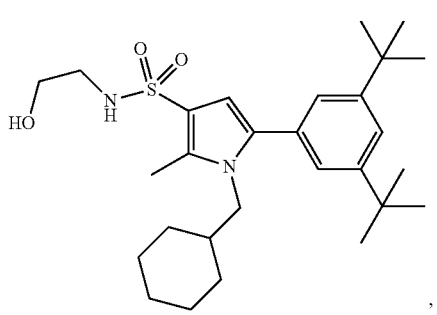
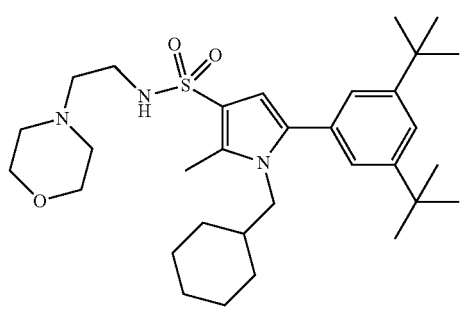
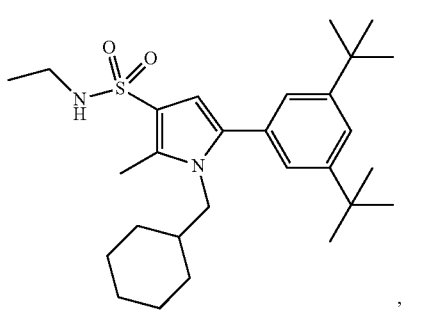
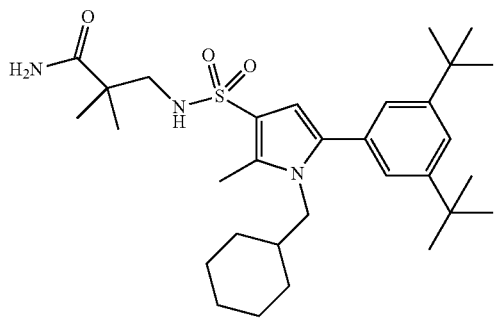
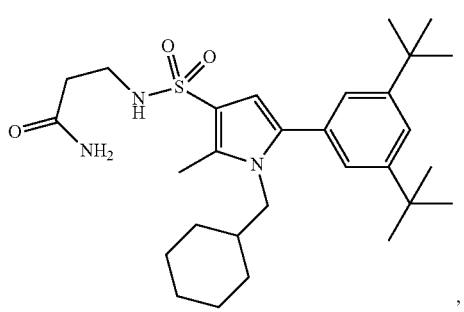
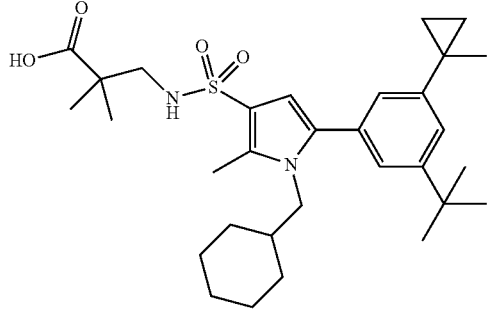
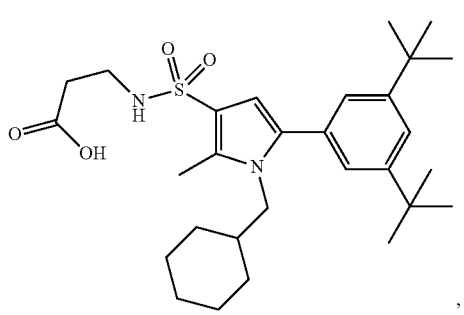
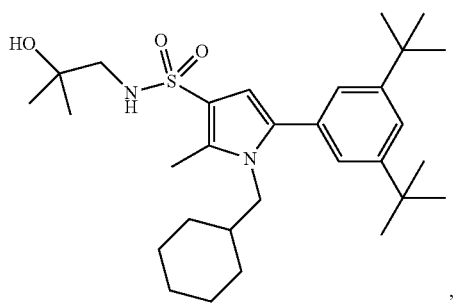

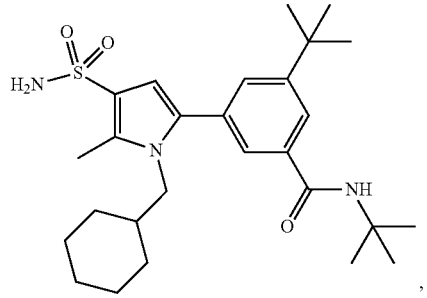
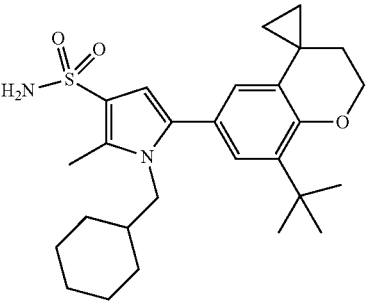
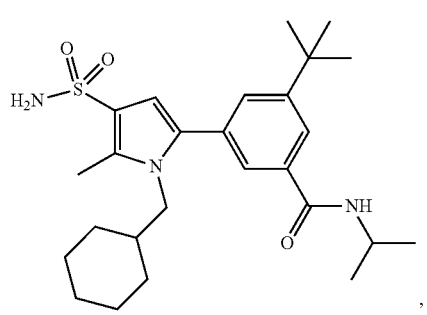
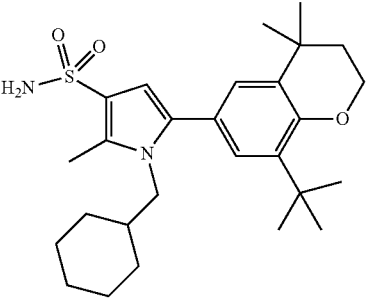
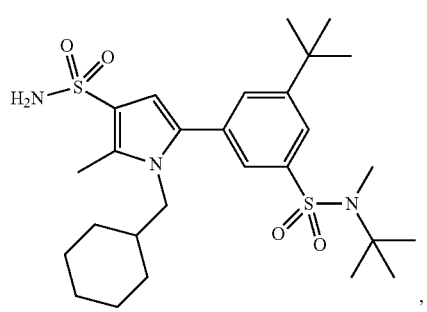
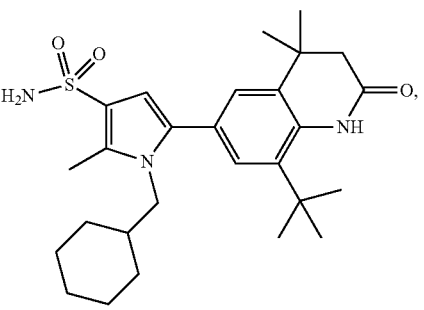
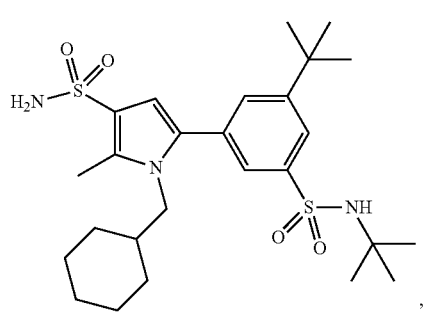
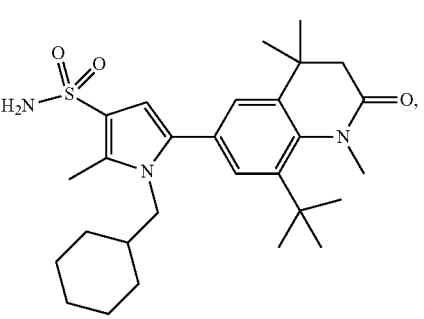
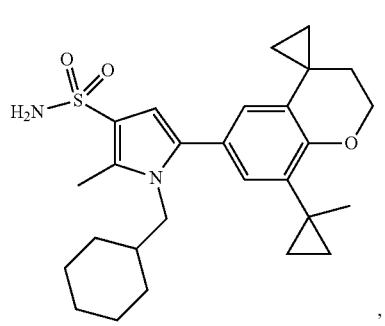
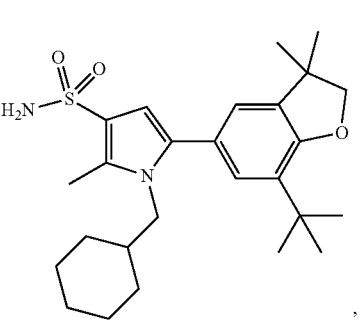

33
-continued
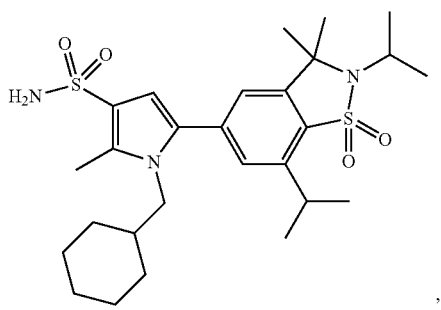
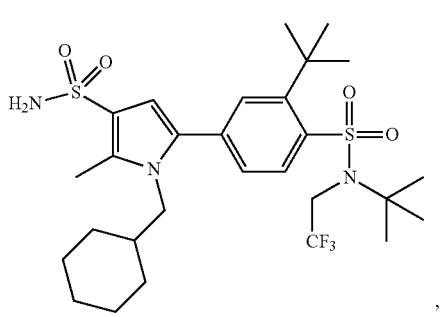
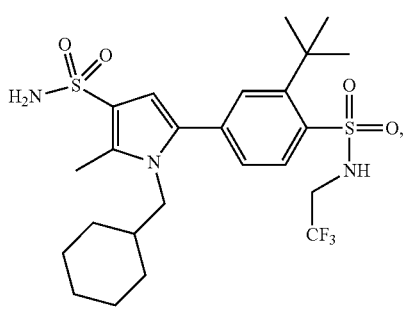
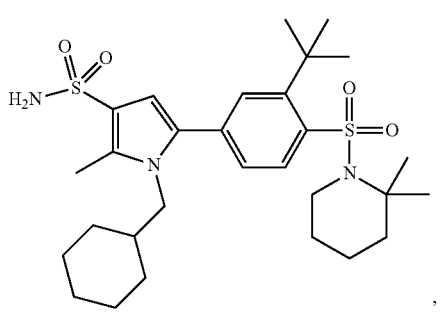
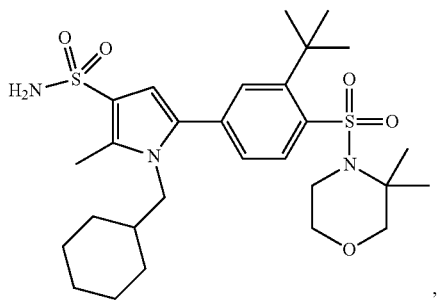
34
-continued
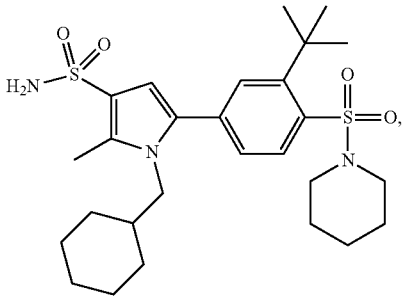
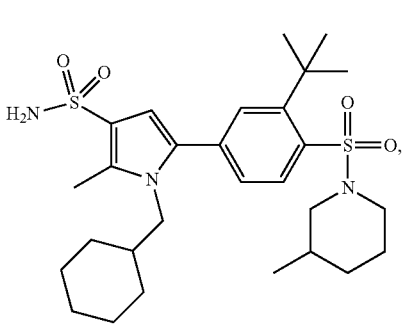
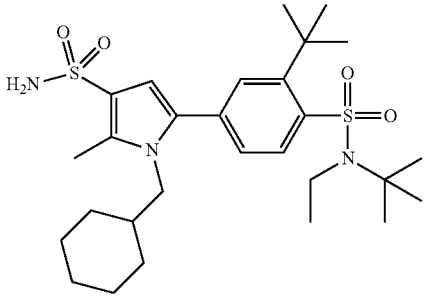
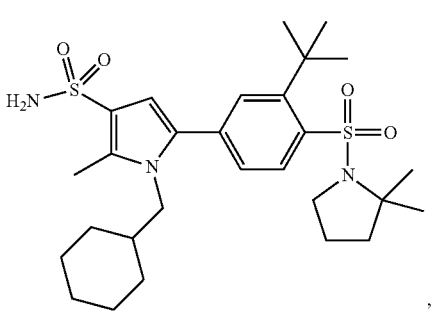
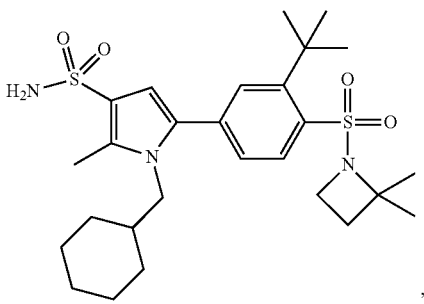

35
-continued
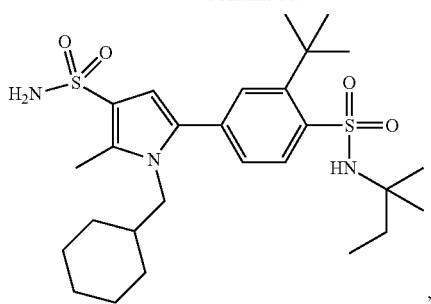
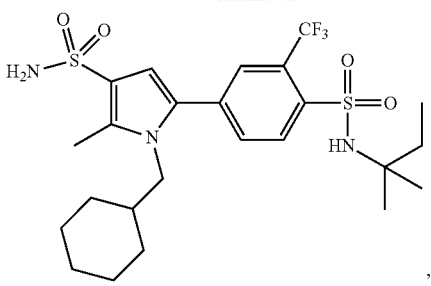
36
-continued
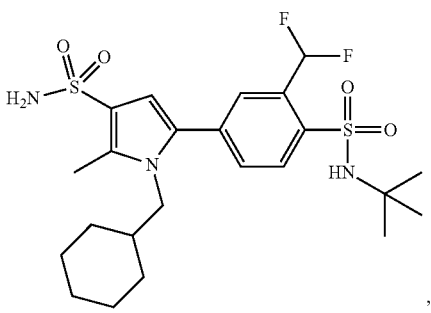
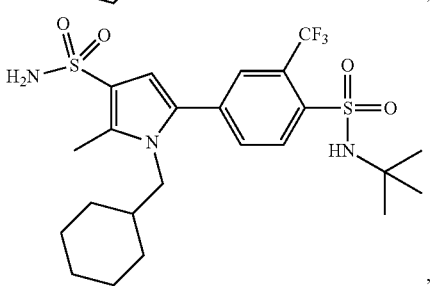
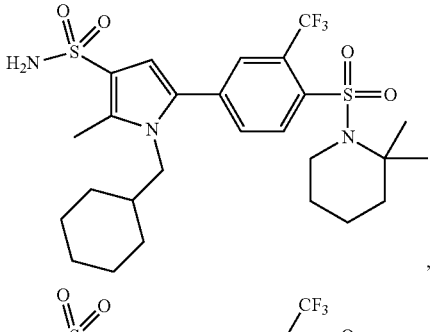
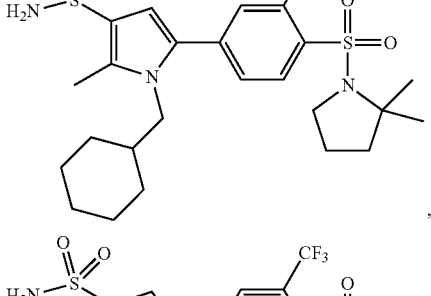
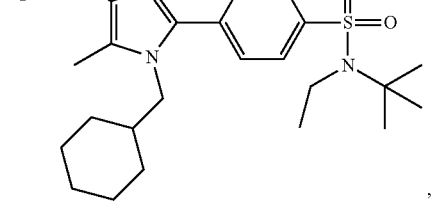

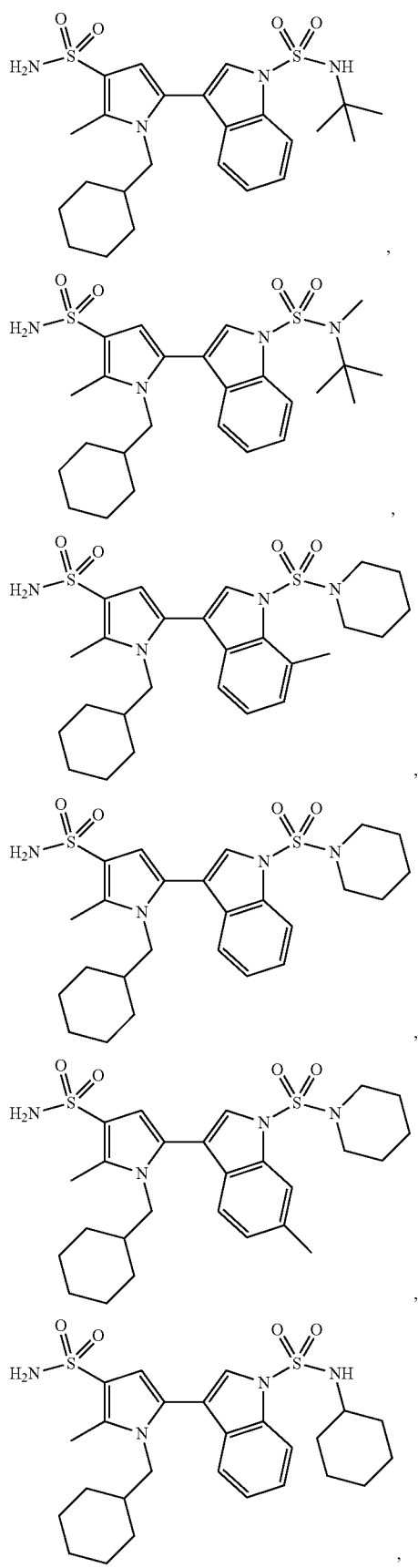
, and
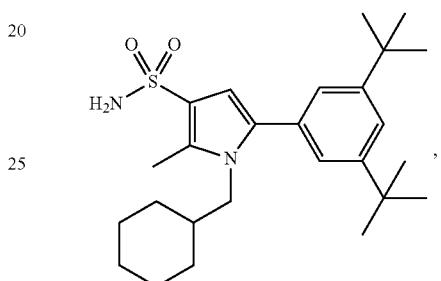
More preferably, the compounds of the present invention are selected from
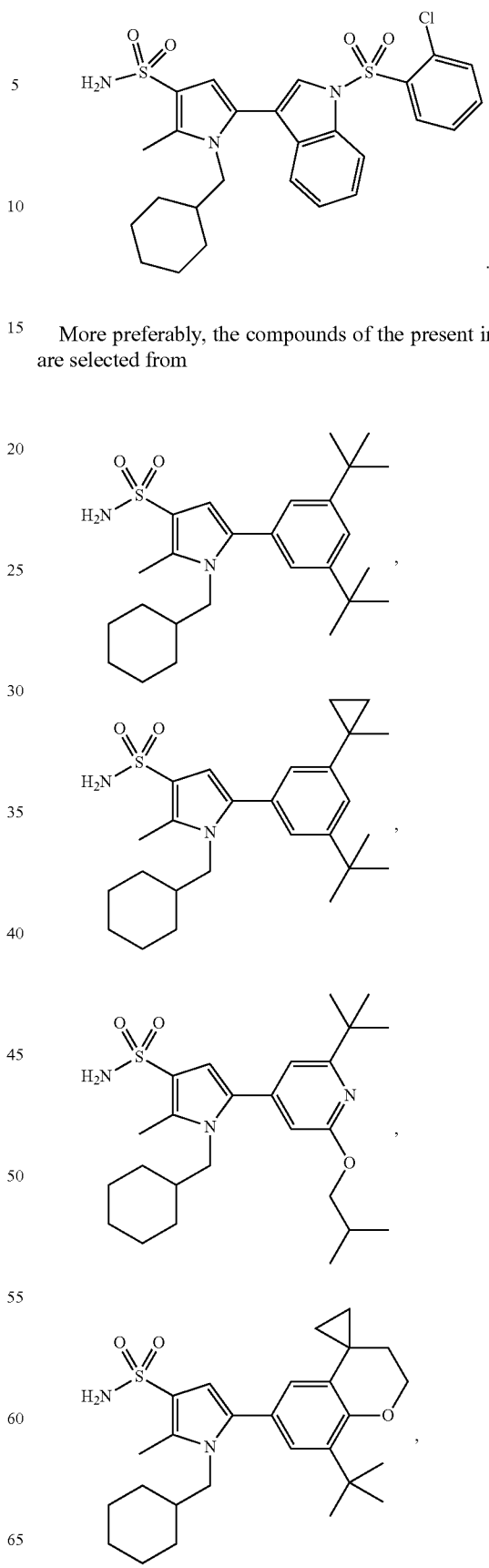

-continued

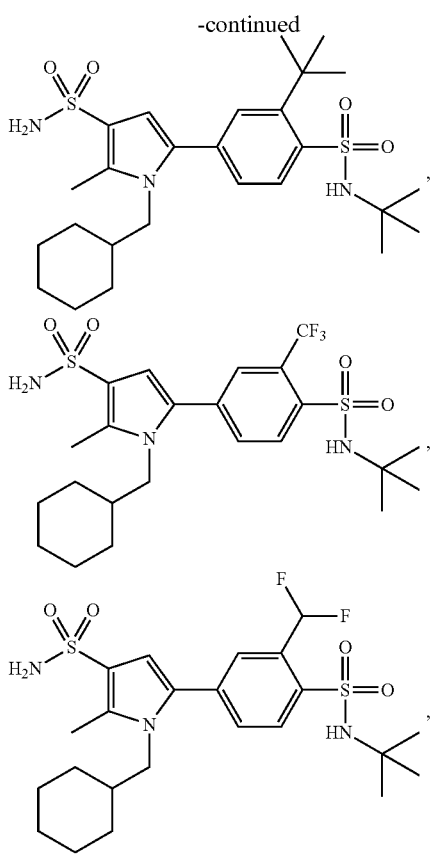

most preferably from

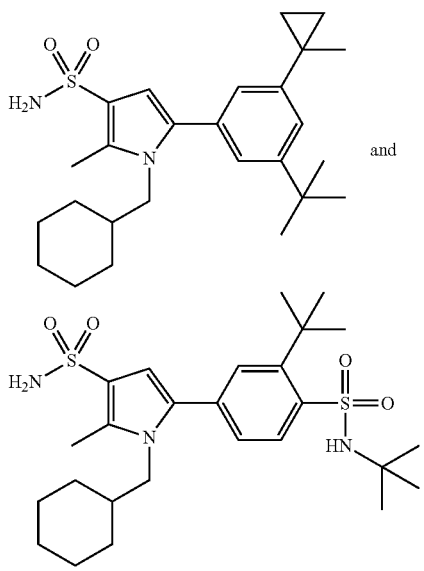

and

In another embodiment, the present invention provides the compounds of the present invention as medicament.

In a further embodiment, the compounds of the present invention are for use in the treatment of diseases or disorders which are Th17 mediated tissue inflammation, or of autoimmune etiology or which are a skin disease with associated symptoms such as pain, itching or excoriations.

In a preferred embodiment in combination with any of the embodiments mentioned above or below, the disease or disorder is selected from the group of rheumatoid arthritis, ankylosing spondylitis, lupus erythematosus, psoriasis, atopic eczema, inflammatory bowel diseases, Crohn's disease, ulcerative colitis, asthma, multiple sclerosis, type 1 diabetes and amyotrophic lateral sclerosis.

In a further embodiment in combination with any of the embodiments mentioned above or below, the compounds of the present invention are for use in the treatment or prophylaxis of a disease or disorder associated with the inhibition or activation of the RORγ receptor.

In another embodiment the present invention provides a pharmaceutical composition comprising a compound according to the present invention and a pharmaceutically acceptable carrier.

In the context of the present invention "$C_{1-10}$ alkyl" means a saturated alkyl chain having 1 to 10 carbon atoms which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl and decyl.

The term "halo-$C_{1-10}$ alkyl" means that one or more hydrogen atoms in the alkyl chain are replaced by a halogen. A preferred example thereof is $CF_3$.

"$C_{1-10}$ alkenyl" means an alkyl chain having 1 to 10 carbon atoms which may be straight chained or branched, containing at least one carbon to carbon double bond. Examples thereof include ethenyl, propenyl, decenyl, 2-methylenehexyl and (2E,4E)-hexa-2,4-dienyl.

"$C_{1-10}$ alkynyl" means an alkyl chain having 1 to 10 carbon atoms which may be straight chained or branched, containing at least one carbon to carbon triple bond. Examples thereof include ethynyl, propynyl and decynyl.

A "$C_{0-6}$ alkylene" means that the respective group is divalent and connects the attached residue with the remaining part of the molecule. Moreover, in the context of the present invention, "$C_0$ alkylene" is meant to be represent a bond.

A $C_{3-10}$ cycloalkyl group means a saturated or partially unsaturated mono-, bi- or multicyclic ring system comprising 3 to 10 carbon atoms. Examples include cyclopropyl, cyclobutyl, cyclopentyl, cyclohexyl, cyclohexenyl, bicyclo[2.2.2]octyl, bicyclo[2.2.1]heptyl, adamantyl and pentacyclo[4.2.0.0$^{2,5}$.0$^{3,8}$.0$^{4,7}$]octyl.

A $C_{3-10}$ heterocycloalkyl group means a saturated or partially unsaturated 3 to 10 membered carbon mono-, bi- or multicyclic ring wherein 1, 2 or 3 carbon atoms are replaced by 1, 2 or 3 heteroatoms, respectively, wherein the heteroatoms are independently selected from N, O and S. Examples thereof include epoxidyl, oxetanyl, pyrrolidinyl, tetrahydrofuranyl, piperidinyl, piperazinyl tetrahydropyranyl, 1,4-dioxanyl, morpholinyl, 4-quinuclidinyl, 1,4-dihydropyridinyl and 3,6-dihydro-2H-thiopyranyl. The $C_{3-10}$ heterocycloalkyl group can be connected via a carbon or nitrogen atom.

A 5-14 membered mono-, bi- or tricyclic heteroaromatic ring system (within the application also referred to as heteroaryl) containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bi- or tricyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl, pyrazolo[1,5-a]pyrimidinyl and dibenzo[b,d]furanyl.

A 6-10 membered mono- or bicyclic aromatic ring system (within the application also referred to as aryl) means an aromatic carbon cycle such as phenyl or naphthalenyl.

Halogen is selected from fluorine, chlorine, bromine and iodine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

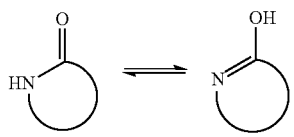

A $C_{3-10}$ cycloalkyl or $C_{3-10}$ heterocycloalkyl group can be connected straight or spirocyclic, e.g. when cyclohexan is substituted with the heterocycloalkyl group oxetane, the following structures are possible:

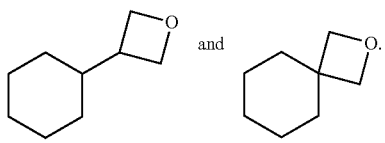 [SMILES: C1CCC(C2COC2)CC1 ; C1CCC2(CC1)COC2]

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing RORγ-mediated conditions for which compounds of Formula (1) are indicated, generally satisfactory results are obtained when the compounds are administered at a daily dosage of from about 0.1 milligram to about 100 milligram per kilogram of mammal body weight, preferably given as a single daily dose or in divided doses two to six times a day, or in sustained release form. For most large mammals, the total daily dosage is from about 1.0 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The present invention describes modulators, in the following also referred to as ligands, which bind to the RORγ receptor. Surprisingly, it has been found that compounds of Formula (1) act as modulators of the RORγ receptor.

The RORγ receptor is considered to be involved in thymocyte development, thus the modulators described herein may be useful in the treatment of inflammatory skin diseases such as atopic eczema and psoriasis. It is further suggested that down-modulation of RORγ transcriptional activity with a ligand could result in a shift of the immune response towards a Th2 type response which could be beneficial in the treatment of certain allergic inflammatory conditions such as rheumatoid arthritis, systemic lupus erythomatosis, inflammatory bowel disease (Crohn's Disease) and multiple sclerosis (Tesmer et. al., *Immunol. Rev.* 2008, 223:97).

The compounds of Formula (1) show antagonistic activity, with respect to the dose dependent modulation of the constitutive interaction of the RORγ ligand binding domain with peptides derived from the co-activators such as SRC-1, TRAP 220 or TIF-2.

It has been surprisingly found that the interaction between RORγ ligand binding domain and the peptides can be determined by a homogenous FRET based ligand-sensing assays. Even more surprising was the identification of compounds of Formula (1) as ligands for RORγ.

The identification of high affinity ligands for RORγ with agonistic and antagonistic properties is the basis to enable experts knowledgeable in the field to establish assays for the identification of novel agonistic and antagonistic RORγ ligands from libraries of small molecules. The identification of ligands which bind to and modulate the activity of RORγ1 and RORγ 2 is the first mandatory step to develop new small molecule based medicines with a potential to be developed for the treatment of diseases which are directly or indirectly controlled by the activity of RORγ1 or RORγ 2. Such diseases include but are not restricted to inflammatory diseases, asthma, rheumatoid arthritis, autoimmune diseases or diseases with an autoimmune component such as systemic lupus erythomatosis, inflammatory bowel disease (Crohn's disease), ulcerative colitis, inflammatory skin diseases such as atopic eczema or psoriasis, multiple sclerosis or similar diseases.

The compounds of the present invention can be prepared by a combination of methods known in the art including the procedures described in Schemes I to VI below.

Scheme I depicts the N-alkylation of a pyrrolo derivative of formula A-1 with an alkylbromide or -mesylate in the presence of an appropriate base in a suitable solvent. The resulting intermediate A-II can be treated with chlorosulfuric acid and subsequently with amine $HNR^1R^2$ similar as described previously in *J. Chem. Soc. Perkin Trans.* 1, 1998, 3285 to give intermediate A-III. Decarboxylation similar as described previously in *J. Chem. Soc. Perkin Trans.* 1, 1998, 3285 affords compound A-IV and subsequently bromination using N-bromosuccinimide affords compound A-V, which subsequently gives rise to target compound A-VI by Pd-catalysed reaction (Suzuki coupling) using a suitable boronic acid or boronic ester.

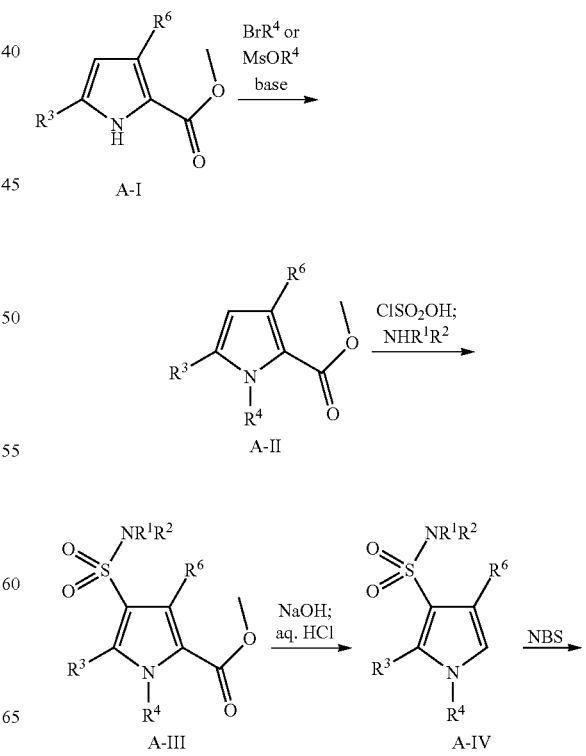

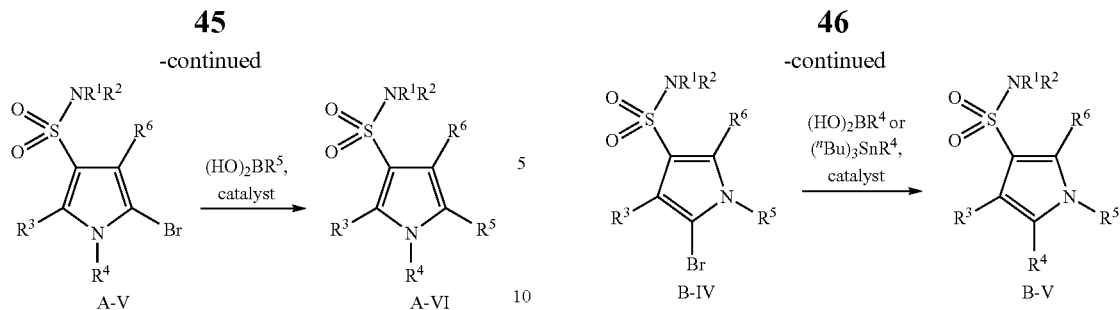

Scheme II depicts the N-arylation of a pyrrolo derivative of formula (B-1, commerically available or synthesized from alkyl-vinylketone and N-[(4-methylphenyl)sulfonyl]-glycine ethyl ester similar as described in WO2008/154271) with a suitable boronic acid ester using Cu(OAc)$_2$ and pyridine as catalyst similar as previously described in *Tetrahedron* 2008, 64:328. The resulting intermediate B-II can be treated with chlorosulfuric acid and subsequently with amine HNR$^1$R$^2$ similar as described previously in *J. Chem. Soc. Perkin Trans.* 1, 1998, 3285 to give intermediate B-III. Decarboxylation similar as described previously in *J. Chem. Soc. Perkin Trans.* 1, 1998, 3285 and subsequently bromination using N-bromo-succinimide (NBS) affords compound B-IV, which subsequently gives rise to target compound B-V by Pd-catalysed reaction using a suitable boronic acid or via a Stille coupling using a suitable stannane derivative (see e.g. *Bioorg. Med. Chem. Lett.* 2006, 16:5203).

As illustrated in Scheme III, N-alkylation of a pyrrolo derivative C-I with alkylbromide R$^6$Br can be performed in the presence of a base to give intermediate C-II. Friedel-Crafts acylation using chloro(methoxy)methane in the presence of AlCl$_3$ as catalyst (*J. Amer. Chem. Soc.* 1987, 109:271) affords aldehyde C-III. Attachment of the R$^{4'}$-group (wherein R$^{4'}$ represents —(CR$^8$R$^8$)$_{x-1}$—R$^{11}$), e.g. by use of a Wittig reaction using an appropriate alkyltriphenylphosphonium bromide with subsequent hydrogenation of the double bond affords derivative C-IV. Derivative V can be obtained by bromination with NBS as previously described for similar compounds in *J. Org. Chem.* 2004, 69:2362. Attachment of the R$^5$-group can be accomplished utilizing a Suzuki-coupling of boronic acid (HO)$_2$BR$^5$ to give derivative C-VI. Saponification and decarboxylation with NaOH (*J. Amer. Chem. Soc.* 2008, 130:2404), treatment with chlorosulfuric acid and subsequently with amine HNR$^1$R$^2$ affords final compound C-VIII.

Scheme II

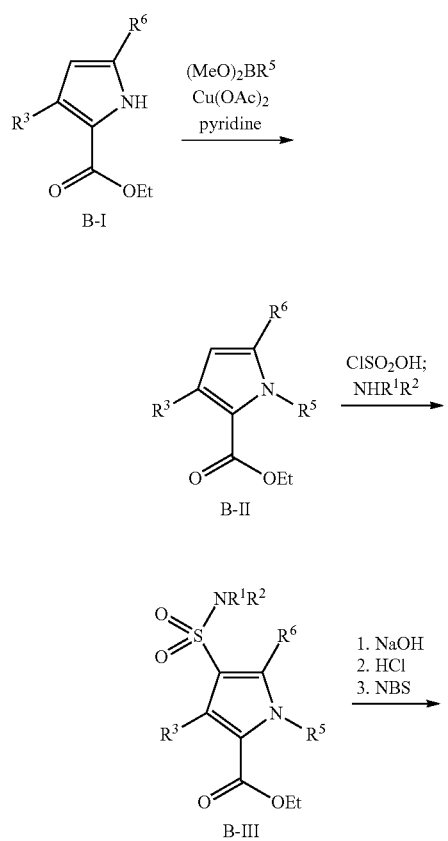

Scheme III

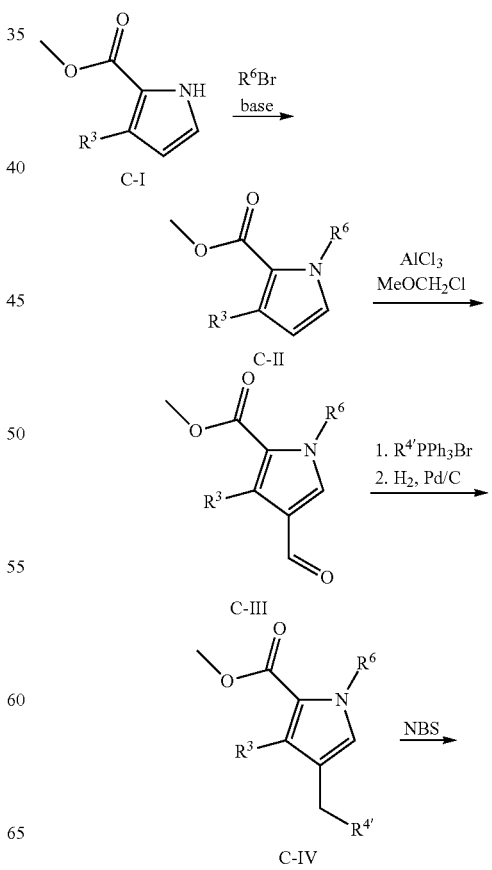

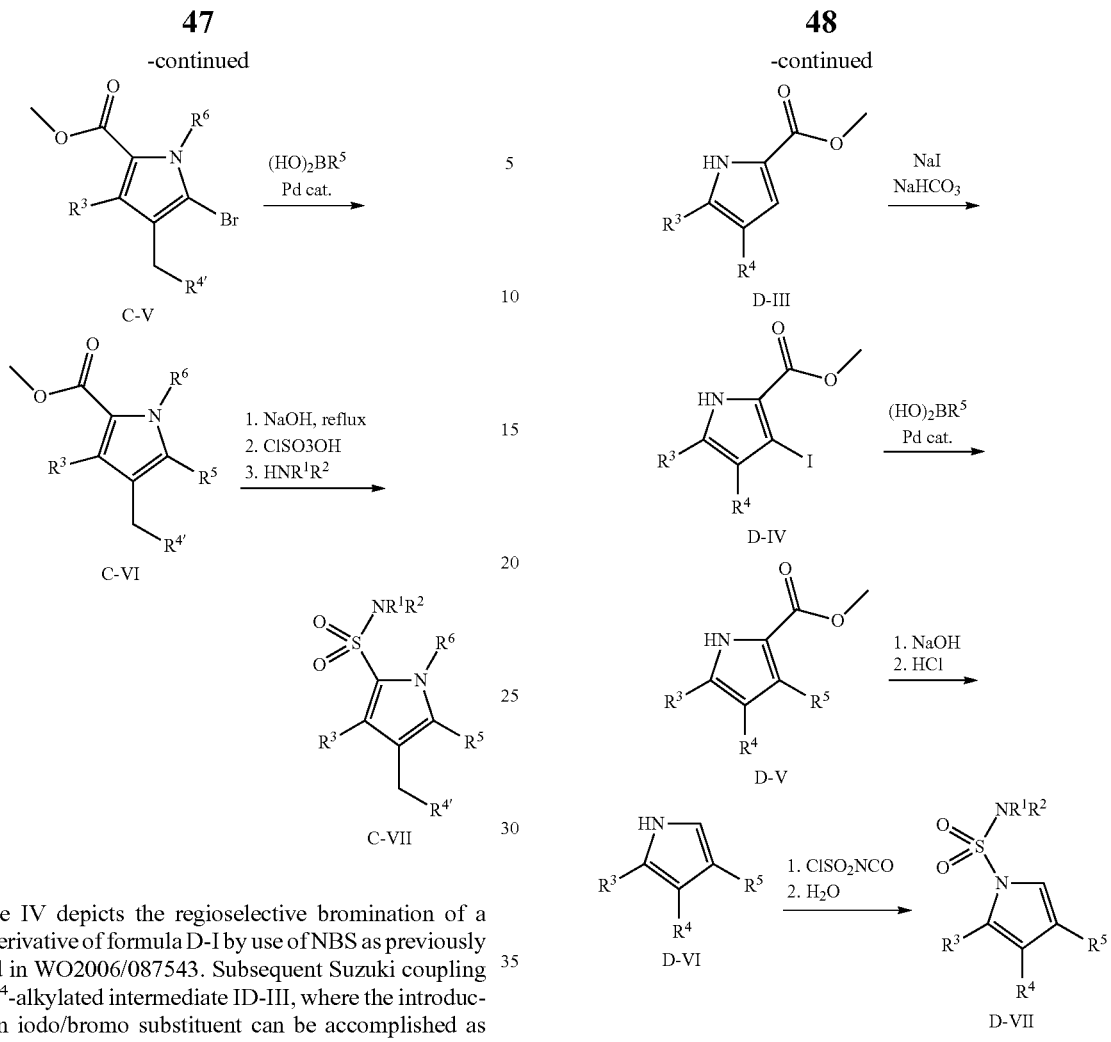

Scheme IV depicts the regioselective bromination of a pyrrolo derivative of formula D-I by use of NBS as previously described in WO2006/087543. Subsequent Suzuki coupling affords $R^4$-alkylated intermediate ID-III, where the introduction of an iodo/bromo substituent can be accomplished as described previously in Faming Zhuanli Shenqing Gongkai Shuomingshu, 1769284, 2006 (for iodo) or *Gazzetta Chimica Italiana* 1986, 116:589 (for bromo) to afford derivative D-IV. Again, by use of a Suzuki coupling substituent $R^5$ can be introduced to give intermediate D-V, which can be decarboxylated as described above. The resulting intermediate D-VI can be treated with chlorosulfonyl isocyanate or $R^1R^2SO_2Cl$ to give target compound D-VII after aqueous workup.

Scheme V depicts the N-alkylation of a pyrrolo derivative of formula E-1 with an alkylbromide in the presence of an appropriate base in a suitable solvent. The resulting intermediate E-II can be treated with acid chloride under Friedel-Crafts conditions. Subsequently the formed ketone can be reduced using a suitable agent, e.g. hydrazine (Wolff-Kishner reduction) to afford intermediate E-III with an $R^{4'}$ substituent ($R^{4'}$ represents $(CR^8R^8)_{x-1}$—$R^{11}$). Regioselective deprotonation can be accomplished with stong bases, e.g. butyl lithium, and quenching with sulfur dioxide affords an intermediate, which can be transformed with NBS to the sulfonyl chloride. Reaction with amine $HNR^1R^2$ can give intermediate E-IV, which can be brominated with NBS. Subsequent Pd-catalysed reaction using a suitable boronic acid or ester can afford the target compound E-V.

Scheme IV

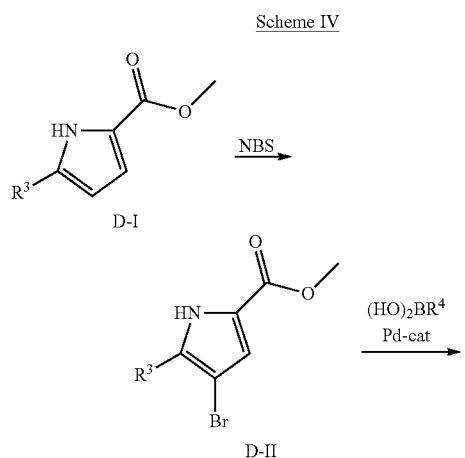

Scheme V

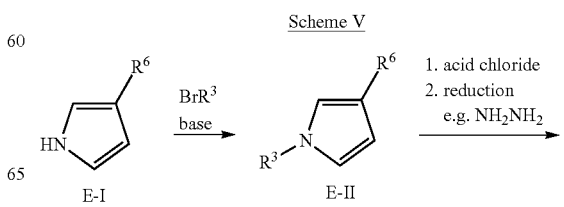

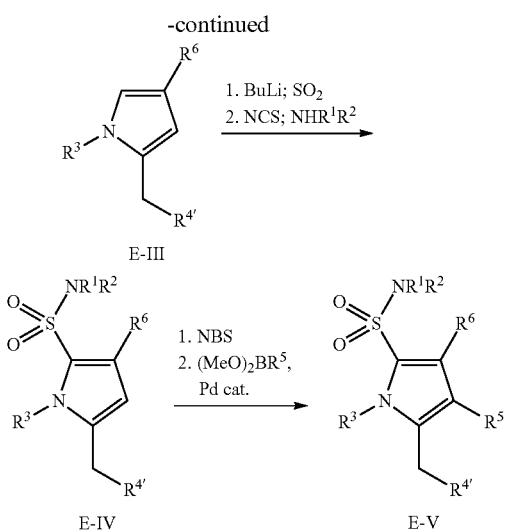

Derivatives with a R⁴ residue linked via a SO₂-group can get synthesized as illustrated in Scheme VI: A suitable substituted pyrrole educt E-I can be halogenated similar as described in *Tetrahedron* 2007, 63:3826. Reaction of intermediate E-II with ClSO₂R⁴' (wherein R⁴' represents —(CR⁸R⁸)$_{y-1}$—R⁷) using a base (e.g. sodium hydride) affords intermediate E-III, where the bromo substituent reacts in a Suzuki coupling to give compound E-IV. Finally, the resulting intermediate can be treated with chlorosulfuric acid and subsequently with amine HNR¹R² similar as described above to give target compound E-V (similar as described in *Tetrahedron* 2006 62:1699).

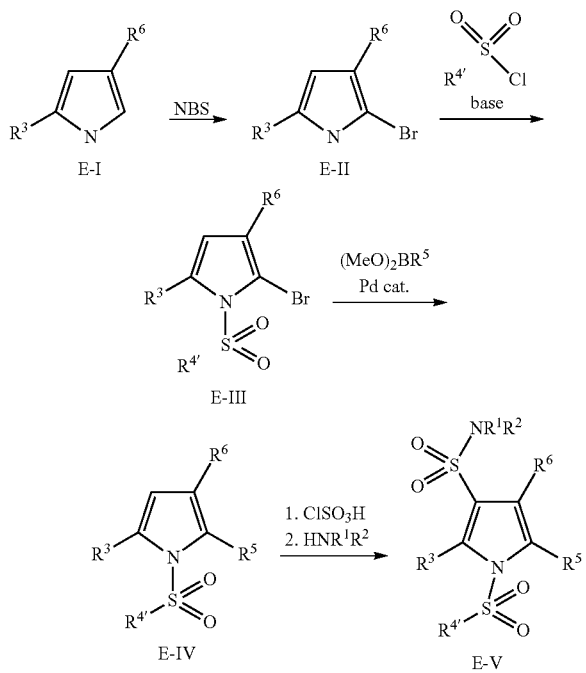

Scheme VI

By using a combination of the reactions described above, the other regioisomers can be prepared.

EXPERIMENTAL SECTION

Abbreviations

ACN acetonitrile
AIBN azobisisobutyronitrile
aq. aqueous
Boc tert-butyloxycarbonyl
CC (flash) chromatography on silica gel
COD cyclooctadiene
CoTPP Cobalt-meso-tetraphenylporphyrine
DAST diethylaminosulfur trifluoride
dba dibenzylideneacetone
DCM dichloromethane
DIBAH diisobutylaluminium hydride
DIPEA diisopropylethylamine
DMF N,N-dimethylformamide
dtbpy 4,4'-di-t-butyl-2,2'-bipyridine
dppf 1,1'-Bis(diphenylphosphino)ferrocene
dppp 1,3-bis(diphenylphosphino)propane
EA ethyl acetate
HATU O-(7-azabenzotriazole-1-yl)-N,N,N',N'-tetramethyluronium hexafluorophosphate
HMDS hexamethyldisilazane
NBS N-bromosuccinimide
NCS N-chloroosuccinimide
PCC pyridinium dichlorochromate
PE petroleum ether
Pin pinacolato (OCMe₂CMe₂O)
sat. saturated
TEA triethylamine
Tf trifluoromethyl
TFA trifluoroacetic acid
THF tetrahydrofuran
TLC thin layer chromatography
TMS trimethlylsilyl
Ts tosyl Preparative Example P1

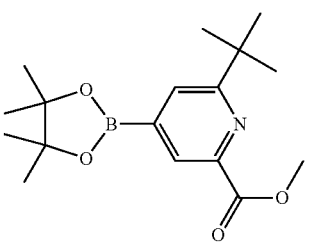

P1

Step 1: Methyl 6-(tert-butyl)picolinate (P1a)

To the solution of 2-bromo-6-(tert-butyl)pyridine (20.0 g, 93.9 mmol) in MeOH (100 mL) was added dppp (3.86 g, 9.39 mmol), Pd(OAc)₂ (6.32 g, 9.39 mmol) and TEA (28.5 g, 281 mmol) and then the mixture was stirred under CO (4 MPa) at 70° C. for 12 h. The reaction mixture was filtered, concentrated and purified by CC (PE/EA=40/1) to give compound P1a (12.0 g, 66%) as a colorless oil.

Step 2: Methyl 6-(tert-butyl)-4-(4,4,5,5-tetramethyl-1,3,2-dioxaborolan-2-yl)picolinate (P1)

The solution of compound P1a (10.0 g, 51.7 mmol), B₂Pin₂ (17.2 g, 68.1 mmol), [(COD)Ir(μ-OMe)]₂ (1.2 g, 1.85 mmol)

and dtbpy (990 mg, 3.69 mmol) in THF (100 mL) was stirred at 80° C. under N$_2$ overnight. The mixture was quenched with water and extracted with EA twice. The combined organic layers were washed with water (3×) and brine consecutively, dried over Na$_2$SO$_4$, filtered, concentrated and purified by CC (PE/EA=30/1) to give compound P1 (7.2 g, 44%) as a white solid.

Preparative Example P2

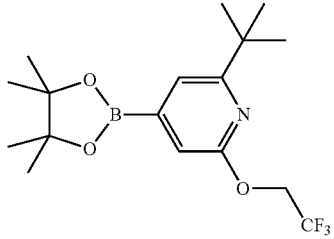

P2

Step 1: 4-Bromo-2-(tert-butyl)-6-(2,2,2-trifluoroethoxy)pyridine (P2a)

To a solution of 4-bromo-6-(tert-butyl)pyridin-2-ol (5.00 g, 21.8 mmol) in dry DMF (50 mL) was added NaH (1.75 g, 43.7 mmol) at 0° C. under N$_2$ and the mixture was stirred at 0° C. for 30 min. Then CF$_3$CH$_2$OTs (11.1 g, 43.7 mmol) was added and the solution was stirred at 70° C. overnight. Water was added and the mixture was extracted with EA twice. The combined organic layers were washed with water (3×) and brine twice, concentrated and purified by CC (PE/EA=30/1) to give compound P2a (1.13 g, 17%) as a white oil.

Step 2: 2-(tert-Butyl)-4-(4,4,5,5-tetramethyl-1,3,2-dioxaborolan-2-yl)-6-(2,2,2-trifluoroethoxy)pyridine (P2)

The solution of compound P2a (1.23 g, 3.95 mmol), B$_2$Pin$_2$ (1.20 g, 4.74 mmol), AcOK (778 mg, 7.91 mmol) and Pd(dppf)Cl$_2$ (200 mg) in dry DMF (20 mL) was heated at 90° C. for 2 h under N$_2$, quenched with water and extracted with EA twice. The combined organic layers were washed with water (3×) and brine consecutively, dried over Na$_2$SO$_4$, filtered, concentrated and purified by CC (PE/EA=20/1) to give compound P2 (922 mg, 65%) as a white solid.

Preparative Example P3

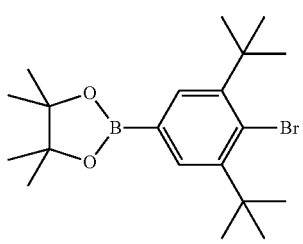

P3

Step 1: 2-Bromo-1,3-bis(bromomethyl)benzene (P3a)

To a stirred solution of 2-bromo-1,3-dimethylbenzene (46.0 g, 250 mmol) in ACN (500 mL) was added NBS (177 g, 1.0 mol) under N$_2$ and the solution was stirred at rt overnight, then filtered, concentrated, diluted with H$_2$O and extracted with Et$_2$O. The organic layer was washed with brine, dried over Na$_2$SO$_4$, filtered and concentrated to give compound P3a (79.5 g, 94%) as a white solid.

Step 2: 2,2'(2-Bromo-1,3-phenylene)diacetonitrile (P3b)

To a stirred solution of compound P3a (75.0 g, 220 mmol) in a mixture of DMF (700 mL) and H$_2$O (140 mL) was added NaCN (42.8 g, 874 mmol) under N$_2$ and the solution was stirred overnight at 50° C. and then extracted with Et$_2$O. The combined organic layers were washed with brine, dried over Na$_2$SO$_4$, filtered, concentrated and purified by CC (PE/EA=3/1) to give compound P3b (30.0 g, 59%) as a white solid.

Step 3: 2,2'-(2-Bromo-1,3-phenylene)bis(2-methylpropanenitrile) (P3c)

To the solution of compound P3b (29.0 g, 126 mmol) in dry THF (500 mL) was added NaH (18.2 g, 756 mmol) with cooling using an icebath. After stirring for 15 min at 5° C., MeI (336 g, 2.37 mol) was added and stirred at rt overnight, then water was added and extracted with EA twice. The combined organic layers were washed with brine, dried over Na$_2$SO$_4$, filtered, concentrated and purified by CC (PE/EA=5/1) to give compound P3c (28.4 g, 78%) as a white solid.

Step 4: 2,2'-(2-Bromo-1,3-phenylene)bis(2-methylpropanal) (P3d)

To a stirred solution of compound P3c (28.0 g, 96.5 mmol) in dry toluene (400 mL) was added a solution of DIBAH (1M in toluene, 250 mL, 250 mmol) at 0° C. under N$_2$ and the solution was stirred for 2 h at rt and then quenched carefully with water. 10% H$_2$SO$_4$ was added and the resulting mixture was stirred for 2 h and extracted with toluene. The organic layer was washed with brine, dried over Na$_2$SO$_4$, filtered, concentrated and purified by CC (PE/EA=10/1) to give compound P3d (23.2 g, 92%) as a white solid.

Step 5: 2-Bromo-1,3-di-tert-butylbenzene (P3e)

The solution of compound P3d (23.0 g, 77.2 mmol), triethylene glycol (230 mL), KOH (26.2 g, 468 mmol), H$_2$O (160 mL) and hydrazine monohydrate (75 mL) was heated at 120° C. for 2 h and then the flask was equipped with a Dean-Stark trap and the reaction mixture was heated for 2 h at 200° C., cooled, poured into water and extracted with Et$_2$O twice. The combined organic layer was washed with brine, dried over Na$_2$SO$_4$, filtered, concentrated and purified by CC (PE) to give compound P3e (16.8 g, 81%) as a colorless oil.

Step 6: 2-(4-Bromo-3,5-di-tert-butylphenyl)-4,4,5,5-tetramethyl-1,3,2-dioxaborolane (P3)

The solution of compound P3e (5.5 g, 20.4 mmol), B$_2$Pin$_2$ (5.7 g, 22.4 mmol), [Ir(COD)(OMe)]$_2$ (0.41 g, 0.61 mmol) and dtbpy (0.32 g, 1.22 mmol) in dry THF (200 mL) was stirred overnight at 80° C. under N₂, concentrated and purified by CC (PE/EA=40/1) to give compound P3 (6.0 g, 76%) as a white solid.

Preparative Example P4

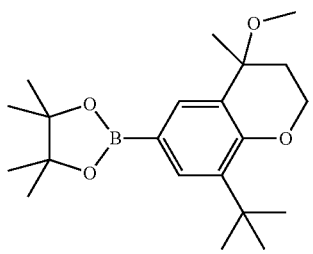

P4

Step 1: 1-(tert-Butyl)-2-(prop-2-yn-1-yloxy)benzene (P4a)

To a stirred solution of 2-(tert-butyl)phenol (5.0 g, 34 mmol) and progargyl bromide (4.8 g, 40 mmol) in dry ACN (50 mL) was added K₂CO₃ (5.5 g, 40 mmol) and the solution was stirred for 2 d at rt, concentrated, redissolved in water and extracted with Et₂O. The combined organic layers were dried over Na₂SO₄, filtered, concentrated and purified by CC (PE) to give compound P4a (4.5 g, 72%) as an oil.

Step 2: 1-(tert-Butyl)-2((3-chloroprop-2-yn-1-yl)oxy)benzene (P4b)

To a stirred mixture of compound P4a (1.0 g, 5.3 mmol) in dry acetone (10 mL) was added NCS (0.85 g, 6.4 mmol) and CH₃COOAg (90 mg, 0.53 mmol) and the solution was heated to reflux for 4 h, cooled, filtered and the filtrate was concentrated, taken up in Et₂O, washed with water and sat. NaHCO₃ solution, dried over Na₂SO₄, filtered and concentrated to give compound P4b (0.5 g, 42%) as an oil.

Step 3: 8-(tert-Butyl)chroman-4-one (P4c)

A solution of compound P4b (0.5 g, 2.3 mmol) in dry ethylene glycol (5 mL) was heated to reflux for 4 h, cooled, poured into water and extracted with Et₂O twice. The combined organic layers were combined, washed with 1N NaOH and sat. (NH₄)₂CO₃, dried over Na₂SO₄, filtered, concentrated and purified by CC (PE) to give compound P4c (0.2 g, 44%) as an oil.

Step 4: 8-(tert-Butyl)-4-methylchroman-4-ol (P4d)

To a solution of compound P4c (6.5 g, 32 mmol) in dry THF (50 mL) was added CH₃MgCl (3M in THF, 32 mL, 96 mmol) under N₂ and the mixture was stirred at 45° C. overnight, quenched with water and extracted with EA twice. The combined organic layers were washed with brine (3 x), concentrated and purified by CC (PE/EA=50/1) to give compound P4d (3.0 g, 42%) as a white solid.

Step 5: 6-Bromo-8-(tert-butyl)-4-methylchroman-4-ol (P4e)

To a stirred mixture of compound P4d (1.5 g, 6.5 mmol) in dry THF (12 mL) was added NBS (1.38 g, 7.76 mmol) and the solution was stirred at rt overnight, quenched with water and extracted with EA twice. The combined organic layers were washed with brine (3×), concentrated and purified by CC (PE/EA=50/1) to give compound P4e (1.4 g, 72%) as a white solid.

Step 6: 8-(tert-Butyl)-4-methyl-6-(4,4,5,5-tetramethyl-1,3,2-dioxaborolan-2-yl)chroman-4-ol (P4f)

To a solution of compound P4e (1.2 g, 4.0 mmol), B₂Pin₂ (1.53 g, 6.02 mmol), AcOK (0.59 g, 6.0 mmol) and Pd(dppf)Cl₂ (30 mg) in dry DMF (10 mL) was heated at 90° C. overnight under N₂, cooled, quenched with water and extracted with EA twice. The combined organic layers were washed with brine (3×), concentrated and purified by CC (PE/EA=5/1) to give compound P4f (0.85 g, 61%) as a white solid.

Step 7: 2-(8-(tert-Butyl)-4-methoxy-4-methylchroman-6-yl)-4,4,5,5-tetramethyl-1,3,2-dioxaborolane (P4)

To a mixture of compound P4f (0.25 g, 0.72 mmol) in dry THF (2 mL) was added NaH (52 mg, 2.2 mmol) and the mixture was stirred at rt for 1 h. Then MeI (0.21 g, 1.5 mmol) was added and the solution was heated to 40° C. overnight, quenched with water and extracted with EA twice. The combined organic layers were washed with brine (3×), concentrated and purified by CC (PE/EA=50/1) to give compound P4 (80 mg, 31%) as a white solid.

Preparative Example P5

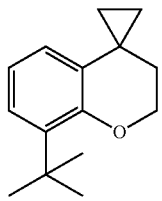

P5

Step 1: 8-(tert-Butyl)spiro[chroman-4,1'-cyclopropane] (P5)

To a stirred mixture of methyl(triphenyl)phosphonium bromide (3.6 g, 10 mmol) in dry THF (20 mL) was added n-BuLi (4 mL, 2.5M) under N₂ at −40° C. and the mixture was stirred for 30 min at this temperature. Then the solution of compound P4c (1.0 g, 5.0 mmol) in dry THF (8 mL) was added dropwise. The solution was stirred at rt overnight, quenched with aq. NH₄Cl at 0° C. and then extracted with EA. The organic layer was concentrated and purified by CC (PE) to give an intermediate. KOH (8.0 g, 140 mmol) was added to a mixture of water (30 mL) and Et₂O (20 mL) and then amino-N-nitrosoamide (0.4 g, 1.0 mmol) was added to the resulting mixture at −20° C. After stirred for 10 min, the organic layer was added to a solution of the above intermediate and Pd(OAc)₂ (100 mg) in dry THF (10 mL) at 0° C. dropwise. The mixture was stirred at rt overnight and then extracted between water and Et₂O. The organic combined layers were concentrated and purified CC (PE/EA=50/1) to give compound P5 (0.8 g, 75%) as a white solid.

Preparative Example P6

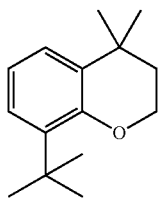

P6

Step 1: 8-(tert-Butyl)-4,4-dimethylchroman (P6)

To a solution of TiCl$_4$ (4.8 mL, 43.6 mmol) in dry CH$_2$Cl$_2$ (40 mL) was added ZnMe$_2$ (36.3 mL, 43.6 mmol) at −30° C. and the mixture was stirred for 20 min. Then a solution of compound P4c (4.0 g, 20 mmol) in dry CH$_2$Cl$_2$ (10 mL) was added dropwise. The mixture was stirred at rt overnight, poured onto ice water and extracted with Et$_2$O. The organic layer was washed with aq. NaHCO$_3$, concentrated and purified by CC (PE) to give compound P6 (3.85 g, 90%) as an oil.

Preparative Example P6/1 to P6/2

Using similar procedures as that described in Preparative Example P4, Step 5 and Step 6, the following Preparative Examples have been prepared:

| # | Structure |
|---|---|
| P6/1 | 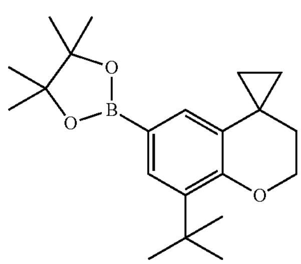 [SMILES: CC(C)(C)c1cc(B2OC(C)(C)C(C)(C)O2)cc2c1OCCC21CC1] |
| P6/2 | 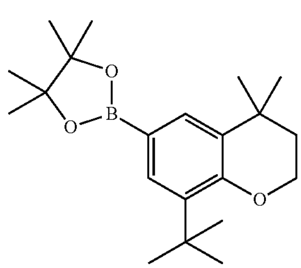 [SMILES: CC(C)(C)c1cc(B2OC(C)(C)C(C)(C)O2)cc2c1OCCC2(C)C] |

Preparative Example P7

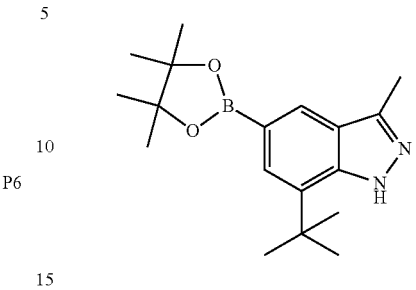

P7

Step 1: 3-(tert-Butyl)-2-hydroxybenzaldehyde (P7a)

A mixture of 2-(tert-butyl)phenol (15 g, 0.1 mol), Et$_3$N (37 g, 374 mmol), MgCl$_2$ (14.3 g, 0.15 mol) and paraformaldehyde (20.2 g, 674 mmol) in ACN (200 mL) was heated at reflux for 5 h, cooled, poured into aq. HCl (2N, 200 mL) and extracted with Et$_2$O. The organic layer was concentrated and purified by CC (PE/EA=8/1) to give compound P7a (13 g, 74%) as a colorless oil.

Step 2: 5-Bromo-3-(tert-butyl)-2-hydroxybenzaldehyde (P7b)

To a solution of compound P7a (3.0 g, 17 mmol) in AcOH (15 mL) was added Br$_2$ (2.95 g, 18 mmol) dropwise at rt and the mixture was stirred for 3 h, quenched with aq. NaHSO$_3$ (50 mL) and extracted with Et$_2$O. The organic layer was concentrated to give crude compound P7b (3.2 g, 73%) as white solid.

Step 3: 4-Bromo-2-(tert-butyl)-6-(1-hydroxyethyl) phenol (P7c)

A solution of compound P7b (1.0 g, 3.9 mmol) in dry THF (10 mL) was added MeMgCl (3M in Et$_2$O, 3.0 mL) dropwise at 0° C. and the mixture was stirred at rt for 1 h. The mixture was quenched with aq. NH$_4$Cl and extracted with Et$_2$O. The organic layer was concentrated to give crude compound P7c (1.0 g, 92%) as a colorless oil.

Step 4: 1-(5-Bromo-3-(tert-butyl)-2-methoxyphenyl) ethanol (P7d)

To a solution of compound P7c (2.0 g, 7.4 mmol) in ACN (20 mL) was added K$_2$CO$_3$ (2.0 g, 15 mmol) and MeI (2.1 g, 15 mmol) and the mixture was stirred at reflux for 12 h, cooled, concentrated, poured into water and extracted with EA (20 mL). The organic layer was concentrated to give crude compound P7d (1 g, 47%) as an oil.

Step 5: 1-(5-Bromo-3-(tert-butyl)-2-methoxyphenyl) ethanone (P7e)

To a solution of compound P7d (1 g, 3.4 mmol) in DCM (10 mL) was added PCC (0.9 g, 4.7 mmol) at rt and the mixture was stirred at rt for 2 h, then silica (1.5 g) was added and the slurry was concentrated. The residue was purified by CC (PE/EA=50/1) to give compound P7e (0.5 g, 50%) as a yellow solid.

Step 6: 1-(5-Bromo-3-(tert-butyl)-2-hydroxyphenyl)ethanone (P7f)

To a solution of compound P7e (0.4 g, 1.4 mmol) in dry DCM (10 mL) was added BBr$_3$ (1.4 g, 5.6 mmol) dropwise at −78° C. under N$_2$ and the mixture was stirred at 0° C. for 30 min, MeOH (2 mL) was added dropwise at −30° C., then concentrated and purified by CC (PE/EA=50/1) to give compound P7f (0.2 g, 55%) as a yellow solid.

Step 7: 2-Acetyl-4-bromo-6-(tert-butyl)phenyl trifluoromethanesulfonate (P7q)

To a mixture of compound P7f (50 mg, 0.18 mmol) and K$_2$CO$_3$ (27 mg, 0.2 mmol) in DMF (2 mL) was added a mixture of PhNTf$_2$ (70 mg, 0.2 mmol) in DMF (0.5 mL) at −20° C., the mixtrue was stirred for 1 h at −20° C. and then overnight at rt, quenched with aq. NH$_4$Cl and extracted with Et$_2$O. The organic layer was concentrated and purified by CC (PE/EA=50/1) to give compound P7g (60 mg, quant.) as a yellow oil.

Step 8: 5-Bromo-7-(tert-butyl)-3-methyl-1H-indazole (P7h)

To a solution of compound P7g (200 mg, 0.58 mmol) in xylene (2 mL) was added NH$_4$OAc (111 mg, 1.45 mmol) and NH$_2$NH$_2$.H$_2$O (58 mg, 1.2 mmol) and the mixture was heated at reflux overnight, concentrated and purified by CC (PE/EA=8/1) to give compound P7h (60 mg, 39%) as a yellow oil.

Step 9: 7-(tert-Butyl)-3-methyl-5-(4,4,5,5-tetramethyl-1,3,2-dioxaborolan-2-yl)-1H-indazole (P7)

To a mixture of compound P7h (90 mg, 0.34 mmol), Pin$_2$B$_2$ (128 mg, 0.50 mmol) and AcOK (49 mg, 0.5 mmol) in DMF (10 mL) was added Pd(dppf)Cl$_2$ (30 mg) under N$_2$ and the mixture was stirred at 90° C. overnight under N$_2$, quenched with water and extracted with EA twice. The combined organic layers were washed with water (3×) and brine (3×) consecutively, concentrated and purified by CC (PE/EA=10/1) to give compound P7 (50 mg, 45%) as a white solid.

Preparative Example P8

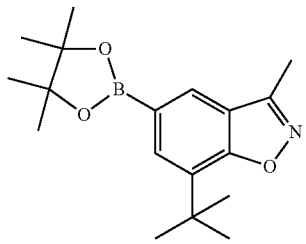

Step 1: 1-(5-Bromo-3-(tert-butyl)-2-hydroxyphenyl)ethanone oxime (P8a)

A mixture of 1-(5-bromo-3-(tert-butyl)-2-hydroxyphenyl)ethanone (0.5 g, 1.8 mmol), NaOAc (246 mg, 3.0 mmol) and NH$_2$OH.HCl (187 mg, 2.7 mmol) in EtOH (10 mL) was heated at reflux for 3 h, concentrated and the obtained solid was washed with water to give compound P8a (0.5 g, 97%) as solid.

Step 2: 1-(5-Bromo-3-(tert-butyl)-2-hydroxyphenyl)ethanone 0-acetyl oxime (P8b)

A solution of compound P8a (0.5 g, 1.7 mmol) in Ac$_2$O (2 mL) was stirred at rt for 4 h, concentrated and purified by CC (PE/EA=15/1) to give compound P8b (0.5 mg, 80%) as a yellow solid.

Step 3: 5-Bromo-7-(tert-butyl)-3-methylbenzo[d]isoxazole (P8c)

Compound P8b (100 mg, 0.3 mmol) was heated to 160° C. for 2 h and then cooled to rt to give compound P8c (50 mg, 60%) as a solid.

Step 4: 7-(tert-butyl)-3-methyl-5-(4,4,5,5-tetramethyl-1,3,2-dioxaborolan-2-yl)benzo[d]isoxazole (P8)

To a mixture of compound P8c (60 mg, 0.225 mmol), Pin$_2$B$_2$ (85 mg, 0.337 mmol) and AcOK (33 mg, 0.34 mmol) in DMF (10 mL) was added Pd(dppf)Cl$_2$ (30 mg) under N$_2$ and the mixture heated at 90° C. overnight, quenched with water and extracted with EA twice. The combined organic layers were washed with water (3×) and brine (3×), concentrated and purified by CC (PE/EA=5/1) to give compound P8 (48 mg, 70%) as a white solid.

Preparative Example P9

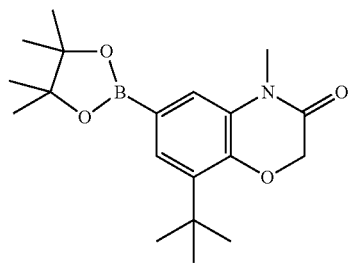

Step 1: 4-Bromo-2-(tert-butyl)phenol (P9a)

To a stirred mixture of 2-(tert-butyl)phenol (20 g, 133 mmol) in dry DCM (200 mL) was added tetrabutyl ammonium tribromide (64.3 g, 133 mmol) at 0° C. and the solution was stirred at rt for 2 h, concentrated and redissolved in Et$_2$O, washed by brine (3×), dried over Na$_2$SO$_4$, filtered and concentrated to give compound P9a (36.6 g, 95%) as an oil.

Step 2: 4-Bromo-2-(tert-butyl)-6-nitrophenol (P9b)

To a solution of compound P9a (10 g, 43.7 mmol) in hexane (62 mL) was slowly added HNO$_3$ (2.3 mL) and then the solution was stirred at rt for 4 h, diluted with Et$_2$O, washed with water and sat. NaHCO$_3$ solution, dried over Na$_2$SO$_4$, filtered, concentrated and purified by CC (PE) to give compound P9b (6.2 g, 52%) as a yellow solid.

Step 3: 2-Amino-4-bromo-6-(tert-butyl)phenol (P9c)

To a solution of compound P9b (10 g, 36.5 mmol) in AcOH (100 mL) was added Zn (9.5 g, 150 mmol) at 30° C. Then one drop of water was added. After stirring for 2 h, the resulting solution was filtrated and the filtrate was concentrated. The residue was extracted between sat. NaHCO₃ solution and EA. The organic layer was dried over Na₂SO₄, filtered and concentrated to give compound P9c (8.0 g, 90%) as a red solid.

Step 4: 6-Bromo-8-(tert-butyl)-2H-benzo[b][1,4]oxazin-3(4H)-one (P9d)

To a stirred solution of compound P9c (8.0 g, 32.8 mmol) in a mixture of dry DCM (40 mL) and sat. NaHCO₃ (40 mL) was added 2-chloroacetyl chloride (4.45 g, 39.3 mmol). After stirring for 1 h, the resulting solution was extracted with EA twice. The combined organic layers were washed with brine and concentrated. The residue was dissolved in DMF (8 mL) and K₂CO₃ (9.05 g, 65.6 mmol) was added. The mixture was heated to 70° C. overnight and then water and EA was added. The combined organic layers were washed with water (3×) and brine, concentrated and purified by CC (PE/EA=10/1) to give compound P9d (5.0 g, 62%) as a solid.

Step 5: 6-Bromo-8-(tert-butyl)-4-methyl-2H-benzo[b][1,4]oxazin-3(4H)-one (P9e)

To a solution of compound P9d (1.5 g, 6.15 mmol) in DMF (15 mL) was added NaH (0.44 g, 18 mmol) at 0° C. and the solution was stirred for 1 h. Then MeI (1.7 g, 12 mmol) was added dropwise and the solution was stirred at 50° C. overnight, quenched with water and extracted with EA. The organic layer was washed with water (3×) and brine, concentrated and purified by CC (PE/EA=20/1) to give compound P9e (0.55 g, 30%) as a white solid.

Step 6: 8-(tert-Butyl)-4-methyl-6-(4,4,5,5-tetramethyl-1,3,2-dioxaborolan-2-yl)-2H-benzo[b][1,4]oxazin-3(4H)-one (P9)

A solution of compound P9e (0.55 g, 1.85 mmol), Pin₂B₂ (0.70 g, 2.77 mmol), AcOK (0.27 g, 2.77 mmol) and Pd(dppf)Cl₂ (30 mg) in dry DMF (10 mL) was heated at 90° C. overnight under N₂. The resulting solution was quenched with water and extracted with EA twice. The combined organic layers were washed with water (3×) and brine, concentrated and purified by CC (PE/EA=10/1) to give compound P9 (0.38 g, 59%) as a white solid.

Preparative Example P10

Using similar procedures as that described in Preparative Example P9, the following compound has been prepared:

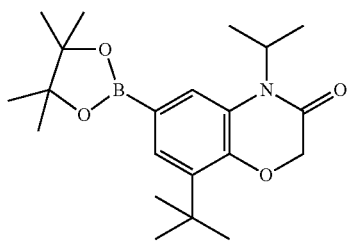

P10

Preparative Example P11

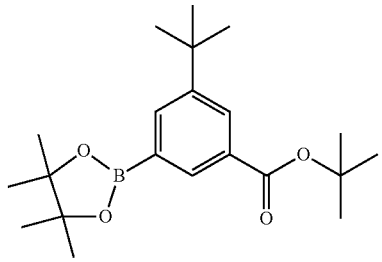

P11

Step 1: tert-Butyl 3-bromo-5-(tert-butyl)benzoate (P11a)

n-BuLi (7.2 mL, 18.0 mmol, 2.5M in THF) was added to a flask under N₂ containing toluene (9 mL) at −10° C. n-BuMgCl (4.5 mL, 9.0 mmol, 2M in THF) was then added at such a rate to keep the temperature below −5° C. The resulting milky slurry was aged at −10° C. for 30 min, then 1,3-dibromo-5-(tert-butyl)benzene (6.2 g, 21.2 mmol) dissolved in toluene (20 mL) was added. The rate of addition was such that the temperature did not increase above −5° C. After addition was complete, the mixture was kept at −10° C. until the metal-halogen reaction was complete. A solution of di-tert-butyl dicarbonate (5.89 g, 27 mmol) in toluene (7.5 mL) was then charged such at a rate to keep the temperature below −5° C. After the addition was complete, the mixture was kept at −10° C. until the aryl-Mg intermediate was completely consumed. The mixture was quenched by the addition of 10% aq. citric acid (40 mL). The phases were separated and the organic layer was washed with another 10% aq. citric acid (40 mL). The organic extracts were dried over MgSO₄ and concentrated. Compound P11a (4.0 g, 60%) was obtained as a brown oil.

Step 2: tert-Butyl 3-(tert-butyl)-5-(4,4,5,5-tetramethyl-1,3,2-dioxaborolan-2-yl)benzoate (P11)

To a mixture of compound P11a (4.0 g, 12.8 mmol), Pin₂B₂ (3.1 g, 31.9 mmol) in dioxane (60 mL), Pd(dppf)Cl₂ (30 μmol) was added under Ar and the mixture was refluxed at 90° C. overnight, diluted with water (200 mL) and extracted with EA (3×200 mL). The organic layer was washed with brine and dried over Na₂SO₄, concentrated and purified by CC (hexane/EA=3/1) to give compound P11 (2.1 g, 46%).

Preparative Example P12

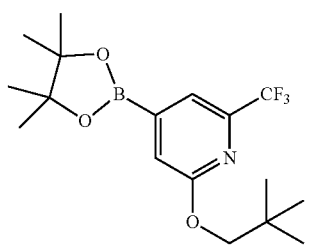

P12

Step 1: 2-(Neopentyloxy)-6-(trifluoromethyl)pyridine (P12a)

To a solution of 6-(trifluoromethyl)pyridin-2-ol (5.00 g, 30.7 mmol) in dry DMF (50 mL) was added NaH (3.71 g, 92.1 mmol) under N₂ and the mixture was stirred at rt for 1 h. Then 1-bromo-2,2-dimethylpropane (11.6 g, 76.7 mmol) was added and the resulting mixture was heated at 100° C. overnight, cooled, quenched with water (10 mL) and extracted with EA twice. The combined organic layers were washed with brine (3×), concentrated and purified by CC on NH silica gel (PE/EA=100/1) to give compound P12a (1.05 g, 15%) as an oil.

Step 2: 2-(Neopentyloxy)-4-(4,4,5,5-tetramethyl-1,3,2-dioxaborolan-2-yl)-6-(trifluoromethyl)pyridine (P12)

To a solution of compound P12a (1.00 g, 4.29 mmol) in THF (20 mL) was added [(COD)Ir(μ-OMe)]₂ (282 mg, 0.43 mmol), dtbpy (232 mg, 0.86 mmol) and B₂Pin₂ (3.32 g, 13.0 mmol). The mixture was stirred overnight at 80° C. under N₂, concentrated and purified by CC (PE/EA=20/1) to give compound P12 (0.91 g, 88%) as a solid.

Preparative Example P13 and Preparative Example P14

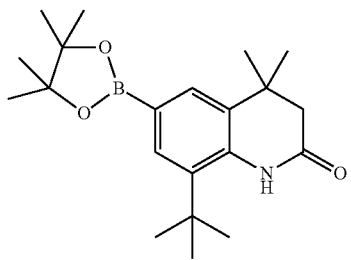

P13

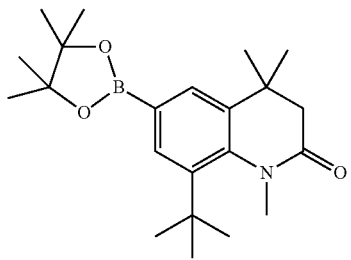

P14

Step 1: 4-Bromo-2-(tert-butyl)aniline (P13a)

To a solution of 2-tert-butylaniline (7.5 g, 50 mmol) in DMF (80 mL) was added NBS (8.9 g, 50 mmol) at 0° C. The reaction mixture was stirred for 2 h, quenched with ice water, extracted with EA (3×100 mL). The combined organic layers were washed with brine, dried over Na₂SO₄, filtered, concentrated and purified by CC to give compound P13a (9.1 g, 80%) as a white solid.

Step 2: N-(4-Bromo-2-(tert-butyl)phenyl)-3-methylbut-2-enamide (P13b)

A mixture of compound P13a (2.3 g, 10 mmol) and 3-methylbut-2-enoyl chloride (1.4 g, 12 mmol) in toluene (20 mL) was stirred overnight, quenched with water and extracted with EA (3×50 mL). The combined organic layers were washed with brine, dried over Na₂SO₄, filtered, concentrated and purified by CC to give P13b (1.5 g, 48%) as a white solid.

Step 3: 6-Bromo-8-(tert-butyl)-4,4-dimethyl-3,4-dihydroquinolin-2(1H)-one (P13c)

AlCl₃ (800 mg, 7.1 mmol) was added in one portion to a solution of P13b (1.24 g, 4.0 mmol) in 1,2-dichloroethane (20 mL). The reaction mixture was stirred for 2 h, quenched with cold H₂O, stirred for 0.5 h and diluted with CH₂Cl₂. The organic layer was washed with H₂O, dried over Na₂SO₄ and concentrated to give P13c (1.1 g, 89%) as a white solid.

Step 4: 8-(tert-Butyl)-4,4-dimethyl-6-(4,4,5,5-tetramethyl-1,3,2-dioxaborolan-2-yl)-3,4-dihydroquinolin-2(1H)-one (P13)

A mixture of P13c (930 mg, 3.0 mmol), B₂Pin₂ (900 mg, 3.6 mmol), Cs₂CO₃ (2.93 g, 9 mmol) and Pd(dppf)Cl₂ (100 mg) in dioxane (20 mL) and water (2 mL) was stirred at 85° C. under Ar overnight, quenched with cold H₂O and diluted with EA. The organic layer was separated and the aq. layer was extracted with EA (3×). The combined organic layer was washed with brine and dried over Na₂SO₄, filtered, concentrated and purified by CC to give P13 (750 mg, 70%) as a white solid.

Step 5: 8-(tert-Butyl)-1,4,4-trimethyl-6-(4,4,5,5-tetramethyl-1,3,2-dioxaborolan-2-yl)-3,4-dihydroquinolin-2(1H)-one (P14)

To a solution of P13 (375 mg, 1.0 mmol) in DMF (20 mL), NaH (120 mg, 3 mmol) was added at 0° C. and subsequently MeI (approx. 1.5 mmol). The mixture was stirred for 1 h, quenched with water and extracted with EA (3×). The combined organic layer was washed with brine and dried over Na₂SO₄, filtered and concentrated to give P14 (350 mg, 95%) as a white solid.

Preparative Example 15

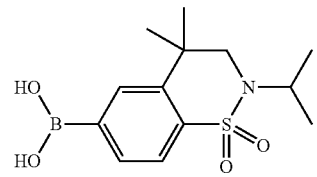

P15

Step 1: Methyl 2-(5-bromo-2-(chlorosulfonyl)phenyl)acetate (P15a)

Methyl 2-(3-bromophenyl)acetate (22 g, 67 mmol) was slowly added into ClSO₃H at −10° C. After 1 h, the mixture was warmed up to rt and stirred overnight, diluted slowly with ice water and extracted with EA. The organic layer was washed with water, dried over Na₂SO₄ and evaporated to give compound P15a (17 g, 54%).

Step 2: Methyl 2-(5-bromo-2-(N-isopropylsulfamoyl)phenyl)acetate (P15b)

To a solution of compound P15a (8.2 g, 25 mmol) and NEt₃ (3.04 g, 30 mmol) in DCM (50 mL) was slowly added propan-2-amine (1.55 g, 26.3 mmol) under ice cooling. The mixture was stirred for 2 h, then washed with HCl solution and water.

The organic layer was dried over Na$_2$SO$_4$ and evaporated to give compound P15b (8.2 g, 94%).

Step 3: 2-(5-Bromo-2-(N-isopropylsulfamoyl)phenyl)acetic acid (P15c)

To a solution of compound P15b (7.4 g, 21 mmol) in THF (80 mL) and H$_2$O was added LiOH (1.33 g, 55 mmol). The mixture was heated to 60° C. and stirred overnight, then diluted with water (30 mL) and extracted with EA. The organic layer was washed with water, dried over Na$_2$SO$_4$ and evaporated to give compound P15c (6.2 g, 87%).

Step 4: 6-Bromo-2-isopropyl-2H-benzo[e][1,2]thiazin-3(4H)-one 1,1-dioxide (P15d)

Compound P15c (6.2 g, 18 mmol) was slowly added into SOCl$_2$. The mixture was heated to 50° C. overnight, concentrated, diluted with aq. Na$_2$CO$_3$ solution and extracted with EA. The organic layer was washed with water, dried over Na$_2$SO$_4$ and evaporated to give compound P15d (4.9 g, 85%).

Step 5: 6-Bromo-2-isopropyl-4,4-dimethyl-2H-benzo[e][1,2]thiazin-3(4H)-one 1,1-dioxide (P15e)

To a solution of compound P15d (3.5 g, 11 mmol) in THF (50 mL) was added under ice cooling NaH (1.06 g, 44 mmol), followed by CH$_3$I (9.37 g, 66 mmol). The mixture was warmed to rt and stirred for 4 h, diluted with water (60 mL) and extracted with EA. The organic layer was washed with water, dried over Na$_2$SO$_4$ and evaporated to give compound P15e (2.6 g, 67%).

Step 6: 6-Bromo-2-isopropyl-4,4-dimethyl-3,4-dihydro-2H-benzo[e][1,2]thiazine 1,1-dioxide (P15f)

To a solution of compound P15e (2.5 g, 7.2 mmol) in THF (30 mL) was slowly added BH$_3$ (1M; 21.7 mL) at 0° C. Then the mixture was heated to 60° C. and stirred overnight, slowly diluted with 6N HCl followed by NaHCO$_3$ and extracted with EA. The organic layer was washed with water, dried over Na$_2$SO$_4$ and evaporated to give compound P15f (1.4 g, 57%).

Step 7: (2-Isopropyl-4,4-dimethyl-1,1-dioxido-3,4-dihydro-2H-benzo[e][1,2]thiazin-6-yl)boronic acid (P15)

To a solution of compound P15f (580 mg, 1.75 mmol) and B(i-PrO)$_3$ (493 mg, 2.62 mmol) in THF (30 mL) was slowly added n-BuLi (2.5M; 1.05 mL) at −78° C. Then the mixture was warmed to rt overnight, diluted with water (15 mL) and extracted with EA. The organic layer was washed with water, dried over Na$_2$SO$_4$ and evaporated to give compound P15 (174 mg, 34%).

Preparative Example P15/1

Using similar procedures as that described in Preparative Example P15, the following Preparative Example has been prepared:

| # | Structure |
|---|---|
| P15/1 | 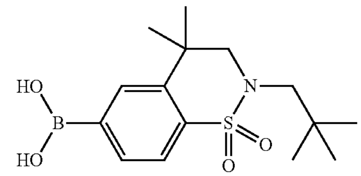 [SMILES: CC(C)(C)CN1CC(C)(C)c2cc(B(O)O)ccc2S1(=O)=O] |

Preparative Example P16

Step 1: 4-Bromo-2,6-diisopropylaniline (P16a)

To a solution of 2,6-diisopropylaniline (12.5 g, 70.6 mmol) in THF was added (C$_4$H$_9$)$_4$NBr$_3$ (47 g, 85 mmol) at rt and stirred overnight. Then sat. NaHSO$_3$ solution (30 mL) was added and the mixture was extracted with Et$_2$O (3×250 mL). The organic layer was washed with brine, dried over Na$_2$SO$_4$ and concentrated to give compound P16a (19 g, 82%).

Step 2: 5-Bromo-2-iodo-1,3-diisopropylbenzene (P16b)

To a solution of compound P16a (12.5 g, 70.6 mmol) in AcOH and H$_2$SO$_4$ were slowly added isoamyl nitrite (16.8 g, 144 mmol) at 0° C. and stirred at 0° C. for 1 h. Then a K$_2$CO$_3$ solution (100 mL) of was slowly added at 0° C. The mixture was warmed up to rt and stirred overnight, diluted with sat. NaHSO$_3$ solution (30 mL) and extracted with hexane (3×250 mL). The organic layer was washed with brine, dried over Na$_2$SO$_4$ and concentrated to give compound P16b (21.7 g, 80%).

Step 3: 4-Bromo-2,6-diisopropylbenzene-1-sulfonyl chloride (P16c)

To a solution of compound P16b (21.7 g, 59.1 mmol) in THF (150 mL) was slowly added n-BuLi (2.5M; 23.7 mL) at −78° C. After 30 min, SO$_2$Cl$_2$ (12 g, 89 mmoL) was added at −78° C. The mixture was warmed up to rt, stirred for 3 h and then extracted with EA. The organic layer was evaporated and purified by CC to give compound P16c (5.3 g, 25%).

Step 4: 4-Bromo-2,6-diisopropylbenzenesulfonyl azide (P16d)

To a solution of compound P16c (5.3 g, 46 mmol) in acetone (80 mL) and H$_2$O (15 mL) was added NaN$_3$ (1.5 g, 23 mmol) at 0° C. Then mixture was warmed up to rt, stirred for 4 h, concentrated and extracted with DCM (3×100 mL). The organic layer was washed with water, dried over Na$_2$SO$_4$ and concentrated to give compound P16d (5.3 g, 98%).

Step 5: 5-Bromo-7-isopropyl-3,3-dimethyl-2,3-dihydrobenzo[d]isothiazole 1,1-dioxide (P16e)

To a suspension of compound P16d (5.33 g, 15.4 mmol) and molecular sieves (5 Å, 7.7 g) in toluene (60 mL) were added CoTPP (203 mg, 0.31 mmol) under N$_2$. Then the mixture was heated to 80° C. and stirred overnight, filtered, evaporated and purified by CC to give compound P16e (3.5 g, 71%).

Step 6: (7-Isopropyl-3,3-dimethyl-1,1-dioxido-2,3-dihydrobenzo[d]isothiazol-5-yl)boronic acid (P16)

To a solution of compound P16e (477 mg, 1.5 mmol) and B(i-PrO)$_3$ (564 mg, 3.0 mmol) in THF (10 mL) was slowly added n-BuLi (2.5M; 1.8 mL) at −78° C. After 30 min, the mixture was warmed up to rt and stirred for 5 h, diluted with HCl (10 mL) and extracted with EA. The organic layer was dried over Na$_2$SO$_4$, evaporated and purified by CC to give compound P16 (240 mg, 57%).

Preparative Example P17

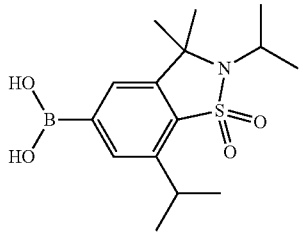

P17

Step 1: 5-Bromo-2,7-diisopropyl-3,3-dimethyl-2,3-dihydrobenzo[d]isothiazole 1,1-dioxide (P17a)

To a suspension of compound P16e (954 mg, 3 mmol), KOH (672 mg, 12 mmol) and tetrabutylammonium bromide (95 mg) was added 2-iodopropane (3.1 g, 18 mmol) at rt. The mixture was heated to 80° C. and stirred overnight, diluted with EA and washed with water. The organic layer was dried over Na$_2$SO$_4$, evaporated and purified by CC to give compound P17a (924 mg, 85%).

Step 2: (2,7-Diisopropyl-3,3-dimethyl-1,1-dioxido-2,3-dihydrobenzo[d]isothiazol-5-yl)boronic acid (P17)

Compound P17 was prepared similar as described in Preparative Example P16, Step 6.

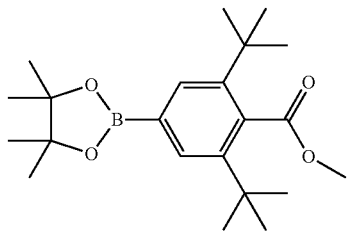

P18

Preparative Example P18

Step 1: 2,6-Di-tert-butylbenzoic acid (P18a)

To a solution of compound P3e (13.5 g, 50 mmol) in dry Et$_2$O (80 mL) was added n-BuLi (2.5M in hexane, 60 mL, 150 mmol) dropwise at rt under N$_2$, stirred for 2 h at reflux and then CO$_2$ was bubbled through the solution for 2 h. The solution was quenched with 3N HCl and extracted with EA twice. The combined organic layers were washed with brine, dried over Na$_2$SO$_4$, filtered, concentrated and purified by CC (PE/EA=5/1) to give compound P18a (4.14 g, 35%) as a yellow solid.

Step 2: Methyl 2,6-di-tert-butylbenzoate (P18b)

To a solution of compound P18a (4.14 g, 17.7 mmol) in Et$_2$O (50 mL) was added dropwise a solution of CH$_2$N$_2$ in Et$_2$O at rt. The mixture was concentrated and purified by CC (PE) to give compound P18b (3.9 g, 89%) as a white solid.

Step 3: Methyl 2,6-di-tert-butyl-4-(4,4,5,5-tetramethyl-1,3,2-dioxaborolan-2-yl)benzoate (P18)

A solution of compound P18b (3.43 g, 14.6 mmol), B$_2$Pin$_2$ (3.86 g, 15.2 mmol), [Ir(COD)(OMe)]$_2$ (0.28 g, 0.44 mmol) and dtbpy (0.22 g, 0.88 mmol) in dry THF (150 mL) was stirred overnight at 80° C. under N$_2$, concentrated and purified by CC (PE/EA=40/1) to give compound P18 (4.69 g, 90%) as a white solid.

Preparative Example P19 and Preparative Example P20

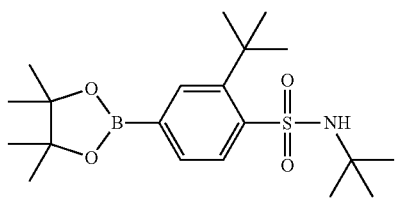

P19

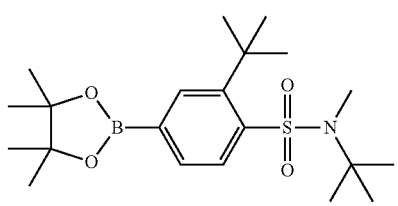

P20

Step 1: 4-Bromo-2-tert-butylaniline (P19a)

To a solution of NBS (218 mg, 1 mmol) in DMF was added a solution of 2-tert-butylaniline (149 mg, 1 mmol) in DMF at rt. The reaction mixture was stirred for 4 h at rt, then water (30 mL) was added and the mixture was extracted with EA (150 mL). The organic layer was washed with brine and dried over $Na_2SO_4$, concentrated and purified by CC (hexane/EA=3/1) to give compound P19a (180 mg, 79%).

Step 2: 4-Bromo-2-tert-butylbenzene-1-sulfonyl chloride (P19b)

4-Bromo-2-tert-butylaniline P19a (20 mmol) was added to a mixture of conc. HCl (11.2 mL) and AcOH (2.24 mL) at −10° C. To this mixture, a solution of $NaNO_2$ (1.52 g, 22 mmol) in minimum amount of water was added dropwise at −10° C. After stirring for 45 min at −10° C. the diazonium salt solution was obtained. $SO_2$ gas was bubbled into AcOH (22.4 mL) in a three-neck flask until saturation (30 min). Then CuCl (0.49 g, 0.49 mmol) was added and stirring was continued until the mixture turned green. The flask was placed in an ice bath and the diazonium salt solution was added dropwise at 5° C. After the addition was complete, the mixture was stirred overnight at rt and poured into ice water. The solid was collected by filtration to give the compound P19b (45%).

Step 3: 4-Bromo-N,2-di-tert-butylbenzenesulfonamide (P19c)

Compound P19b (1.0 mmol) and $NEt_3$ (2.0 mmol) were added into a solution of 2-methylpropan-2-amine (88 mg, 1.2 mmol) in toluene (20 mL). The mixture was stirred for 4 h at reflux, evaporated, poured into water and extracted with EA. The combined organic layers were washed with brine, dried over $Na_2SO_4$, filtered and evaporated to give compound P19c as a solid (330 mg, 85%)

Step 4: N,2-Di-tert-butyl-4-(4,4,5,5-tetramethyl-1,3,2-dioxaborolan-2-yl)benzenesulfonamide (P19)

A flask charged with $Pd(dppf)Cl_2$ (30 μmol), KOAc (294 mg, 3.0 mmol) and compound 19c (279 mg, 1.0 mmol) was flushed with $N_2$, then 1,4-dioxane (6 mL) and $B_2Pin_2$ (1.2 mmol) were added. After being stirred at 80° C. for an appropriate period, the product was extracted with benzene, washed with water and dried over $MgSO_4$. Kugelrohr distillation in vacuo gave compound P19 (200 mg, 50%).

Step 5: N,2-Di-tert-butyl-N-methyl-4-(4,4,5,5-tetramethyl-1,3,2-dioxaborolan-2-yl)benzenesulfonamide (P20)

To a cooled solution of compound P19 (395 mg, 1.0 mmol) and $K_2CO_3$ (2.0 mmol) in DCM (25 mL) at 0° C. was added dropwise over 30 min a solution containing MeI (1.2 mmol) in DCM (2 mL). The reaction mixture was stirred for 1 h at 0° C., 2 h at rt and then concentrated, redissolved in EA (20 mL) and washed successively with brine (20 mL) and water (20 mL), dried over $MgSO_4$ and evaporated to afford compound P20 (400 mg, 74%) as a colorless oil.

Preparative Example P19/1 to P19/6

Using similar procedures as that described in Preparative Example P19/P20, the following Preparative Examples have been prepared:

| # | Structure |
|---|---|
| P19/1 | 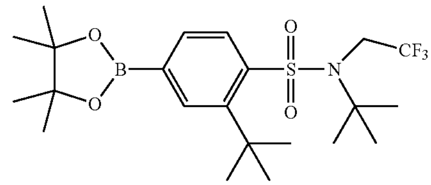 [SMILES: CC(C)(C)c1cc(B2OC(C)(C)C(C)(C)O2)ccc1S(=O)(=O)N(CC(F)(F)F)C(C)(C)C] |
| P19/2 | 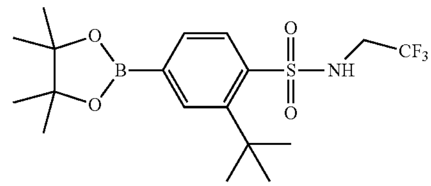 [SMILES: CC(C)(C)c1cc(B2OC(C)(C)C(C)(C)O2)ccc1S(=O)(=O)NCC(F)(F)F] |
| P19/3 | 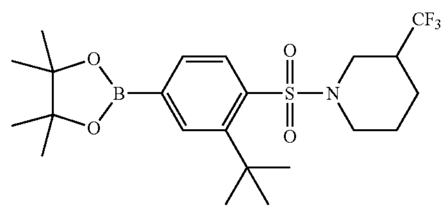 [SMILES: CC(C)(C)c1cc(B2OC(C)(C)C(C)(C)O2)ccc1S(=O)(=O)N1CCCC(C(F)(F)F)C1] |
| P19/4 | 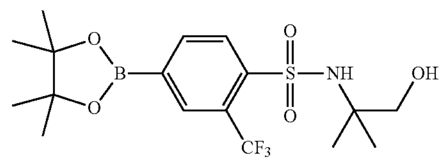 [SMILES: CC(C)(CO)NS(=O)(=O)c1ccc(B2OC(C)(C)C(C)(C)O2)cc1C(F)(F)F] |
| P19/5 | 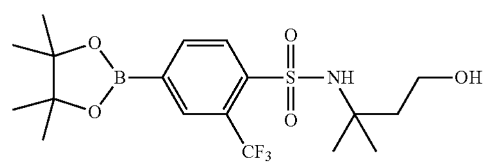 [SMILES: CC(C)(CCO)NS(=O)(=O)c1ccc(B2OC(C)(C)C(C)(C)O2)cc1C(F)(F)F] |
| P19/6 | 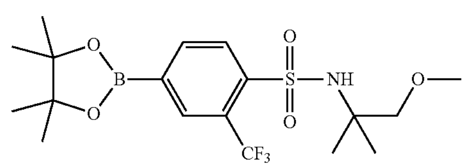 |

Preparative Example P21 and Preparative Example P22

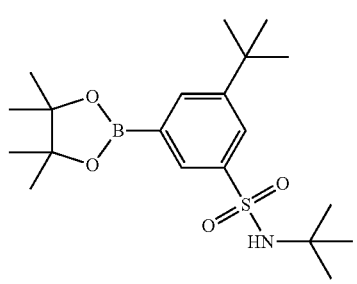

P21

-continued

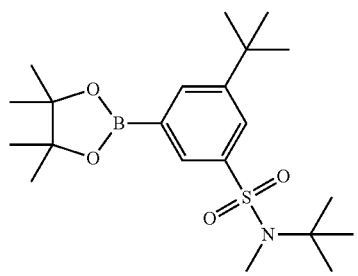

Step 1: Benzyl(3-bromo-5-tert-butylphenyl)sulfane (P21a)

1,3-Dibromo-5-tert-butylbenzene (2.89 g, 10 mmol) in dioxane (160 mL) was stirred under Ar. Then DIPEA (3.09 mL, 16 mmol), Xantphos (0.28 g, 0.48 mmol) and Pd$_2$(dba)$_3$ (0.24 g, 0.24 mmol) were added and the reaction was heated to 100° C. Phenyl-methanethiol (0.94 mL, 8 mmol) was slowly added and the reaction was stirred for 6 h, quenched by the addition of H$_2$O (15 mL) and extracted with EA (3×). The combined organic layers were washed with water, dried over Na$_2$SO$_4$, filtered, evaporated and purified by CC to afford compound P21a (1.7 g, 72%).

Step 2: 3-Bromo-5-tert-butylbenzene-1-sulfonyl chloride (P21b)

Intermediate P21a (3.98 g, 11.9 mmol) was dissolved in DCM (100 mL) and treated with water (0.86 mL, 48 mmol), AcOH (3.4 mL, 60 mmol) and SO$_2$Cl$_2$ (3.9 mL, 48 mmol) at 0° C. After stirring for 5 min at 0° C. and 20 min at rt the reaction was cooled to 0° C. and quenched by addition of water (10 mL) and extracted with DCM. The combined organic layers were washed with water, dried over Na$_2$SO$_4$ and evaporated to afford crude intermediate P21b (3.12 g).

Step 3: 3-Bromo-N,5-di-tert-butylbenzenesulfonamide (P21c)

The crude compound P21b (310 mg, approx. 1.0 mmol), triethylamine (270 µL, 2.0 mmol) and DMAP (122 mg, 1.0 mmol) was added into a solution of 2-methylpropan-2-amine (88 mg, 1.2 mmol) in DCM (20 mL). The mixture was stirred at rt, evaporated, poured into water and extracted with EA. The organic layer was washed with brine, dried over Na$_2$SO$_4$, filtered and concentrated to afford compound P21c as a crude solid (300 mg, 86%).

Step 4: N,3-Di-tert-butyl-5-(4,4,5,5-tetramethyl-1,3, 2-dioxaborolan-2-yl)benzenesulfonamide (P21) and Step 5: N,3-Di-tert-butyl-N-methyl-5-(4,4,5,5-tetramethyl-1,3,2-dioxaborolan-2-yl)benzenesulfonamide (P22)

Boronic ester intermediates P21 and P22 were obtained in a similar fashion as outlined in Preparative Example P19 and Preparative Example P20, Step 4 and Step 5, respectively.

Preparative Example P23

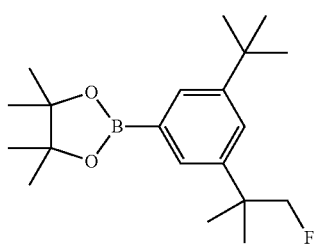

Step 1: 2-(3-Bromo-5-(tert-butyl)phenyl)propan-2-ol (P23a)

To a solution of 1,3-dibromo-5-tert-butylbenzene (404 mg) in dry THF (10 mL) was added n-BuLi (0.84 mL) at −78° C. and after 20 min, acetone was added dropwise to the above solution at −78° C. and the mixture was stirred at this temperature for 30 min and at rt for 1 h, diluted with sat. NH$_4$Cl and extracted with EA (3×30 mL). The organic layer was dried over Na$_2$SO$_4$, evaporated and purified by CC to give compound P23a (380 mg, 70%) as a white solid.

Step 2: 2-(3-Bromo-5-(tert-butyl)phenyl)-2-methylpropanenitrile (P23b)

To a solution of compound P23a (271 mg, 1.0 mmol) in DCM (6 mL) was added TMSCN (495 mg, 5.0 mmol) at 0° C. followed by slow addition of SnCl$_4$ (104 mg, 0.40 mmol). The mixture was warmed to rt overnight, K$_2$CO$_3$ and KF.2H$_2$O were added, followed by dropwise addition of H$_2$O. The mixture was filtered and washed with DCM (3×50 mL). The combined organic layers were washed with sat. NaHCO$_3$, dried over MgSO$_4$, concentrated and purified by CC to give compound P23b (200 mg, 71%) as a pale yellow solid.

Step 3: 2-(3-Bromo-5-(tert-butyl)phenyl)-2-methylpropanal (P23c)

To a solution of compound P23b (1.38 g, 5 mmol) in THF (20 mL) was added diisobutylaluminium hydride (6.5 mL, 1M) at 15° C. The mixture was allowed to warm to rt for 2 h, hydrolyzed by a cold solution of H$_2$SO$_4$ (10%) and allowed to warm to 25° C. and stirred for additional 2 h. The organic layer was separated and the aq. phase was extracted with EA (3×50 mL). The combined organic layers were dried over Na$_2$SO$_4$ and evaporated to give compound P23c (1.0 g, 72%) as a white solid.

Step 4: 2-(3-Bromo-5-(tert-butyl)phenyl)-2-methylpropan-1-ol (P23d)

To a solution of compound P23c (283 mg, 1.0 mmol) in MeOH (5 mL) was added NaBH$_4$ (57 mg, 1.5 mmol). The mixture was stirred at rt for 3 h, then aq. NH₄Cl was added and stirred for another 1 h, evaporated and extracted by EA (3×20 mL). The organic phase was dried over Na₂SO₄ and evaporated to give compound P23d (180 mg, 64%) as a white solid.

Step 5: 1-Bromo-3-(tert-butyl)-5-(1-fluoro-2-methyl-propan-2-yl)benzene (P23e)

To a cooled solution of compound P23d (180 mg, 0.64 mmol) in dry DCM (5 mL) was added DAST (150 mg, 0.95 mmol) under N₂ at −78° C. The mixture was stirred at −78° C. for 1 h and warmed to rt for overnight, quenched with aq. NaHCO₃, extracted by DCM (3×20 mL), dried and evaporated to give compound P23e (100 mg, 54%) as a pale yellow oil.

Step 6: 2-(3-(tert-Butyl)-5-(1-fluoro-2-methylpropan-2-yl)phenyl)-4,4,5,5-tetramethyl-1,3,2-dioxaborolane (P23)

Boronic ester intermediate P23 was obtained in a similar fashion as outlined in Preparative Example P19, Step 4.

Preparative Example P24

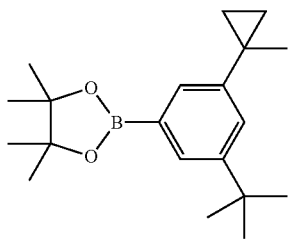

P24

Step 1: 1-Bromo-3-(tert-butyl)-5-(prop-1-en-2-yl)benzene (P24a)

To a solution of 1,3-dibromo-5-(tert-butyl)benzene (2.92 g, 10 mmol) in dioxane (20 mL) was added Pd(PPh₃)₄ (3.0 g, 2.6 mmol), prop-1-en-2-ylboronic acid (1.0 g, 12 mmol), K₂CO₃ (2.8 g, 20 mmol) and H₂O (1 mL) under N₂. The resulting mixture was stirred at 90° C. overnight, concentrated and purified by CC (hexane) to give compound P24a (2.5 g, 100%; 80% by GC/MS) as a liquid.

Step 2: 1-Bromo-3-(tert-butyl)-5-(1-methylcyclopropyl)benzene (P24b)

To a solution of Et₂Zn (20 mL of 1M solution in hexanes, 20 mmol) in dry DCM (20 mL) at 0° C. was added freshly distilled TFA (1.8 mL, 20 mmol) in DCM (20 mL) over a period of approx. 30 min. The gray mixture was stirred at 0° C. for 20 min at which time CH₂I₂ (2.0 mL, 20 mmol) dissolved in DCM (20 mL) was added to the reaction flask by cannulation. The resulting slurry was stirred for 20 min before the addition of compound P24a (2.5 g, 10 mmol) dissolved in DCM (15 mL). The slurry was allowed to warm to rt over 30 min, quenched with sat. NH₄Cl (50 mL) and extracted with hexanes. The combined organic layers were dried over MgSO₄. Evaporation and purification by CC (hexane) afforded compound P24b (1.6 g, 60%) as a colorless oil.

Step 3: 2-(3-(tert-Butyl)-5-(1-methylcyclopropyl)phenyl)-4,4,5,5-tetramethyl-1,3,2-dioxaborolane (P24)

To a suspension of compound P24b (1.6 g, 70 mmol), B₂Pin₂ (3.0 g, 15 mmol), KOAc (2.32 g, 24 mmol) in dioxane (40 mL) was added Pd(dppf)Cl₂ (0.16 g) under N₂. The mixture was heated to 100° C. for 16 h, evaporated and purified by CC (PE/EA=4/1) to afford compound P24 (1.5 g, 68%) as a white solid.

Preparative Example P25

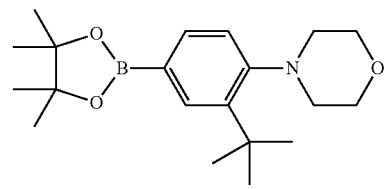

P25

Step 1: 4-Bromo-2-(tert-butyl)aniline (P25a)

To a solution of 2-tert-butylaniline (14.9 g, 100 mmol) was added a solution of NBS (17.8 g, 100 mmol) in DMF at rt. The reaction mixture was stirred for 1 h at rt, diluted with water (30 mL) and extracted with Et₂O (3×250 mL). The organic layer was washed with brine, dried over Na₂SO₄, concentrated and purified by CC to give compound P25a (19 g, 83%).

Step 2: 4-(4-Bromo-2-(tert-butyl)phenyl)morpholine (P25b)

To a microwave vial (20 mL) equipped with a magnetic bar was added compound P25a (1.0 g, 4.4 mmol), 1-chloro-2-(2-chloroethoxy)ethane (1.1 g, 7.6 mmol), KI (2.2 g, 13.2 mmol) and K₂CO₃ (1.2 g, 8.8 mmol) in DMF. The mixture was stirred under microwave irradiation at 120° C. for 1 h, cooled, poured into water (20 mL) and extracted with Et₂O (3×25 mL). The combined organic layers were dried over Na₂SO₄, evaporated and purified by CC to afford compound P25b (200 mg, 15%).

Step 3: 4-(2-(tert-Butyl)-4-(4,4,5,5-tetramethyl-1,3,2-dioxaborolan-2-yl)phenyl)morpholine (P25)

A flask charged with Pd(dppf)Cl₂ (2 mg), KOAc (59 mg, 0.6 mmol), and compound P25b (60 mg, 0.2 mmol) was flushed with N₂. Dioxane (3 mL) and B₂Pin₂ (0.24 mmol) were then added. After being stirred at 80° C. for 35 min, the mixture was extracted with EA. The combined organic layers were washed with water, dried over Na₂SO₄, concentrated and purified by CC to afford compound P25 (30 mg, 43%) as a colorless solid.

Preparative Example P26

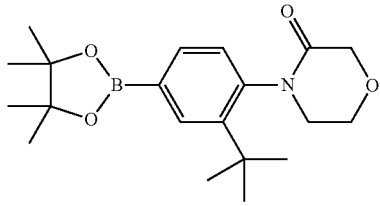

Step 1: N-(4-Bromo-2-(tert-butyl)phenyl)-2-(2-chloroethoxy)acetamide (P26a)

A mixture of compound P25a (2.28 g, 10 mmol) and 2-(2-chloroethoxy)acetyl chloride (1.57 g, 10 mmol) in toluene was heated at 110° C. for 1.5 h, concentrated, diluted with water (100 mL) and extracted with EA. The combined organic layers were washed with brine, dried over $Na_2SO_4$, concentrated and purified by CC to give compound P26a (2.3 g, 64%).

Step 2: 4-(4-Bromo-2-(tert-butyl)phenyl)morpholin-3-one (P26b)

A mixture of compound P25a (3.48 g, 10 mmol) and $K_2CO_3$ (1.57 g, 10 mmol) in ACN was heated at 80° C. for 15 h, evaporated, diluted with water (100 mL) and extracted with EA. The combined organic layers were washed with brine, dried over $Na_2SO_4$, concentrated and purified by CC to give compound P26b (2.3 g, 72%).

Step 3: 4-(2-(tert-Butyl)-4-(4,4,5,5-tetramethyl-1,3,2-dioxaborolan-2-yl)phenyl)morpholin-3-one (P26)

A flask charged with $Pd(dppf)Cl_2$ (20 mg), KOAc (590 mg, 6 mmol) and compound P26b (620 mg, 2 mmol) was flushed with $N_2$. Dioxane (30 mL) and $Pin_2B_2$ (2.4 mmol) were then added. After being stirred at 80° C. for 35 min, the mixture was extracted with EA and the combined organic layers were washed with water, dried over $Na_2SO_4$, concentrated and purified by CC to give compound P26 (370 mg, 52%) as colorless solid.

Preparative Example 27

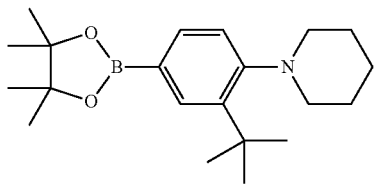

Step 1: 1-(4-Bromo-2-(tert-butyl)phenyl)piperidine (P27a)

To a solution of NaH (72 mg, 3.0 mmol) in dry DMF was added P25a (228 mg, 1.0 mmol) and the mixture was stirred at 25° C. for 0.5 h. Then 1,5-dibromopentane was added dropwise and the mixture was stirred at 80° C. for 40 h, cooled, poured into water (20 mL) and extracted with $Et_2O$ (3×25 mL). The combined organic layers were dried over $Na_2SO_4$, evaporated and purified by CC to afford compound P27a (50 mg, 19%) as yellow oil.

Step 2: 1-(2-(tert-Butyl)-4-(4,4,5,5-tetramethyl-1,3,2-dioxaborolan-2-yl)phenyl)piperidine (P27)

Boronic ester intermediate P27 was obtained in a similar fashion as outlined in Preparative Example P26, Step 3.

Preparative Example P28

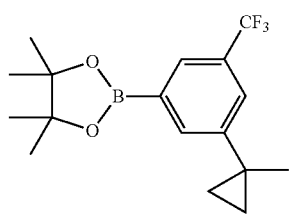

Step 1: 1-Bromo-3-(prop-1-en-2-yl)-5-(trifluoromethyl)benzene (P28a)

To a solution of 1,3-dibromo-5-(trifluoromethyl)benzene (3.03 g, 10 mmol) in dioxane (20 mL) was added $Pd(PPh_3)_4$ (300 mg, 0.26 mmol), prop-1-en-2-ylboronic acid (1.0 g, 12 mmol), $K_2CO_3$ (2.8 g, 20 mmol) and water (1 mL) under $N_2$. The mixture was stirred at 90° C. overnight, concentrated and purified by CC (hexane) to afford compound P28a (1.9 g, 71%) as an oil.

Step 2: 1-Bromo-3-(1-methylcyclopropyl)-5-(trifluoromethyl)benzene (P28b)

To a solution of $Et_2Zn$ (4 mL of 1.0 M solution in hexanes, 4 mmol) in dry DCM (4 mL) at 0° C. was added freshly distilled TFA (0.36 mL, 4 mmol) in DCM (4 mL) very slowly (ca. 30 min). The grey mixture was stirred at 0° C. for 20 min while adding $CH_2I_2$ (0.4 mL, 4 mmol) in DCM (4 mL), stirred for additional 20 min before compound P28a (0.53 g, 2 mmol) dissolved in DCM (3 mL) was added. The slurry was allowed to warm to rt over 30 min, quenched with sat. $NH_4Cl$ (5 mL) and extracted with hexanes. The combined organic layers were dried ($MgSO_4$), evaporated and purified by CC (hexane) to afford P28b (300 mg, 46%) as a colorless oil.

Step 3: 4,4,5,5-Tetramethyl-2-(3-(1-methylcyclopropyl)-5-(trifluoromethyl)phenyl)-1,3,2-dioxaborolane (P28)

To a suspension of compound P28b (300 mg, 1.0 mmol), $B_2Pin_2$ (380 mg, 1.5 mmol), KOAc (290 mg, 3 mmol) in dioxane (5 mL) was added $Pd(dppf)Cl_2$ (20 mg) under $N_2$.

The mixture was heated to 100° C. for 16 h, evaporated and purified by CC (PE/EA=4/1) to give compound P28 (200 mg, 68%) as a white solid.

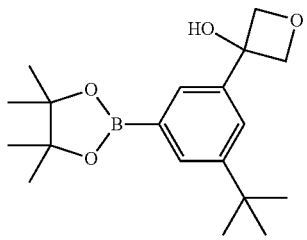

P50

Preparative Example P29

Step 1: 3-(3-bromo-5-(tert-butyl)phenyl)oxetan-3-ol (P29a)

To a solution of 1,3-dibromo-5-(tert-butyl)benzene (316 mg, 1.05 mmol) in dry THF (15 mL), n-BuLi (1 mL, 2.5M) was added dropwise under N₂ at −78° C. The mixture was stirred at this temperature for 1 h. Then oxetan-3-one (91 mg, 1.27 mmol) was added and the mixture was stirred at rt overnight, diluted with aq. NH₄Cl (20 mL) and extracted with EA. The combined organic layers were washed with brine, dried over Na₂SO₄ and concentrated to give the product P29a (120 mg, 40%) as a yellow solid.

Step 2: 3-(3-(tert-Butyl)-5-(4,4,5,5-tetramethyl-1,3, 2-dioxaborolan-2-yl)phenyl)oxetan-3-ol (P29)

Compound P29 was prepared similar as described for Example P44, Step 3 and was obtained as a white solid (45%).

Preparative Example P30

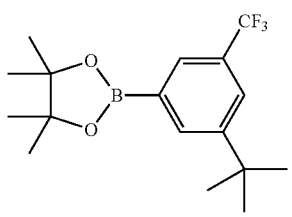

P30

Step 1: 3-Bromo-N-methoxy-N-methyl-5-(trifluoromethyl)benzamide (P30a)

To a solution of 3-bromo-5-(trifluoromethyl)benzoic acid (5.34 g, 20 mmol) in DCM (120 mL) was added O,N-dimethylhydroxylamine hydrochloride (2.9 g, 30 mmol), HATU (9.2 g, 30 mmol) and Et₃N (8.0 g, 80 mmol). The mixture was stirred at rt overnight, concentrated and purified by CC (hexane) to afford compound P30a (5.1 g, 83%) as a solid.

Step 2: 1-(3-Bromo-5-(trifluoromethyl)phenyl)ethanone (P30b)

To a solution of compound P30a (5.0 g, 16 mmol) in dry THF (100 mL) at 0° C. was added a MeMgBr solution (1M, 32 mL, 32 mmol) under N₂. After stirring at rt for 2 h, the reaction was quenched with sat. NH₄Cl (15 mL) and extracted with EA. The combined organic layers were dried over MgSO₄, evaporated and purified by CC (PE/EA=20/1) to afford compound P30b (2.7 g, 65%) as a pale yellow solid.

Step 3: 1-Bromo-3-(tert-butyl)-5-(trifluoromethyl) benzene (P30c)

An oven dried flask was charged with DCM (15 mL) and TiCl₄ (2.3 g, 12 mmol) and ZnMe₂ (1M, 12 mL) were added. The mixture was cooled to −30° C. and stirred at constant temperature for 0.5 h. A solution of compound P30b (1.6 g, 6.0 mmol) was added dropwise and the solution was allowed to warm to 0° C. over 40 min, stirred at rt for 2 h, 45 min at 45° C. and at 40° C. overnight, diluted with water (20 mL) and extracted with EA. The organic layer was washed with brine, dried over Na₂SO₄ and concentrated give compound P30c as a yellow oil (400 mg, 23%).

Step 4: 2-(3-(tert-Butyl)-5-(trifluoromethyl)phenyl)- 4,4,5,5-tetramethyl-1,3,2-dioxaborolane (P30)

To a suspension of compound P30c (400 mg, 1.4 mmol), B₂Pin₂ (760 mg, 3 mmol) and KOAc (400 mg, 4.2 mmol) in dioxane (15 mL) was added Pd(dppf)Cl₂ (40 mg) under N₂. The mixture was heated to 100° C. for 16 h, evaporated and purified by CC (PE/EA=4/1) to give compound P30 (320 mg, 71%) as a colorless solid.

Preparative Example P31

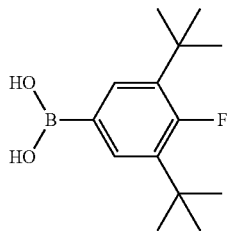

P31

Step 1: 1,3,5-Tri-tert-butyl-2-fluorobenzene (P31a)

A solution of 1,3,5-tri-tert-butylbenzene (442 mg, 2.0 mmol) in ACN (20 mL) was cooled to 0° C. under N₂. Selectfluor (1.06 g, 3.0 mmol) was added, keeping the temperature close to 0° C. The reaction was stirred overnight warming up to rt, poured into aq. Na₂CO₃ (15 mL) and extracted with Et₂O (30 mL). The organic layer was washed with brine, dried with Na₂SO₄, filtered and evaporated to give compound P31a (430 mg, 81%).

Step 2: 1,3-Di-tert-butyl-2-fluoro-5-nitrobenzene (P31 b)

Fuming HNO₃ (1 mL) was added dropwise to a cooled (−5° C.) solution of compound P31a (430 mg, 1.63 mmol) in cyclohexane/nitromethane (10 mL, 1:1). The mixture was stirred at rt for 2 d, diluted with water (15 mL) and extracted with cyclohexane (3×15 mL). The organic layer was washed with water and 10% NaOH, dried over Na₂SO₄ and evaporated to give crude product (102 mg). Crystallization from EtOH/acetone (1:1) afforded compound P31b (56 mg, 14%).

Step 3: 3,5-Di-tert-butyl-4-fluoroaniline (P31c)

SnCl$_2$ (2.4 g, 10.6 mmol) dissolved in conc. HCl (4 mL) was added to a refluxing solution of compound P31b (507 mg, 2 mmol) in AcOH (5 mL). After stirring for 2 h the product was isolated by hydrolysis with 10% aq. NaOH, followed by extraction with Et$_2$O (4×15 mL). After evaporation, crude compound P31c (168 mg, 36%) was obtained as a brown oil.

Step 4: 1,3-Di-tert-butyl-2-fluoro-5-iodobenzene (P31 d)

AcOH (3 mL) and H$_2$SO$_4$ (1 mL) were added to compound P31c (168 mg, 0.73 mmol) and the hot mixture was stirred for 30 min. Isoamyl nitrite was added at 0° C. and the mixture was stirred for 20 min at 0° C., diluted with a solution of KI (242 mg, 1.46 mmol) in water (2 mL) and gradually warmed to 20° C. and stirred for 12 h, diluted with an aq. solution of Na$_2$SO$_3$ (5 mL) and extracted with hexane. The organic layer was washed with brine, dried over Na$_2$SO$_4$, filtered, concentrated and purified by CC (pentane) to give compound P31d (160 mg, 66%).

Step 5: (3,5-Di-tert-butyl-4-fluorophenyl)boronic acid (P31)

To a cooled (−78° C.) solution of compound P31d (160 mg, 0.48 mmol) and triisopropyl borate (135 mg, 0.72 mmol) in dry THF was added n-BuLi (2.5M in hexane, 0.3 mL) under N$_2$ and the mixture was stirred at rt for 3 h, quenched with 3N HCl (2 mL) and extracted with EA (3×10 mL). The combined organic layer was washed with brine (2×10 mL), dried over Na$_2$SO$_4$, concentrated and purified by prep-TLC (EA/PE=1/3) to afford compound P31 (30 mg, 25%) as a colorless solid.

Preparative Example P32

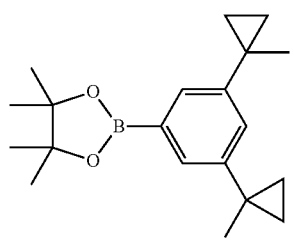

P32

Step 1: 5-Bromo-N1,N3-dimethoxy-N1,N3-dimethylisophthalamide (P32a)

1,1'-Carbonyldiimidazole (2.53 g, 25 mmol) was added portionwise to a solution of 5-bromoisophthalic acid (2.45 g, 10 mmol) in DCM and the mixture was stirred at rt for 1 h, then a suspension of N,O-dimethylhydroxylamine (2.34 g, 24 mmol) in DCM was added, stirred at rt overnight, washed with water and brine, dried over Na$_2$SO$_4$ and concentrated to afford compound P32a (3.2 g, 97%) as a pale oil.

Step 2: 1,1'-(5-Bromo-1,3-phenylene)diethanone (P32b)

A suspension of CH$_3$MgI (40 mmol) in Et$_2$O was added to a solution of compound P32a (3.3 g, 10 mmol) in THF at 0° C. The mixture was stirred at rt overnight and then treated with H$_2$O and extracted with Et$_2$O. The combined organic layer was dried over Na$_2$SO$_4$ and concentrated to afford compound P32b (2.0 g, 83%) as a yellow solid.

Step 3: 1-Bromo-3,5-di(prop-1-en-2-yl)benzene (P32c)

To a solution of NaH (2.0 g, 84 mmol) in THF (20 mL) was added PPh$_3$CH$_3$Br (26.4 g, 74 mmol) portionwise and stirred at rt for 3 h. Then a solution of compound P32b (8.1 g, 33.6 mmol) was added and stirred for 2 h. Water was added and the mixture was extracted with EA. The organic layer was dried with Na$_2$SO$_4$, evaporated and purified by CC to give compound P32c (5.2 g, 65%) as a colorless oil.

Step 4: 1-Bromo-3,5-bis(1-methylcyclopropyl)benzene (P32d)

To a solution of Et$_2$Zn (119 mL, 1.0 M) in dry DCM was added freshly distilled TFA (13.6 g, 119 mmol) in DCM very slowly. The gray mixture was stirred at 0° C. for 20 min at which time CH$_2$I$_2$ (31.8 g, 119 mmol) in DCM was added to the flask by cannulation. The resulting slurry was stirred for 20 min before addition of compound P32c (4.7 g, 19.8 mmol) dissolved in DCM. The slurry was allowed to warm to rt over 30 min, quenched with sat. NH$_4$Cl and the layers were separated. The aq. layer was extracted with hexane (2×), dried over Na$_2$SO$_4$, evaporated and purified by CC to give compound P32d (5.0 g, 95%) as colorless oil.

Step 5: 2-(3,5-Bis(1-methylcyclopropyl)phenyl)-4,4,5,5-tetramethyl-1,3,2-dioxaborolane (P32)

A flask charged with Pd(dppf)Cl$_2$ (50 mg), KOAc (1.44 g, 14.7 mmol), and compound P32d (1.3 g, 4.9 mmol) was flushed with N$_2$. Dioxane (15 mL) and B$_2$Pin$_2$ (5.8 mmol) were added and the mixture was stirred at 80° C. for 35 min, then extracted with EA and the combined organic layer was washed with water, dried over Na$_2$SO$_4$, concentrated and purified by CC to give compound P32 (600 mg, 39%) as a white solid.

Preparative Example P33

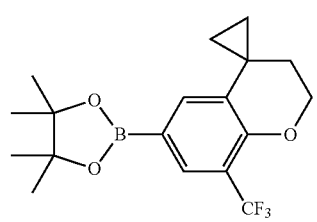

P33

Step 1: 1-(Prop-2-yn-1-yloxy)-2-(trifluoromethyl)benzene (P33a)

To a stirred solution of 2-(trifluoromethyl)phenol (50.0 g, 0.31 mol) and progargyl bromide (44.0 g, 0.37 mol) in ACN (500 mL) was added $K_2CO_3$ (51.0 g, 0.37 mol) and the mixture was stirred overnight at rt, concentrated, diluted with water and extracted with $Et_2O$. The combined organic layers were dried over $Na_2SO_4$, filtered, concentrated and purified by CC (PE/EA=40/1) to give compound P33a (59.7 g, 97%) as an oil.

Step 2: 1((3-Chloroprop-2-yn-1-yl)oxy)-2-(trifluoromethyl)benzene (P33b)

To a stirred mixture of compound P33a (54.0 g, 0.27 mol) in acetone (500 mL) was added NCS (43.3 g, 0.32 mol) and $CH_3COOAg$ (4.5 g, 0.027 mol) and the solution was heated to reflux for 6 h, cooled to rt, filtered, concentrated, diluted with $Et_2O$, washed with water and sat. $NaHCO_3$, dried over $Na_2SO_4$, filtered and concentrated to give crude compound P33b (60.0 g, 95%) as an oil.

Step 3: 8-(Trifluoromethyl)chroman-4-one (P33c)

Compound P33b (60.0 g, 0.26 mol) was dissolved in conc. $H_2SO_4$ (400 mL) at 0° C. and the mixture was stirred at rt for 2 h, poured into ice water and extracted with $Et_2O$. The combined organic layers were washed with brine, dried over $Na_2SO_4$, filtered, concentrated and purified by CC (PE/EA=40/1) to give compound P33c (9.8 g, 18%) as an oil.

Step 4: 8-(Trifluoromethyl)spiro[chroman-4,1'-cyclopropane] (P33d)

To a stirred mixture of $PPh_3CH_3Br$ (23.8 g, 67.0 mmol) in dry THF (70 mL) was added n-BuLi (2.5M, 26.6 mL, 66.5 mmol) under $N_2$ at −40° C. and the mixture was stirred for 30 min at this temperature. Then a solution of compound P33c (7.2 g, 33.0 mmol) in dry THF (30 mL) was added dropwise and the mixture was stirred at rt for 1.5 h, quenched with aq. $NH_4Cl$ at 0° C. and extracted with EA twice. The combined organic layers were concentrated and purified by CC (PE) to give the intermediate. A solution of $CH_2N_2$ in $Et_2O$ (2M, 150 mL) was added dropwise at 10° C. to a solution of this intermediate together with $Pd(OAc)_2$ (300 mg) in dry THF (30 mL) and the mixture was stirred at rt for 2 h, filtered, concentrated and purified by CC (PE) to give compound P33d (2.7 g, 36%) as a brown oil.

Step 5: 4,4,5,5-Tetramethyl-2-(8-(trifluoromethyl)spiro[chroman-4,1'-cyclopropan]-6-yl)-1,3,2-dioxaborolane (P33)

To a solution of compound P33d (2.5 g, 10.9 mmol) in dry THF (30 mL) was added $Ir(OMe)_2(COD)_2$ (217 mg, 0.33 mmol), dtbpy (178 mg, 0.66 mmol) and $B_2Pin_2$ (2.78 g, 10.9 mmol) and the mixture was stirred overnight at 80° C. under $N_2$, concentrated and purified by CC (PE) to give compound P33 (1.10 g, 28%) as a solid.

Preparative Example P34

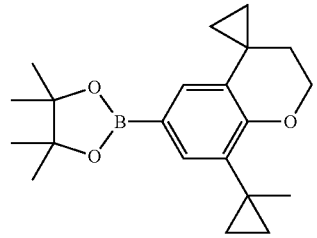

P34

Step 1: 1-Bromo-2-(prop-2-yn-1-yloxy)benzene (P34a)

To a stirred solution of 2-bromophenol (50.0 g, 289 mmol) and progargyl bromide (41.3 g, 347 mmol) in dry ACN (500 mL) was added $K_2CO_3$ (47.9 g, 347 mmol) and the solution was stirred overnight at rt. The solvent was removed and the residue was poured into water and extracted with $Et_2O$. The combined organic layers were dried over $Na_2SO_4$, filtered and concentrated to give compound P34a (60 g, 98%) as an oil.

Step 2: 1-Bromo-2((3-chloroprop-2-yn-1-yl)oxy)benzene (P34b)

To a stirred mixture of compound P34a (61.3 g, 291 mmol) in dry acetone (600 mL) was added NCS (46.6 g, 349 mmol) and AcOAg (4.86 g, 29.1 mmol) and the solution was heated at reflux for 2 d. After cooling, the mixture was filtered and the filtrate was concentrated. The residue was taken up in $Et_2O$ and the obtained filtrate was washed with water and sat. $NaHCO_3$ solution, dried over $Na_2SO_4$, filtered, concentrated and purified by CC (PE) to give compound P34b (50.3 g, 70%) as an oil.

Step 3: 8-Bromochroman-4-one (P34c)

The solution of compound P34b (2.0 g, 8.15 mmol) in ethylene glycol (20 mL) was heated at reflux for 4 h. The reaction mixture was cooled, poured into water and extracted with $Et_2O$ twice. The combined organic layers were combined, washed with 1M aq. NaOH and sat. ammonium carbonate, dried over $Na_2SO_4$, filtered, concentrated and purified by CC (PE/EA=50/1) to give compound P34c (0.88 g, 48%) as a yellow solid.

Step 4: 8-Bromo-4-methylenechroman (P34d)

To a stirred mixture of $PPh_3CH_3Br$ (25.4 g, 71.1 mmol) in dry THF (250 mL) was added n-BuLi (2.5M, 28.5 mL, 71.3 mmol) under $N_2$ at −40° C. and the mixture was stirred for 30 min at that temperature. Then a solution of compound P34c (8.0 g, 35.6 mmol) in dry THF (80 mL) was added dropwise. The solution was stirred at rt for 2 h, then quenched with aq. $NH_4Cl$ at 0° C. and extracted with EA. The organic layer was concentrated and purified by CC (PE/EA=50/1) to give P34d (5.2 g, 66%) as an oil.

Step 5: 8-Bromospiro[chroman-4,1'-cyclopropane] (P34e)

KOH (50 g, 893 mmol) was added to a mixture of water (300 mL) and Et$_2$O (200 mL), and then amino-N-nitrosoamide (25 g, 62.5 mmol) was added to the resulting mixture at 20° C. After stirring for 10 min, the organic layer was added to a solution of compound P34d (5.2 g, 23.5 mmol) and Pd(OAc)$_2$ (500 mg) in dry THF (50 mL) at 0° C. dropwise. The mixture was stirred at rt for 1 h, filtered, concentrated and purified by CC (PE) to give compound P34e (4.5 g, 81%) as an oil.

Step 6: 1-(Spiro[chroman-4,1'-cyclopropan]-8-yl)ethanone (P34f)

A solution of compound P34e (500 mg, 2.11 mmol) and NEt$_3$ (852 mg, 8.44 mmol) in dry DMF (5 mL) was degassed with N$_2$ for 15 min, then butyl vinyl ether (633 mg, 6.23 mmol), dppp (87 mg, 0.21 mmol) and Pd(OAc)$_2$ (50 mg, 0.21 mmol) were added under N$_2$. The mixture was stirred at 80° C. overnight, cooled, poured into water and extracted with EA twice. The combined organic layers were washed with brine, dried over Na$_2$SO$_4$, filtered, concentrated and purified by CC (PE/EA=50/1) to give compound P34f (120 mg, 28%) as an oil.

Step 7: 8-(Prop-1-en-2-yl)spiro[chroman-4,1'-cyclopropane] (P34g)

To a stirred mixture of PPh$_3$CH$_3$Br (5.7 g, 16 mmol) in dry THF (57 mL) was added n-BuLi (2.5M, 6.4 mL, 16 mmol) under N$_2$ at −40° C. and the mixture was stirred for 30 min at that temperature. Then the solution of compound P34f (1.6 g, 8.0 mmol) in dry THF (16 mL) was added dropwise and the solution was stirred at rt for 2 h, quenched with aq. NH$_4$Cl at 0° C. and extracted with EA. The organic layer was concentrated and purified by CC (PE) to give compound P34g (1.2 g, 76%) as an oil.

Step 8: 8-(1-Methylcyclopropyl)spiro[chroman-4,1'-cyclopropane] (P34h)

KOH (10 g, 178 mmol) was added to a mixture of water (100 mL) and Et$_2$O (120 mL) and then amino-N-nitrosoamide (5 g, 12.5 mmol) was added to the resulting mixture at −20° C. After stirred for 10 min, the organic layer was added to a solution of compound P34g (1.2 g, 6.12 mmol) and Pd(OAc)$_2$ (150 mg) in dry THF (12 mL) at 0° C. dropwise. The mixture was stirred at rt for 1 h, filtered, concentrated and purified by CC (PE) to give compound P34h (780 mg, 61%) as an oil.

Step 9: 6-Bromo-8-(1-methylcyclopropyl)spiro[chroman-4,1'-cyclopropane] (P34i)

To a stirred mixture of compound P34h (700 mg, 3.33 mmol) in dry THF (7 mL) was added NBS (712 mg, 4.00 mmol) and the solution was stirred at rt for 1.5 h, quenched with water and extracted with EA. The combined organic layers were washed with brine, concentrated and purified by CC (PE) to give compound P34i (350 mg, 36%) as a white solid.

Step 10: 4,4,5,5-Tetramethyl-2-(8-(1-methylcyclopropyl)spiro[chroman-4,1'-cyclopropan]-6-yl)-1,3,2-dioxaborolane (P34)

A solution of compound P34i (220 mg, 0.76 mmol), B$_2$Pin$_2$ (290 mg, 1.14 mmol), Pd(dppf)Cl$_2$ (20 mg) and K$_2$CO$_3$ (157 mg, 1.14 mmol) in DMF (5 mL) under N$_2$ was stirred at 90° C. overnight, concentrated and purified by CC (PE) to give compound P34 (180 mg, 70%) as a white solid.

Preparative Example P35

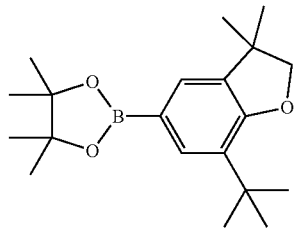

P35

Step 1: 2,4-Dibromo-6-(tert-butyl)phenol (P35a)

To a solution of 2-(tert-butyl)phenol (25 g, 167 mmol) in MeOH was added dropwise Br$_2$ at rt. The reaction was stirred at rt until completed by TLC and then concentrated to afford a yellow solid, which was washed with water and dried in vacuo to provide crude compound 35a (45 g, 90%).

Step 2: 1,5-Dibromo-3-(tert-butyl)-2((2-methylallyl)oxy)benzene (P35b)

A mixture of compound P35a (7.0 g, 22.7 mmol), 3-chloro-2-methylprop-1-ene (3.5 mL, 33.9 mmol), K$_2$CO$_3$ (3.76 g, 27 mmol) and NaI (0.338 g, 2.27 mmol) in acetone was vigorously stirred at rt for 56 h, filtered, evaporated to give an oil which was dissolved in hexanes and stirred with silica gel. The slurry was filtered through a pad of Celite and eluted with additional hexanes. The filtrate was evaporated to give crude compound P35b (7.2 g, 87%) as a yellow oil.

Step 3: 5-Bromo-7-(tert-butyl)-3,3-dimethyl-2,3-dihydrobenzofuran (P35c)

A mixture of dioxane (400 mL), compound P35b (7.8 g, 21.6 mmol), dry hypophosphorus acid (43 g, 652 mmol) and Et$_3$N (90 mL, 650 mmol) was degassed (N$_2$) for 30 min and then was kept under N$_2$. A solution of AIBN (20 mL of a 0.7 M solution in degassed dioxane) was added via a syringe and the mixture was refluxed. Every 0.5 h additional AIBN solution (20 mL) was injected. After 3 h, the reaction was allowed to reflux for further 14 h and then cooled to rt, extracted twice with a mixture of brine (250 mL) and 1N HCl (100 mL). The organic layer was dried over MgSO$_4$, filtered and evaporated to give a yellow oil admixed with a white solid. This was triturated with hexanes (300 mL) and the insolubles were filtered off and rinsed with fresh hexanes (50 mL). The combined filtrates were evaporated to give P35c (7.0 g, quant.) as a clear yellow oil.

Step 4: 2-(7-(tert-Butyl)-3,3-dimethyl-2,3-dihydrobenzofuran-5-yl)-4,4,5,5-tetramethyl-1,3,2-dioxaborolane (P35)

Compound P35 has been prepared using a similar procedure as that described in Preparative Example P34, Step 10 (180 mg, 43%).

Preparative Example P36

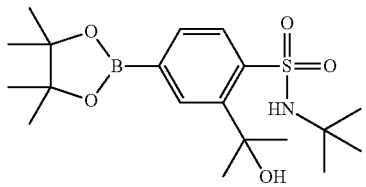

Step 1: 2-Amino-5-bromobenzonitrile (P36a)

To a solution of 2-aminobenzonitrile (14.9 g, 100 mmol) was added a solution of NBS (17.8 g, 100 mmol) in DMF at rt. The mixture was stirred overnight at rt, then water (30 mL) was added and the mixture was extracted with $Et_2O$ (3×250 mL). The organic layer was washed with brine, dried over $Na_2SO_4$, concentrated and purified by CC to give compound P36a (19 g, 83%).

Step 2: 4-Bromo-2-cyanobenzene-1-sulfonyl chloride (P36b)

Compound P36a (10 g, 51 mmol) was added to a mixture of conc. HCl (28 mL) and AcOH (5.6 mL) at −10° C. Then a solution of $NaNO_2$ (3.8 g, 55 mmol) in a minimum amount of water was added dropwise at −10° C. After stirring for 45 min at −10° C. a diazonium salt solution was obtained. $SO_2$ gas was bubbled into AcOH (56 mL) until saturation (60 min). Then $CuCl_2$ (3 g) was added and stirring was continued until the mixture turned green. The flask was placed in an ice bath and the diazonium salt solution was added dropwise at 5° C. After addition was complete, the mixture was stirred overnight at rt and poured into ice water. The solid was collected by filtration to give the crude compound P36b (9 g, 71%)

Step 3: 4-Bromo-N-(tert-butyl)-2-cyanobenzenesulfonamide (P36c)

To a solution of compound P36b (5.0 g, 18 mmol) in pyridine (20 mL) was added 2-methylpropan-2-amine (3.3 g, 45 mmol) and the reaction was purged with $N_2$, heated at 50° C. for 1 h, cooled and concentrated. The residue was purified by CC (DCM/MeOH=100/1) to give compound P36c (3.0 g, 53%) as a yellow solid.

Step 4: 2-Acetyl-4-bromo-N-(tert-butyl)benzenesulfonamide (P36d)

A suspension of compound P36c (2 g, 6.3 mmol) in THF (20 mL) was added slowly to MeMgBr (6.3 mL, 3M in $Et_2O$, 19 mmol) and the mixture was heated to reflux for 3 h, placed in an ice bath and 6N HCl (58 mL) was added slowly. The mixture was then heated to reflux, cooled, made alkaline by addition of solid $Na_2CO_3$ and extracted with EA. The combined organic phases were dried over $Na_2SO_4$, evaporated and purified by CC (n-heptan/EA=100/0 to 60/40) to give compound P36d (0.6 g, 34%).

Step 5: 4-Bromo-N-(tert-butyl)-2-(2-hydroxypropan-2-yl)benzenesulfonamide (P36e)

Compound P36d (200 mg, 0.60 mmol) was dissolved in THF (15 mL) at 0° C. A 3M solution of MeMgBr in $Et_2O$ (1 mL, 3.0 mmol) was added slowly and the reaction mixture was stirred at rt for 3 h, then another portion of a MeMgBr in $Et_2O$ (1 mL, 3.0 mmol) was added. The mixture was evaporated, diluted with water (20 mL) and extracted with $Et_2O$. The organic layer was dried over $MgSO_4$, filtered, evaporated and purified by HPLC (DCM/MeOH=100/0 to 70/30) to give compound P36e (100 mg, 39%; 47% purity).

Step 6: N-(tert-Butyl)-2-(2-hydroxypropan-2-yl)-4-(4,4,5,5-tetramethyl-1,3,2-dioxaborolan-2-yl)benzenesulfonamide (P36)

To a solution of compound P36e (200 mg, 0.57 mmol), $Pin_2B_2$ (290 mg, 1.14 mmol) and KOAc (160 mg, 1.7 mmol) in dioxane (10 mL) at rt under $N_2$ was added $Pd(dppf)Cl_2$ (42 mg, 0.05 mmol). The resulting mixture was stirred at rt for 1 h, then heated to 110° C. for 2 h, diluted with water (50 mL) and extracted with EA. The combined organic layers were concentrated and purified by CC(PE/EA=5/1) to give compound P36 (100 mg, 43%) as a colorless solid.

Preparative Example P37 and Preparative Example P38

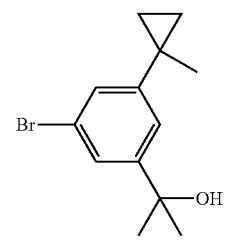

P37

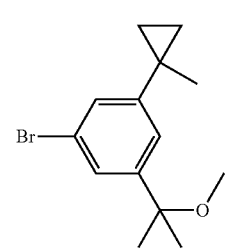

P38

Step 1: 3,5-Dibromo-N-methoxy-N-methylbenzamide (P37a)

The solution of 3,5-dibromobenzoic acid (26 g, 93 mmol) in $SOCl_2$ (100 mL) was heated at reflux for 2 h, concentrated, diluted with dry DCM (300 mL) and added slowly to a stirred solution of N,O-dimethylhydroxylamine hydrochloride (9.75 g, 100 mmol) and EtN₃ (28 g, 277 mmol) in dry DCM (300 mL) at 0° C. The solution was stirred for 1 h at rt, poured into water and the organic layer was separated. The organic layer was washed with water and brine, dried over Na₂SO₄, filtered and concentrated to give crude compound P37a (28 g, 93%) as an oil.

Step 2: 1-(3,5-Dibromophenyl)ethanone (P37b)

To a solution of compound P37a (1.0 g, 3.1 mmol) in dry THF (10 mL) was added MeMgCl (3M in Et₂O, 1 mL, 3.0 mmol) dropwise at 0° C. and the solution was stirred for 4 h at rt, then quenched with aq. NHCl₄ and extracted with tert-butylmethylether. The organic layer was washed with water and brine consecutively, dried over Na₂SO₄, filtered and concentrated to give crude compound P37b (0.70 g, 66%) as a yellow oil.

Step 3: 1,3-Dibromo-5-(prop-1-en-2-yl)benzene (P37c)

To a stirred solution of PPh₃CH₃Br (5.10 g, 14.4 mmol) in dry THF (50 mL) was added n-BuLi (2.5 M in n-hexane, 5.76 mL, 14.4 mmol) dropwise at −40° C. After stirring at this temperature for 0.5 h, a solution of compound P37b (2.0 g, 7.2 mmol) in dry THF (10 mL) was added dropwise. The resulting solution was allowed to warm to rt and stirred for 1 h, quenched with aq. NHCl₄ and extracted with Et₂O. The organic layer was concentrated and purified by CC (PE) to give compound P37c (1.6 g, 80%) as a light yellow oil.

Step 4: 1,3-Dibromo-5-(1-methylcyclopropyl)benzene (P37d)

To a solution of compound P37c (1.6 g, 5.8 mmol) and Pd(OAc)₂ (350 mg) in THF (20 mL) was added dropwise at 0° C. a solution of CH₂N₂ (487 mg, 11.6 mmol) in Et₂O (20 mL) and the mixture was stirred for 1 h at rt. The suspension was filtered and the filtrate was concentrated and purified by CC (PE) to give compound P37d (1.4 g, 82%) as a colorless oil.

Step 5: 2-(3-Bromo-5-(1-methylcyclopropyl)phenyl) propan-2-ol (P37)

To a stirred solution of compound P37d (0.5 g, 1.7 mmol) in dry THF (5 mL) was added dropwise n-BuLi (0.74 mL, 1.87 mmol) at −78° C. After 1 h at this temperature, dry acetone (118 mg, 2.04 mmol) was added dropwise. The solution was allowed to warm to rt and stirred overnight, then quenched with aq. NHCl₄ and extracted with EA. The combined organic layers were concentrated and purified by CC (PE/EA=20/1) to give compound P37 (250 mg, 52%) as a colorless oil.

Step 6: 1-Bromo-3-(2-methoxypropan-2-yl)-5-(1-methylcyclopropyl)benzene (P38)

To a solution of compound P37 (1.5 g, 5.6 mmol) in dry THF (10 mL) was added NaH (450 mg, 11.2 mmol) under N₂ and the suspension was stirred for 1 h at rt. Then MeI (2.3 g, 16.8 mmol) was added and the solution was stirred at 70° C. in a sealed tube overnight, poured into water and extracted with Et₂O. The organic layer was washed with brine, dried over Na₂SO₄, filtered, concentrated and purified by CC (PE) to give compound P38 (1.6 g, 100%) as a colorless oil.

Preparative Example P39 and Preparative Example P40

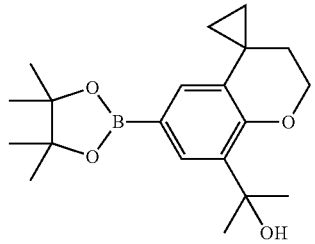

P39

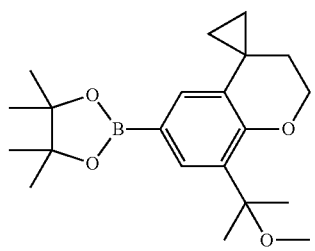

P40

Step 1: 2-(Spiro[chroman-4,1'-cyclopropan]-8-yl) propan-2-ol (P39a)

To a stirred solution of compound P34f (7.4 g, 36.7 mmol) in dry THF (74 mL) was added CH₃MgBr (3M, 24.5 mL, 73.5 mmol), and the mixture was stirred at it for 2.5 h, quenched with aq. NH₄Cl at 0° C. and extracted with EA. The organic layer was concentrated and purified by CC (PE/EA=40/1) to give compound P39a (5.1 g, 64%) as an oil.

Step 2: 2-(6-Bromospiro[chroman-4,1'-cyclopropan]-8-yl)propan-2-ol (P39)

To a solution of compound P39a (1.0 g, 4.58 mmol) in dry THF (10 mL) was added NBS (980 mg, 5.5 mmol) and the mixture was heated at reflux overnight, cooled, poured into water and extracted with EA twice. The combined organic layers were washed with brine, dried over Na₂SO₄, filtered, concentrated and purified by CC (PE/EA=100/1) to give compound P39 (180 mg, 14%) as a colorless oil.

Step 3: 6-Bromo-8-(2-methoxypropan-2-yl)spiro [chroman-4,1'-cyclopropane] (P40)

To a solution of compound P39 (160 mg, 0.54 mmol) in dry THF (1.6 mL) was added NaH (26 mg, 1.08 mmol). After 30 min, MeI (230 mg, 1.62 mmol) was added and the mixture was stirred at 50° C. overnight, cooled, poured into water and extracted with EA twice. The combined organic layers were washed with brine, dried over Na₂SO₄, filtered, concentrated and purified by CC (PE/EA=10/1) to give compound P40 (144 mg, 86%) as a colorless solid.

Preparative Example P41/1 to P41/3

Boronic ester intermediates P41/1 to P41/3 was obtained in a similar fashion as outlined above.

| # | Structure | MW (g/mol) |
|---|---|---|
| P41/1 | 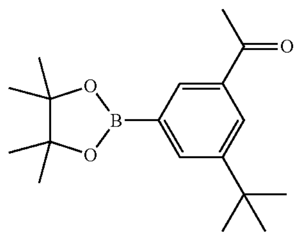 [SMILES: CC(=O)c1cc(B2OC(C)(C)C(C)(C)O2)cc(C(C)(C)C)c1] | 302.2 |
| P41/2 | 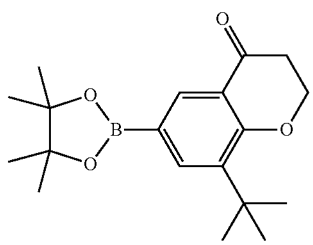 [SMILES: CC(C)(C)c1cc(B2OC(C)(C)C(C)(C)O2)cc2c1OCCC2=O] | 390.2 |
| P41/3 | 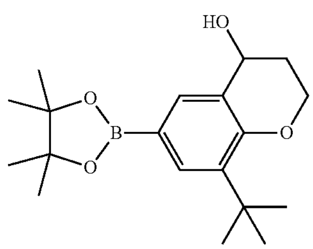 [SMILES: CC(C)(C)c1cc(B2OC(C)(C)C(C)(C)O2)cc2c1OCCC2O] | 392.2 |

Preparative Example P42

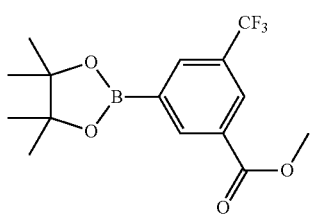

P42

Step 1: Methyl 3-bromo-5-(trifluoromethyl)benzoate (P42a)

To a solution of 3-bromo-5-(trifluoromethyl)benzoic acid (3.00 g, 11.2 mmol) in $Et_2O$ (50 mL) was added a solution of $CH_2N_2$ in $Et_2O$ (2M, 50 mL, 100 mmol) at rt and the mixture was stirred for 10 min, concentrated and purified by CC (PE/EA=10/1) to give compound P42a (2.51 g, 80%) as a colorless oil.

Step 2: Methyl 3-(4,4,5,5-tetramethyl-1,3,2-dioxaborolan-2-yl)-5-(trifluoromethyl)benzoate (P42)

A solution of compound P42a (2.51 g, 8.90 mmol), $B_2Pin_2$ (2.71 g, 10.7 mmol), AcOK (1.75 g, 17.8 mmol) and Pd(dppf)Cl$_2$ (300 mg) in dry DMF (40 mL) was heated at 90° C. for 2 h under $N_2$. The mixture was quenched with water and extracted with EA. The combined organic layers were washed with water and brine consecutively, dried over $Na_2SO_4$, filtered, concentrated and purified by CC (PE/EA=50/1) to give compound P42 (2.11 g, 72%) as a white solid.

Preparative Example P43

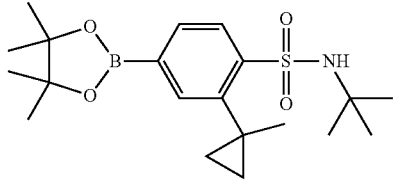

P43

Step 1: (1-Methylcyclopropyl)benzene (P43a)

To a solution of $ZnEt_2$ (165 mL, 169 mmol) in DCM (160 mL) at 0° C. was added a solution of TFA (6.5 mL, 85 mmol) in DCM (80 mL) dropwise and the mixture was stirred at 0° C. for 30 min. Then to above mixture was added $CH_2I_2$ (6.6 mL, 85 mmol) in DCM (80 mL) dropwise and the mixture was stirred at 0° C. for 20 min, followed by adding dropwise a solution of prop-1-en-2-ylbenzene (5.0 g, 42.3 mmol) in DCM (80 mL). The mixture was stirred at rt for 30 min, quenched by brine (100 mL), extracted with DCM (2×100 mL) and the combined organic layers were dried over $Na_2SO_4$, filtered, concentrated and purified by CC (PE/EA=1/0 to 100/1) to afford compound P43a (3.4 g, 60%) as a yellow oil.

Step 2: 1-(1-Methylcyclopropyl)-2-nitrobenzene (P43b)

To a solution of compound P43a (3.4 g, 26 mmol) in DCM (50 mL) was added a solution of $HNO_3$ (2.2 g, 31 mmol) in $Ac_2O$ (7.9 g, 77 mmol) dropwise at 0° C. and the mixture was stirred at 0° C. for 30 min, poured into ice (100 mL), extracted with DCM (2×100 mL). The combined organic layers were washed with brine (100 mL), dried over $Na_2SO_4$, filtered, concentrated and purified by CC (PE/EA=1/0 to 50/1) to afford compound P43b (2.4 g, 53%) as a brown oil.

Step 3: 2-(1-Methylcyclopropyl)aniline (P43c)

To a solution of compound P43b (2.4 g, 14 mmol) in EA (50 mL) was added Pd/C (10%, 0.5 g) under Ar and then the resulting suspension was stirred under $H_2$ overnight. The catalyst was filtered off and the filtrate was concentrated to give compound P43c (1.5 g, 75%) as pale oil.

Step 4: 4-Bromo-2-(1-methylcyclopropyl)aniline (P43d)

To a solution of compound P43c (1.4 g, 9.5 mmol) in DCM (30 mL) was added a solution of NBS (1.69 g, 9.5 mmol) in DCM (5 mL) dropwise at 0° C. and the resulting mixture was stirred at rt for 1 h, quenched with sat. aq. $Na_2SO_3$ (50 mL), extracted with DCM (2×50 mL). The combined organic layers were washed with brine (50 mL), dried over Na$_2$SO$_4$, filtered and concentrated to give compound P43d (1.8 g, 84%) as a brown oil.

Step 5: 4-Bromo-2(1-methylcyclopropyl)benzene-1-sulfonyl chloride (P43e)

To a suspension of compound P43d (600 mg, 2.67 mmol) in a mixture of conc. HCl (6 mL) and HOAc (2 mL) was added a solution of NaNO$_2$ (220 mg, 3.2 mmol) in H$_2$O (0.5 mL) dropwise at −10° C. and the resulting mixture was stirred at −10° C. to 5° C. for 30 min. HOAc (5 mL) was placed in a 100 mL flask, and SO$_2$ is introduced until saturation. CuCl$_2$.2H$_2$O (113 mg, 0.67 mmol) and CuCl (66 mg, 0.67 mmol) was added and the mixture was stirred for 30 min. The diazotization mixture was added at 10° C. dropwise and the stirring at rt was continued overnight. The reaction was quenched with ice-water (100 mL), extracted with EA (2×100 mL) and the combined organic layers were washed with brine (100 mL), dried over Na$_2$SO$_4$, filtered, concentrated and purified by CC (PE/EA=1/0 to 100/1) to afford compound P43e (0.26 g, 31%) as a brown solid.

Step 6: 4-Bromo-N-(tert-butyl)-2-(1-methylcyclopropyl)benzenesulfonamide (P43f)

To a solution of compound P43e (250 mg, 0.81 mmol) in DCM (20 mL) was added TEA (250 mg, 2.43 mmol), followed by 2-methylpropan-2-amine (120 mg, 1.62 mmol) and the mixture was stirred at rt for 4 h, concentrated and purified by CC (PE/EA=100/1 to 10/1) to afford compound P43f (180 mg, 64%) as a brown solid.

Step 7: N-(tert-Butyl)-2-(1-methylcyclopropyl)-4-(4,4,5,5-tetramethyl-1,3,2-dioxaborolan-2-yl)benzenesulfonamide (P43)

To a solution of compound P43f (150 mg, 0.43 mmol) in dioxane (20 mL) was added Pin$_2$B$_2$ (166 mg, 0.65 mmol) and KOAc (85 mg, 0.86 mmol), followed by PdCl$_2$(dppf) (35 mg, 43 µmol) under Ar and the resulting suspension was heated to 100° C. overnight, concentrated and purified by CC (PE/EA=30/1 to 10/1) to afford compound P43 (157 mg, 93%) as an off-white solid.

Preparative Example P44

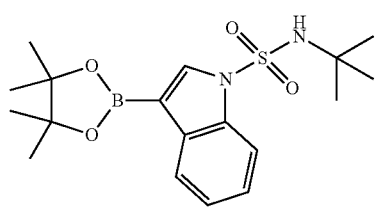

P44

Step 1: tert-Butylsulfamoyl chloride (P44a)

To a solution of tert-butylamine (21.9 g, 0.30 mol) in ACN (150 mL) was added SO$_2$Cl$_2$ (80 mL) dropwise and the reaction mixture was heated to reflux for 24 h, cooled and concentrated to afford the crude product P44a as a yellow oil (48.0 g, 93%).

Step 2: 3-Bromo-N-(tert-butyl)-1H-indole-1-sulfonamide (P44b)

To a solution of 3-bromo-1H-indole (2.0 g, 10 mmol) in THF (30 mL) was added NaH (60%, 1.22 g, 51 mmol) at 0° C. under N$_2$. The reaction mixture was stirred at 10° C. for 30 min, then cooled to 0° C., then a solution of P44a (5.25 g, 31 mmol) in THF (20 mL) was added dropwise, stirred at rt overnight, quenched with water and extracted with EA (3×50 mL): The combined organic phase was washed with brine, dried over Na$_2$SO$_4$, filtered, concentrated and purified by CC (PE/EA=8/1) to afford compound P44b (0.5 g, 15%) as a yellow solid.

Step 3: N-(tert-Butyl)-3-(4,4,5,5-tetramethyl-1,3,2-dioxaborolan-2-yl)-1H-indole-1-sulfonamide (P44)

To a solution of P44b (400 mg, 1.21 mmol), KOAc (360 mg, 3.62 mmol) and B$_2$Pin$_2$ (460 mg, 1.81 mmol), in 1,4-dioxane (8 mL) was added Pd(dppf)Cl$_2$ (88 mg, 120 µmol). The reaction was stirred at 120° C. for 40 min in a microwave oven, cooled to rt, diluted with water and extracted with EA (3×30 mL). The combined organic layers were washed with water and brine, dried over Na$_2$SO$_4$, filtered, concentrated and purified by CC (PE/EA=10/1) to give compound P44 (120 mg, 26%) as a yellow oil.

Preparative Example P44/1 to P44/3

Using similar procedures as that described in Preparative Example P44, the following Preparative Examples have been prepared:

| # | Structure |
|---|-----------|
| P44/1 | 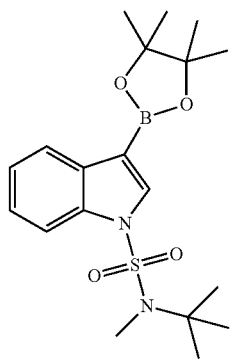 [SMILES: CN(C(C)(C)C)S(=O)(=O)n1cc(B2OC(C)(C)C(C)(C)O2)c2ccccc21] |

| # | Structure |
|---|---|
| P44/2 | 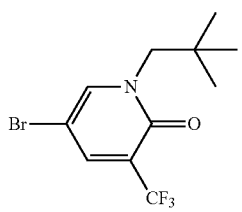 |
| P44/3 | 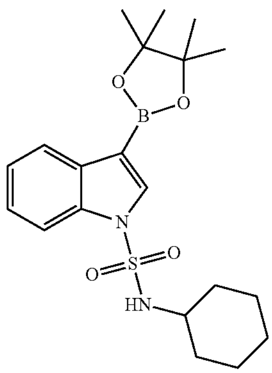 [SMILES: CC1(C)OB(c2cn(S(=O)(=O)NC3CCCCC3)c3ccccc23)OC1(C)C] |

Preparative Example P45

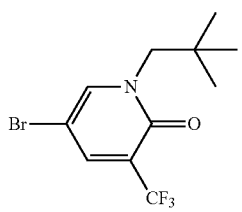

P45

Step 1: 5-Bromo-3-(trifluoromethyl)pyridin-2(1H)-one (P45a)

To a solution of 3-(trifluoromethyl)pyridin-2(1H)-one (25.0 g, 0.15 mol) in AcOH (300 mL) were added NaOAc (15.1 g, 0.18 mol) and dropwise Br$_2$ (8.6 mL, 0.17 mol). Then the mixture was stirred at 80° C. overnight, concentrated, diluted with sat aq. NaHCO$_3$ and extracted with EtOAc twice. The combined organic layers were washed with brine, dried over Na$_2$SO$_4$, filtered, concentrated and purified by CC (PE/EA=7/2) to give compound P45a (29.7 g, 80%) as a white solid.

Step 2: 5-Bromo-1-neopentyl-3-(trifluoromethyl)pyridin-2(1H)-one (P45)

To a solution of compound P45a (10.0 g, 41.3 mmol) in DMF (130 mL) was added portionwise NaH (4.1 g, 103 mmol) at 0° C. After stirring for 40 min, 1-bromo-2,2-dimethyl-propane (18.7 g, 124 mmol) was added and the solution was stirred at 100° C. overnight, diluted with water and extracted with EA twice. The combined organic layers were washed with water and brine consecutively (3×), dried over Na$_2$SO$_4$, filtered, concentrated and purified by CC (PE/EA=5/1) to give compound P45 (1.4 g, 11%) as a yellow solid.

Preparative Example P46

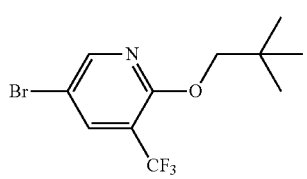

P46

Step 1:
5-Bromo-2-chloro-3-(trifluoromethyl)pyridine (P46a)

A solution of compound P45a (11.0 g, 45.8 mmol) in phenylphosphonicdichloride (22 mL) was heated at 140° C. overnight, cooled to rt, poured into ice water and extracted with EA. The organic layer was washed with sat. aq. NaHCO$_3$ and brine consecutively, dried over NaSO$_4$, filtered, concentrated and purified by CC (PE/EA=5/1) to give compound P46a (10.5 g, 88%) as a yellow liquid.

Step 2: 5-Bromo-2-(neopentyloxy)-3-(trifluoromethyl)pyridine (P46)

To a solution of compound P46a (4.0 g, 15.4 mmol) and 2,2-dimethyl-propan-1-ol (1.5 g, 16.9 mmol) in dry THF (50 mL) was added NaH (0.74 g, 18.4 mmol) at 0° C. and the solution was stirred at reflux for 4 h, cooled, diluted with water and extracted with EA. The organic layer was washed with brine, dried over Na$_2$SO$_4$, filtered, concentrated and purified by CC (PE/EA=50/1) to give compound P46 (1.4 g, 29%) as a pale yellow oil.

Preparative Example P47

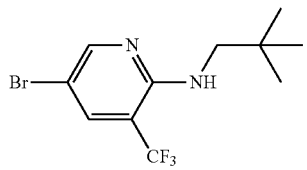

P47

Step 1: 5-Bromo-N-neopentyl-3-(trifluoromethyl)pyridin-2-amine (P47)

A solution of compound P46a (3.0 g, 12 mmol) and 1,1-dimethylethylamine (5.6 mL, 46 mmol) in DMF (6 mL) was heated at 70° C. overnight, cooled to rt, poured into water and textracted with EA (3×). The combined organic layers were washed with water (3×) and brine consecutively and dried over NaSO₄, filtered, concentrated and purified by CC (PE/EA=10/1) to give compound P47 (1.5 g, 42%) as a light yellow liquid.

Preparative Example P48

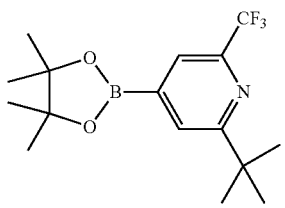 [SMILES: CC(C)(C)c1cc(B2OC(C)(C)C(C)(C)O2)cc(C(F)(F)F)n1]

Step 1: 6-(Trifluoromethyl)pyridin-2(1H)-one (P48a)

To the solution of 6-(trifluoromethyl)pyridin-2(1H)-one (2.0 g, 12.3 mmol) in dry pyridine (25 mL) at 0° C. was rapidly added Tf₂O (4.27 g, 15.1 mmol). The solution was stirred at 0° C. for 1 h, diluted with water and then extracted with DCM. The combined organic layers were washed with water and brine consecutively, dried over Na₂SO₄, filtered, concentrated and purified by CC (PE/EA=10/1) to give compound P48a (2.79 g, 78%) as a pale yellow oil.

Step 2: 2-(tert-Butyl)-6-(trifluoromethyl)pyridine (P48b)

tert-Butyl lithium (1.3M, 44 mL, 56 mmol) was added to a suspension of copper cyanide (2.7 g, 30.6 mmol) in dry THF (20 mL) under N₂ at 40° C. A solution of compound P48a in THF (30 mL) was added slowly to the reaction mixture. The mixture was slowly warmed up to rt and stirred for 16 h, quenched with sat. NH₄Cl (50 mL) and diluted with EA. The aq. phase was extracted with EA and the organic layer was washed with brine, dried with Na₂SO₄, filtered, concentrated and purified by CC (PE) to give compound P48b (1.35 g, 70%) as a colorless oil.

Step 3: 2-(tert-Butyl)-4-(4,4,5,5-tetramethyl-1,3,2-dioxaborolan-2-yl)-6-(trifluoromethyl)pyridine (P48)

The compound P48 was prepared similar as described for Example 18, Step 1 and was obtained as a white solid (59%).

P49

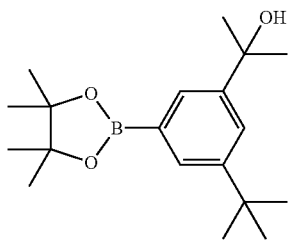

Preparative Example P49

Step 1: 1-(3-Bromo-5-(tert-butyl)phenyl)ethanone (P49a)

To a solution of 1,3-dibromo-5-(tert-butyl)benzene (664 mg, 2.22 mmol) in toluene (15 mL) were added tri-n-butyl-1-ethoxyvinyl tin (965 mg, 2.66 mmol) and Pd(PPh₃)₂Cl₂ (150 mg 0.22 mmol) under N₂. The mixture was stirred at 95° C. for 3 h, evaporated, diluted with 1,4-dioxane and 2N HCl, stirred rapidly at 25° C. for 1 h and then extracted with EA. The combined organic layers were washed with brine, dried over Na₂SO₄, concentrated and purified by CC to afford compound P49a (310 mg, 55%).

Step 2: 2-(3-Bromo-5-(tert-butyl)phenyl)propan-2-ol (P49b)

An oven dried flask was charged with THF (10 mL) and compound P49a (300 mg, 0.91 mmol) and cooled to 0° C. CH₃MgBr (2N, 2 mL) was added dropwise and the mixture was stirred at rt overnight, diluted with aq. NH₄Cl (20 mL) and extracted with EA. The combined organic layers were washed with brine, dried over Na₂SO₄ and concentrated to give crude compound P49b (110 mg, 45%) as a yellow solid.

Step 3: 2-(3-(tert-Butyl)-5-(4,4,5,5-tetramethyl-1,3,2-dioxaborolan-2-yl)phenyl)propan-2-ol (P49)

Compound P49 was prepared similar as described for Example P44, Step 3 and was obtained as a white solid (45%).

Example 1

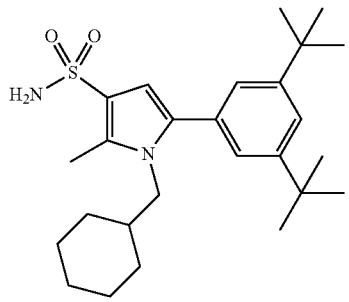

Step 1: Ethyl 1-(cyclohexylmethyl)-5-methyl-1H-pyrrole-2-carboxylate (1a)

A solution of ethyl 5-methyl-1H-pyrrole-2-carboxylate (15.0 g, 98.0 mmol), (bromo-methyl)cyclohexane (17.6 g, 100 mmol) and K₂CO₃ (41.4 g, 300 mmol) in dry DMF (150 mL) was stirred at 50° C. overnight, then cooled to rt and filtered. To the filtrate was added NaH (12.0 g, 60%, 300 mmol) slowly. Then the mixture was stirred overnight at 50° C. The reaction mixture was quenched with water and extracted with EA twice. The combined organic phases were washed with water (3×) and brine (2×), dried over Na₂SO₄, filtered, concentrated and purified by CC (EA/PE=1/20) to give compound 1a (19.9 g, 82%) as a white solid.

Step 2: Ethyl 1-(cyclohexylmethyl)-5-methyl-4-sulfamoyl-1H-pyrrole-2-carboxylate (1 b)

The solution of compound 1a (19.9 g, 79.9 mmol) in ClSO$_3$H (50 mL) was stirred at 0° C. for 36 h. The resulting mixture was quenched with water and extracted with EA twice. The combined organic phases were dried over Na$_2$SO$_4$, filtered and concentrated to give the residue as a brown oil. To the solution of this oil in dry THF (200 mL) was added a NH$_3$ solution (6N in THF, 300 mL) at 0° C. and stirred overnight at rt, concentrated and purified by CC (DCM) to give compound 1 b (21.2 g, 81%) as a white solid.

Step 3: 1-(Cyclohexylmethyl)-2-methyl-1H-pyrrole-3-sulfonamide (1c)

To a solution of compound 1b (21.2 g, 64.6 mmol) in EtOH (300 mL) was added 6N HCl (200 mL) and then this mixture was refluxed overnight, cooled to rt and concentrated. The residue was diluted with EA, washed with brine, dried over Na$_2$SO$_4$, filtered, concentrated and purified by CC (EA/PE=1/2) to give recovered compound 1b (7 g) and compound 1c (7.4 g, 45%) as a white solid.

Step 4: 5-Bromo-1-(cyclohexylmethyl)-2-methyl-1H-pyrrole-3-sulfonamide (1 d)

To a solution of compound 1c (7.4 g, 29 mmol) in THF (70 mL) at 78° C. was added NBS (5.2 g, 29 mmol) and the solution was stirred for 2 h at −78° C. Hexane and water was added to this resulting solution and it was extracted with EA twice. The combined organic layers were dried over Na$_2$SO$_4$, filtered and concentrated to give crude compound 1d (8.8 g) as a yellow oil.

Step 5: 1-(Cyclohexylmethyl)-5-(3,5-di-tert-butylphenyl)-2-methyl-1H-pyrrole-3-sulfonamide (1)

The solution of compound 1d (3.0 g, 9.0 mmol), (3,5-di-tert-butylphenyl)boronic acid (4.2 g, 18 mmol), Pd(dppf)Cl$_2$ (300 mg) and K$_2$CO$_3$ (2.8 g, 27 mmol) in DMF (80 mL) was heated at 120° C. under N$_2$ for 16 h. The resulting solution was concentrated, diluted with water and extracted with EA twice. The combined organic layers were washed with brine, dried over Na$_2$SO$_4$, filtered, concentrated and purified by CC (PE/EA=4/1) to give compound 1 (1.13 g, 28%) as a white solid. $^1$H-NMR (300 MHz, DMSO-d$_6$) δ: 0.63-0.67 (m, 2H), 0.90-0.98 (m, 3H), 1.22-1.26 (m, 3H), 1.31 (s, 18H), 1.44-1.51 (m, 3H), 2.43 (s, 3H), 3.76 (d, J=6.9 Hz, 2H), 6.28 (s, 1H), 6.90 (s, 2H), 7.14 (d, J=1.5 Hz, 2H), 7.38-7.39 (m, 1H). MS Calcd.: 444; MS Found: 445 (M+1).

Examples 1/1 to 1/43

The following Examples were prepared similar as described in Example 1 (using boronic acid building blocks) or similar as described in Example 10 (using boronic ester building blocks):

| # | Structure | Analytical data |
|---|-----------|-----------------|
| 1/1 | 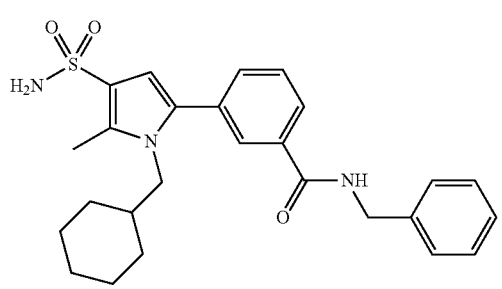 [SMILES: Cc1c(S(N)(=O)=O)cc(-c2cccc(C(=O)NCc3ccccc3)c2)n1CC1CCCCC1] | 465.2; 466 |
| 1/2 | 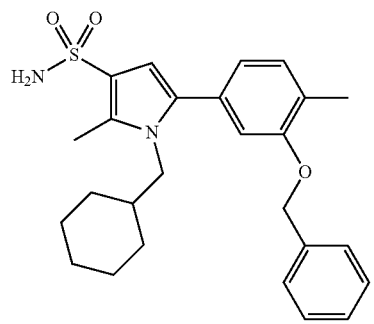 [SMILES: Cc1ccc(-c2cc(S(N)(=O)=O)c(C)n2CC2CCCCC2)cc1OCc1ccccc1] | 452.2; 453 |

| # | Structure | Analytical data |
|---|---|---|
| 1/3 | 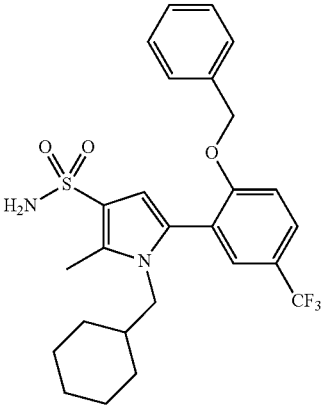 [SMILES: Cc1c(S(N)(=O)=O)cc(-c2cc(C(F)(F)F)ccc2OCc2ccccc2)n1CC1CCCCC1] | 506.2; 507 |
| 1/4 | 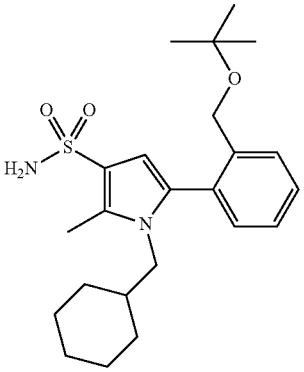 [SMILES: Cc1c(S(N)(=O)=O)cc(-c2ccccc2COC(C)(C)C)n1CC1CCCCC1] | 418.2; 419 |
| 1/5 | 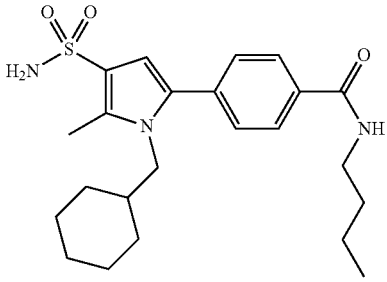 [SMILES: CCCCNC(=O)c1ccc(-c2cc(S(N)(=O)=O)c(C)n2CC2CCCCC2)cc1] | 431.2; 432 |
| 1/6 | 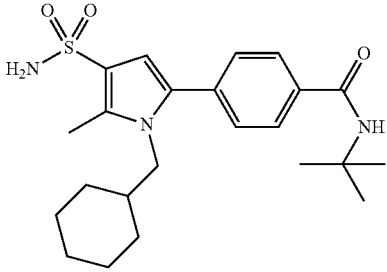 [SMILES: Cc1c(S(N)(=O)=O)cc(-c2ccc(C(=O)NC(C)(C)C)cc2)n1CC1CCCCC1] | 431.2; 432 |

-continued
| # | Structure | Analytical data |
|---|---|---|
| 1/7 | 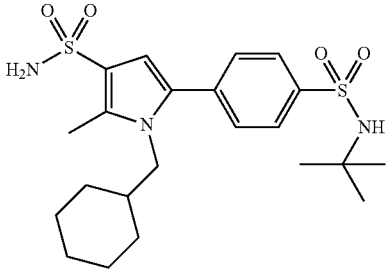 [SMILES: Cc1c(S(N)(=O)=O)cc(-c2ccc(S(=O)(=O)NC(C)(C)C)cc2)n1CC1CCCCC1] | ¹H-NMR (400 MHz, CDCl₃) δ: 7.86 (d, J = 6.8 Hz, 2H), 7.36 (d, J = 6.8 Hz, 2H), 6.48 (s, 1H), 4.72 (br s, 2H), 4.60 (s, 1H), 3.72 (d, J = 5.6 Hz, 2H), 2.49 (s, 3H), 1.55-1.43 (m, 3H), 1.29-1.21 (m, 3H), 1.18 (s, 3H), 0.96-0.89 (m, 3H), 0.60-0.49 (m, 2H). MS Calcd.: 467.2; MS Found: 468 (M + 1). |
| 1/8 | 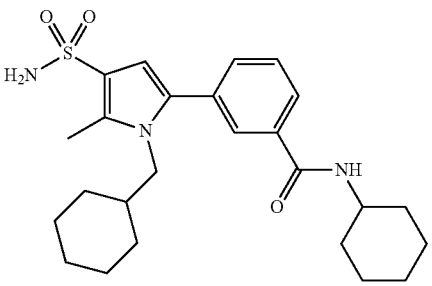 [SMILES: Cc1c(S(N)(=O)=O)cc(-c2cccc(C(=O)NC3CCCCC3)c2)n1CC1CCCCC1] | 457.2; 458 |
| 1/9 | 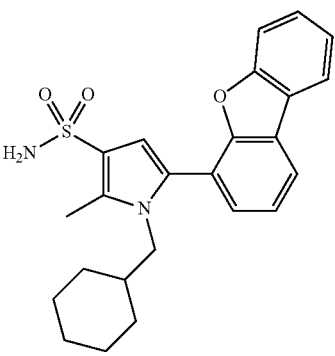 [SMILES: Cc1c(S(N)(=O)=O)cc(-c2cccc3c2oc2ccccc23)n1CC1CCCCC1] | 422.2; 422.3 |
| 1/10 | 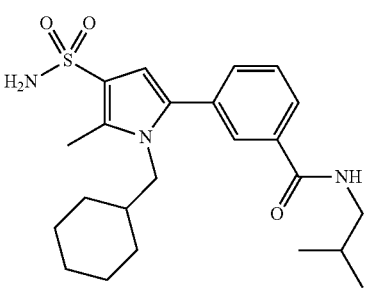 [SMILES: Cc1c(S(N)(=O)=O)cc(-c2cccc(C(=O)NCC(C)C)c2)n1CC1CCCCC1] | 431.2; 432 |
| 1/11 | 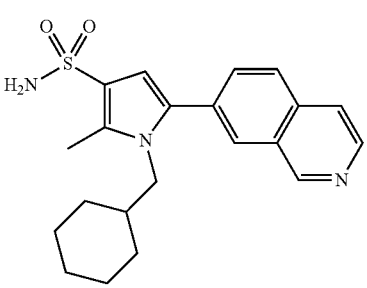 [SMILES: Cc1c(S(N)(=O)=O)cc(-c2ccc3ccncc3c2)n1CC1CCCCC1] | 383.2; 384 |

| # | Structure | Analytical data |
|---|---|---|
| 1/12 | 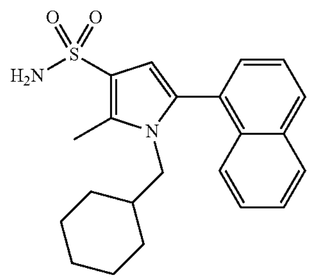 [SMILES: Cc1c(S(N)(=O)=O)cc(-c2cccc3ccccc23)n1CC1CCCCC1] | 382.2; 383 |
| 1/13 | 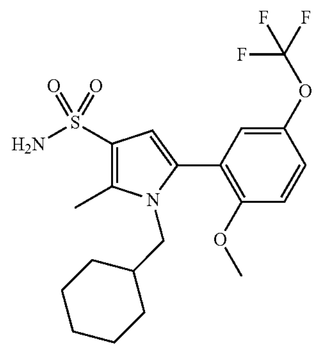 [SMILES: COc1ccc(OC(F)(F)F)cc1-c1cc(S(N)(=O)=O)c(C)n1CC1CCCCC1] | 446.2; 447 |
| 1/14 | 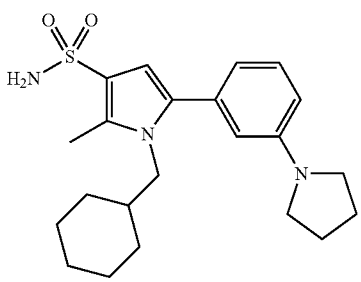 [SMILES: Cc1c(S(N)(=O)=O)cc(-c2cccc(N3CCCC3)c2)n1CC1CCCCC1] | 401.2; 402 |
| 1/15 | 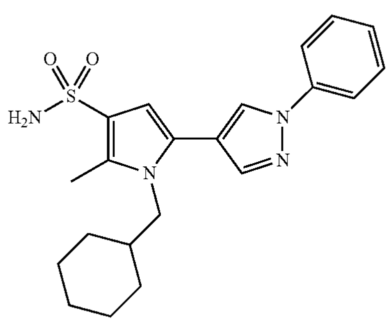 [SMILES: Cc1c(S(N)(=O)=O)cc(-c2cnn(-c3ccccc3)c2)n1CC1CCCCC1] | 398.2; 399 |
| 1/16 | 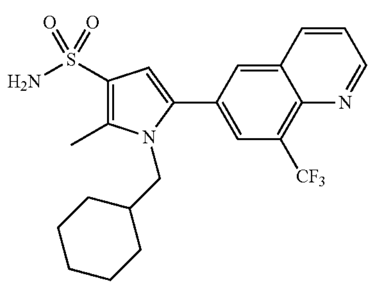 [SMILES: Cc1c(S(N)(=O)=O)cc(-c2cc(C(F)(F)F)c3ncccc3c2)n1CC1CCCCC1] | $^1$H-NMR (400 MHz, DMSO-d$_6$) δ: 9.10-9.08 (m, 1H), 8.62-8.59 (m, 1H), 8.37 (s, 1H), 8.13 (s, 1H), 7.98-7.74 (m, 1H), 7.04 (s, 2H), 6.58 (s, 1H), 3.96 (d, J = 5.6 Hz, 2H), 2.50 (s, 3H), 1.50-1.41 (m, 3H), 1.39-1.22 (m, 3H), 0.98-0.90 (m, 3H), 0.70-0.59 (m, 2H). MS Calcd.: 451.2; MS Found: 452 (M + 1). |

-continued

| # | Structure | Analytical data |
|---|-----------|-----------------|
| 1/17 | 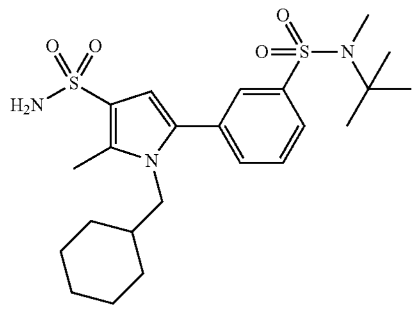 [SMILES: Cc1c(S(N)(=O)=O)cc(-c2cccc(S(=O)(=O)N(C)C(C)(C)C)c2)n1CC1CCCCC1] | 481.2; 482 |
| 1/18 | 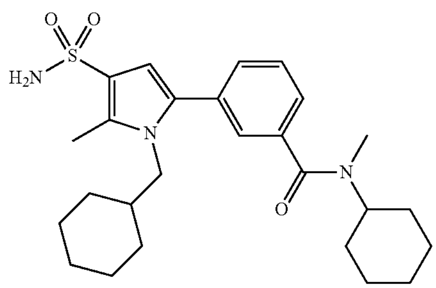 [SMILES: Cc1c(S(N)(=O)=O)cc(-c2cccc(C(=O)N(C)C3CCCCC3)c2)n1CC1CCCCC1] | 471.3; 472 |
| 1/19 | 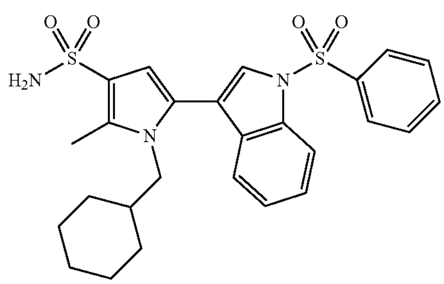 [SMILES: Cc1c(S(N)(=O)=O)cc(-c2cn(S(=O)(=O)c3ccccc3)c3ccccc23)n1CC1CCCCC1] | ¹H-NMR (400 MHz, DMSO-d₆) δ: 8.05-8.02 (m, 3H), 7.98 (s, 1H), 7.76-7.70 (m, 1H), 7.60-7.57 (m, 2H), 7.49-7.41 (m, 2H), 7.37-7.30 (m, 1H), 6.96 (s, 2H), 6.44 (s, 1H), 3.77 (d, J = 5.8 Hz, 2H), 2.45 (s, 3H), 1.42-1.35 (m, 3H), 1.20-1.13 (m, 3H), 0.84-0.73 (m 3H), 0.46-0.38 (m, 2H). MS Calcd.: 511.2, MS Found 512 (M + 1). |
| 1/20 | 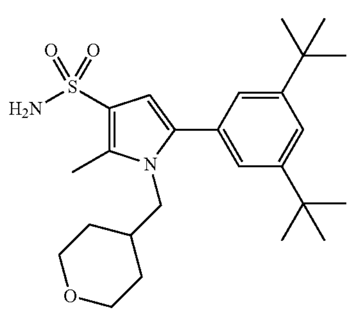 [SMILES: Cc1c(S(N)(=O)=O)cc(-c2cc(C(C)(C)C)cc(C(C)(C)C)c2)n1CC1CCOCC1] | ¹H-NMR (300 MHz, CDCl₃) δ: 0.96-1.06 (2H, m), 1.20-1.26 (2H, m), 1.34 (18H, s), 1.54-1.64 (1H, m), 2.56 (3H, s), 3.13 (2H, dt, J = 1.8 Hz, 11.7 Hz), 3.76-3.82 (4H, m), 4.69 (2H, s), 6.48 (1H, s), 7.13 (2H, d, J = 1.8 Hz), 7.42-7.44 (1H, t, J = 1.8 Hz). MS Calcd.: 446; MS Found: 447 (M + 1). |
| 1/21 | 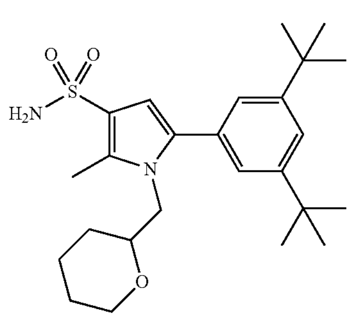 [SMILES: Cc1c(S(N)(=O)=O)cc(-c2cc(C(C)(C)C)cc(C(C)(C)C)c2)n1CC1CCCCO1] | ¹H-NMR (300 MHz, CDCl₃) δ: 0.99-1.14 (1H, m), 1.27-1.59 (4H, s), 1.34 (18H, s), 1.73-1.80 (1H, m), 2.59 (3H, s), 3.23-3.26 (1H, m), 3.32 (1H, m), 3.74 (1H, dd, J = 4.2 Hz, 15.0 Hz), 3.89-3.97 (2H, m), 4.69 (2H, s), 6.49 (1H, s), 7.26 (2H, m), 7.41-7.42 (1H, t, J = 1.8 Hz). MS Calcd.: 446; MS Found: 447 (M + 1). |

| # | Structure | Analytical data |
|---|---|---|
| 1/22 | 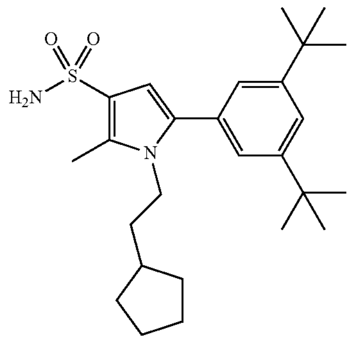 [SMILES: Cc1c(S(N)(=O)=O)cc(-c2cc(C(C)(C)C)cc(C(C)(C)C)c2)n1CCC1CCCC1] | $^1$H-NMR (300 MHz, CDCl$_3$) δ: 0.88-0.89 (2H, m), 1.34 (18H, s), 1.39-1.57 (9H, m), 2.56 (3H, s), 3.80 (2H, t, J = 6.6 Hz), 4.81 (2H, s), 6.47 (1H, s), 7.16 (2H, s), 7.43 (1H, s). MS Calcd.: 444; MS Found: 445 (M + 1). |
| 1/23 | 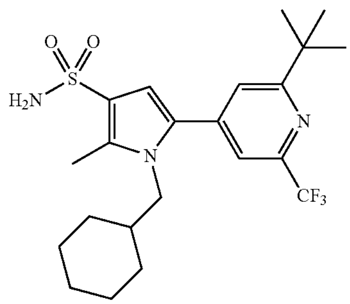 [SMILES: Cc1c(S(N)(=O)=O)cc(-c2cc(C(C)(C)C)nc(C(F)(F)F)c2)n1CC1CCCCC1] | $^1$H-NMR (CDCl$_3$, 300 MHz) δ: 7.45-7.41 (m, 2H), 6.65 (s, 1H), 4.74 (s, 1H), 3.82 (d, 2H, J = 7.2 Hz), 2.56 (s, 3H), 1.56 (m, 3H), 1.40 (s, 9H), 1.30-1.38 (m, 3H), 0.97-1.03 (m, 3H), 0.63 (m, 2H). MS Calcd.: 457; MS Found: 458 (M + 1). |
| 1/24 | 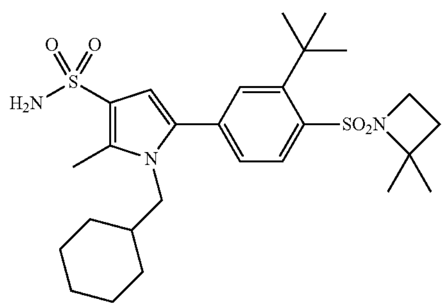 | $^1$H-NMR (400 MHz, CDCl$_3$) δ: 8.17 (d, J = 8.0 Hz, 1H), 7.55 (d, J = 1.6 Hz, 1H), 7.24 (dd, J = 8.0 Hz, J = 1.6 Hz, 1H), 6.53 (s, 1H), 4.68 (s, 2H), 3.77 (d, J = 7.2 Hz, 2H), 3.72 (t, J = 7.2 Hz, 2H), 2.55 (s, 3H), 2.06 (t, J = 7.2 Hz, 2H), 1.60 (s, 6H), 1.59 (s, 9H), 1.46-1.57 (m, 3H), 1.29-1.40 (m, 3H), 0.94-1.06 (m, 3H), 0.57-0.70 (m, 2H). MS Calcd.: 535; MS Found: 536 (M + 1). |
| 1/25 | 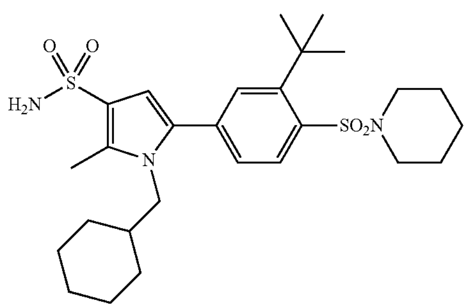 | $^1$H-NMR (300 MHz, DMSO-d$_6$) δ: 7.78 (d, J = 8.0 Hz, 1H), 7.61 (s, 1H), 7.43 (d, J = 8.0 Hz, 1H), 6.98 (s, 2H), 6.45 (s, 1H), 3.87 (d, J = 6.3 Hz, 2H), 3.22 (m, 4H), 2.46 (s, 3H), 1.56-1.53 (m, 14H), 1.48-1.45 (m, 3H), 1.26-1.23 (m, 4H), 0.97-0.91 (m, 3H), 0.67-0.64 (m, 2H). MS Calcd.: 535; MS Found: 536 (M + 1). |
| 1/26 | 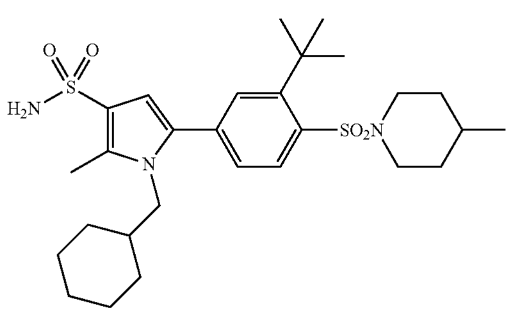 | $^1$H-NMR (300 MHz, CDCl$_3$) δ: 7.74 (d, J = 8.1 Hz, 1H), 7.75 (s, 1H), 7.17 (d, J = 8.1 Hz, 1H), 6.64 (s, 2H), 4.66 (s, 1H), 3.71 (m, 4H), 2.79-2.72 (m, 2H), 2.49 (s, 3H), 1.67-1.52 (m, 14H), 1.28-1.19 (m, 6H), 0.95-0.90 (m, 6H), 0.59-0.56 (m, 2H). MS Calcd.: 549; MS Found: 550 (M + 1). |

| # | Structure | Analytical data |
|---|---|---|
| 1/27 | 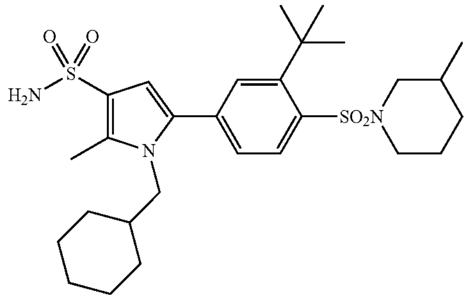 | ¹H-NMR (300 MHz, CDCl₃) δ: 7.77 (d, J = 8.2 Hz, 1H), 7.62 (s, 1H), 7.26 (d, J = 8.2 Hz, 1H), 6.55 (s, 2H), 4.70 (s, 1H), 3.80-3.72 (m, 4H), 2.83 (m, 1H), 2.58 (s, 3H), 2.54-2.51 (m, 1H), 1.84-1.61 (m, 15H), 1.37-1.34 (m, 4H), 1.09-1.04 (m, 4H), 0.94 (d, J = 6.3 Hz, 3H), 0.68-0.65 (m, 2H). MS Calcd.: 549; MS Found: 550 (M + 1). |
| 1/28 | 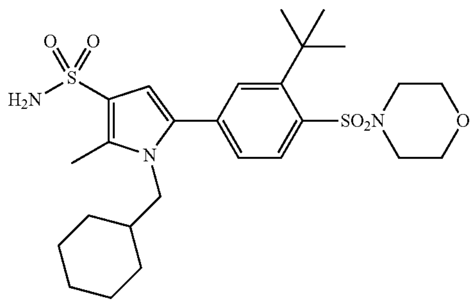 | ¹H-NMR (300 MHz, CDCl₃) δ: 7.89 (d, J = 8.1 Hz, 1H), 7.63 (s, 1H), 7.28 (d, J = 8.1 Hz, 1H), 6.54 (s, 2H), 4.67 (s, 1H), 3.79-3.75 (m, 6H), 3.33 (t, J = 4.5 Hz, 3H), 2.56 (s, 3H), 1.59 (s, 9H), 1.53-1.49 (m, 3H), 1.38-1.32 (m, 3H), 1.03-0.98 (m, 3H), 0.94 (d, J = 6.3 Hz, 3H), 0.68-0.62 (m, 2H). MS Calcd.: 537; MS Found: 538 (M + 1). |
| 1/29 | 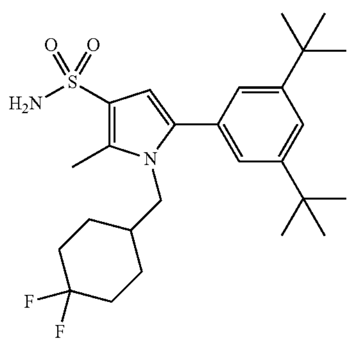 [SMILES: Cc1c(S(N)(=O)=O)cc(-c2cc(C(C)(C)C)cc(C(C)(C)C)c2)n1CC1CCC(F)(F)CC1] | ¹H-NMR (CDCl₃, 300 MHz) δ: 1.00-1.05 (2H, m), 1.34 (18H, s), 1.36-1.58 (5H, m), 1.84-1.88 (2H, m), 2.55 (3H, s), 3.81 (2H, d, J = 7.2 Hz), 4.69 (2H, s), 6.49 (1H, s), 7.13 (2H, d, J = 1.8 Hz), 7.43-7.44 (1H, t, J = 1.8 Hz). MS Calcd.: 480; MS Found: 481 (M + 1). |
| 1/30 | 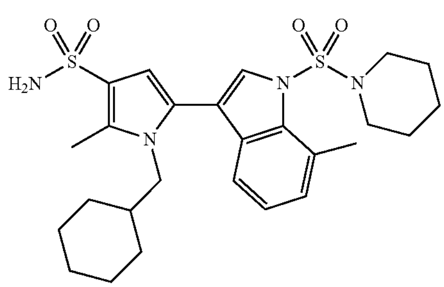 [SMILES: Cc1cccc2c(-c3cc(S(N)(=O)=O)c(C)n3CC3CCCCC3)cn(S(=O)(=O)N3CCCCC3)c12] | ¹H-NMR (300 MHz, CDCl₃) δ: 7.81 (d, J = 8.4 Hz, 1H), 7.41 (m, 2H), 7.32 (m, 1H), 7.22 (m, 1H), 6.49 (s, 1H), 5.07 (d, J = 8.1 Hz, 1H), 4.75 (s, 2H), 3.65 (d, J = 6.6 Hz, 2H), 3.15 (m, 1H), 2.50 (s, 3H), 1.60-0.48 (m, 21H). MS Calcd.: 532; MS Found: 533 (M + 1). |
| 1/31 | 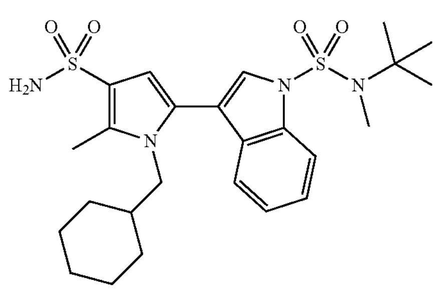 [SMILES: Cc1c(S(N)(=O)=O)cc(-c2cn(S(=O)(=O)N(C)C(C)(C)C)c3ccccc23)n1CC1CCCCC1] | ¹H-NMR (300 MHz, DMSO-d₆) δ: 7.80-7.70 (m, 2H), 7.55-7.30 (m, 3H), 6.97 (s, 2H), 6.44 (s, 1H), 3.81 (d, J = 6.9 Hz, 2H), 3.14 (s, 3H), 2.48 (s, 3H), 1.55-1.41 (m, 3H), 1.40-1.30 (m, 3H), 1.26 (s, 9H), 0.98-0.82 (m, 3H), 0.70-0.51 (m, 2H). MS Calcd.: 520; MS Found: 521 (M + 1). |

| # | Structure | Analytical data |
|---|-----------|-----------------|
| 1/32 | 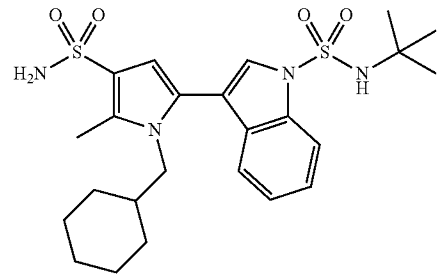 [SMILES: Cc1c(S(N)(=O)=O)cc(-c2cn(S(=O)(=O)NC(C)(C)C)c3ccccc23)n1CC1CCCCC1] | ¹H-NMR (300 MHz, CDCl₃) δ: 7.72 (d, J = 8.1 Hz, 1H), 7.40 (m, 4H), 6.49 (s, 1H), 4.88 (s, 1H), 4.61 (s, 2H), 3.67 (d, J = 7.2 Hz, 2H), 2.51 (s, 3H), 1.40-1.10 (m, 6H) 1.09 (s, 9H), 0.98-0.88 (m, 3H), 0.64-0.50 (m, 2H). MS Calcd.: 506; MS Found: 507 (M + 1). |
| 1/33 | 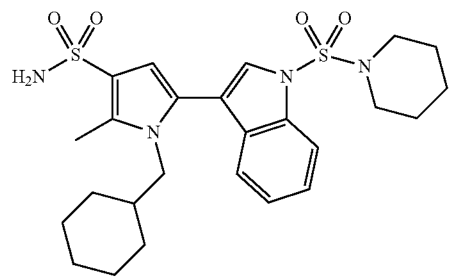 [SMILES: Cc1c(S(N)(=O)=O)cc(-c2cn(S(=O)(=O)N3CCCCC3)c3ccccc23)n1CC1CCCCC1] | ¹H-NMR (400 MHz, DMSO-d₆) δ: 7.94 (d, J = 6.8 Hz, 1H), 7.80 (s, 1H), 7.51 (m, 1H), 7.41 (m, 1H), 7.33 (m, 1H), 7.00 (s, 2H), 6.45 (s, 1H), 3.83 (d, J = 5.6 Hz, 2H), 3.18 (m, 4H), 2.48 (s, 3H), 1.47-1.45 (m, 7H), 1.33-1.32 (m, 5H), 0.91 (m, 3H), 0.61 (m, 2H). MS Calcd.: 518; MS Found: 519 (M + 1). |
| 1/34 | 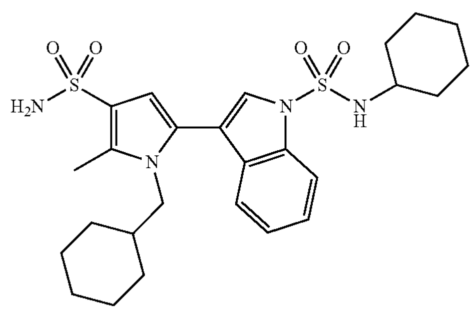 [SMILES: Cc1c(S(N)(=O)=O)cc(-c2cn(S(=O)(=O)NC3CCCCC3)c3ccccc23)n1CC1CCCCC1] | ¹H-NMR (300 MHz, CDCl₃) δ: 7.81 (d, J = 8.4 Hz, 1H), 7.41 (m, 2H), 7.32 (m, 1H), 7.22 (m, 1H), 6.49 (s, 1H), 5.07 (d, J = 8.1 Hz, 1H), 4.75 (s, 2H), 3.65 (d, J = 6.6 Hz, 2H), 3.15 (m, 1H), 2.50 (s, 3H), 1.60-0.48 (m, 21H). MS Calcd.: 532; MS Found: 533 (M + 1). |
| 1/35 | 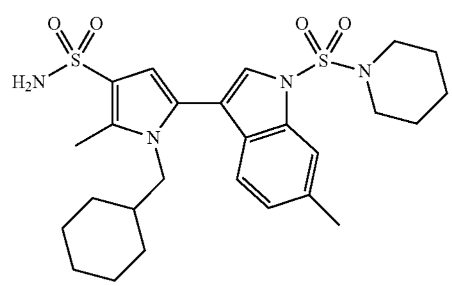 [SMILES: Cc1ccc2c(-c3cc(S(N)(=O)=O)c(C)n3CC3CCCCC3)cn(S(=O)(=O)N3CCCCC3)c2c1] | ¹H-NMR (300 MHz, CDCl₃) δ: 7.70 (s, 1H), 7.26 (d, J = 5.7 Hz, 2H), 7.02 (d, J = 8.4 Hz, 1H), 6.50 (s, 1H), 4.65 (s, 2H), 3.65 (d, J = 6.9 Hz, 2H), 3.13 (m, 4H), 2.50 (s, 3H), 2.43 (s, 3H), 1.18-1.50 (m, 12H), 0.89 (m, 3H), 0.58 (m, 2H). MS Calcd.: 532; MS Found: 533 (M + 1). |
| 1/36 | 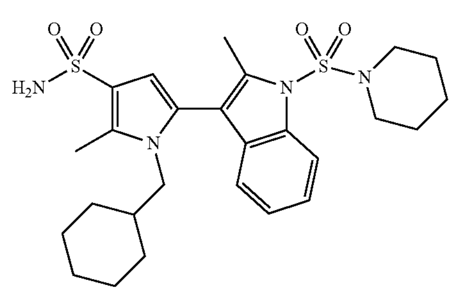 [SMILES: Cc1c(S(N)(=O)=O)cc(-c2c(C)n(S(=O)(=O)N3CCCCC3)c3ccccc23)n1CC1CCCCC1] | ¹H-NMR (400 MHz, DMSO-d₆) δ: 7.94 (d, J = 6.8 Hz, 1H), 7.80 (s, 1H), 7.51 (m, 1H), 7.41 (m, 1H), 7.33 (m, 1H), 7.00 (s, 2H), 6.45 (s, 1H), 4.63 (s, 2H), 3.83 (d, J = 5.6 Hz, 2H), 3.18 (m, 4H), 2.48 (s, 3H), 1.47-1.45 (m, 7H), 1.33-1.32 (m, 5H), 0.91 (m, 3H), 0.61 (m, 2H). MS Calcd.: 532; MS Found: 533 (M + 1). |

-continued

| # | Structure | Analytical data |
|---|---|---|
| 1/37 | 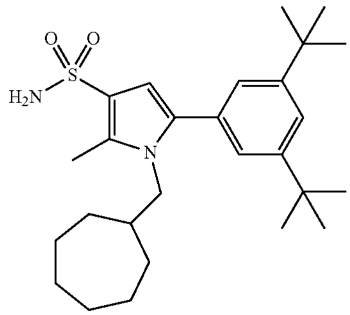 [SMILES: Cc1c(S(N)(=O)=O)cc(-c2cc(C(C)(C)C)cc(C(C)(C)C)c2)n1CC1CCCCCC1] | ¹H-NMR (CDCl₃, 300 MHz) δ: 0.83-0.93 (2H, m), 1.04-1.17 (2H, m), 1.26-1.30 (3H, m), 1.33 (18H, s), 1.36-1.43 (5H, m), 1.59 (1H, m), 2.53 (3H, s), 3.71 (2H, d, J = 7.8 Hz), 4.72 (2H, d, J = 10.2 Hz), 6.47 (1H, s), 7.14 (2H, d, J = 1.8 Hz), 7.41 (1H, J = 1.8 Hz). MS Calcd.: 458; MS Found: 459 (M + 1). |
| 1/38 | 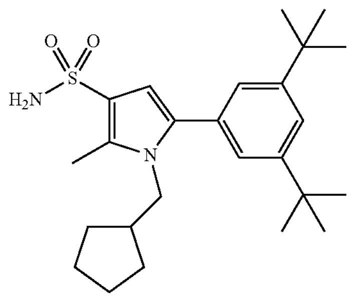 [SMILES: Cc1c(S(N)(=O)=O)cc(-c2cc(C(C)(C)C)cc(C(C)(C)C)c2)n1CC1CCCC1] | ¹H-NMR (400 MHz, CDCl₃) δ: 7.40 (s, 1H), 7.15 (s, 2H), 6.47 (s, 1H), 4.67 (br s, 2H), 3.83 (d, 2H), 2.57 (s, 3H), 1.96 (m, 1H), 1.46-1.43 (m, 2H), 1.41-1.28 (m, 22H), 0.95-0.90 (m, 2H). Calcd.: 430; MS Found: 431 (M + 1). |
| 1/39 | 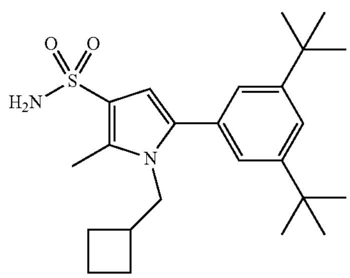 [SMILES: Cc1c(S(N)(=O)=O)cc(-c2cc(C(C)(C)C)cc(C(C)(C)C)c2)n1CC1CCC1] | ¹H-NMR (400 MHz, CDCl₃) δ: 7.42 (t, 1H), 7.14 (d, 2H), 6.45 (s, 1H), 4.67 (br s, 2H), 3.90 (d, 2H), 2.55 (s, 3H), 2.41 (m, 1H), 1.87-1.82 (m, 2H), 1.80-1.73 (m, 1H), 1.67-1.55 (m, 1H), 1.43-1.38 (m, 2H), 1.34 (m, 18H). Calcd.: 416; MS Found: 417 (M + 1). |
| 1/40 | 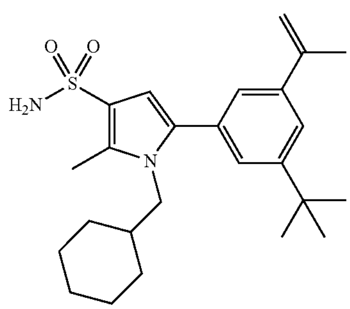 [SMILES: C=C(C)c1cc(-c2cc(S(N)(=O)=O)c(C)n2CC2CCCCC2)cc(C(C)(C)C)c1] | 428.3; 429 |
| 1/41 | 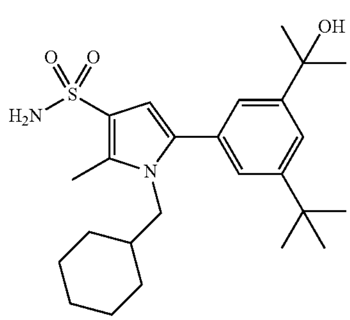 [SMILES: Cc1c(S(N)(=O)=O)cc(-c2cc(C(C)(C)C)cc(C(C)(C)O)c2)n1CC1CCCCC1] | ¹H-NMR (400 MHz, CDCl₃) δ: 7.56 (s, 1H), 7.21 (m, 2H), 6.47 (s, 1H), 4.69 (br s, 2H), 3.72 (d, 2H), 2.54 (s, 3H), 1.55 (s, 6H), 1.56-1.55 (m, 3H), 1.33-1.37 (m, 12H), 0.99 (m, 3H), 0.63-0.66 (m, 2H). MS Calcd.: 446 MS Found: 447 (M + 1). |

-continued

| # | Structure | Analytical data |
|---|---|---|
| 1/42 | 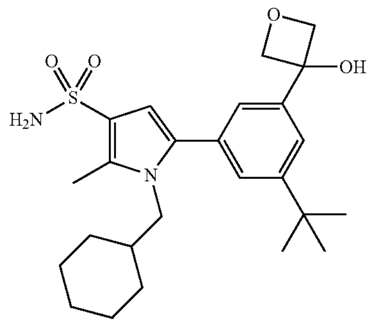 [SMILES: Cc1c(S(N)(=O)=O)cc(-c2cc(C(C)(C)C)cc(C3(O)COC3)c2)n1CC1CCCCC1] | $^1$H-NMR (400 MHz, CDCl$_3$) δ: 7.61 (s, 1H), 7.39 (s, 1H), 7.32 (s, 1H), 6.49 (s, 1H), 4.91-4.96 (m, 4H), 4.69 (br s, 2H), 3.74 (d, 2H), 2.55 (s, 3H), 1.56-1.55 (m, 3H), 1.37-1.36 (m, 12H), 0.99-1.00 (m, 3H), , 0.62-0.66 (m, 2H). MS Calcd.: 460; MS Found: 461 (M + 1). |
| 1/43 | by reacting Example 1/19 with Boc$_2$O | 611.2; 612 |

Example 2

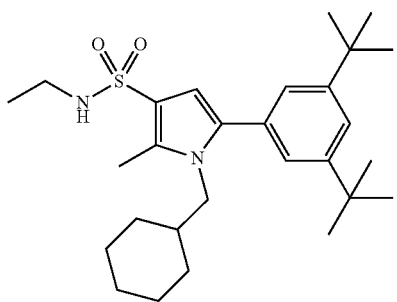

1-(Cyclohexylmethyl)-5-(3,5-di-tert-butylphenyl)-N-ethyl-2-methyl-1H-pyrrole-3-sulfonamide (2)

To a solution of compound 1 (500 mg, 1.10 mmol) in dry THF (20 mL) was added LiHMDS (1.0 mL, 1.0 mmol) at −10° C. under N$_2$. After stirring for 30 min, iodoethane (312 mg, 2.0 mmol) was added. The solution was stirred for another 3 h at 35° C., then quenched with water and extracted with EA twice. The combined organic phases were washed with water and brine, dried over Na$_2$SO$_4$, filtered, concentrated and purified by CC (EA/PE=1/5) to give compound 2 (50 mg, 10%) as a solid. $^1$H-NMR (400 MHz, CDCl$_3$) δ: 0.63-0.65 (m, 2H), 0.97-1.03 (m, 3H), 1.13-1.17 (m, 3H), 1.34 (s, 18H), 1.32-1.35 (m, 3H), 1.50-1.55 (m, 3H), 2.52 (s, 3H), 3.04-3.07 (m, 2H), 3.72 (d, J=6.8 Hz, 2H), 4.12 (m, 1H), 6.41 (s, 1H), 7.15 (s, 2H), 7.40 (s, 1H). MS Calcd.: 472; MS Found: 473 (M+1).

Example 2/1 to 2/6

Using similar procedures as that described in Example 2, the following Examples have been prepared:

| # | Structure | Analytical data |
|---|---|---|
| 2/1 | 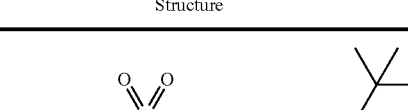 | $^1$H-NMR (400 MHz, CDCl$_3$) δ: 0.62-0.65 (m, 2H), 0.98-1.03 (m, 3H), 1.34 (s, 18H), 1.32-1.36 (m, 3H), 1.49-1.53 (m, 3H), 2.51 (s, 3H), 3.14-3.18 (m, 2H), 3.32 (s, 3H), 3.46-3.49 (m, 2H), 3.72 (d, J = 6.8 Hz, 2H), 4.67-4.70 (m, 1H), 6.41 (s, 1H), 7.14 (s, 2H), 7.40 (s, 1H). MS Calcd.: 502; MS Found: 503 (M + 1). |

| # | Structure | Analytical data |
|---|---|---|
| 2/2 | 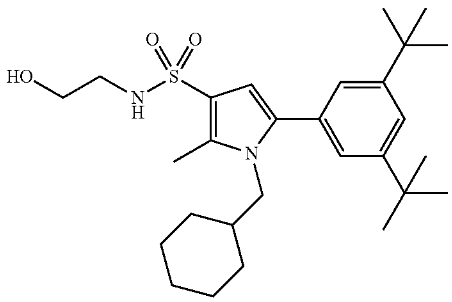 [SMILES: Cc1c(S(=O)(=O)NCCO)cc(-c2cc(C(C)(C)C)cc(C(C)(C)C)c2)n1CC1CCCCC1] | ¹H-NMR (400 MHz, CDCl₃) δ: 0.63-0.66 (m, 2H), 0.98-1.03 (m, 3H), 1.34 (s, 18H), 1.30-1.36 (m, 3H), 1.53-1.55 (m, 3H), 2.53 (s, 3H), 3.14-3.18 (m, 2H), 3.71-3.77 (m, 4H), 4.70 (m, 1H), 6.42 (s, 1H), 7.14 (s, 2H), 7.41 (s, 1H). MS Calcd.: 488; MS Found: 489 (M + 1). |
| 2/3 | 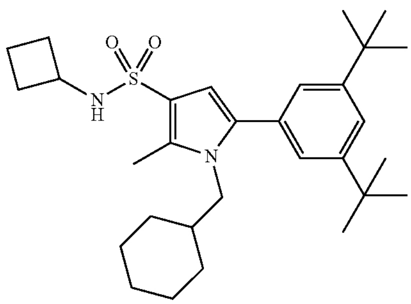 [SMILES: Cc1c(S(=O)(=O)NC2CCC2)cc(-c2cc(C(C)(C)C)cc(C(C)(C)C)c2)n1CC1CCCCC1] | ¹H-NMR (300 MHz, CD₃OD) δ: 0.59-0.67 (m, 2H), 0.96-1.00 (m, 3H), 1.34 (s, 18H), 1.30-1.35 (m, 3H), 1.49-1.66 (m, 5H), 1.85-1.93 (m, 2H), 2.01-2.14 (m, 2H), 2.49 (s, 3H), 3.65-3.71 (m, 1H), 3.80 (d, J = 6.6 Hz, 2H), 6.30 (s, 1H), 7.15 (s, 2H), 7.46 (s, 1H). MS Calcd.: 498; MS Found: 499 (M + 1). |
| 2/4 | 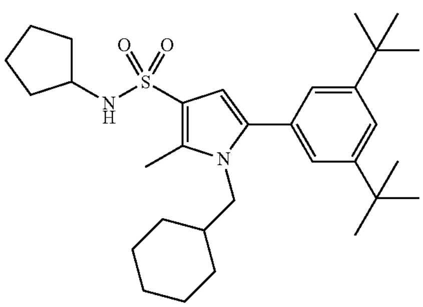 [SMILES: Cc1c(S(=O)(=O)NC2CCCC2)cc(-c2cc(C(C)(C)C)cc(C(C)(C)C)c2)n1CC1CCCCC1] | ¹H-NMR (400 MHz, CDCl₃) δ: 0.62-0.67 (m, 2H), 0.96-1.00 (m, 3H), 1.34 (s, 18H), 1.30-1.35 (m, 3H), 1.41-1.56 (m, 6H), 1.62-1.67 (m, 2H), 1.83-1.88 (m, 2H), 2.52 (s, 3H), 3.64-3.65 (m, 1H), 3.73 (d, J = 6.8 Hz, 2H), 4.21 (d, J = 6.4 Hz, 1H), 6.43 (s, 1H), 7.15 (s, 2H), 7.40 (m, 1H). MS Calcd.: 512; MS Found: 513 (M + 1). |
| 2/5 | 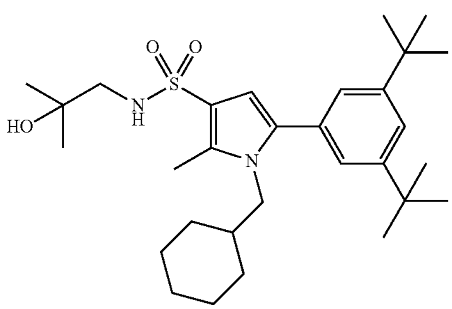 [SMILES: Cc1c(S(=O)(=O)NCC(C)(C)O)cc(-c2cc(C(C)(C)C)cc(C(C)(C)C)c2)n1CC1CCCCC1] | ¹H-NMR (300 MHz, CDCl₃) δ: 0.60-0.65 (2H, m), 0.93-1.02 (3H, m), 1.25 (6H, s), 1.27-1.36 (3H, m), 1.34 (18H, s), 1.51-1.55 (3H, m), 2.51 (3H, s), 2.94 (2H, d, J = 6.6 Hz), 3.72 (2H, d, J = 6.9 Hz), 4.67 (1H, m), 6.41 (1H, s), 7.14 (2H, d, J = 1.8 Hz), 7.41 (1H, t, J = 1.8 Hz). MS Calcd.: 516; MS Found: 517 (M + 1). |
| 2/6 | 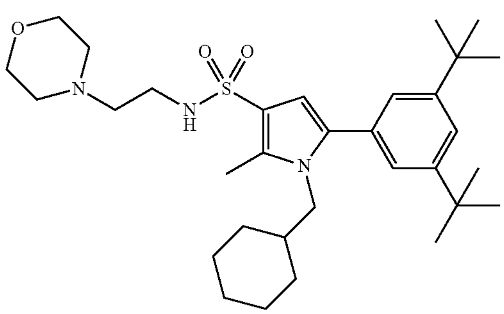 [SMILES: Cc1c(S(=O)(=O)NCCN2CCOCC2)cc(-c2cc(C(C)(C)C)cc(C(C)(C)C)c2)n1CC1CCCCC1] | ¹H-NMR (300 MHz, CDCl₃) δ: 0.60-0.65 (2H, m), 0.93-1.02 (3H, m), 1.25 (6H, s), 1.27-1.36 (3H, m), 1.34 (18H, s), 1.51-1.55 (3H, m), 2.34-2.36 (4H, m), 2.47-2.56 (5H, m), 3.02-3.06 (2H, m), 3.62-3.73 (6H, m), 5.00 (1H, s), 6.41 (1H, s), 7.14 (2H, d, J = 1.8 Hz), 7.40 (1H, m). MS Calcd.: 557; MS Found: 558 (M + 1). |

Example 3

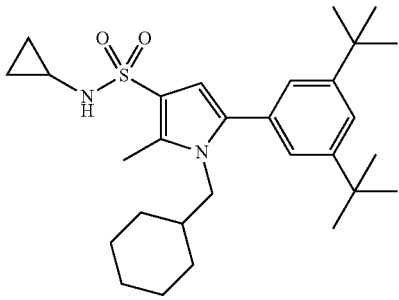

Step 1: Ethyl 1-(cyclohexylmethyl)-4-(N-cyclopropylsulfamoyl)-5-methyl-1H-pyrrole-2-carboxylate (3a)

The solution of intermediate 1a (10.0 g, 40.0 mmol) in ClSO$_3$H (50 mL) was stirred at 0° C. for 36 h. This resulting mixture was quenched with water and extracted with EA twice. The combined organic phases were dried over Na$_2$SO$_4$, filtered and concentrated to give the residue as a brown oil. The residue oil was dissolved in dry THF (200 mL) and cyclopropylamine (6.80 g, 120 mmol) was added to this mixture at 0° C. and this solution was stirred overnight at rt. This solution was concentrated and purified by CC (DCM) to give compound 3a (12.2 g, 82%) as an oil.

Step 2: 1-(Cyclohexylmethyl)-4-(N-cyclopropylsulfamoyl)-5-methyl-1H-pyrrole-2-carboxylic acid (3b)

To a solution of compound 3a (8.0 g, 22.0 mmol) in MeOH (200 mL) was added a solution of LiOH (4.2 g, 100 mmol) in water (50 mL) and the solution was warmed to 50° C. overnight, cooled to rt and concentrated. The residue was diluted with water and acidified to pH~4 with 4N aq. HCl and the solution was extracted with EA twice. The combined organic layers were washed with brine, dried over Na$_2$SO$_4$, filtered, concentrated and purified by CC (PE/EA=2/1) to give compound 3b (6.0 g, 80%) as a white solid.

Step 3: 1-(Cyclohexylmethyl)-N-cyclopropyl-2-methyl-1H-pyrrole-3-sulfonamide (3c)

To a solution of compound 3b (6.0 g, 17.6 mmol) in EtOH (100 mL) was added 4N aq. HCl (50 mL) and the solution was refluxed for 5 h, cooled to rt and concentrated. The residue was diluted with EA, washed with brine, dried over Na$_2$SO$_4$, filtered, concentrated and purified by CC (EA/PE=1/5) to give compound 3c (3.2 g, 61%) as a white solid.

Step 4: 5-Bromo-1-(cyclohexylmethyl)-N-cyclopropyl-2-methyl-1H-pyrrole-3-sulfonamide (3d)

To a solution of compound 3c (3.0 g, 10.0 mmol) in THF (80 mL) at −78° C. was added a solution of NBS (1.78 g, 10.0 mmol) in THF (50 mL) and the solution was stirred for 2 h at −78° C. Water was added and the solution was extracted with EA twice. The combined organic layers were dried over Na$_2$SO$_4$, filtered, concentrated and purified CC (EA/PE=1/5) to give compound 3d (3.2 g, 85%) as a white solid.

Step 5: 1-(Cyclohexylmethyl)-N-cyclopropyl-5-(3,5-di-tert-butylphenyl)-2-methyl-1H-pyrrole-3-sulfonamide (3)

The solution of compound 3d (600 mg, 1.60 mmol), (3,5-di-tert-butylphenyl)boronic acid (700 mg, 3.00 mmol), Pd(dppf)Cl$_2$ (80 mg) and K$_2$CO$_3$ (483 mg, 3.50 mmol) in DMF (30 mL) was heated at 120° C. under N$_2$ for 16 h. The resulting solution was concentrated, diluted with water and extracted with EA twice. The combined organic layers were washed with water (3×) and brine (3×) consecutively, dried over Na$_2$SO$_4$, filtered, concentrated and purified by CC (PE/EA=10/1) to give compound 3 (70 mg, 10%) as a white solid. $^1$H-NMR (300 MHz, CDCl$_3$) δ: 0.58-0.66 (m, 6H), 0.95-1.00 (m, 3H), 1.34 (s, 18H), 1.30-1.35 (m, 3H), 1.40-1.55 (m, 3H), 2.32-2.35 (m, 1H), 2.54 (s, 3H), 3.73 (d, J=7.2 Hz, 2H), 4.69 (s, 11-1), 6.44 (s, 1H), 7.15 (s, 2H), 7.40 (s, 1H). MS Calcd.: 484; MS Found: 485 (M+1).

Example 4

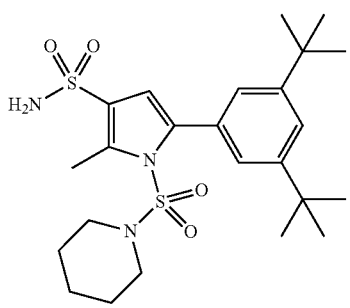

Step 1: Ethyl 2-methyl-1-(piperidin-1-ylsulfonyl)-1H-pyrrole-3-carboxylate (4a)

To a solution of ethyl 2-methyl-1H-pyrrole-3-carboxylate (3.06 g, 20 mmol) in dry DMF (40 mL) was added NaH (0.96 mg, 24 mmol) in portions and the mixture was stirred at rt for 30 min. Then a solution of piperidine-1-sulfonyl chloride (4.4 g, 24 mmol) in dry DMF (10 mL) was added and the resulting mixture was stirred overnight, diluted with EA, washed with water and brine, dried over Na$_2$SO$_4$, concentrated and purified by CC (PE/EA=1/0 to 10/1) to give compound 4a (4.77 g, 78%).

Step 2: Ethyl 5-bromo-2-methyl-1-(piperidin-1-ylsulfonyl)-1H-pyrrole-3-carboxylate (4b)

To a solution of compound 4a (4.77 g, 15.9 mmol) in dry DMF (20 mL) and dry THF (20 mL) was added NBS (3.12 g, 17.5 mmol) in portions at 0° C. The mixture was stirred at rt overnight, diluted with EA, washed with water and brine, dried over Na$_2$SO$_4$, concentrated and purified by CC (PE/EA=1/0 to 15/1) to give compound 4b (4.2 g, 63%).

Step 3: Ethyl 5-(3,5-di-tert-butylphenyl)-2-methyl-1-(piperidin-1-ylsulfonyl)-1H-pyrrole-3-carboxylate (4c)

A mixture of compound 4b (2.1 g, 5.0 mmol), (3,5-di-tert-butylphenyl)boronic acid (1.9 g, 8.1 mmol), Na$_2$CO$_3$ (1.9 g, 17.9 mmol) and Pd(PPh$_3$)$_4$ (100 mg) in dioxane (50 mL) and H$_2$O (15 mL) was heated to 100° C. for 1 h, evaporated and dissolved in EA. The mixture was washed with water (4×80 mL) and brine, dried with Na$_2$SO$_4$, concentrated and purified by CC to afford compound 4c (1.5 g, 61%) as a right red oil.

Step 4: 5-(3,5-Di-tert-butylphenyl)-2-methyl-1-(piperidin-1-ylsulfonyl)-1H-pyrrole-3-carboxylic acid (4d)

To a solution of NaOH (2.72 g, 67.8 mmol) in H$_2$O was added to compound 4c (800 mg, 1.7 mmol) in MeOH (60 mL) and refluxed for 3 h, evaporated, diluted with H$_2$O, acidified with conc. HCl to pH ~2, extracted with EA (3×30 mL), washed by brine, dried with Na$_2$SO$_4$ and concentrated to get the compound 4d (700 mg, 90%) as a white solid.

Step 5: 1-((2-(3,5-Di-tert-butylphenyl)-5-methyl-1H-pyrrol-1-yl)sulfonyl)piperidine (4e)

A solution of compound 4d (700 mg, 1.5 mmol) in TFA (5 mL) was heated to 100° C. for 30 min, evaporated and redissolved in EA, washed with aq. NaHCO$_3$ (3×50 mL) and brine, dried with Na$_2$SO$_4$, concentrated and purified by CC (PE/EA=1/0 to 7/1) to get compound 4e (260 mg, 41%).

Step 6: 5-(3,5-Di-tert-butylphenyl)-2-methyl-1-(piperidin-1-ylsulfonyl)-1H-pyrrole-3-sulfonamide (4)

To a solution of compound 4e (195 mg, 0.46 mmol) in DCM (0.9 mL) was added ClSO$_3$H (0.45 mL, 7.02 mmol) at −40° C. under Ar. The mixture was slowly warmed to rt and stirred for 48 h. To the mixture was added dropwise to NH$_3$ (3N in THF, 20 mL) at −20° C. and the mixture was stirred for 2 h, evaporated, redissolved in water, extracted with EA, washed with brine, dried with Na$_2$SO$_4$, concentrated and purified by prep-HPLC to afford compound 4 (16 mg, 8%) as light yellow solid. $^1$H-NMR (400 MHz, CDCl$_3$) δ: 8.28 (s, 1H), 7.49 (t, J=1.8 Hz, 1H), 7.33 (d, J=1.6 Hz, 2H), 5.71 (s, 2H), 2.88 (m, 4H), 2.57 (s, 3H), 1.35-1.27 (m, 24H). LC-MS (ESI+) m/z: 496.6 [M+1]$^+$.

Example 5

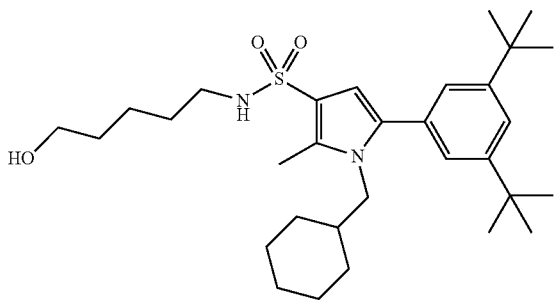

Step 1: 1-(3,5-Di-tert-butylphenyl)pentane-1,4-dione (5a)

To a solution of 3,5-di-tert-butylbenzaldehyde (10.9 g, 50 mmol) in EtOH (200 mL) was added DIPEA (12.9 g, 100 mmol), but-3-en-2-one (3.5 g, 50 mmol) and 3-ethyl-5-(2-hydroxyethyl)-4-methylthiazolium bromide (2.5 g, 10 mmol). This mixture was heated to 75-80° C. overnight, evaporated, diluted with water (50 mL) and extracted with EA. The organic layer was washed with brine, dried, concentrated and purified by CC (EA/PE=1/100) to afford compound 5a (6.4 g, 44%) as colorless oil.

Step 2: 1-(Cyclohexylmethyl)-2-(3,5-di-tert-butylphenyl)-5-methyl-1H-pyrrole (5b)

To a solution of 5a (6.4 g, 22.2 mmol) in toluene (100 mL) was added cyclohexylmethanamine (2.8 g, 24.4 mmol) and TsOH (0.3 g). This mixture was refluxed for 20 h, cooled, concentrated and purified by CC to afford compound 5b (7.5 g, 93%) as yellow oil.

Step 3: 1-(Cyclohexylmethyl)-5-(3,5-di-tert-butylphenyl)-2-methyl-1H-pyrrole-3-sulfonic acid (5c)

To a solution of compound 5b (1.0 g, 2.7 mmol) in THF (10 mL) was added dropwise ClSO$_3$H (3 mL) at −78° C. This mixture was stirred at −78° C. for 3 h, then EA and cooled water was added and extracted with EA. The organic layer was washed with aq. NaHCO$_3$, dried and concentrated to afford compound 5c (1.0 g, 83%) as yellow oil.

Step 4: 1-(Cyclohexylmethyl)-5-(3,5-di-tert-butylphenyl)-2-methyl-1H-pyrrole-3-sulfonyl chloride (5d)

To a solution of compound 5c (1.0 g, 2.2 mmol) in CH$_2$Cl$_2$ (10 mL) was added (COCl)$_2$ (0.8 g, 6.6 mmol) dropwise at 0° C. Then this mixture was stirred at 0° C. for 2 h and concentrated to obtain compound 5d (1.0 g, 100%).

Step 5: 2,6-Di-tert-butyl-4-(1-(cyclohexylmethyl)-4-(N-(5-hydroxypentyl)sulfamoyl)-5-methyl-1H-pyrrol-2-yl)benzoic acid (5)

To a solution of compound 5d (1.0 eq.) in CH$_2$Cl$_2$ (20 mL) was added Et$_3$N (0.2 g) and 5-aminopentan-1-ol (1.0 eq.). Then this mixture was stirred at rt for 2 h, concentrated and purified by pre-HPLC to afford compound 5 (60 mg, 68%) as yellow solid. $^1$H-NMR (300 MHz, CDCl$_3$) δ: 7.39 (s, 1H), 7.16 (d, J=1.5 Hz, 2H), 6.99 (t, J=6.0 Hz, 1H), 6.26 (s, 1H), 4.31 (t, J=4.8 Hz, 1H), 3.79 (d, J=6.9 Hz, 2H), 3.37-3.32 (m, 2H), 2.73 (dd, 2H), 2.43 (s, 3H), 1.47-1.20 (m, 30H), 0.95-0.89 (m, 3H), 0.69-0.61 (m, 2H). MS Calcd.: 530.4; MS Found: 531.5 (M$_+$1).

Example 5/1 to 5/11

Using similar procedures as that described in Example 5, the following Examples have been prepared:

| # | Structure | Analytical data |
|---|---|---|
| 5/1 | 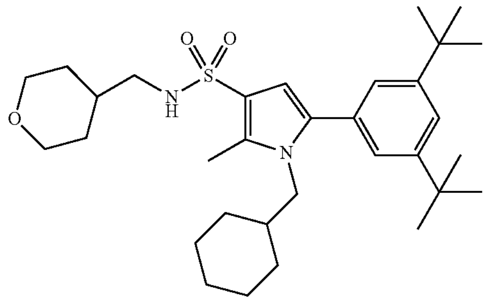 [SMILES: Cc1c(S(=O)(=O)NCC2CCOCC2)cc(-c2cc(C(C)(C)C)cc(C(C)(C)C)c2)n1CC1CCCCC1] | $^1$H-NMR (300 MHz, CDCl$_3$) δ: 7.41 (t, J = 1.8 Hz, 1H), 7.14 (d, J = 1.8 Hz, 2H), 6.41 (s, 1H), 3.97-3.92 (dd, 2H), 3.72 (d, J = 7.2 Hz, 2H), 3.34 (td, 2H), 2.88 (d, J = 6.6 Hz, 2H), 2.52 (s, 3H), 1.73-1.52 (m, 7H), 1.34-1.23 (m, 22H), 1.00-0.85 (m, 3H), 0.66-0.62 (m, 2H). MS Calcd.: 542.4; MS Found: 543.4 (M + 1). |
| 5/2 | 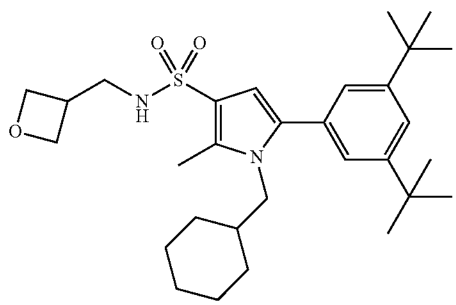 [SMILES: Cc1c(S(=O)(=O)NCC2COC2)cc(-c2cc(C(C)(C)C)cc(C(C)(C)C)c2)n1CC1CCCCC1] | $^1$H-NMR (300 MHz, CDCl$_3$) δ: 7.41 (t, J = 1.8 Hz, 1H), 7.15 (d, J = 1.8 Hz, 2H), 6.41 (s, 1H), 4.77 (dd, 2H), 4.34 (dd, 3H), 3.73 (d, J = 7.2 Hz, 2H), 3.32 (t, 2H), 3.17-3.13 (m, 1H), 2.53 (s, 3H), 1.52-1.49 (m, 3H), 1.37-1.21 (m, 21H), 1.00-0.96 (m, 3H), 0.66-0.60 (m, 2H). MS Calcd.: 514.3; MS Found: 515.1 (M + 1). |
| 5/3 | 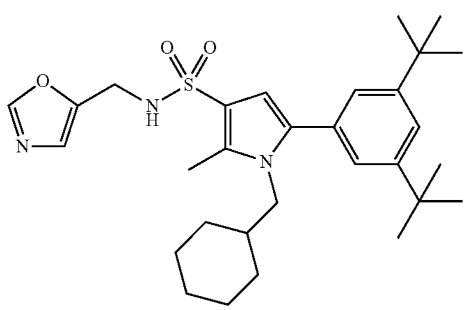 [SMILES: Cc1c(S(=O)(=O)NCc2cnco2)cc(-c2cc(C(C)(C)C)cc(C(C)(C)C)c2)n1CC1CCCCC1] | $^1$H-NMR (300 MHz, CDCl$_3$) δ: 7.77 (s, 1H), 7.42 (t, J = 1.8 Hz, 1H), 7.13 (d, J = 1.8 Hz, 2H), 6.90 (s, 1H), 6.39 (s, 1H), 4.65 (br s, 1H), 4.29 (d, J = 3.9 Hz, 2H), 3.70 (d, J = 7.2 Hz, 2H), 2.49 (s, 3H), 1.55-1.53 (m, 3H), 1.37-1.25 (m, 21H), 1.01-0.98 (m, 3H), 0.66-0.61 (m, 2H). MS Calcd.: 525.3; MS Found: 526.3 (M + 1). |
| 5/4 | 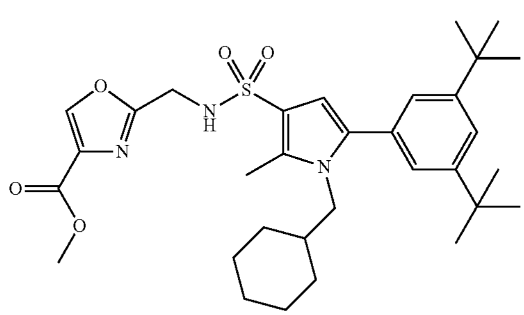 [SMILES: COC(=O)c1coc(CNS(=O)(=O)c2cc(-c3cc(C(C)(C)C)cc(C(C)(C)C)c3)n(CC3CCCCC3)c2C)n1] | $^1$H-NMR (300 MHz, CDCl$_3$) δ: 8.12 (s, 1H), 7.41 (t, J = 1.8 Hz, 1H), 7.09 (d, J = 1.8 Hz, 2H), 6.38 (s, 1H), 5.01 (t, 1H), 4.37 (m, J = 5.1 Hz, 2H), 3.91 (s, 1H), 3.66 (d, J = 7.2 Hz, 2H), 2.52 (s, 3H), 1.55-1.50 (m, 3H), 1.36-1.25 (m, 21H), 1.01-0.94 (m, 3H), 0.65-0.60 (m, 2H). MS Calcd.: 583.3; MS Found: 584.0 (M + 1). |

| # | Structure | Analytical data |
|---|---|---|
| 5/5 | 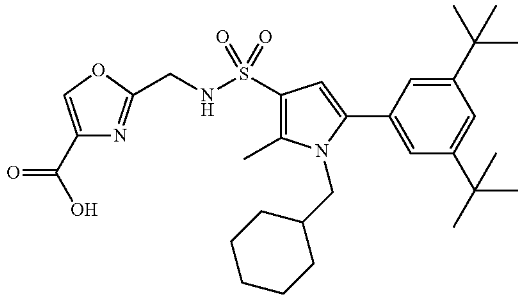 [SMILES: Cc1c(S(=O)(=O)NCc2nc(C(=O)O)co2)cc(-c2cc(C(C)(C)C)cc(C(C)(C)C)c2)n1CC1CCCCC1] | $^1$H-NMR (300 MHz, CDCl$_3$) δ: 8.19 (s, 1H), 7.41 (s, 1H), 7.10 (d, J = 1.2 Hz, 2H), 6.38 (s, 1H), 5.20 (br s, 1H), 4.39 (d, 2H), 3.67 (d, J = 7.2 Hz, 2H), 2.52 (s, 3H), 1.53-1.49 (m, 3H), 1.34-1.25 (m, 21H), 1.00-0.94 (m, 3H), 0.65-0.55 (m, 2H). |
| 5/6 | 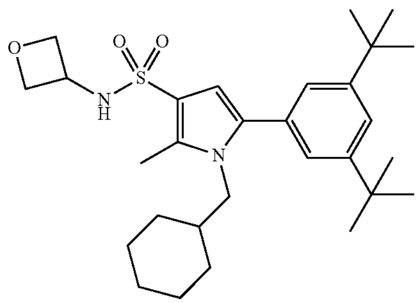 [SMILES: Cc1c(S(=O)(=O)NC2COC2)cc(-c2cc(C(C)(C)C)cc(C(C)(C)C)c2)n1CC1CCCCC1] | $^1$H-NMR (300 MHz, DMSO-d$_6$) δ: 7.97 (d, J = 7.8 Hz, 1H), 7.40 (s, 1H), 7.15 (d, J = 1.5 Hz, 2H), 6.24 (s, 1H), 4.53 (br s, 2H), 4.32 (br s, 3H), 3.78 (d, J = 6.9 Hz, 2H), 2.44 (s, 3H), 1.47-1.44 (m, 3H), 1.31-1.19 (m, 21H), 0.99-0.90 (m, 3H), 0.67-0.60 (m, 2H). MS Calcd.: 500.3; MS Found: 501.4 (M + 1). |
| 5/7 | 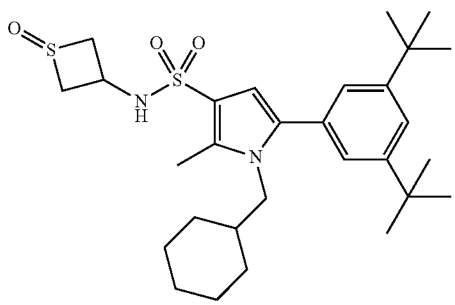 [SMILES: Cc1c(S(=O)(=O)NC2CS(=O)C2)cc(-c2cc(C(C)(C)C)cc(C(C)(C)C)c2)n1CC1CCCCC1] | $^1$H-NMR (300 MHz, CDCl$_3$) δ: 7.43 (t, J = 1.8 Hz, 1H), 7.12 (d, J = 1.8 Hz, 2H), 6.39 (s, 1H), 5.00 (d, J = 6.9 Hz, 2H), 3.99-3.93 (m, 2H), 3.87-3.82 (m, 1H), 3.73 (d, J = 7.2 Hz, 2H), 3.17-3.11 (m, 2H), 2.51 (s, 3H), 1.57-1.50 (m, 3H), 1.37-1.25 (m, 21H), 1.00-0.96 (m, 3H), 0.67-0.61 (m, 2H). MS Calcd.: 532.3; MS Found: 533.2 (M + 1). |
| 5/8 | 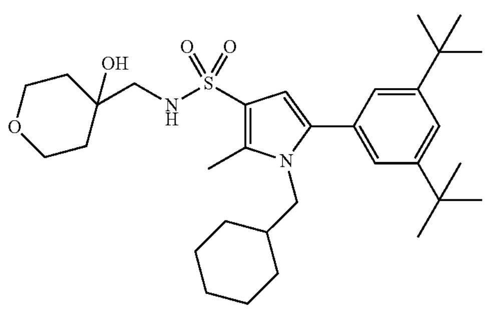 [SMILES: Cc1c(S(=O)(=O)NCC2(O)CCOCC2)cc(-c2cc(C(C)(C)C)cc(C(C)(C)C)c2)n1CC1CCCCC1] | $^1$H-NMR (300 MHz, DMSO-d$_6$) δ: 7.39 (s, 1H), 7.16 (d, J = 1.5 Hz, 2H), 6.94 (t, J = 6.6 Hz, 2H), 6.29 (s, 1H), 4.37 (s, 1H), 3.79 (d, J = 7.2 Hz, 2H), 3.57-3.54 (m, 4H), 2.70 (d, J = 6.3 Hz, 2H), 2.45 (s, 3H), 1.61-1.44 (m, 5H), 1.31-1.20 (m, 23H), 0.95-0.92 (m, 3H), 0.67-0.63 (m, 2H). MS Calcd.: 558.4; MS Found: 559.5 (M + 1). |
| 5/9 | 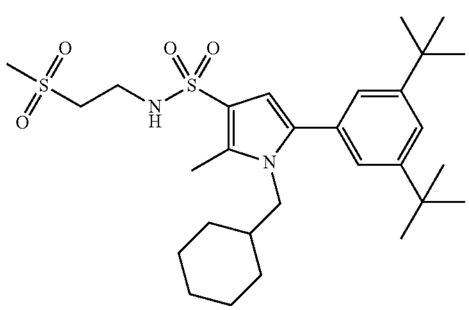 [SMILES: Cc1c(S(=O)(=O)NCCS(C)(=O)=O)cc(-c2cc(C(C)(C)C)cc(C(C)(C)C)c2)n1CC1CCCCC1] | $^1$H-NMR (300 MHz, DMSO-d$_6$) δ: 7.40 (s, 1H), 7.35 (br t, 1H), 7.18 (s, 2H), 6.31 (s, 1H), 3.80 (d, J = 6.6 Hz, 2H), 3.23-3.16 (m, 4H), 3.00 (s, 3H), 2.45 (s, 3H), 1.47-1.44 (m, 3H), 1.31-1.21 (m, 21H), 0.95-0.92 (m, 3H), 0.67-0.63 (m, 2H). MS Calcd.: 550.3; MS Found: 551.4 (M + 1). |

-continued

| # | Structure | Analytical data |
|---|---|---|
| 5/10 | 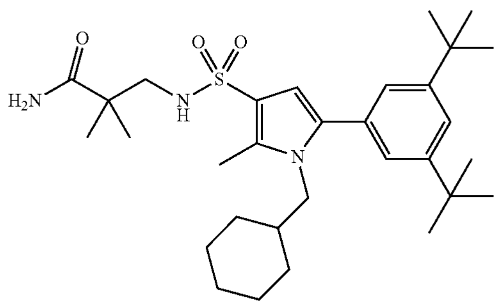 [SMILES: Cc1c(S(=O)(=O)NCC(C)(C)C(N)=O)cc(-c2cc(C(C)(C)C)cc(C(C)(C)C)c2)n1CC1CCCCC1] | $^1$H-NMR (300 MHz, DMSO-d$_6$) δ: 7.39 (s, 1H), 7.17 (s, 2H), 7.09 (br s, 1H), 6.88-6.82 (m, 2H), 6.30 (s, 1H), 3.80 (d, J = 6.9 Hz, 2H), 2.78 (d, J = 6.9 Hz, 2H), 2.44 (s, 3H), 1.47-1.44 (m, 3H), 1.31-1.19 (m, 21H), 1.04-0.92 (m, 9H), 0.67-0-63 (m, 2H). MS Calcd.: 543.4; MS Found: 544.4 (M + 1). |
| 5/11 | 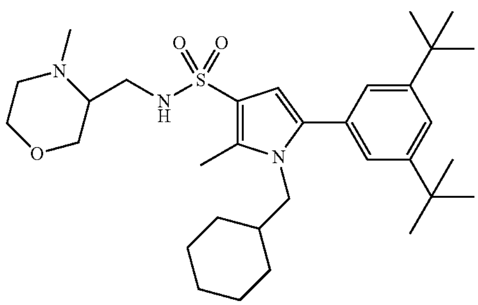 [SMILES: Cc1c(S(=O)(=O)NCC2COCCN2C)cc(-c2cc(C(C)(C)C)cc(C(C)(C)C)c2)n1CC1CCCCC1] | $^1$H-NMR (300 MHz, CDCl$_3$) δ: 7.42 (t, 1H), 7.14 (d, 2H), 6.37 (s, 1H), 5.95 (br s, 1H), 4.06-3.26 (m, 10H), 2.99-2.96 (m, 4H), 2.51 (s, 3H), 1.54-1.52 (m, 3H), 1.30-1.23 (m, 21H), 1.00-0.96 (m, 3H), 0.65-0.57 (m, 2H). MS Calcd.: 557.4; MS Found: 558.1 (M + 1). |

Example 6 and Example 7

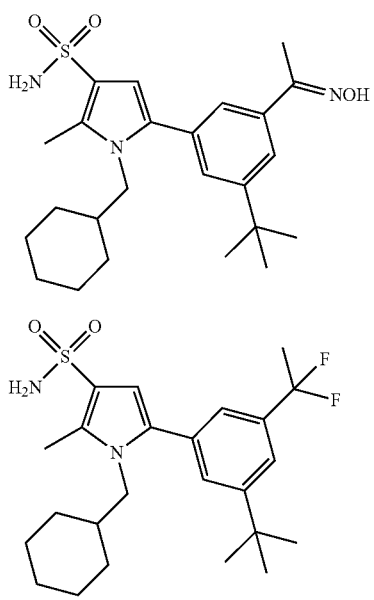

Step 1: 5-(3-(tert-Butyl)-5-(1-(hydroxyimino)ethyl)phenyl)-1-(cyclohexylmethyl)-2-methyl-1H-pyrrole-3-sulfonamide (6)

To a solution of compound 12/27 (100 mg, 0.23 mmol) and pyridine (55 mg, 0.70 mmol) in EtOH (10 mL) was added NH$_2$OH.HCl (21 mg, 0.30 mmol) in one portion at rt and the mixture was stirred at reflux overnight, concentrated and purified by CC (PE/EA=4/1) to give compound 6 (50 mg, 49%) as a white solid. $^1$H-NMR (400 MHz, CDCl$_3$) δ: 7.65-7.66 (m, 1H), 7.33-7.36 (m, 2H), 6.48 (s, 1H), 4.84 (s, 2H), 3.73 (d, 2H, J=7.2 Hz), 2.54 (s, 3H), 2.30 (s, 3H), 1.54-1.56 (m, 3H), 1.35 (s, 11H), 0.98-1.01 (m, 3H), 0.62-0.65 (m, 2H). MS Calcd.: 445; MS Found: 446 (M+1)$^+$.

Step 2: 5-(3-(tert-Butyl)-5-(1,1-difluoroethyl)phenyl)-1-(cyclohexylmethyl)-2-methyl-1H-pyrrole-3-sulfonamide (7)

To a solution of NOBF$_4$ (390 mg, 3.3 mmol) and HF.pyridine (70%, 1.5 mL) in dry CHCl$_3$ (3 mL) was added a solution of compound 6 (446 mg, 1.0 mmol) in dry CHCl$_3$ (6 mL) at 0° C. under dry N$_2$ and the mixture was refluxed overnight, cooled, washed with water twice and brine consecutively, dried over Na$_2$SO$_4$, filtered, concentrated and purified by CC (PE/EA=3/1) and then prep-HPLC to give compound 7 (20 mg, 4.4%) as a white solid. $^1$H-NMR (400 MHz, CDCl$_3$) δ: 7.51 (s, 1H), 7.39 (s, 1H), 7.26 (s, 1H), 6.49 (s, 1H), 4.75 (s, 2H), 3.72 (d, 2H, J=6.8 Hz), 2.54 (s, 3H), 1.93 (t, 3H, J=18.0 Hz), 1.50-1.60 (m, 3H), 1.35-1.49 (m, 12H), 0.98-1.00 (m, 3H), 0.63-0.68 (m, 2H). MS Calcd.: 452; MS Found: 453 (M+1)$^+$.

Example 6/1

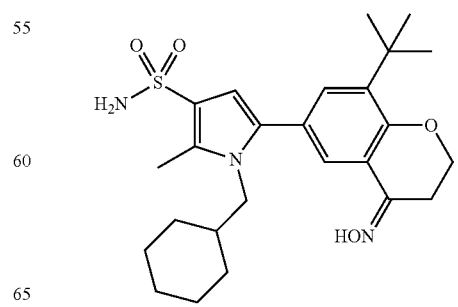

5-(8-(tert-Butyl)-4-(hydroxyimino)chroman-6-yl)-1-(cyclohexylmethyl)-2-methyl-1H-pyrrole-3-sulfonamide (6/1)

Using similar procedures as that described in Example 6, the Example 6/1 has been prepared. ¹H-NMR (400 MHz, CDCl₃) δ: 7.65-7.66 (m, 1H), 7.51 (s, 1H), 7.18-7.19 (m, 1H), 6.42 (s, 1H), 4.71-4.73 (m, 2H), 4.27 (t, 2H, J=6.0 Hz), 3.69 (d, 2H, J=7.2 Hz), 3.01 (t, 2H, J=6.0 Hz), 2.52 (s, 3H), 1.58 (s, 3H), 1.37-1.41 (m, 12H), 1.01-1.03 (m, 3H), 0.66-0.69 (m, 2H). MS Calcd.: 473; MS Found: 474 (M+1)⁺.

Example 8

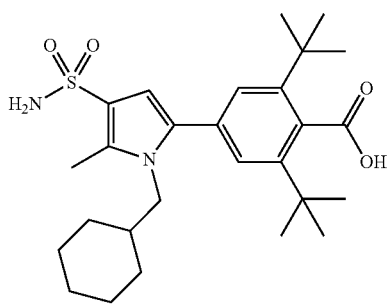

2,6-Di-tert-butyl-4-(1-(cyclohexylmethyl)-5-methyl-4-sulfamoyl-1H-pyrrol-2-yl)benzoic acid (8)

The solution of compound 12/24 (200 mg, 398 μmol) and t-BuOK (446 mg, 3.98 mmol) in a mixture of DMSO (5 mL) and H₂O (one drop) was stirred overnight at 100° C. Then water was added and the resulting solution was acidified to pH=3-4 by 1N HCl. The resulting solution was extracted with EA twice. The combined organic layers were washed with brine, dried over Na₂SO₄, filtered, concentrated and purified by CC (PE/EA=2/1) to give compound 8 (130 mg, 62%) as a white solid. ¹H-NMR (CDCl₃, 300 MHz) δ: 7.32 (s, 2H), 6.44 (s, 1H), 4.68 (s, 2H), 3.72 (d, 2H, J=7.2 Hz), 2.52 (s, 3H), 1.61-1.58 (m, 3H), 1.39-1.34 (m, 21H), 1.03-1.05 (m, 3H), 0.66-0.69 (m, 2H). MS Calcd.: 488; MS Found: 489 (M+1).

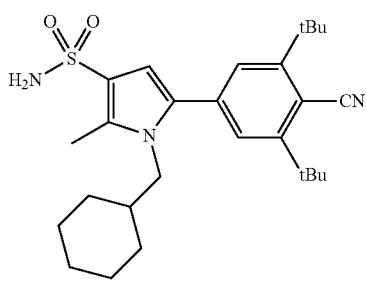

Example 9

Step 1: 1-(Cyclohexylmethyl)-5-(3,5-di-tert-butyl-4-cyanophenyl)-2-methyl-1H-pyrrole-3-sulfonamide (9)

Compound 12/23 (230 mg, 490 μmol) was treated with dry K₄[Fe(CN)₆] and CuI as described in Chem. Eur. J. 2007, 13:6249 to give compound 9 (30 mg, 14%) as a white solid. ¹H-NMR (CDCl₃, 400 MHz) δ: 7.30 (s, 2H), 6.54 (s, 1H), 4.68 (s, 2H), 3.73 (d, 2H, J=7.2 Hz), 2.55 (s, 3H), 1.61-1.58 (m, 21H), 1.40-1.36 (m, 3H), 1.03-1.05 (m, 3H), 0.66-0.69 (m, 2H). MS Calcd.: 469; MS Found: 470 (M+1).

Example 10 and Example 11

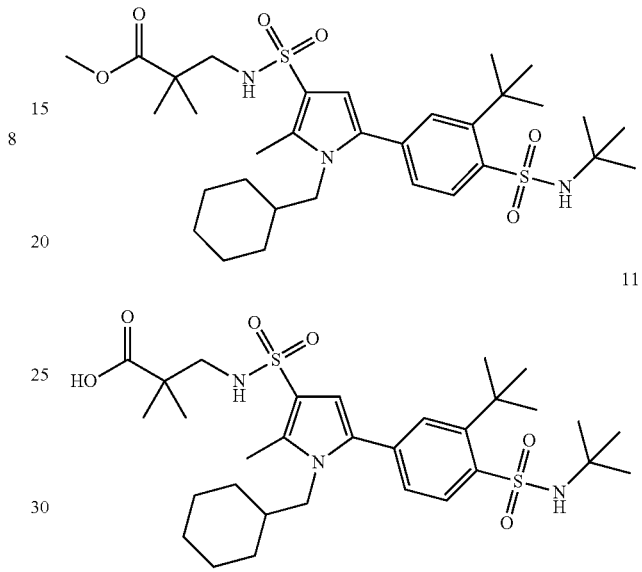

Step 1: Methyl 3-(5-bromo-1-(cyclohexylmethyl)-2-methyl-1H-pyrrole-3-sulfonamido)-2,2-dimethylpropanoate (10a)

To a solution of compound 1d (500 mg, 1.5 mmol) in dry DMF (20 mL) was added NaH (60%, 250 mg, 3.74 mmol). The mixture was stirred at 0° C. for 1 h and then methyl 3-bromo-2,2-dimethylpropanoate (452 mg, 1.64 mmol) was added and stirred overnight, quenched with aq. NH₄Cl and extracted with EA. The organic layer was separated and washed with brine, dried over Na₂SO₄, concentrated and purified by CC (EA/PE. 1/4) to give compound 10a (403 mg, 60%) as white solid.

Step 2: Methyl 3-(5-(3-(tert-butyl)-4-(N-(tert-butyl)sulfamoyl)phenyl)-1-(cyclohexylmethyl)-2-methyl-1H-pyrrole-3-sulfonamido)-2,2-dimethylpropanoate (10)

A mixture of bromide 10a (100 mg, 0.22 mmol), boronic ester P19 (106 mg, 0.27 mmol), Cs₂CO₃ (181 mg, 0.56 mmol) and Pd(dppf)Cl₂ (50 mg) in dioxane and water (10:1, 100 mL) was heated at 100° C. overnight. The solvent was removed, diluted with water, extracted with EA (3×), the combined organic layers were washed with brine, dried over Na₂SO₄ and concentrated to give product 10 (62 mg, 44%) as yellow solid.

Step 3: 3-(5-(3-(tert-Butyl)-4-(N-(tert-butyl)sulfamoyl)phenyl)-1-(cyclohexylmethyl)-2-methyl-1H-pyrrole-3-sulfonamido)-2,2-dimethylpropanoic acid (11)

To a solution of ester 10 (60 mg, 0.09 mmol) in MeOH (5 mL) was added 6N NaOH (1 mL). The mixture was stirred at rt overnight, the solvent was removed and the residue was adjusted ph<2 with 4N HCl, then extracted with EA (3×) and the combined organic layers were washed with brine and dried over Na$_2$SO$_4$, evaporated and purified by prep-HPLC to give acid 11 (38 mg, 65%) as white solid. $^1$H-NMR (400 MHz, DMSO-d$_6$) δ: 12.29 (s, 1H), 8.15 (d, J=8.4 Hz, 1H), 7.81 (s, 1H), 7.53 (s, 1H), 7.47 (d, J=8.4 Hz, 1H), 7.14 (t, J=6.8 Hz, 1H), 6.47 (s, 1H), 3.87 (d, J=6.8 Hz, 2H), 2.83 (d, J=7.2 Hz, 2H), 2.45 (s, 3H), 1.55 (s, 9H), 1.44 (d, 3H), 1.19-1.16 (m, 12H), 1.05 (s, 6H), 0.89-0.84 (m, 3H), 0.66-0.57 (m, 2H). MS Calcd.: 623.3; MS Found: 624.2 (M+1).

Examples 11/1 to 11/2

Using similar procedures as that described in Example 10/11, the following Examples have been prepared:

| # | Structure | Analytical data |
|---|---|---|
| 11/1 | 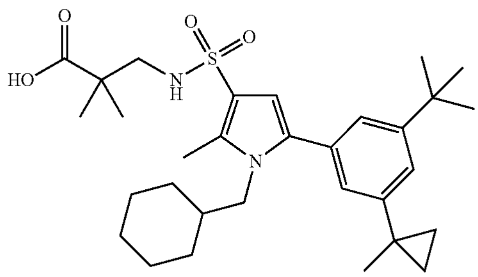 [SMILES: Cc1c(S(=O)(=O)NCC(C)(C)C(=O)O)cc(-c2cc(C(C)(C)C)cc(C3(C)CC3)c2)n1CC1CCCCC1] | $^1$H-NMR (400 MHz, CDCl$_3$) δ: 7.27 (t, 1H), 7.13 (t, 1H), 7.01 (t, 1H), 6.39 (s, 1H), 5.56 (br s, 1H), 3.72 (d, J = 7.2 Hz, 2H), 3.00 (d, J = 5.2 Hz, 2H), 2.51 (s, 3H), 1.54 (d, 3H), 1.42 (s, 3H), 1.38-1.32 (m, 12H), 1.27 (s, 6H), 0.99 (m, 3H), 0.86 (dd, 2H), 0.75 (dd, 2H), 0.67-0.60 (m, 2H). MS Calcd.: 542.3; MS Found: 543.2 (M + 1). |
| 11/2 | 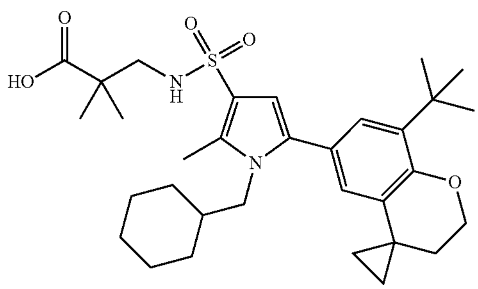 [SMILES: Cc1c(S(=O)(=O)NCC(C)(C)C(=O)O)cc(-c2cc(C(C)(C)C)c3c(c2)C2(CCO3)CC2)n1CC1CCCCC1] | $^1$H-NMR (400 MHz, CDCl$_3$) δ: 12.28 (s, 1H), 7.03 (t, J = 7.2 Hz, 1H), 6.90 (d, J = 1.6 Hz, 1H), 6.51 (d, J = 1.6 Hz, 1H), 6.18 (s, 1H), 4.28 (t, J = 4.8 Hz, 2H), 3.71 (d, J = 7.2 Hz, 2H), 2.81 (d, 2H), 2.41 (s, 3H), 1.85 (t, J = 4.8 Hz, 2H), 1.51 (m, 3H), 1.34-1.23 (m, 12H), 1.04 (s, 6H), 1.02-0.95 (m, 5H), 0.89-0.86 (m, 2H), 0.71-0.64 (m, 2H). MS Calcd.: 470.3; MS Found: 471.3 (M + 1). |

Examples 12/1 to 12/45

The following Examples were prepared similar as described in Example 1 (using boronic acid building blocks) or similar as described in Example 10 (using boronic ester building blocks):

| # | Structure | Analytical data |
|---|---|---|
| 12/1 | 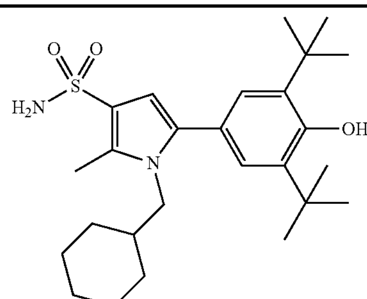 | $^1$H-NMR (400 MHz, CDCl$_3$) δ: 0.66-0.73 (m, 2H), 0.99-1.03 (m, 3H), 1.34-1.38 (m, 3H), 1.45 (s, 18H), 2.53 (s, 3H), 3.65 (d, J = 7.2 Hz, 2H), 4.66 (s, 2H), 5.31 (s, 1H), 6.41 (s, 1H), 7.08 (s, 2H). MS Calcd.: 460; MS Found: 461 (M + 1). |
| 12/2 | 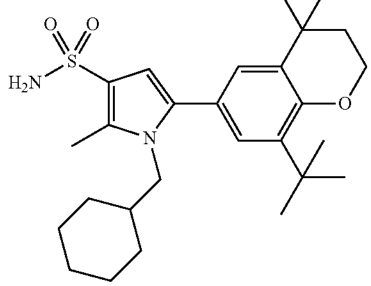 | $^1$H-NMR (400 MHz, CDCl$_3$) δ: 0.66-0.69 (m, 2H), 1.02-1.03 (m, 3H), 1.33-1.40 (m, 18H), 1.52-1.57 (m, 3H), 1.85-1.88 (t, J = 10.8 Hz, 2H), 2.53 (s, 3H), 3.49-3.50 (d, J = 5.2 Hz, 2H), 4.20-4.23 (t, J = 10.4 Hz, 2H), 4.64 (s, 2H), 6.41 (s, 1H), 6.99 (s, 1H), 7.08 (s, 1H). MS Calcd.: 472; MS Found: 473 (M + 1). |

| # | Structure | Analytical data |
|---|---|---|
| 12/3 | 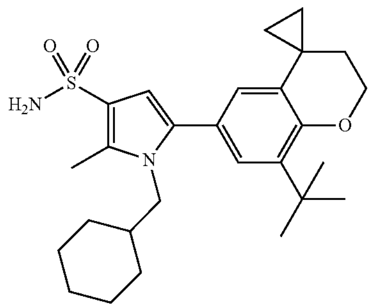 [SMILES: Cc1c(S(N)(=O)=O)cc(-c2cc(C(C)(C)C)c3c(c2)C2(CCO3)CC2)n1CC1CCCCC1] | ¹H-NMR (400 MHz, CDCl₃) δ: 0.68-0.70 (m, 2H), 0.84-0.87 (m, 2H), 0.98-1.04 (m, 5H), 1.28 (s, 12H), 1.55-1.60 (m, 3H), 1.89-1.91 (t, J = 10.0 Hz, 2H), 2.52 (s, 3H), 3.63-3.65 (d, J = 7.2 Hz, 2H), 4.32-4.35 (t, J = 10.0 Hz, 2H), 4.63 (s, 1H), 6.35 (s, 1H), 6.43 (s, 1H), 6.96 (s, 1H). MS Calcd.: 470; MS Found: 471 (M + 1). |
| 12/4 | 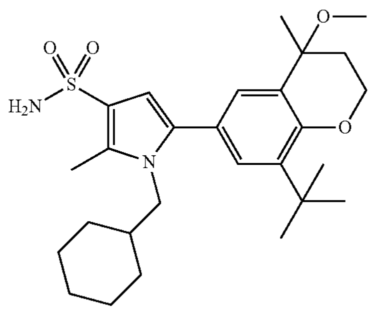 [SMILES: COC1(C)CCOc2c(C(C)(C)C)cc(-c3cc(S(N)(=O)=O)c(C)n3CC3CCCCC3)cc21] | ¹H-NMR (400 MHz, CDCl₃) δ: 0.63-0.68 (m, 2H), 0.97-1.05 (m, 3H), 1.24 (s, 12H), 1.52-1.56 (m, 6H), 1.84-1.90 (m, 1H), 2.31-2.38 (m, 1H), 2.52 (s, 3H), 3.10 (s, 3H), 3.69-3.71 (d, J = 7.2 Hz, 2H), 4.19-4.25 (m, 1H), 4.36-4.41 (s, 1H), 6.53 (m, 1H), 4.64 (s, 2H), 6.42 (s, 1H), 7.10 (s, 1H), 7.19 (s, 1H). MS Calcd.: 488; MS Found: 457 (M – 31). |
| 12/5 | 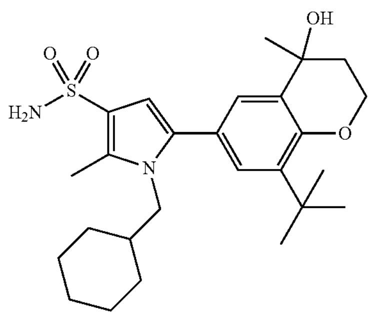 [SMILES: Cc1c(S(N)(=O)=O)cc(-c2cc(C(C)(C)C)c3c(c2)C(C)(O)CCO3)n1CC1CCCCC1] | ¹H-NMR (400 MHz, CDCl₃) δ: 0.69-0.72 (m, 2H), 1.04 (s, 3H), 1.36-1.43 (m, 12H), 1.55-1.63 (m, 6H), 1.81 (s, 1H), 2.11-2.14 (m, 2H), 2.53 (s, 3H), 3.67-3.69 (d, J = 6.8 Hz, 2H), 4.29-4.32 (t, J = 11.2 Hz, 2H), 4.64 (s, 2H), 6.41 (s, 1H), 7.11 (s, 1H), 7.32 (s, 1H). MS Calcd.: 474; MS Found: 457 (M + 1 – H₂O). |
| 12/6 | 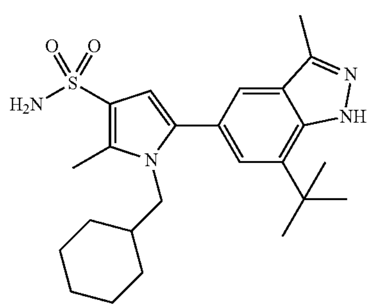 [SMILES: Cc1n[nH]c2c(C(C)(C)C)cc(-c3cc(S(N)(=O)=O)c(C)n3CC3CCCCC3)cc12] | ¹H-NMR (400 MHz, CDCl₃) δ: 0.58-0.67 (m, 2H), 0.94-1.04 (m, 3H), 1.25-1.44 (m, 3H), 1.51 (s, 9H), 1.55 (m, 1H), 1.57 (m, 2H), 2.52-2.53 (s, 3H), 2.58 (s, 3H), 3.72-3.74 (d, J = 7.6 Hz, 2H), 4.69 (s, 2H), 6.47 (s, 1H), 7.22 (s, 1H), 7.46 (s, 1H), 9.90 (s, 1H). MS Calcd.: 442; MS Found: 443 (M + 1). |
| 12/7 | 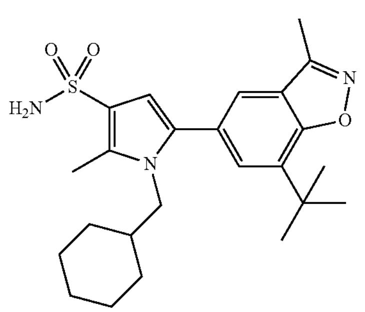 [SMILES: Cc1noc2c(C(C)(C)C)cc(-c3cc(S(N)(=O)=O)c(C)n3CC3CCCCC3)cc12] | ¹H-NMR (400 MHz, CDCl₃) δ: 0.62-0.64 (m, 2H), 0.98-1.00 (m, 3H), 1.49 (s, 9H), 1.51-1.55 (m, 3H), 2.56 (s, 3H), 2.58 (s, 3H), 3.71-3.72 (d, J = 6.8 Hz, 2H), 4.68 (s, 2H), 6.49 (s, 1H), 7.33 (s, 1H), 7.40 (s, 1H). MS Calcd.: 443; MS Found: 444 (M + 1). |

| # | Structure | Analytical data |
|---|---|---|
| 12/8 | 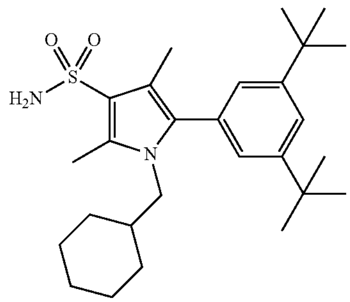 [SMILES: Cc1c(S(N)(=O)=O)c(C)n(CC2CCCCC2)c1-c1cc(C(C)(C)C)cc(C(C)(C)C)c1] | ¹H-NMR (300 MHz, CDCl₃) δ: 0.59-0.63 (m, 2H), 0.98 (m, 3H), 1.25-1.30 (m, 3H), 1.33 (s, 21H), 1.49-1.54 (m, 3H), 2.14 (s, 3H), 2.53 (s, 3H), 3.58 (d, J = 6.9 Hz, 2H), 4.68 (s, 2H), 7.05 (d, J = 1.8 Hz, 2H), 7.39 (m, 1H). MS Calcd.: 458; MS Found: 459 (M + 1). |
| 12/9 | 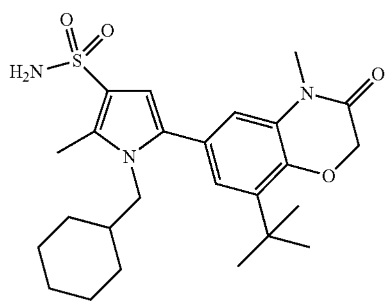 [SMILES: Cc1c(S(N)(=O)=O)cc(-c2cc3c(c(C(C)(C)C)c2)OCC(=O)N3C)n1CC1CCCCC1] | ¹H-NMR (400 MHz, CDCl₃) δ: 0.68-0.71 (m, 2H), 1.02-1.04 (m, 3H), 1.39-1.44 (m, 12H), 1.56-1.60 (m, 3H), 2.55 (s, 3H), 3.35 (s, 3H), 3.71-3.72 (d, J = 6.8 Hz, 2H), 4.62 (s, 2H), 4.67 (s, 2H), 6.45 (s, 1H), 6.82 (s, 1H), 6.96 (s, 1H). MS Calcd.: 473; MS Found: 474 (M + 1). |
| 12/10 | 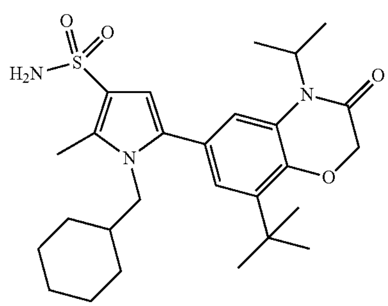 [SMILES: Cc1c(S(N)(=O)=O)cc(-c2cc3c(c(C(C)(C)C)c2)OCC(=O)N3C(C)C)n1CC1CCCCC1] | ¹H-NMR (400 MHz, CDCl₃) δ: 0.69-0.72 (m, 2H), 1.04 (m, 3H), 1.38-1.45 (m, 12H), 1.54-1.60 (m, 9H), 2.55 (s, 3H), 3.70-3.72 (d, J = 6.8 Hz, 2H), 4.48 (s, 2H), 4.62-4.68 (m, 3H), 6.44 (s, 1H), 6.93 (s, 1H), 6.97 (s, 1H). MS Calcd.: 501; MS Found: 502 (M + 1). |
| 12/11 | 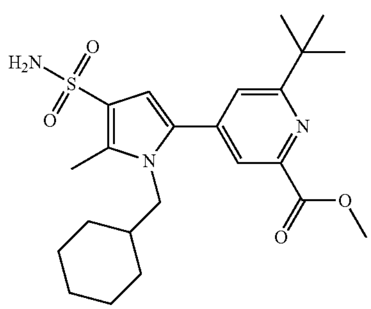 [SMILES: COC(=O)c1cc(-c2cc(S(N)(=O)=O)c(C)n2CC2CCCCC2)cc(C(C)(C)C)n1] | n.d. |
| 12/12 | 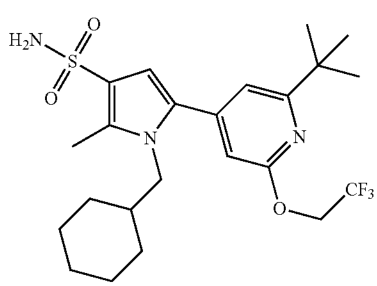 [SMILES: Cc1c(S(N)(=O)=O)cc(-c2cc(OCC(F)(F)F)nc(C(C)(C)C)c2)n1CC1CCCCC1] | ¹H-NMR (400 MHz, CDCl₃) δ: 0.66-0.84 (2H, m), 1.02-1.04 (3H, m), 1.34-1.37 (14H, m), 1.57 (1H, m), 2.55 (3H, s), 3.82 (2H, d, J = 7.2 Hz), 4.69 (2H, s), 4.82 (2H, q, J = 8.8 Hz), 6.57 (1H, s), 6.60 (1H, d, J = 1.2 Hz), 6.92 (1H, d, J = 1.2 Hz). MS Calcd.: 487.2; MS Found: 488.1 (M + 1)⁺. |

| # | Structure | Analytical data |
|---|---|---|
| 12/13 | 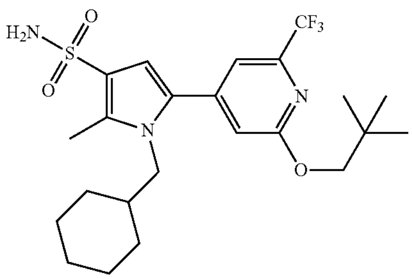 [SMILES: Cc1c(S(N)(=O)=O)cc(-c2cc(OCC(C)(C)C)nc(C(F)(F)F)c2)n1CC1CCCCC1] | ¹H-NMR (300 MHz, CDCl₃) δ: 0.69-0.72 (2H, m), 0.98-1.04 (12H, m), 1.35-1.39 (3H, m), 1.57 (3H, m), 2.55 (3H, s), 3.84 (2H, d, J = 6.9 Hz), 4.07 (2H, s), 4.74 (2H, s), 6.64 (1H, s), 6.86 (1H, s), 7.19 (1H, s). MS Calcd.: 487.2; MS Found: 488.2 (M + 1)⁺. |
| 12/14 | 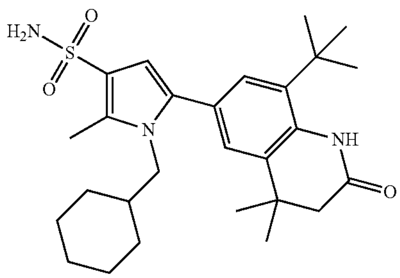 [SMILES: Cc1c(S(N)(=O)=O)cc(-c2cc(C(C)(C)C)c3c(c2)C(C)(C)CC(=O)N3)n1CC1CCCCC1] | ¹H-NMR (400 MHz, CDCl₃) δ: 7.81 (s, 1H), 7.18 (d, J = 2.0 Hz, 1H), 7.15 (d, J = 1.2 Hz, 1H), 6.45 (s, 1H), 4.73 (s, 2H), 3.69 (d, J = 7.2 Hz, 2H), 2.54 (s, 3H), 2.52 (s, 2H), 1.59-1.57 (m, 3H), 1.46 (s, 9H), 1.43-133 (m, 9H), 1.05-1.02 (m, 3H), 0.74-0.66 (m, 2H). MS Calcd.: 485.3; MS Found: 486.2 (M + 1). |
| 12/15 | 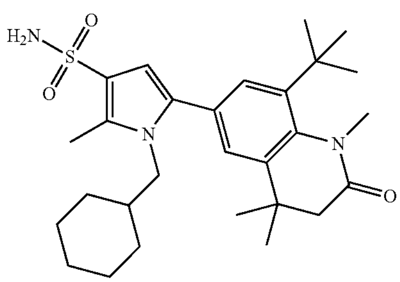 [SMILES: Cc1c(S(N)(=O)=O)cc(-c2cc(C(C)(C)C)c3c(c2)C(C)(C)CC(=O)N3C)n1CC1CCCCC1] | ¹H NMR (400 MHz, CDCl₃) δ: 7.32 (d, J = 2.0 Hz, 1H), 7.03 (d, J = 2.0 Hz, 1H), 6.47 (s, 1H), 4.68 (s, 2H), 3.73 (d, J = 7.2 Hz, 2H), 3.28 (s, 3H), 2.55-2.53 (m, 5H), 1.48-1.44 (m, 3H), 1.44 (m, 9H), 1.42-1.15 (m, 9H), 1.15-0.99 (m, 3H), 0.73-0.64 (m, 2H). MS Calcd.: 499.3; MS Found: 500.1 (M + 1). |
| 12/16 | 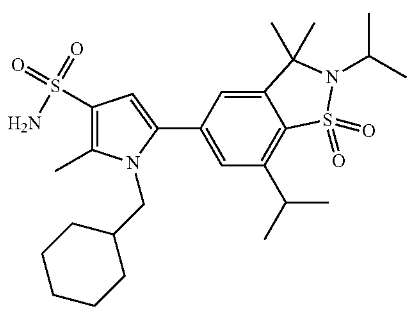 [SMILES: Cc1c(S(N)(=O)=O)cc(-c2cc(C(C)C)c3c(c2)C(C)(C)N(C(C)C)S3(=O)=O)n1CC1CCCCC1] | ¹H-NMR (300 MHz, CDCl₃) δ: 7.23 (s, 1H), 7.04 (s, 1H), 6.47 (s, 1H), 4.64 (s, 2H), 3.74-3.65 (m, 4H), 2.48 (s, 3H), 1.57 (d, J = 6.9 Hz, 6H), 1.51 (m, 9H), 1.30-1.18 (m, 9H), 0.95 (m, 3H), 0.61-0.54 (m, 2H). MS Calcd.: 535.3; MS Found: 536.0 (M + 1). |
| 12/17 | 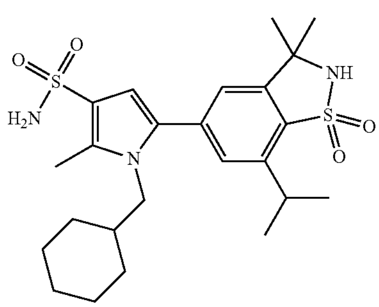 [SMILES: Cc1c(S(N)(=O)=O)cc(-c2cc(C(C)C)c3c(c2)C(C)(C)NS3(=O)=O)n1CC1CCCCC1] | ¹H-NMR (300 MHz, CDCl₃) δ: 7.26 (s, 1H), 7.07 (s, 1H), 6.49 (s, 1H), 4.70 (s, 2H), 4.59 (s, 1H), 3.69-3.55 (m, 3H), 2.49 (s, 3H), 1.65 (s, 6H), 1.59-1.49 (m, 3H), 1.37-1.18 (m, 9H), 0.95 (m, 3H), 0.59-0.55 (m, 2H). MS Calcd.: 493.2; MS Found: 494.2 (M + 1). |

| # | Structure | Analytical data |
|---|---|---|
| 12/18 | 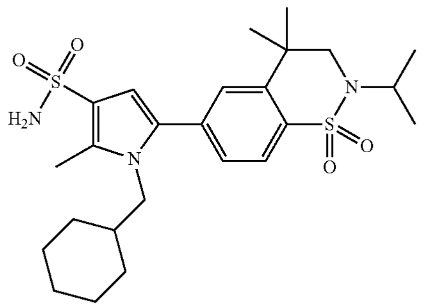 [SMILES: Cc1c(S(N)(=O)=O)cc(-c2ccc3c(c2)C(C)(C)CN(C(C)C)S3(=O)=O)n1CC1CCCCC1] | ¹H-NMR (300 MHz, CDCl₃) δ: 7.80 (d, J = 8.4 Hz, 1H), 7.22 (s, 2H), 6.43 (s, 1H), 4.69 (s, 2H), 4.50-4.41 (m, 1H), 3.67 (d, J = 6.9 Hz, 2H), 3.28 (s, 3H), 2.48 (s, 3H), 1.51-1.49 (m, 3H), 1.30 (s, 6H), 1.22-1.19 (m, 9H), 0.95 (m, 3H), 0.57-0.53 (m, 2H). MS Calcd.: 507.2; MS Found: 507.9 (M + 1). |
| 12/19 | 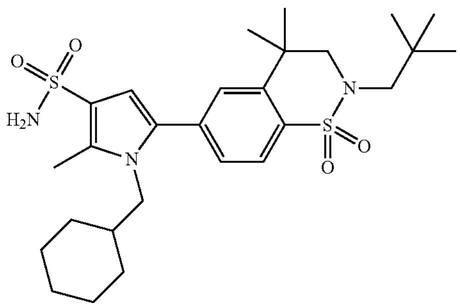 [SMILES: Cc1c(S(N)(=O)=O)cc(-c2ccc3c(c2)C(C)(C)CN(CC(C)(C)C)S3(=O)=O)n1CC1CCCCC1] | ¹H-NMR (300 MHz, CDCl₃) δ: 7.91 (d, J = 8.3 Hz, 1H), 7.32 (s, 2H), 6.52 (s, 1H), 4.71 (s, 2H), 3.77 (d, J = 6.9 Hz, 2H), 3.65 (s, 2H), 3.19 (s, 2H), 2.57 (s, 3H), 1.59 (m, 3H), 1.42-1.341 (m, 9H), 1.06 (m, 12H), 0.67-0.64 (m, 2H). MS Calcd.: 535.2; MS Found: 535.9 (M + 1). |
| 12/20 | 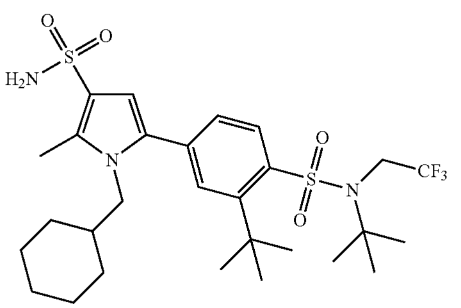 [SMILES: Cc1c(S(N)(=O)=O)cc(-c2ccc(S(=O)(=O)N(CC(F)(F)F)C(C)(C)C)c(C(C)(C)C)c2)n1CC1CCCCC1] | ¹H-NMR (400 MHz, CDCl₃) δ: 7.83 (d, J = 6.4 Hz, 1H), 7.60 (d, J = 1.2 Hz, 1H), 7.24 (d, J = 1.6 Hz, 1H), 6.55 (s, 1H), 4.70 (s, 2H), 4.22 (br d, J = 6.8 Hz, 2H), 3.77 (d, J = 5.6 Hz, 1H), 2.55 (s, 3H), 1.62 (s, 9H), 1.55-1.57 (m, 3H), 1.40 (s, 9H), 1.31-1.34 (m, 3H). 0.97-1.01 (m, 3H), 0.60-0.66 (m, 2H). MS Calcd.: 605.3; MS Found: 606.7 (M + 1). |
| 12/21 | 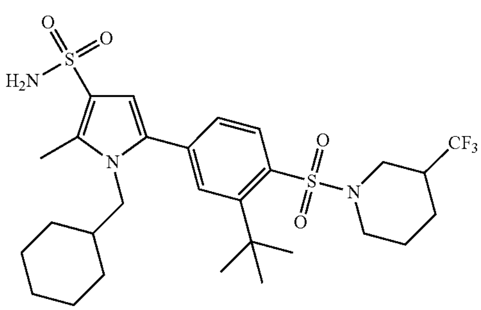 [SMILES: Cc1c(S(N)(=O)=O)cc(-c2ccc(S(=O)(=O)N3CCCC(C(F)(F)F)C3)c(C(C)(C)C)c2)n1CC1CCCCC1] | ¹H-NMR (400 MHz, CDCl₃) δ: 7.70 (d, J = 6.8 Hz, 1H), 7.56 (d, J = 1.2 Hz, 1H), 7.18 (d, J = 1.2 Hz, 1H), 6.47 (s, 1H), 4.69 (br s, 2H), 3.93-3.97 (m, 1H), 3.82 (br d, J = 9.6 Hz, 1H), 3.71 (d, J = 5.2 Hz, 2H), 2.71-2.77 (m, 2H), 2.49 (s, 3H), 2.32-2.42 (m, 1H), 2.04-2.07 (m, 1H), 1.80-1.83 (m, 1H), 0.65-1.66 (m, 22H). MS Calcd.: 603.2; MS Found: 604.3 (M + 1). |
| 12/22 | 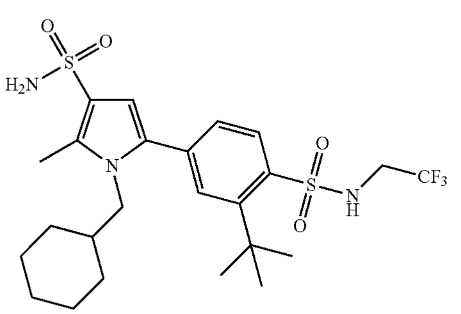 [SMILES: Cc1c(S(N)(=O)=O)cc(-c2ccc(S(=O)(=O)NCC(F)(F)F)c(C(C)(C)C)c2)n1CC1CCCCC1] | ¹H-NMR (400 MHz, CDCl₃) δ: 8.12 (d, J = 6.4 Hz, 1H), 7.61 (d, J = 1.2 Hz, 1H), 7.28 (d, J = 1.2 Hz, 1H), 6.54 (s, 1H), 5.20 (t, J = 5.6 Hz, 1H), 4.75 (br s, 2H), 3.73-3.80 (m, 4H), 2.56 (s, 3H), 1.60 (s, 9H), 1.56-1.59 (m, 3H), 1.30-1.33 (m, 3H), 0.97-1.00 (m, 3H), 0.60-0.65 (m, 2H). MS Calcd.: 549.2; MS Found: 550.0 (M + 1). |

| # | Structure | Analytical data |
|---|---|---|
| 12/23 | 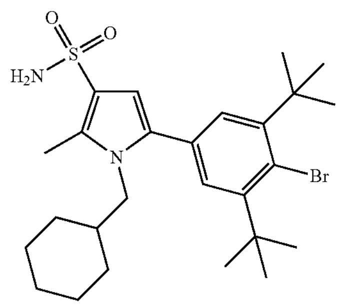 [SMILES: Cc1c(S(N)(=O)=O)cc(-c2cc(C(C)(C)C)c(Br)c(C(C)(C)C)c2)n1CC1CCCCC1] | $^1$H-NMR (300 MHz, CDCl$_3$) δ: 7.31 (s, 2H), 6.49 (s, 1H) 4.72 (s. 2H), 3.72 (d, 2H, J = 7.5 Hz), 2.56 (s, 3H), 1.61-1.58 (m, 21H), 1.40-1.36 (m, 3H), 1.05 (m, 3H) 0.70 (m, 2H). MS Calcd.: 522; MS Found: 523 (M + 1). |
| 12/24 | 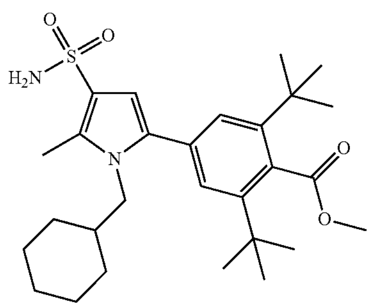 [SMILES: COC(=O)c1c(C(C)(C)C)cc(-c2cc(S(N)(=O)=O)c(C)n2CC2CCCCC2)cc1C(C)(C)C] | $^1$H-NMR (300 MHz, CDCl$_3$): δ 7.31 (s, 2H), 6.45 (s, 1H), 4.66 (s, 2H), 3.86 (s, 3H), 3.72 (d, 2H, J = 6.9 Hz), 2.54 (s, 3H), 1.61-1.58 (m, 3H), 1.39-1.34 (m, 21H), 1.03-1.05 (m, 3H), 0.66-0.69 (m, 2H). MS Calcd.: 502; MS Found: 503 (M + 1). |
| 12/25 | 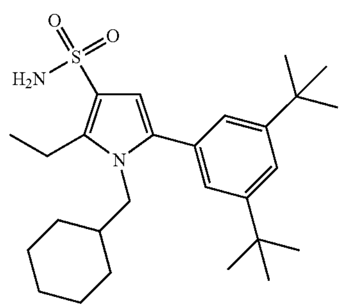 [SMILES: CCc1c(S(N)(=O)=O)cc(-c2cc(C(C)(C)C)cc(C(C)(C)C)c2)n1CC1CCCCC1] | $^1$H NMR (300 MHz, CDCl$_3$) δ: 0.62-0.66 (m, 2H), 0.90-0.98 (m, 3H), 1.23-1.38 (m, 24H), 1.51-1.55 (m, 3H), 2.96-3.03 (m, 2H), 3.72 (d, J = 6.6 Hz, 2H), 4.67 (s, 2H), 6.45 (s, 1H), 7.15 (d, J = 1.5 Hz, 2H), 7.41 (s, 1H). MS Calcd.: 458.3; MS Found: 459.4 (M + 1). |
| 12/26 | 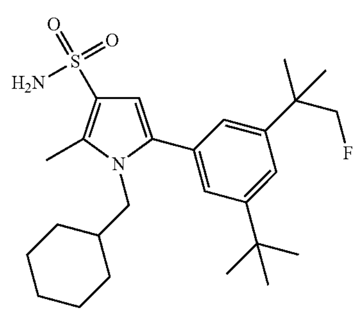 [SMILES: Cc1c(S(N)(=O)=O)cc(-c2cc(C(C)(C)C)cc(C(C)(C)CF)c2)n1CC1CCCCC1] | $^1$H NMR (300 MHz, CDCl$_3$) δ: 7.21 (s, 2H), 7.00 (s, 1H), 6.46 (s, 1H), 4.66 (s, 2H), 3.75 (d, J = 9.3 Hz, 2H), 2.92 (d, J = 20.7 Hz, 2H), 2.54 (s, 3H), 1.55-1.51 (m, 3H), 1.37-1.30 (m, 18H), 0.99-0.94 (m, 3H), 0.64-0.59 (m, 2H). MS Calcd.: 462.3; MS Found: 463.4 (M + 1). |
| 12/27 | 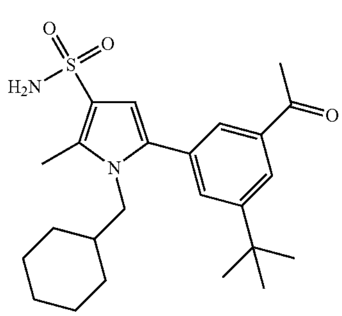 [SMILES: CC(=O)c1cc(-c2cc(S(N)(=O)=O)c(C)n2CC2CCCCC2)cc(C(C)(C)C)c1] | $^1$H-NMR (400 MHz, CDCl$_3$) δ: 8.00-8.01 (m, 1H), 7.71-7.73 (m, 1H), 7.56-7.58 (m, 1H), 6.53 (s, 1H), 4.70-4.72 (m, 2H), 3.75 (d, 2H, J = 9.2 Hz), 2.64 (s, 3H), 2.56 (s, 3H), 1.56-1.59 (m, 3H), 1.35-1.38 (m, 12H), 0.98-1.01 (m, 3H), 0.62-0.65 (m, 2H). MS Calcd.: 430; MS Found: 431 (M + 1)$^+$. |

| # | Structure | Analytical data |
|---|---|---|
| 12/28 | 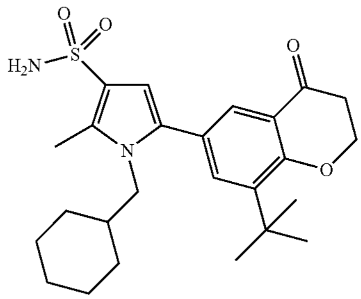 [SMILES: Cc1c(S(N)(=O)=O)cc(-c2cc3c(c(C(C)(C)C)c2)OCCC3=O)n1CC1CCCCC1] | ¹H-NMR (400 MHz, CDCl₃) δ: 7.75-7.76 (m, 1H), 7.41-7.42 (m, 1H), 6.44 (s, 1H), 4.60-4.69 (m, 3H), 3.71 (d, 2H, J = 9.2 Hz), 2.87 (t, 2H, J = 8.8 Hz), 2.54 (s, 3H), 1.58 (s, 3H), 1.37-1.41 (m, 12H), 1.01-1.07 (m, 3H), 0.61-0.69 (m, 2H). MS Calcd.: 458; MS Found: 459 (M + 1)⁺. |
| 12/29 | 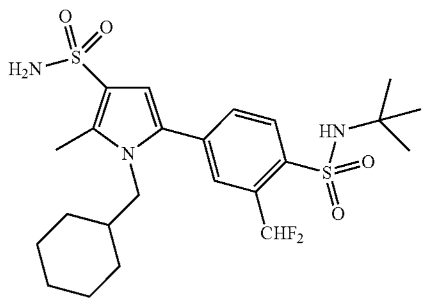 [SMILES: Cc1c(S(N)(=O)=O)cc(-c2ccc(S(=O)(=O)NC(C)(C)C)c(C(F)F)c2)n1CC1CCCCC1] | ¹H-NMR (400 MHz, CDCl₃) δ: 8.13 (d, J = 8.4 Hz, 1H), 7.80 (s, 1H), 7.55 (d, J = 10.8 Hz), 7.53 (t, J = 54.8 Hz, 1H), 6.62 (s, 1H), 4.70 (br s, 2H), 4.54 (s, 1H), 3.81 (d, J = 6.8 Hz, 2H), 2.56 (s, 3H), 1.55-1.58 (m, 3H), 1.32-1.35 (m, 3H), 1.26 (s, 9H), 0.96-1.00 (m, 3H), 0.60-0.65 (m, 2H). MS Calcd.: 517; MS Found: 518 (M + 1). |
| 12/30 | 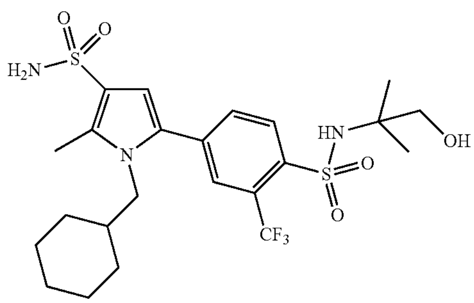 [SMILES: Cc1c(S(N)(=O)=O)cc(-c2ccc(S(=O)(=O)NC(C)(C)CO)c(C(F)(F)F)c2)n1CC1CCCCC1] | n.d. |
| 12/31 | 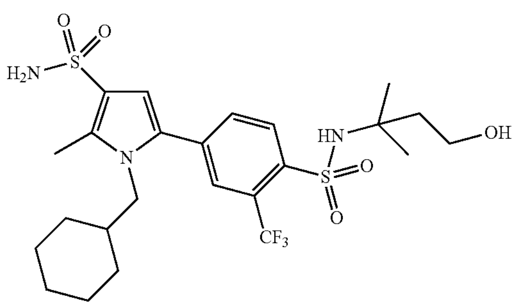 [SMILES: Cc1c(S(N)(=O)=O)cc(-c2ccc(S(=O)(=O)NC(C)(C)CCO)c(C(F)(F)F)c2)n1CC1CCCCC1] | ¹H NMR (400 MHz, CDCl₃) δ: 8.32 (d, 1H, J = 8.4 Hz), 7.78 (s, 1H), 7.61 (dd, 1H, J = 1.6 Hz, J = 8.4 Hz), 6.63 (s, 1H), 6.32 (s, 1H), 4.76 (s, 2H), 3.93-3.91 (m, 2H), 3.79 (d, 2H, J = 6.8 Hz), 2.57 (s, 3H), 1.78 (t, 2H, J = 1.8 Hz), 1.74 (s, 1H), 1.59 (s, 3H), 1.35-1.30 (m, 9H), 1.02-0.98 (m, 3H), 0.66-0.61 (m, 2H). MS Calcd.: 565; MS Found: 566 (M + 1)⁺. |
| 12/32 | 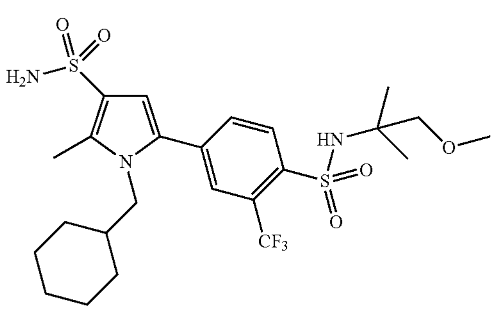 [SMILES: COCC(C)(C)NS(=O)(=O)c1ccc(-c2cc(S(N)(=O)=O)c(C)n2CC2CCCCC2)cc1C(F)(F)F] | ¹H NMR (400 MHz, CDCl₃) δ: 8.32 (d, 1H, J = 8.0 Hz), 7.79 (s, 1H), 7.62 (d, 1H, J = 8.0 Hz), 6.62 (s, 1H), 5.30 (s, 1H), 4.73 (s, 2H), 3.80 (d, 2H, J = 6.8 Hz), 3.26 (s, 3H), 3.17 (s, 2H), 2.57 (s, 3H), 1.58-1.54 (m, 3H), 1.35-1.32 (m, 3H), 1.23 (s, 6H), 1.02-0.98 (m, 3H), 0.66-0.62 (m, 2H). MS Calcd.: 565; MS Found: 566 (M + 1)⁺. |

| # | Structure | Analytical data |
|---|---|---|
| 12/33 | 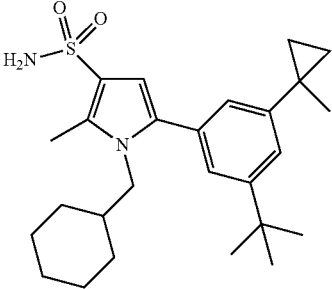 [SMILES: Cc1c(S(N)(=O)=O)cc(-c2cc(C(C)(C)C)cc(C3(C)CC3)c2)n1CC1CCCCC1] | ¹H-NMR (400 MHz, CDCl₃) δ: 7.28 (s, 1H), 7.12 (s, 1H), 7.00 (s, 1H), 6.45 (s, 1H), 4.67 (s, 2H), 3.71 (d, 2H, J = 6.8 Hz), 2.54 (s, 3H), 1.54-1.56 (m, 3H), 1.42 (s, 3H), 1.32-1.40 (m, 12H), 0.95-1.07 (m, 3H), 0.85-0.87 (m, 2H), 0.74-0.76 (m, 2H), 0.62-0.68 (m, 2H). MS Calcd.: 442; MS Found: 443 (M + 1). |
| 12/34 | 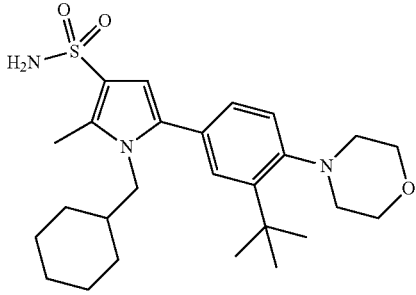 [SMILES: Cc1c(S(N)(=O)=O)cc(-c2ccc(N3CCOCC3)c(C(C)(C)C)c2)n1CC1CCCCC1] | ¹H-NMR (300 MHz, CDCl₃) δ: 7.30 (d, J = 8.0 Hz, 1H), 7.23 (s, 1H), 7.09 (d, J = 8.0 Hz, 1H), 6.37 (s, 1H), 4.58 (s, 2H), 3.87-3.64 (m, 6H), 3.00 (t, 2H), 2.66 (m, 2H), 2.47 (s, 3H) 1.48 (s, 3H), 1.38 (s, 9H), 1.29-1.19 (m, 3H), 0.94-0.92 (m, 3H), 0.61-0.58 (m, 2H). MS Calcd.: 473; MS Found: 474 (M + 1). |
| 12/35 | 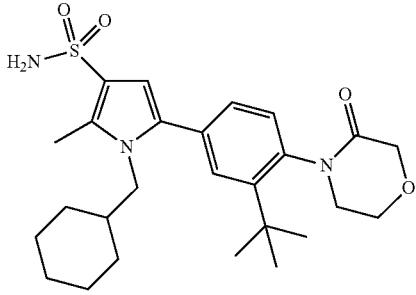 [SMILES: Cc1c(S(N)(=O)=O)cc(-c2ccc(N3CCOCC3=O)c(C(C)(C)C)c2)n1CC1CCCCC1] | ¹H-NMR (300 MHz, CDCl₃) δ: 7.47 (s, 1H), 7.20 (d, J = 8.1 Hz, 1H), 7.09 (d, J = 8.1 Hz, 1H), 6.46 (s, 1H), 4.66 (s, 2H), 4.33 (m, 2H), 4.10-4.03 (m, 4H), 3.83-3.73 (m, 3H), 3.67-3.60 (m, 1H), 2.53 (s, 3H), 1.56-1.50 (m, 3H), 1.35-1.19 (m, 12H), 1.03-0.97 (m, 3H), 0.73-0.62 (m, 2H). MS Calcd.: 487; MS Found: 488 (M + 1). |
| 12/36 | 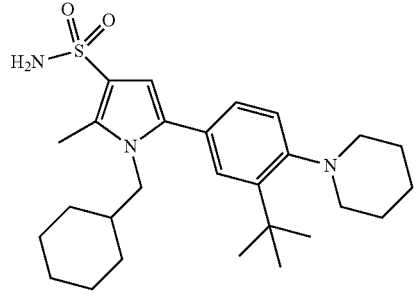 [SMILES: Cc1c(S(N)(=O)=O)cc(-c2ccc(N3CCCCC3)c(C(C)(C)C)c2)n1CC1CCCCC1] | ¹H-NMR (300 MHz, CDCl₃) δ: 7.26 (d, J = 8.4 Hz, 1H), 7.19 (s, 1H), 7.05 (d, J = 8.4 Hz, 1H), 6.37 (s, 1H), 4.58 (s, 2H), 3.64 (d, J = 6.9 Hz, 2H), 2.81-2.77 (m, 2H), 2.67-2.58 (m, 2H), 2.46 (s, 3H) 1.79-1.63 (m, 5H), 1.48 (m, 2H), 1.36 (s, 9H), 1.29-1.15 (m, 5H), 0.93-0.81 (m, 3H), 0.65-0.57 (m, 2H). MS Calcd.: 471; MS Found: 472 (M + 1). |
| 12/37 | 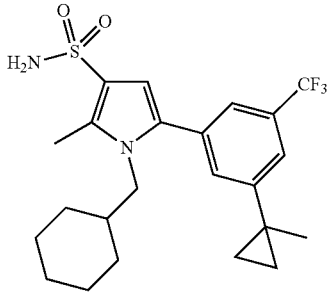 | ¹H-NMR (400 MHz, CDCl₃) δ: 7.48 (s, 1H), 7.36 (s, 2H), 6.50 (s, 1H), 4.66 (s, 2H), 3.72 (d, 2H), 2.55 (s, 3H), 1.57 (m, 4H), 1.44 (s, 3H), 1.37 (m, 3H), 1.00 (m, 2H), 0.92 (m, 2H), 0.85 (m, 2H), 0.64 (m, 2H). MS Calcd.: 454; MS Found: 455 (M + 1). |

| # | Structure | Analytical data |
|---|---|---|
| 12/38 | 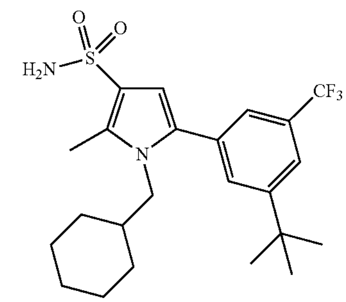 [SMILES: Cc1c(S(N)(=O)=O)cc(-c2cc(C(C)(C)C)cc(C(F)(F)F)c2)n1CC1CCCCC1] | ¹H-NMR (400 MHz, CDCl₃) δ: 7.62 (s, 1H), 7.52 (s, 1H), 7.39 (s, 1H), 6.51 (s, 1H), 4.67 (s, 2H), 3.71 (t, 2H), 2.55 (s, 3H), 1.55 (m, 6H), 1.34 (m, 9H), 0.99 (m, 3H), 0.63 (m, 2H). MS Calcd.: 456; MS Found: 457 (M + 1). |
| 12/39 | 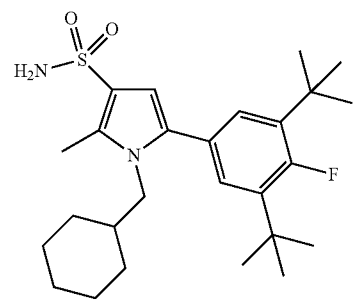 [SMILES: Cc1c(S(N)(=O)=O)cc(-c2cc(C(C)(C)C)c(F)c(C(C)(C)C)c2)n1CC1CCCCC1] | ¹H-NMR (300 MHz, CDCl₃) δ: 7.10 (d, J = 6.9 Hz, 2H), 6.44 (s, 1H), 4.68 (s, 2H), 3.67 (d, J = 6.9 Hz, 2H), 2.53 (s, 3H), 1.57 (m, 3H), 1.39 (m, 21H), 1.02 (m, 3H), 0.70 (m, 2H). MS Calcd.: 462; MS Found: 463 (M + 1). |
| 12/40 | 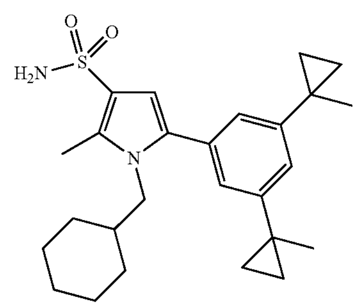 [SMILES: Cc1c(S(N)(=O)=O)cc(-c2cc(C3(C)CC3)cc(C3(C)CC3)c2)n1CC1CCCCC1] | ¹H-NMR (300 MHz, CDCl₃) δ: 7.15 (s, 1H), 6.98 (d, J = 1.5 Hz, 2H), 6.43 (s, 1H), 4.66 (s, 2H), 3.70 (d, J = 6.6 Hz, 2H), 2.53 (s, 3H), 1.25-1.40 (m, 12H), 1.01 (m, 3H), 0.72-0.86 (m, 10H). MS Calcd.: 440; MS Found: 441 (M + 1). |
| 12/41 | 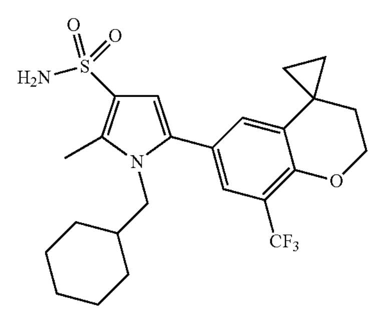 [SMILES: Cc1c(S(N)(=O)=O)cc(-c2cc(C(F)(F)F)c3c(c2)C2(CCO3)CC2)n1CC1CCCCC1] | ¹H-NMR (300 MHz, CDCl₃) δ: 0.65-0.68 (m, 2H), 0.87-0.95 (m, 2H), 0.98-1.06 (m, 3H), 1.23-1.25 (m, 5H), 1.31-1.42 (m, 3H), 1.93 (t, J = 5.1 Hz, 2H), 2.51 (s, 3H), 3.64 (d, J = 7.2 Hz, 2H), 4.43 (t, J = 5.1 Hz, 2H), 4.77 (s, 2H), 6.38 (s, 1H), 6.73 (d, J = 1.8 Hz, 1H), 7.25 (d, J = 1.8 Hz, 1H). MS Calcd.: 482; MS Found: 483 (M + 1)⁺. |
| 12/42 | 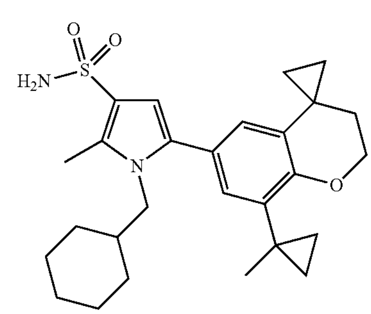 [SMILES: Cc1c(S(N)(=O)=O)cc(-c2cc(C3(C)CC3)c3c(c2)C2(CCO3)CC2)n1CC1CCCCC1] | ¹H-NMR (400 MHz, CDCl₃) δ: 0.63-0.73 (6H, m), 0.84-0.87 (2H, m), 0.98-1.04 (5H, m), 1.32 (3H, s), 1.35-1.55 (3H, m), 1.55-1.57 (3H, m), 1.89-1.92 (2H, t, J = 10 Hz), 2.51 (3H, s), 3.64-3.66 (2H, d, J = 7.2 Hz), 4.37-4.40 (2H, t, J = 10.4 Hz), 4.62 (2H, s), 6.34 (1H, s), 6.42 (1H, s), 6.96 (1H, s). MS Calcd.: 468; MS Found: 469 (M + 1). |

| # | Structure | Analytical data |
|---|---|---|
| 12/43 | 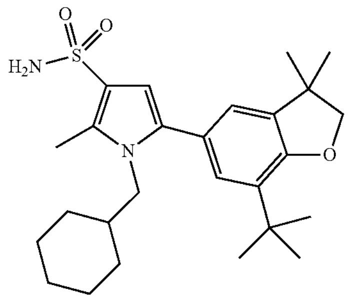 [SMILES: Cc1c(S(N)(=O)=O)cc(-c2cc(C(C)(C)C)c3c(c2)C(C)(C)CO3)n1CC1CCCCC1] | ¹H-NMR (300 MHz, CDCl₃) δ: 6.98 (s, 1H), 6.88 (s, 1H), 6.41 (s, 1H), 4.66 (s, 2H), 4.27 (s, 2H), 3.67 (d, J = 6.6 Hz, 2H), 2.52 (s, 3H), 1.56 (s, 3H), 1.35-1.25 (m, 18H), 1.01 (m, 3H), 0.70 (m, 2H). Calcd.: 458; MS Found: 459 (M + 1). |
| 12/44 | 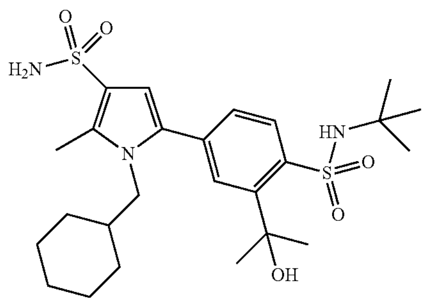 [SMILES: Cc1c(S(N)(=O)=O)cc(-c2ccc(S(=O)(=O)NC(C)(C)C)c(C(C)(C)O)c2)n1CC1CCCCC1] | ¹H-NMR (400 MHz, CDCl₃) δ: 8.21 (d, 1H), 7.29 (m, 2H), 6.55 (s, 1H), 6.26 (s, 1H), 4.70 (s, 2H), 4.41 (br s, 1H), 3.76 (d, 2H), 2.55 (s, 3H), 1.69 (s, 6H), 1.56 (m, 3H), 1.32 (m, 3H), 1.28 (s, 9H), 0.99 (m, 3H), 0.60 (m, 2H). Calcd.: 525; MS Found: 508 (M − H₂O + 1). |
| 12/45 | 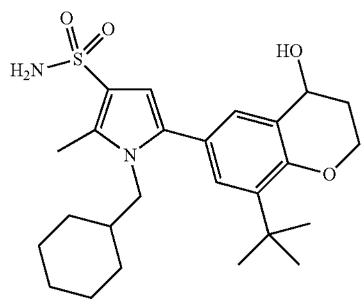 [SMILES: Cc1c(S(N)(=O)=O)cc(-c2cc3c(c(C(C)(C)C)c2)OCCC3O)n1CC1CCCCC1] | ¹H-NMR (400 MHz, CDCl₃) δ: 7.13 (s, 1H), 6.39 (s, 1H), 4.78-4.80 (m, 1H), 4.64-4.66 (m, 2H), 4.29-4.38 (m, 2H), 3.69 (d, 2H, J = 6.8 Hz), 2.52 (s, 3H), 2.04-2.17 (m, 2H), 1.81-1.83 (m, 1H), 1.53-1.56 (m, 3H), 1.33-1.43 (m, 12H), 1.02-1.04 (m, 3H), 0.67-0.70 (m, 2H). MS Calcd.: 460; MS Found: 461 (M + 1)⁺. |

Example 13

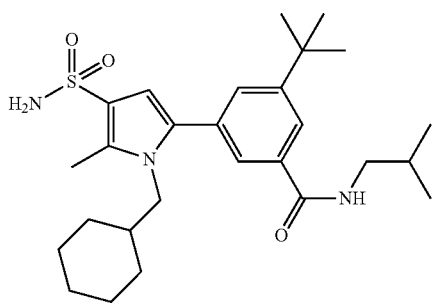

13

Step 1: tert-Butyl 3-(tert-butyl)-5-(1-(cyclohexylmethyl)-5-methyl-4-sulfamoyl-1H-pyrrol-2-yl)benzoate (13a)

Using similar procedures as described in Example 1, compound 13a has been prepared.

Step 2: 3-(tert-Butyl)-5-(1-(cyclohexylmethyl)-5-methyl-4-sulfamoyl-1H-pyrrol-2-yl)benzoic acid (13b)

Compound 13a (180 mg, 0.37 mmol) was treated with a mixture of TFA (0.5 mL) and DCM (5 mL) and stirred at rt overnight. After the reaction was complete (monitored by LC-MS), the mixture was concentrated to give compound 13b (145 mg, 91%). ¹H-NMR (400 MHz, CDCl₃) δ: 8.12 (s, 1H), 7.88 (s, 1H), 7.58 (s, 1H), 6.51 (s, 1H), 4.77-4.75 (m, 2H), 3.76 (m, 2H), 2.56 (s, 3H), 1.53 (s, 3H), 1.37-1.35 (m, 12H), 1.00-0.99 (m, 3H), 0.64-0.63 (m, 2H). MS Found: 433 (M+1).

Step 3: 3-(tert-Butyl)-5-(1-(cyclohexylmethyl)-5-methyl-4-sulfamoyl-1H-pyrrol-2-yl)-N-isobutylbenzamide (13)

A mixture of compound 13b (90 mg, 0.21 mmol), DIPEA (134 mg, 1.04 mmol) and HATU (157 mg, 0.41 mmol) in DMF was stirred at rt for 1 h, then 2-methylpropan-1-amine (18 mg, 0.25 mmol) was added. The mixture was stirred at rt overnight and concentrated. The product was isolated by CC to get compound 13 (45 mg, 45%). ¹H-NMR (400 MHz, DMSO-d₆) δ: 8.57 (m, 1H), 7.85 (s, 1H), 7.67 (s, 1H), 7.52 (s, 1H), 6.94 (s, 2H), 6.39 (s, 1H), 3.82 (d, J=5.6 Hz, 2H), 3.09 (s, 2H), 2.45 (s, 3H), 1.85-1.84 (m, 1H), 1.46 (s, 3H), 1.33-1.25 (m, 12H), 0.94-0.88 (m, 9H), 0.66-0.63 (m, 2H). MS Found: 488 (M+1).

Examples 13/1 to 13/14

Using similar procedures as that described in Example 13, the following Examples have been prepared:

| # | Structure | Analytical data |
|---|---|---|
| 13/1 | 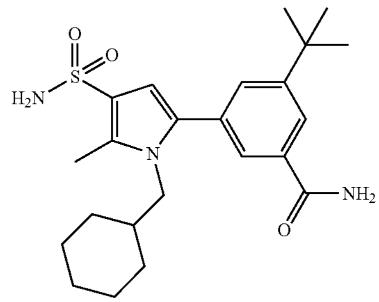 [SMILES: Cc1c(S(N)(=O)=O)cc(-c2cc(C(N)=O)cc(C(C)(C)C)c2)n1CC1CCCCC1] | $^1$H-NMR (400 MHz, DMSO-d$_6$) δ: 8.10 (s, 1H), 7.88 (s, 1H), 7.68 (s, 1H), 7.51 (m, 1H), 7.41 (s, 1H), 6.94 (s, 2H), 6.37 (s, 1H), 3.82 (d, J = 5.6 Hz, 3H), 2.45 (s, 3H), 1.46 (s, 3H), 1.33-1.27 (m, 12H), 0.94 (m, 3H), 0.63 (m, 2H). MS Found: 432 (M + 1). |
| 13/2 | 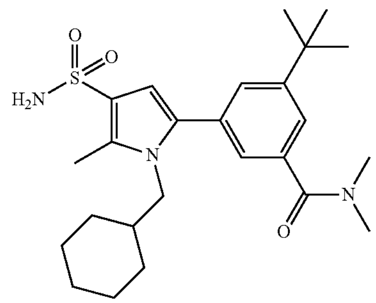 [SMILES: Cc1c(S(N)(=O)=O)cc(-c2cc(C(=O)N(C)C)cc(C(C)(C)C)c2)n1CC1CCCCC1] | $^1$H-NMR (400 MHz, DMSO-d$_6$) δ: 7.42 (s, 1H), 7.37 (s, 1H), 7.15 (s, 1H), 6.94 (s, 2H), 6.34 (s, 1H), 3.82 (s, 2H), 2.99 (s, 3H), 2.91 (s, 3H), 2.44 (s, 3H), 1.45 (m, 3H), 1.32-1.23 (m, 12H), 0.92-0.93 (m, 3H), 0.62-0.61 (m, 2H). MS Found: 460 (M + 1). |
| 13/3 | 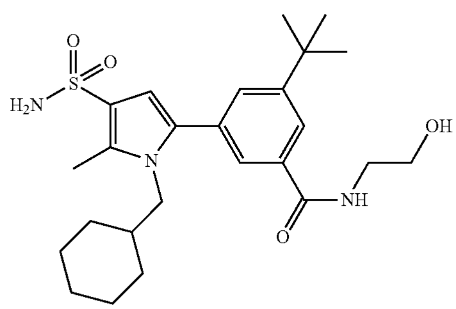 [SMILES: Cc1c(S(N)(=O)=O)cc(-c2cc(C(=O)NCCO)cc(C(C)(C)C)c2)n1CC1CCCCC1] | $^1$H-NMR (400 MHz, DMSO-d$_6$) δ: 8.60-8.57 (m, 1H), 7.86 (s, 1H), 7.66 (s, 1H), 7.52 (s, 1H), 6.94 (s, 2H), 6.39 (s, 1H), 3.83 (d, J = 5.6 Hz, 3H), 3.51 (d, J = 4.8 Hz, 3H), 3.34 (d, J = 4.4 Hz, 2H), 1.47-1.46 (m, 3H), 1.33-1.25 (m, 13H), 0.94-0.93 (m, 3H), 0.63-0.62 (m, 2H). MS Found: 476 (M + 1). |
| 13/4 | 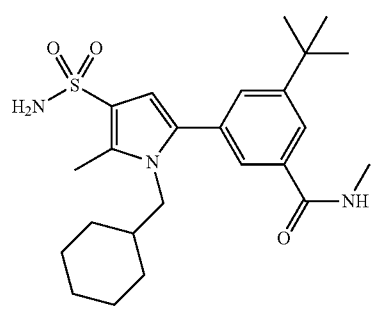 [SMILES: CNC(=O)c1cc(-c2cc(S(N)(=O)=O)c(C)n2CC2CCCCC2)cc(C(C)(C)C)c1] | $^1$H-NMR (400 MHz, CDCl$_3$) δ: 7.81 (s, 1H), 7.47-7.46 (m, 2H), 6.49 (s, 1H), 6.20-6.19 (m, 1H), 4.69-4.66 (m, 2H), 3.74-3.73 (m, 2H), 3.04 (d, J = 4 Hz, 3H), 2.54 (s, 3H), 1.55-1.54 (m, 3H), 1.36-1.32 (m, 12H), 1.02-0.98 (m, 3H), 0.63-0.61 (m, 2H). MS Found: 446 (M + 1). |

| # | Structure | Analytical data |
|---|---|---|
| 13/5 | 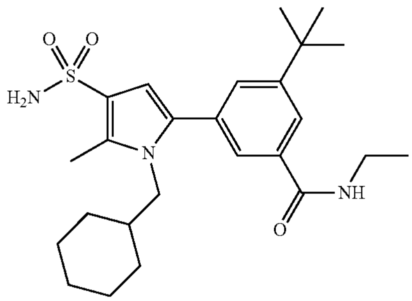 [SMILES: CCNC(=O)c1cc(-c2cc(S(N)(=O)=O)c(C)n2CC2CCCCC2)cc(C(C)(C)C)c1] | ¹H-NMR (400 MHz, CDCl₃) δ: 7.84 (s, 1H), 7.47-7.46 (m, 2H), 6.49 (s, 1H), 6.17-6.16 (m, 1H), 4.73-4.72 (m, 2H), 3.73 (d, J = 6 Hz, 3H), 2.54 (s, 3H), 1.56-1.55 (m, 3H), 1.36-1.33 (m, 12H), 1.29-1.26 (m, 3H), 1.00-0.98 (m, 3H), 0.64-0.61 (m, 2H). MS Found: 460 (M + 1). |
| 13/6 | 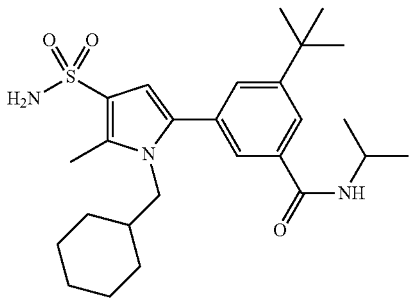 [SMILES: Cc1c(S(N)(=O)=O)cc(-c2cc(C(=O)NC(C)C)cc(C(C)(C)C)c2)n1CC1CCCCC1] | ¹H-NMR (400 MHz, CDCl₃) δ: 7.85-7.84 (m, 1H), 7.46-7.43 (m, 2H), 6.50 (s, 1H), 6.03-6.01 (m, 1H), 4.78-4.77 (m, 2H), 4.32-4.28 (m, 1H), 3.73-3.72 (m, 2H), 2.55 (s, 3H), 1.56-1.55 (m, 3H), 1.38-1.34 (m, 12H), 1.29-1.26 (m, 6H), 1.00-0.99 (m, 3H), 0.64-0.62 (m, 2H). MS Found: 474 (M + 1). |
| 13/7 | 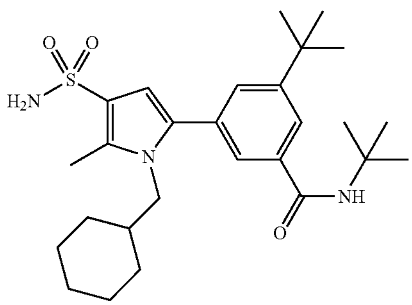 [SMILES: Cc1c(S(N)(=O)=O)cc(-c2cc(C(=O)NC(C)(C)C)cc(C(C)(C)C)c2)n1CC1CCCCC1] | ¹H-NMR (400 MHz, CDCl₃) δ: 7.81-7.80 (m, 1H), 7.47-7.46 (m, 1H), 7.35 (s, 1H) 6.50 (s, 1H), 5.97 (s, 1H), 4.68-4.66 (m, 2H), 3.72 (d, J = 5.6 Hz, 2H), 2.55 (s, 3H), 1.56-1.55 (m, 3H), 1.50 (s, 9H), 1.35-1.34 (m, 12H), 1.01-0.99 (m, 3H), 0.64-0.62 (m, 2H). MS Found: 488 (M + 1). |
| 13/8 | 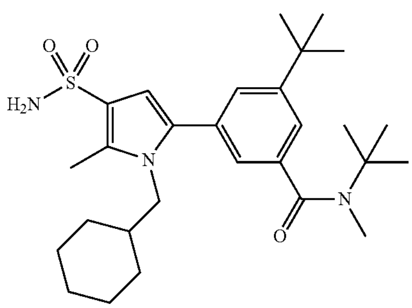 [SMILES: Cc1c(S(N)(=O)=O)cc(-c2cc(C(=O)N(C)C(C)(C)C)cc(C(C)(C)C)c2)n1CC1CCCCC1] | ¹H-NMR (400 MHz, CDCl₃) δ: 7.48 (s, 1H), 7.35 (s, 1H), 7.14 (s, 1H), 6.47 (s, 1H), 4.81-4.80 (m, 2H), 3.73 (d, J = 7.2 Hz, 2H), 2.87 (s, 3H), 2.54 (s, 3H), 1.55-1.51 (m, 12H), 1.40-1.33 (m, 12H), 0.99-0.97 (m, 3H), 0.65-0.62 (m, 2H). MS Found: 502 (M + 1). |
| 13/9 | 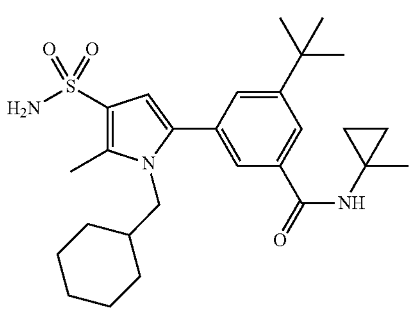 [SMILES: Cc1c(S(N)(=O)=O)cc(-c2cc(C(=O)NC3(C)CC3)cc(C(C)(C)C)c2)n1CC1CCCCC1] | ¹H-NMR (400 MHz, CDCl₃) δ: 7.52 (s, 1H), 7.37 (s, 1H), 7.26 (s, 2H), 6.47 (s, 1H), 4.67-4.66 (m, 2H), 3.75 (d, J = 6 Hz, 2H), 3.11 (s, 3H), 2.54 (s, 3H), 1.56-1.55 (m, 3H), 1.37-1.34 (m, 12H), 0.99-0.98 (m, 3H), 0.64-0.60 (m, 4H), 0.48-0.47 (m, 2H). MS Found: 486 (M + 1). |

| # | Structure | Analytical data |
|---|---|---|
| 13/10 | 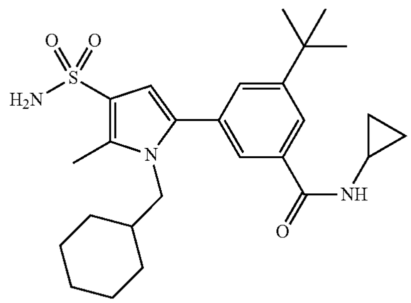 [SMILES: Cc1c(S(N)(=O)=O)cc(-c2cc(C(=O)NC3CC3)cc(C(C)(C)C)c2)n1CC1CCCCC1] | $^1$H-NMR (400 MHz, CDCl$_3$) δ: 7.74 (s, 1H), 7.40 (s, 1H), 7.35 (s, 1H), 6.42 (s, 1H), 6.20 (s, 1H), 4.63 (s, 2H), 3.66 (d, J = 6.8 Hz, 2H), 2.85 (s, 1H), 2.47 (s, 3H), 1.50-1.48 (m, 3H), 1.31-1.18 (m, 12H), 0.93-0.91 (m, 3H), 0.83-0.82 (m, 2H), 0.59-0.53 (m, 4H). MS Found: 472 (M + 1). |
| 13/11 | 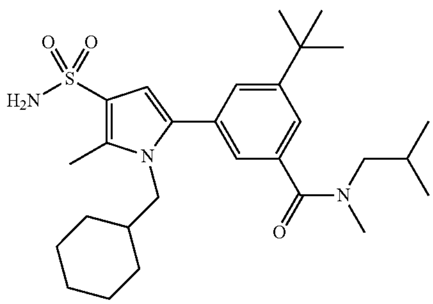 [SMILES: Cc1c(S(N)(=O)=O)cc(-c2cc(C(=O)N(C)CC(C)C)cc(C(C)(C)C)c2)n1CC1CCCCC1] | $^1$H-NMR (400 MHz, CDCl$_3$) δ: 7.43-7.37 (m, 2H), 7.40 (s, 1H), 7.12-7.10 (m, 1H), 6.48 (s, 1H), 4.69-4.68 (m, 2H), 3.74 (s, 2H), 3.41 (d, J = 7.2 Hz, 2H), 3.09 (s, 3H), 2.98-2.90 (m, 2H), 2.55 (s, 3H), 1.56-1.55 (m, 3H), 1.40-1.34 (m, 12H), 1.01-1.00 (m, 6H), 0.78-0.77 (m, 3H), 0.64-0.63 (m, 2H). MS Found: 502 (M + 1). |
| 13/12 | 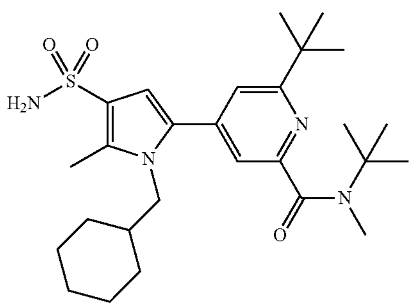 | $^1$H-NMR (300 MHz, CDCl$_3$) δ: 7.30 (d, 1H, J = 1.5 Hz), 7.25 (d, 1H, J = 1.5 Hz), 6.60 (s, 1H), 4.69 (s, 2H), 3.82 (d, 2H, J = 6.9 Hz), 2.90 (d, 3H, J = 2.7 Hz), 2.54 (s, 3H), 1.60 (m, 3H), 1.52 (s, 9H), 1.42 (s, 9H), 1.30-1.38 (m, 3H), 0.97-1.03 (m, 3H), 0.63 (m, 2H). MS Calcd.: 502; MS Found: 503 (M + 1). |
| 13/13 | 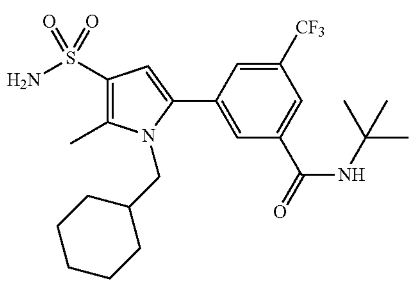 [SMILES: Cc1c(S(N)(=O)=O)cc(-c2cc(C(=O)NC(C)(C)C)cc(C(F)(F)F)c2)n1CC1CCCCC1] | $^1$H-NMR (300 MHz, CDCl$_3$) δ: 7.95 (s, 1H), 7.84 (s, 1H), 7.67 (s, 1H), 6.56 (s, 1H), 5.98 (s, 1H), 4.73 (s, 2H), 3.76 (d, 2H, J = 6.9 Hz), 2.55 (s, 3H), 1.61 (m, 5H), 1.50 (s, 9H), 1.33-1.38 (m, 3H), 0.99-1.03 (m, 3H), 0.66 (m, 2H). MS Calcd.: 499; MS Found: 500 (M + 1). |
| 13/14 | 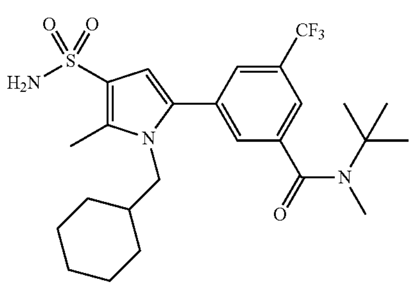 [SMILES: Cc1c(S(N)(=O)=O)cc(-c2cc(C(=O)N(C)C(C)(C)C)cc(C(F)(F)F)c2)n1CC1CCCCC1] | $^1$H-NMR (300 MHz, CDCl$_3$) δ: 7.70 (s, 1H), 7.59 (s, 1H), 7.54 (s, 1H), 6.54 (s, 1H), 4.70 (s, 2H), 3.76 (d, 2H, J = 6.9 Hz), 2.87 (s, 3H), 2.55 (s, 3H), 1.57 (m, 5H), 1.50 (s, 9H), 1.33-1.38 (m, 3H), 0.99-1.03 (m, 3H), 0.70 (m, 2H). MS Calcd.: 513; MS Found: 514 (M + 1). |

Example 14 to Example 16

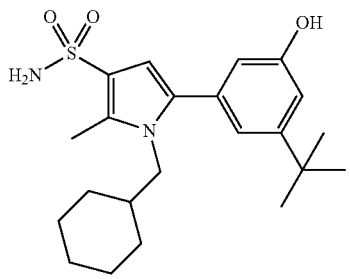

14

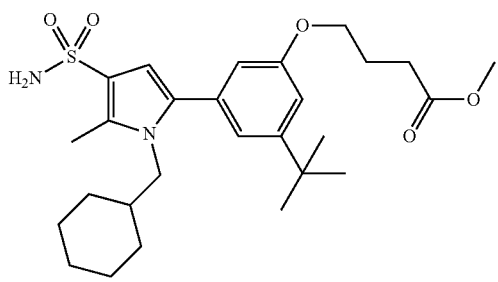

15

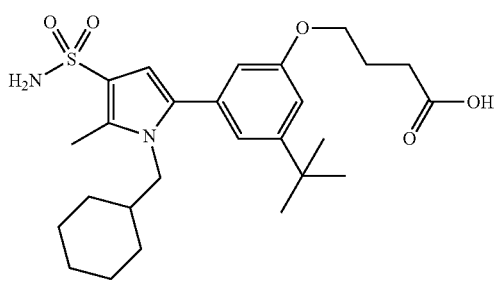

16

Step 1: 1-Bromo-3-(tert-butyl)-5-methoxybenzene (14a)

To a solution of 1,3-dibromo-5-tert-butylbenzene (289 mg, 1 mmol) in DMF (20 mL) were added NaOMe (2 eq) and CuI (0.03 eq). The mixture was stirred at 80° C. for 3 h and then was poured into water and extracted with EA. The combined organic layers were washed with brine and dried over $Na_2SO_4$. After filtration, the filtrate was evaporated to give compound 14a as solid (200 mg, 82%).

Step 2: 2-(3-(tert-Butyl)-5-methoxyphenyl)-4,4,5,5-tetramethyl-1,3,2-dioxaborolane (14b)

A vial was charged with $Pd(dppf)Cl_2$ (0.03 mmol), $B_2Pin_2$ (0.140 g, 0.55 mmol) and KOAc (0.147 g, 1.5 mmol), sealed and purged with Ar. Compound 14a (122 mg, 0.5 mmol) in dioxane (3 mL) was added. The resulting mixture was then stirred at 80° C. until the reaction was complete, diluted with water, extracted with $Et_2O$, separated and dried over $MgSO_4$. The product was purified by CC to give compound 14b (100 mg, 69%).

Step 3: 3-(tert-Butyl)-5-(4,4,5,5-tetramethyl-1,3,2-dioxaborolan-2-yl)phenol (14c)

Compound 14b (290 mg, 1 mol) was dissolved in DCM (25 mL). To the solution was added $BBr_3$ (4 eq) dropwise at 0° C. under $N_2$. The stirred mixture was then allowed to stand at 0° C. for 2 h, after which it was poured carefully dropwise into icewater and extracted with DCM. The organic phase was dried ($MgSO_4$), evaporated and purified by CC to give compound 14c (220 mg, 80%).

Step 4: 5-(3-(tert-Butyl)-5-hydroxyphenyl)-1-(cyclohexylmethyl)-2-methyl-1H-pyrrole-3-sulfonamide (14)

A mixture of compound 14c (276 mg, 1 mmol) of and compound 1d (335 mg, 1 mmol) in dioxane (80 mL) and water (8 mL) was stirred at rt. $Cs_2CO_3$ (2 eq) was added, followed by $Pd(dppf)Cl_2$ (0.03 eq) and then the mixture was heated to reflux under $N_2$ for 7 h. The reaction mixture was cooled to rt and the dioxane was removed. The residue was poured into water and extracted with $CH_2Cl_2$. The organic layer was dried over $MgSO_4$, filtered and purified by CC (EA/hexane=1/9) to give compound 14 (280 mg, 64%). $^1$H-NMR (400 MHz, $CDCl_3$) δ: 6.90-6.87 (m, 2H), 6.60 (s, 1H), 6.44 (s, 1H), 3.76-3.74 (m, 2H), 2.53 (s, 3H), 1.56-1.55 (m, 3H), 1.36-1.33 (m, 12H), 1.01-0.99 (m, 3H), 0.66-0.64 (m, 2H). MS Found: 405 (M+1).

Step 5: Methyl 4-(3-(tert-butyl)-5-(1-(cyclohexylmethyl)-5-methyl-4-sulfamoyl-1H-pyrrol-2-yl)phenoxy)butanoate (15)

To a solution of compound 14 (202 mg, 0.5 mmol) in DMF (20 mL) were added $Cs_2CO_3$ (325 mg, 1 mmol) and methyl 4-bromobutanoate (99 mg, 0.55 mmol). The reaction mixture was stirred for 4 h at 40° C., then water (30 mL) was added and the reaction mixture was extracted with EA (150 mL). The organic layer was washed with brine and dried over $Na_2SO_4$, concentrated and purified by CC (hexane/EA=3/1) to give compound 15 (176 mg, 70%).

Step 6: 4-(3-(tert-Butyl)-5-(1-(cyclohexylmethyl)-5-methyl-4-sulfamoyl-1H-pyrrol-2-yl)phenoxy)butanoic acid (16)

To a solution of compound 15 (126 mg, 0.25 mmol) in methanol and THF (30 mL; 1:1) was added LiOH (25 mg, 1 mmol) and the mixture was stirred at rt overnight. The residue was concentrated and then poured into water and extracted with $CH_2Cl_2$. The organic layer was dried over $MgSO_4$, filtered, evaporated and purified by CC to give compound 16 (98 mg, 80%). $^1$H-NMR (400 MHz, DMSO-$d_6$) δ: 12.2 (br s, 1H), 6.91-6.89 (m, 4H), 6.68 (s, 1H), 6.29 (s, 1H), 4.02-3.98 (m, 2H), 3.81-3.79 (m, 2H), 2.43 (s, 3H) 2.40-2.36 (m, 5H), 1.94-1.91 (m, 2H), 1.48-1.46 (m, 3H), 1.27-1.24 (m, 12H), 0.96-0.94 (m, 3H), 0.66-0.64 (m, 2H). MS Found: 491 (M+1).

Examples 16/1 to 16/11

Using similar procedures as that described in Example 14 to Example 16, the following Examples have been prepared:

| # | Structure | Analytical data |
|---|---|---|
| 16/1 | 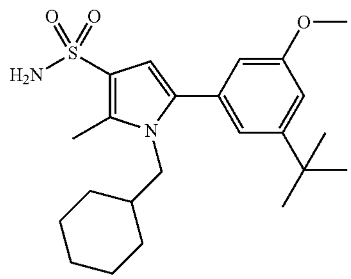 [SMILES: COc1cc(-c2cc(S(N)(=O)=O)c(C)n2CC2CCCCC2)cc(C(C)(C)C)c1] | $^1$H-NMR (400 MHz, CDCl$_3$) δ: 6.95-6.93 (m, 2H), 6.66-6.65 (m, 1H), 6.47 (s, 1H), 3.83 (s, 3H), 3.76 (d, J = 7.2 Hz, 1H), 2.54 (s, 3H), 1.56-1.55 (m, 3H), 1.38-1.32 (m, 12H), 1.01-0.99 (m, 3H), 0.67-0.64 (m, 2H). MS Found: 419 (M + 1). |
| 16/2 | 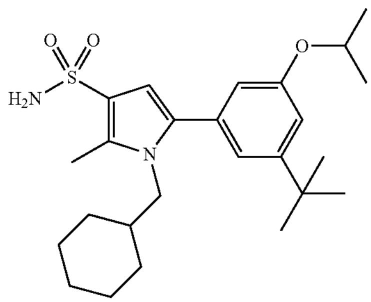 [SMILES: Cc1c(S(N)(=O)=O)cc(-c2cc(OC(C)C)cc(C(C)(C)C)c2)n1CC1CCCCC1] | $^1$H-NMR (400 MHz, CDCl$_3$) δ: 6.91-6.87 (m, 4H), 6.70 (s, 1H), 6.31 (s, 1H), 4.69-4.66 (m, 1H), 3.83 (d, J = 6.8 Hz, 2H), 2.53-2.52 (m, 3H), 1.51-1.49 (m, 3H), 1.29-1.27 (m, 18H), 0.99-0.97 (m, 3H), 0.69-0.67 (m, 2H). MS Found: 447 (M + 1). |
| 16/3 | 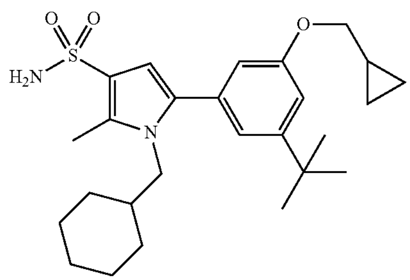 [SMILES: Cc1c(S(N)(=O)=O)cc(-c2cc(OCC3CC3)cc(C(C)(C)C)c2)n1CC1CCCCC1] | $^1$H-NMR (400 MHz, CDCl$_3$) δ: 6.94-6.92 (m, 4H), 6.69 (s, 1H), 6.31 (s, 1H), 3.87-3.83 (m, 4H), 2.45 (s, 3H), 1.51-1.49 (m, 3H), 1.30-1.26 (m, 13H), 0.69-0.57 (m, 4H), 0.35-0.34 (m, 2H). MS Found: 459 (M + 1). |
| 16/4 | 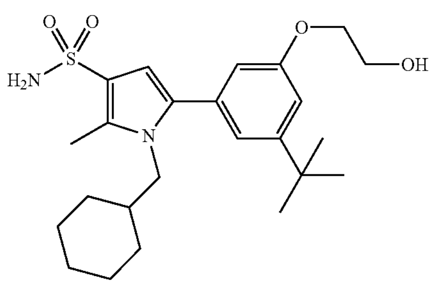 [SMILES: Cc1c(S(N)(=O)=O)cc(-c2cc(OCCO)cc(C(C)(C)C)c2)n1CC1CCCCC1] | $^1$H-NMR (400 MHz, CDCl$_3$) δ: 6.93-6.91 (m, 4H), 6.69 (s, 1H), 6.29 (s, 1H), 4.89-4.88 (m, 1H), 4.02-4.00 (m, 2H), 3.83-3.81 (m, 2H), 3.73-3.71 (m, 2H), 2.44 (s, 3H), 1.49-1.47 (m, 3H), 1.28-1.26 (m, 12H), 0.98-0.96 (m, 3H), 0.67-0.65 (m, 2H). MS Found: 449 (M + 1). |
| 16/5 | 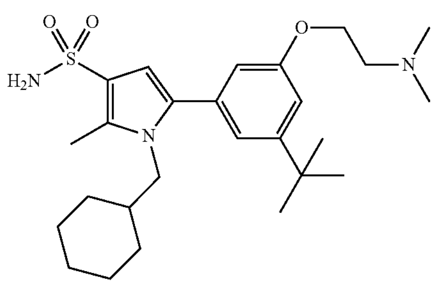 [SMILES: Cc1c(S(N)(=O)=O)cc(-c2cc(OCCN(C)C)cc(C(C)(C)C)c2)n1CC1CCCCC1] | $^1$H-NMR (400 MHz, CDCl$_3$) δ: 7.00-6.94 (m, 4H), 6.79 (s, 1H), 6.31 (s, 1H), 4.36-4.35 (m, 2H), 3.84-3.82 (m, 2H), 3.52-3.51 (m, 2H), 2.88-2.87 (br s, 6H), 2.44 (s, 3H), 1.49-1.48 (m, 3H), 1.29-1.28 (m, 12H), 0.96-0.95 (m, 3H), 0.67-0.65 (m, 2H). MS Found: 476 (M + 1). |

-continued

| # | Structure | Analytical data |
|---|---|---|
| 16/6 | 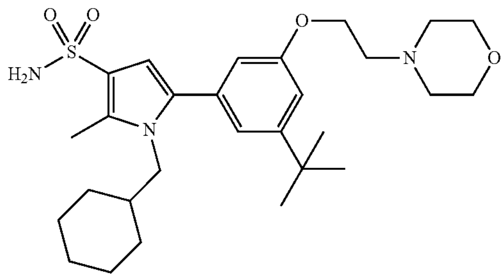 [SMILES: Cc1c(S(N)(=O)=O)cc(-c2cc(OCCN3CCOCC3)cc(C(C)(C)C)c2)n1CC1CCCCC1] | ¹H-NMR (400 MHz, CDCl₃) δ: 6.99-6.93 (m, 4H), 6.79 (s, 1H), 6.30 (s, 1H), 4.39-4.36 (m, 2H), 3.97-3.96 (m, 2H), 3.83-3.73 (m, 6H), 3.56-3.55 (m, 4H), 2.43 (s, 3H), 1.49-1.47 (m, 3H), 1.26-1.25 (m, 12H), 0.97-0.95 (m, 3H), 0.67-0.64 (m, 2H). MS Found: 518 (M + 1). |
| 16/7 | 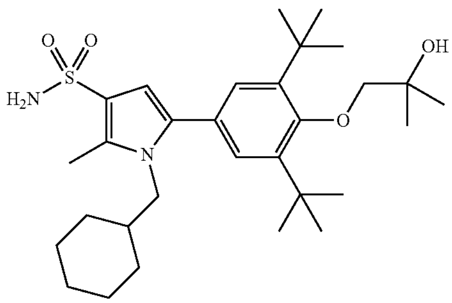 [SMILES: Cc1c(S(N)(=O)=O)cc(-c2cc(C(C)(C)C)c(OCC(C)(C)O)c(C(C)(C)C)c2)n1CC1CCCCC1] | ¹H-NMR (400 MHz, DMSO-d₆) δ: 7.16 (s, 2H), 6.90 (s, 2H), 6.27 (s, 1H), 4.61 (br s, 1H), 3.73 (m, 2H), 2.24 (s, 2H), 2.41 (s, 3H), 1.43 (m, 21H), 1.28 (s, 6H), 1.24-1.20 (m, 3H), 1.02-0.86 (m, 3H), 0.72-0.61 (m, 2H). MS Found: 533 (M + 1). |
| 16/8 | 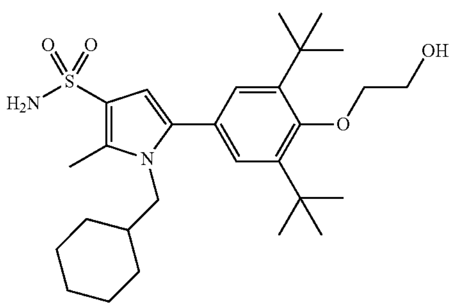 [SMILES: Cc1c(S(N)(=O)=O)cc(-c2cc(C(C)(C)C)c(OCCO)c(C(C)(C)C)c2)n1CC1CCCCC1] | ¹H-NMR (400 MHz, DMSO-d₆) δ: 7.16 (s, 2H), 6.90 (br s, 2H), 6.29 (s, 1H), 4.81 (m, 1H), 3.81-3.70 (m, 6H), 2.42 (s, 3H), 1.50-1.37 (m, 21H), 1.24-1.17 (m, 3H), 1.03-0.84 (m, 3H), 0.75-0.62 (m, 2H). MS Found: 505 (M + 1). |
| 16/9 | 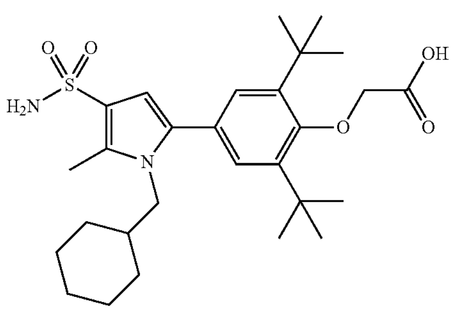 [SMILES: Cc1c(S(N)(=O)=O)cc(-c2cc(C(C)(C)C)c(OCC(=O)O)c(C(C)(C)C)c2)n1CC1CCCCC1] | ¹H-NMR (400 MHz, DMSO-d₆) δ: 13.16 (br s, 1H), 7.18 (s, 2H), 6.91 (s, 2H), 6.27 (s, 1H), 3.73 (m, 2H), 2.42 (s, 3H), 1.50-1.43 (m, 3H), 1.48-1.42 (m, 3H), 1.38 (s, 18H), 1.27-1.18 (m, 3H), 1.02-0.85 (m, 3H), 0.73-0.62 (m, 2H). MS Found: 519 (M + 1). |
| 16/10 | 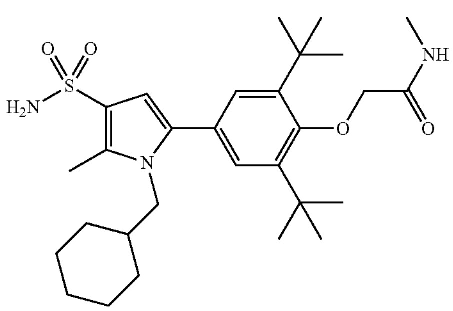 [SMILES: CNC(=O)COc1c(C(C)(C)C)cc(-c2cc(S(N)(=O)=O)c(C)n2CC2CCCCC2)cc1C(C)(C)C] | ¹H-NMR (400 MHz, DMSO-d₆) δ: 8.01-7.97 (q, J = 4.8 Hz, 1H), 7.18 (s, 2H), 6.91 (s, 2H), 6.28 (s, 1H), 4.09 (s, 2H), 3.78-3.74 (m, 2H), 2.73 (d, J = 4.8 Hz, 3H), 2.42 (s, 3H), 1.51-1.44 (m, 3H), 1.48-1.41 (m, 3H), 1.38 (s, 18H), 1.28-1.19 (m, 3H), 1.01-0.87 (m, 3H), 0.73-0.61 (m, 2H). MS Found: 532 (M + 1). |

| # | Structure | Analytical data |
|---|---|---|
| 16/11 | 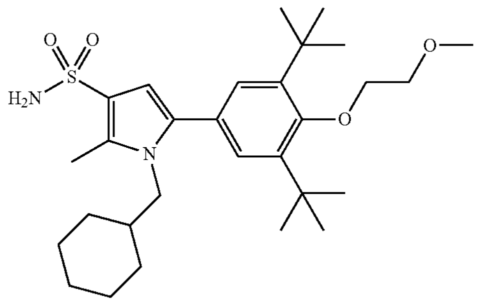 [SMILES: COCCOc1c(C(C)(C)C)cc(-c2cc(S(N)(=O)=O)c(C)n2CC2CCCCC2)cc1C(C)(C)C] | $^1$H-NMR (400 MHz, DMSO-d$_6$) δ: 7.16 (s, 2H), 6.91 (s, 2H), 6.26 (s, 1H), 3.84-3.80 (m, 2H), 3.78-3.71 (m, 4H), 3.35 (s, 3H), 2.42 (s, 3H), 1.49-1.35 (m, 21H), 1.25-1.17 (m, 3H), 1.00-0.83 (m, 3H), 0.75-0.61 (m, 2H). MS Found: 519 (M + 1). |

Example 17

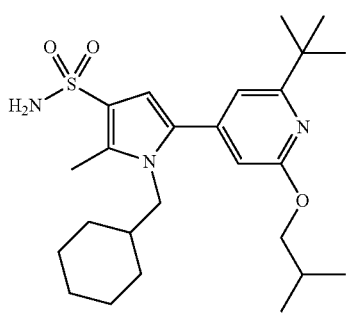

Step 1: 6-tert-Butyl-4-hydroxypyridin-2(1H)-one (17a)

A mixture of 6-(tert-butyl)-4-hydroxy-2H-pyran-2-one (38 g, 168 mmol) and aq. NH$_4$OH (150 mL, 30%) in dry toluene (200 mL) was heated at reflux for 1 h. The resulting mixture was concentrated and purified by CC (PE/EA=5/1) to give compound 17a (22.5 g, 80%) as a white solid.

Step 2: 4-Bromo-6-tert-butylpyridine-2(1H)-one (17b)

To a solution of compound 17a (9.7 g, 60 mmol) in DMF (100 mL) was added POBr$_3$ (17.2 g, 60 mmol) and the mixture was heated at 90° C. for 2 h. Then the resulting mixture was concentrated. Water was added and the mixture was extracted with EA. The organic layer was washed with brine, concentrated and purified by CC (PE/EA=5/1) to give compound 17b (11 g, 80%) as a yellow solid.

Step 3: 4-Bromo-2-tert-butyl-6-isobutoxypyridine (17c)

To a solution of compound 17b (1.0 g, 4.33 mmol) in dry DMF (10 mL) was added NaH (0.31 g, 13 mmol) under N$_2$ and the mixture was stirred at rt for 1 h. Then 1-iodo-2-methylpropane (1.35 g, 7.3 mmol) was added and the resulting mixture was heated at 80° C. overnight. The mixture was quenched with water (5 mL) and extracted with EA twice. The combined organic layers were washed with brine (3×), concentrated and purified by CC (PE/EA=50/1) to give compound 17c (1.0 g, 91%) as an oil.

Step 4: 2-tert-Butyl-6-isobutoxy-4-(4,4,5,5-tetramethyl-1,3,2-dioxaborolan-2-yl)pyridine (17d)

A mixture of compound 17c (1.0 g, 3.88 mmol), B$_2$Pin$_2$ (1.48 g, 5.81 mmol), KOAc (0.57 g, 5.81 mmol) and Pd(dppf)Cl$_2$ (30 mg) in dry DMF (10 mL) was heated to 90° C. under N$_2$ overnight. The mixture was quenched with water and extracted with EA twice. The combined organic layers were washed with brine (3×), concentrated and purified by CC (PE/EA=50/1) to give compound 17d (0.79 g, 67%) as an oil.

Step 5: 5-(2-tert-Butyl-6-isobutoxypyridin-4-yl)-1-(cyclohexylmethyl)-2-methyl-1H-pyrrole-3-sulfonamide (17)

A mixture of compound 17d (0.79 g, 2.58 mmol), compound 1d (0.724 g, 2.16 mmol), K$_2$CO$_3$ (0.45 g, 3.24 mmol) and Pd(dppf)Cl$_2$ (30 mg) in dry DMF (10 mL) was heated at 120° C. overnight under N$_2$, concentrated and purified by prep-HPLC to give compound 17 (44 mg, 12%) as a white solid; $^1$H-NMR (300 MHz, CDCl$_3$) δ: 0.67-0.71 (m, 2H), 0.97-1.06 (m, 10H), 1.59 (m, 1H), 2.04-2.17 (m, 1H), 2.53 (s, 3H), 3.79-3.82 (d, J=7.2 Hz, 2H), 4.11-4.13 (d, J=6.6 Hz, 2H), 4.66 (s, 2H), 6.46 (s, 1H), 6.53 (s, 1H), 6.78-6.92 (s, 1H). MS Calcd.: 461, MS Found: 462 (M+1).

Examples 17/1 to 17/4

Using similar procedures as that described in Example 17, the following Examples have been prepared:

| # | Structure | Analytical data |
|---|---|---|
| 17/1 | 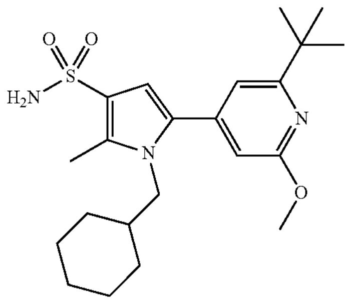 [SMILES: COc1cc(-c2cc(S(N)(=O)=O)c(C)n2CC2CCCCC2)cc(C(C)(C)C)n1] | $^1$H-NMR (300 MHz, CDCl$_3$) δ: 0.69-0.72 (m, 2H), 1.04-1.06 (m, 3H), 1.37-1.39 (m, 12H), 1.61 (m, 3H), 2.57 (s, 3H), 3.82-3.84 (d, J = 7.2 Hz, 2H), 3.99 (s, 3H), 4.73 (s, 3H), 6.50 (s, 1H), 6.56 (s, 1H), 6.84 (s, 1H). MS Calcd.: 419; MS Found: 420 (M + 1). |
| 17/2 | 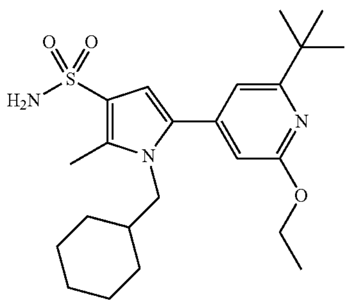 [SMILES: CCOc1cc(-c2cc(S(N)(=O)=O)c(C)n2CC2CCCCC2)cc(C(C)(C)C)n1] | $^1$H-NMR (300 MHz, CDCl$_3$) δ: 0.69-0.73 (m, 2H), 0.97-1.05 (m, 3H), 1.27-1.42 (m, 16H), 1.57-1.59 (m, 1H), 2.53 (s, 3H), 3.79-3.81 (d, J = 7.2 Hz, 2H), 4.37-4.44 (q, J = 7.2 Hz, 2H), 4.67-4.69 (s, 2H), 6.44 (s, 1H), 6.53 (s, 1H), 6.79 (s, 1H). MS Calcd.: 433; MS Found: 434 (M + 1). |
| 17/3 | 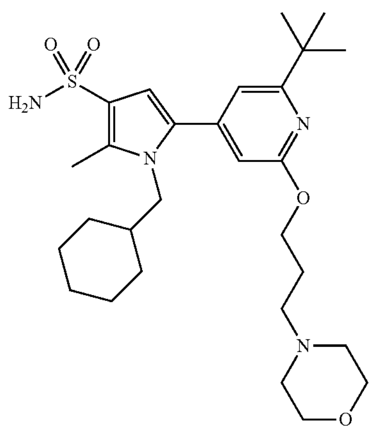 [SMILES: Cc1c(S(N)(=O)=O)cc(-c2cc(OCCCN3CCOCC3)nc(C(C)(C)C)c2)n1CC1CCCCC1] | $^1$H-NMR (300 MHz, CDCl$_3$) δ: 0.66-0.70 (m, 2H), 1.00-1.05 (m, 3H), 1.35-1.39 (m, 14H), 1.57-1.06 (m, 1H), 1.93-2.04 (m, 2H), 2.46-2.55 (m, 10H), 3.71-3.74 (t, J = 9.6 Hz, 4H), 3.79-3.81 (d, J = 7.2 Hz, 2H), 4.39-4.43 (t, J = 12.9 Hz, 2H), 6.66-6.67 (s, 2H), 6.45 (s, 1H), 6.53 (s, 1H), 6.80 (s, 1H). MS Calcd.: 532; MS Found: 533 (M + 1). |
| 17/4 | 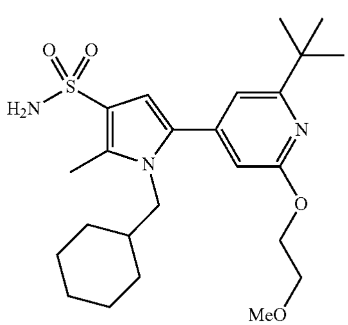 [SMILES: COCCOc1cc(-c2cc(S(N)(=O)=O)c(C)n2CC2CCCCC2)cc(C(C)(C)C)n1] | $^1$H-NMR (300 MHz, CDCl$_3$) δ: 0.64-0.72 (m, 2H), 0.97-1.61 (m, 3H), 1.25-1.50 (m, 14H), 1.51-1.55 (m, 1H), 2.53 (s, 3H), 3.45 (s, 3H), 3.76-3.81 (m, 4H), 4.51-4.55 (t, J = 9.6 Hz, 2H), 4.65 (s, 2H), 6.52-6.53 (m, 2H), 6.80-6.89 (s, 1H). MS Calcd.: 463; MS Found: 464 (M + 1). |

Example 18

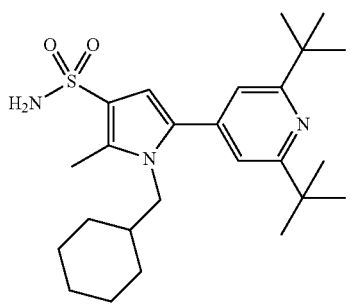

Step 1: 2,6-Di-tert-butyl-4-(4,4,5,5-tetramethyl-1,3,2-dioxaborolan-2-yl)pyridine (18a)

Under $N_2$, a catalyst stock solution was prepared by weighing [Ir(OMe)cod]$_2$ (104 mg, 0.312 mmol Ir), dtbpy (84 mg, 312 μmol) and B$_2$Pin$_2$ (2.64 g, 10.4 mmol) into a vial followed by the volumetric addition of methyl tert-butylether to make up a 25 mL solution and shaken developing a deep red color (*Org. Lett.* 2009, 11:3586). The solution was transferred to a vial and sealed with a rubber septum. Under $N_2$, a vial was charged with 2,6-di-tert-butylpyridine (1.91 g, 10.0 mmol) followed by 25 mL of the catalyst stock solution. The reaction was heated at 80° C. for 2 h, concentrated and purified by CC (PE/EA=8/1) to give compound 18a (1.89 g, 60%) as a white solid.

Step 2: 1-(Cyclohexylmethyl)-5-(2,6-di-tert-butylpyridin-4-yl)-2-methyl-1H-pyrrole-3-sulfonamide (18)

Similar to Example 1, Step 5, compound 18 (41 mg, 17%) was obtained as a white solid. $^1$H-NMR (400 MHz, CDCl$_3$) δ: 0.65-0.70 (m, 2H), 0.99-1.03 (m, 3H), 1.36 (m, 21H), 1.52-1.57 (m, 3H), 2.55 (s, 3H), 3.77-3.79 (d, J=7.2 Hz, 2H), 4.67 (s, 2H), 6.55 (s, 1H), 7.04 (s, 2H). MS Calcd.: 445; MS Found: 446 (M+1).

Example 19 and Example 20

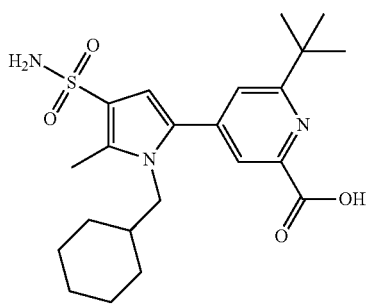

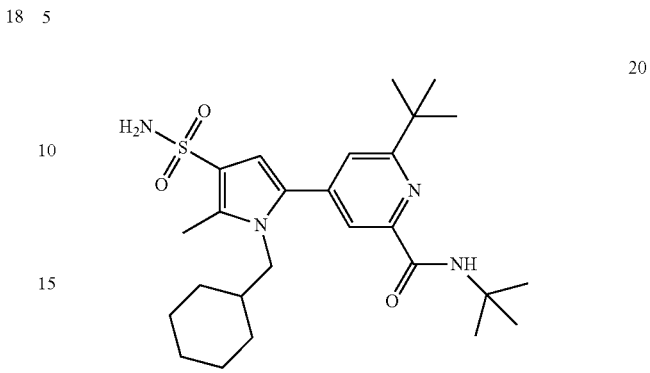

Step 1: 6-(tert-Butyl)-4-(1-(cyclohexylmethyl)-5-methyl-4-sulfamoyl-1H-pyrrol-2-yl)picolinic acid (19)

To a stirred solution of compound 12/11 (1.8 g, 4.0 mmol) in a mixture of THF (15 mL) and H$_2$O (5 mL) was added LiOH.H$_2$O (300 mg, 5.64 mmol) and this mixture was stirred at 60° C. for 3 h. The reaction solution was adjusted to pH=2~3 with 1N HCl and then extracted with EA. The organic layer was washed with brine, dried over Na$_2$SO$_4$, concentrated and purified by CC (PE/EA=2/1) to give compound 19 (1.4 g, 80%) as a white powder.

Step 2: N,6-Di-tert-butyl-4-(1-(cyclohexylmethyl)-5-methyl-4-sulfamoyl-1H-pyrrol-2-yl)picolinamide (20)

A mixture of compound 19 (150 mg, 0.34 mmol), tert-butylamine (36 mg, 0.48 mmol), HATU (207 mg, 0.54 mmol) and DIPEA (146 mg, 1.14 mmol) in DMF (5 mL) was stirred at rt for 20 min, diluted with water and extracted with EA. The organic layer was washed with brine, dried over Na$_2$SO$_4$, concentrated and purified by CC (PE/EA=2/1) to give compound 20 (46 mg, 30%) as a white powder. $^1$H-NMR (300 MHz, CDCl$_3$) δ: 8.17 (s, 1H), 7.93 (d, 1H, J=1.5 Hz), 7.40 (d, 1H, J=1.5 Hz), 6.61 (s, 1H), 4.70 (d, 2H, J=5.4 Hz), 3.84 (d, 2H, J=6.9 Hz), 2.55 (s, 3H), 1.61 (m, 3H), 1.50 (s, 9H), 1.42 (s, 9H), 1.30-1.38 (m, 3H), 0.97-1.03 (m, 3H), 0.63 (m, 2H). MS Calcd.: 488; MS Found: 489 (M+1).

Example 20/1 to Example 20/3

Similar to Example 20 the following compounds were obtained.

| # | Structure | Analytical data |
|---|-----------|-----------------|
| 20/1 | 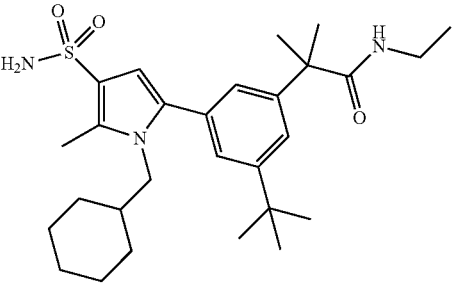 [SMILES: CCNC(=O)C(C)(C)c1cc(-c2cc(S(N)(=O)=O)c(C)n2CC2CCCCC2)cc(C(C)(C)C)c1] | $^1$H-NMR (CDCl$_3$, 400 MHz) δ: 0.59-0.67 (2H, m), 0.95-1.05 (5H, m), 1.33 (12H, m), 1.54-1.57 (10H, m), 2.54 (3H, s), 3.23 (2H, m), 3.72 (2H, d, J = 6.8 Hz), 4.69 (2H, s), 5.14 (1H, s), 6.48 (1H, s), 7.13 (1H, s), 7.24 (1H, s), 7.35 (1H, s). MS Calcd.: 501; MS Found: 502 (M + 1). |
| 20/2 | 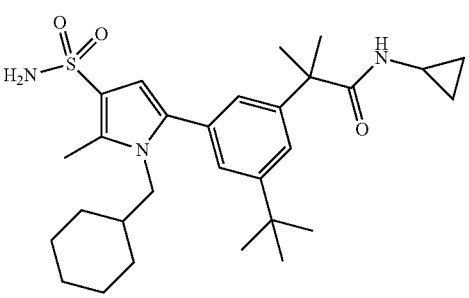 [SMILES: Cc1c(S(N)(=O)=O)cc(-c2cc(C(C)(C)C)cc(C(C)(C)C(=O)NC3CC3)c2)n1CC1CCCCC1] | $^1$H-NMR (CDCl$_3$, 400 MHz) δ: 0.33 (2H, m), 0.63 (2H, m), 0.72 (2H, m), 1.00 (3H, m), 1.32 (12H, s), 1.55 (9H, m), 2.54 (3H, s), 2.64 (1H, m), 3.72 (2H, d, J = 7.2 Hz), 4.69 (2H, s), 5.22 (1H, s), 6.47 (1H, s), 7.10 (1H, s), 7.23 (1H, s), 7.31 (1H, s). MS Calcd.: 513; MS Found: 514 (M + 1). |
| 20/3 | 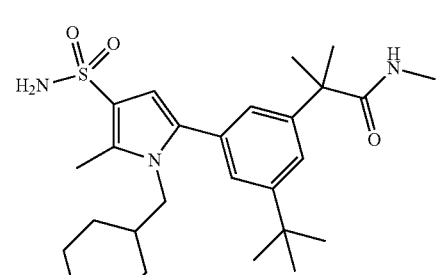 | $^1$H-NMR (CDCl$_3$, 400 MHz) δ: 0.61-0.64 (2H, m), 0.99-1.01 (3H, m), 1.24-1.33 (12H, m), 1.54-1.58 (9H, m), 2.54 (3H, s), 2.74 (3H, d, J = 4.8 Hz), 3.72 (2H, d, J = 6.8 Hz), 4.68 (2H, s), 5.19 (2H, s, br), 6.47 (1H, s), 7.10 (1H, s), 7.24 (1H, s), 7.37 (1H, s). MS Calcd.: 487; MS Found: 488 (M + 1). |

Example 21

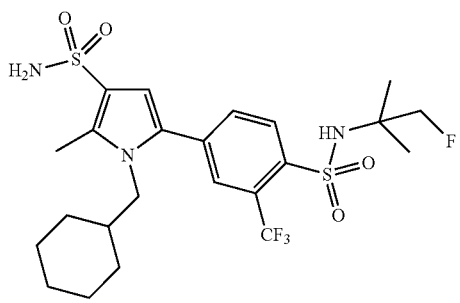

A solution of alcohol 12/30 (88 mg, 150 μmol) in DCM (6 mL) was added DAST (100 mg, 0.6 mmol) under ice-cooling and the solution was stirred at rt overnight. The resulting mixture was washed with water and extracted with CH$_2$Cl$_2$, dried over MgSO$_4$, filtered, concentrated and purified by CC (PE/EA=1/1) to give compound 21 (40 mg, 45%) as a white solid. $^1$H-NMR (400 MHz, CDCl$_3$) δ: 8.22 (d, 1H, J=8.0 Hz), 7.82 (s, 1H), 7.64 (d, 1H, J=8.0 Hz), 6.63 (s, 1H), 5.07 (t, 1H, J=5.8 Hz), 4.80 (s, 2H), 3.80 (d, 2H, J=6.8 Hz), 3.17 (dd, 2H, J=20.0 Hz, J=6.0 Hz), 2.57 (s, 3H), 1.59 (b s, 3H), 1.40-1.25 (m, 9H), 1.03-1.01 (m, 3H), 0.67-0.62 (m, 2H). MS Calcd.: 553.2; MS Found: 552.2 (M−1)$^−$.

Example 21/1

Similar to Example 21 the following compounds were obtained from alcohol showed above.

| # | Structure | Analytical data |
|---|---|---|
| 21/1 | 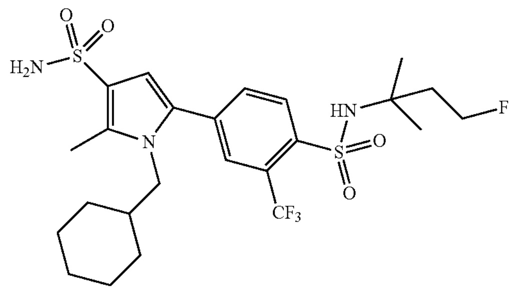 [SMILES: Cc1c(S(N)(=O)=O)cc(-c2ccc(S(=O)(=O)NC(C)(C)CCF)c(C(F)(F)F)c2)n1CC1CCCCC1] | $^1$H-NMR (400 MHz, CDCl$_3$) δ: 8.33 (d, 1H, J = 11.2 Hz), 7.82 (d, 1H, J = 2.0 Hz), 7.64 (dd, 1H, J = 11.2 Hz, J = 2.0 Hz), 6.65 (s, 1H), 4.98-4.99 (br d, 1H), 4.74-4.71 (m, 2H), 4.57 (t, 1H, J = 7.6 Hz), 3.81 (d, 2H, J = 9.2 Hz), 2.58 (s, 3H), 2.05 (dt, 2H, J = 63.4 Hz, J = 7.4 Hz), 1.62-1.50 (m, 4H), 1.37-1.27 (m, 9H), 1.03-0.97 (m, 3H), 0.69-0.61 (m, 2H). MS Calcd.: 567.2; MS Found: 566.2 (M − 1)$^-$. |

Example 22/1 to Example 22/18

The following Examples were prepared similar as described in Example 1 (using boronic acid building blocks) or similar as described in Example 10 (using boronic ester building blocks):

| # | Structure | Analytical data |
|---|---|---|
| 22/1 | 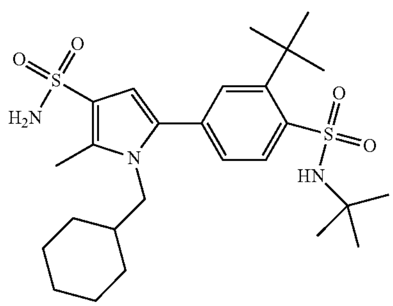 [SMILES: Cc1c(S(N)(=O)=O)cc(-c2ccc(S(=O)(=O)NC(C)(C)C)c(C(C)(C)C)c2)n1CC1CCCCC1] | $^1$H-NMR (400 MHz, DMSO-d$_6$): δ 8.15 (d, J = 8.4 Hz, 1H), 7.80 (s, 1H), 7.51 (s, 1H), 7.44 (d, J = 8.0 Hz, 1H), 6.98 (s, 2H), 6.44 (s, 1H), 3.84 (d, J = 6.8 Hz, 1H), 2.44 (s, 3H), 1.54 (s, 9H), 1.46-1.43 (m, 3H), 1.22-1.17 (m, 3H), 1.17 (s, 9H), 0.91-0.86 (m, 3H), 0.63-0.60 (m, 2H). MS Calcd.: 523; MS Found: 524 (M + 1). |
| 22/2 | 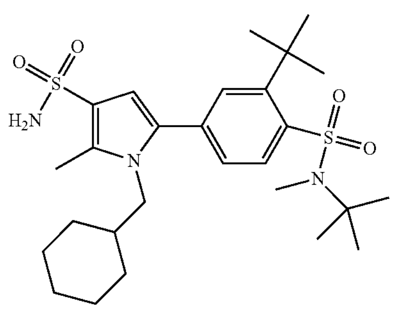 | $^1$H-NMR (400 MHz, DMSO-d$_6$): 7.80 (d, J = 8.4 Hz, 1H), 7.41 (m, 1H), 7.55-7.54 (m, 1H), 6.99-6.97 (m, 2H), 6.44 (s, 1H), 3.86-3.84 (m, 2H), 3.09 (s, 3H), 2.44 (s, 3H), 1.54 (s, 9H), 1.46-1.44 (m, 3H), 1.31 (s, 9H), 1.23-1.22 (m, 3H), 0.92-0.90 (m, 3H), 0.65-0.62 (m, 2H). MS Calcd.: 537; MS Found: 538 (M + 1). |
| 22/3 | 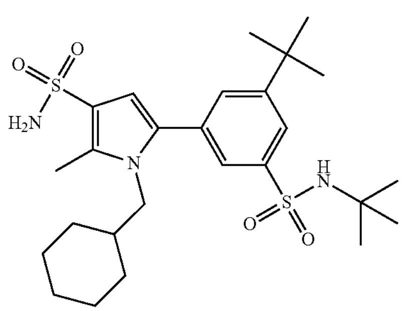 [SMILES: Cc1c(S(N)(=O)=O)cc(-c2cc(C(C)(C)C)cc(S(=O)(=O)NC(C)(C)C)c2)n1CC1CCCCC1] | $^1$H-NMR (400 MHz, DMSO-d$_6$): 7.85 (s, 1H), 7.64-7.60 (m, 3H), 6.99 (s, 2H), 6.40 (s, 1H), 3.86-3.84 (m, 2H), 3.09 (s, 3H), 2.44 (s, 3H), 1.48-1.46 (m, 3H), 1.33 (s, 9H), 1.23-1.22 (m, 3H), 1.08 (s, 9H), 0.92-0.90 (m, 3H), 0.65-0.62 (m, 2H). MS Calcd.: 523; MS Found: 524 (M + 1). |

| # | Structure | Analytical data |
|---|---|---|
| 22/4 | 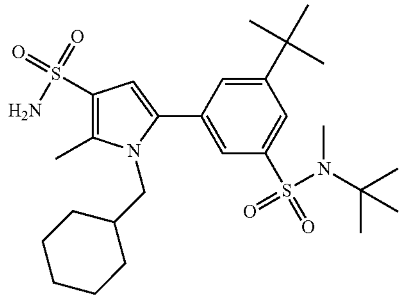 [SMILES: Cc1c(S(N)(=O)=O)cc(-c2cc(C(C)(C)C)cc(S(=O)(=O)N(C)C(C)(C)C)c2)n1CC1CCCCC1] | ¹H-NMR (400 MHz, DMSO-d₆): 7.70-7.68 (m, 2 H), 7.50 (s, 1H), 6.99 (s, 2H), 6.41 (s, 1H), 3.84-3.82 (m, 2H), 2.96 (s, 3H), 2.44 (s, 3H), 1.49-1.47 (m, 3H), 1.33 (s, 9H), 1.23-1.22 (m, 12H), 0.92-0.90 (m, 3H), 0.65-0.62 (m, 2H). MS Calcd.: 537; MS Found: 538 (M + 1). |
| 22/5 | 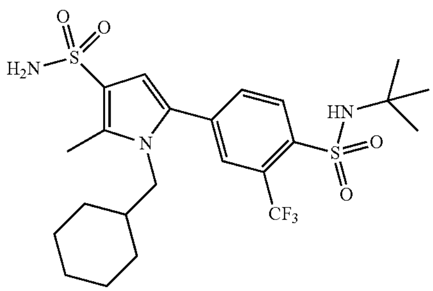 [SMILES: Cc1c(S(N)(=O)=O)cc(-c2ccc(S(=O)(=O)NC(C)(C)C)c(C(F)(F)F)c2)n1CC1CCCCC1] | ¹H-NMR (400 MHz, DMSO-d₆) δ: 8.25 (d, J = 6.8 Hz, 1H), 7.93 (d, J = 6.8 Hz, 1H), 7.88-7.86 (m, 2H), 7.02 (s, 2H), 6.60 (s, 1H), 3.90 (d, J = 5.2 Hz, 2H), 2.47 (s, 3H), 1.48-1.42 (m, 3H), 1.23-1.20 (m, 3H), 1.19 (s, 9H), 0.98-0.85 (m, 3H), 0.70-0.58 (m, 2H). MS Calcd.: 535; MS Found: 536 (M + 1). |
| 22/6 | 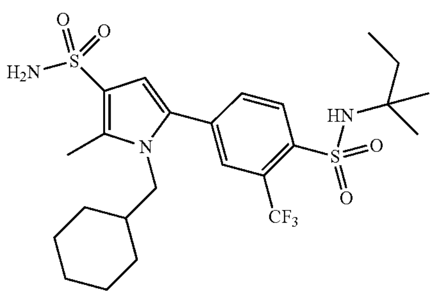 [SMILES: CCC(C)(C)NS(=O)(=O)c1ccc(-c2cc(S(N)(=O)=O)c(C)n2CC2CCCCC2)cc1C(F)(F)F] | ¹H-NMR (400 MHz, DMSO-d₆): δ 8.24 (d, 1H, J = 8.4 Hz), 7.93 (d, 2H, J = 8.4 Hz), 7.86 (s, 1H), 7.73 (s, 1H), 7.03 (s, 1H), 6.59 (s, 1H), 7.78 (d, 2H, J = 6.8 Hz), 2.64 (m, 3H), 1.54-1.45 (m, 5H), 1.24-1.22 (m, 3H), 1.18-1.16 (m, 6H), 1.08 (m, 3H), 0.96-0.75 (m, 3H), 0.67-0.62 (m, 2H). MS Calcd.: 549; MS Found: 550 (M + 1). |
| 22/7 | 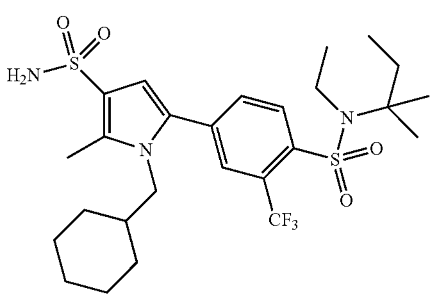 | ¹H NMR (400 MHz, DMSO-d₆) δ: 8.00 (d, 1H, J = 8.0 Hz), 7.89 (d, 2H, J = 8.0 Hz), 7.03 (s, 1H), 6.59 (s, 1H), 3.89 (d, 2H, J = 6.8 Hz), 3.63-3.58 (m, 2H), 2.47 (m, 3H), 1.48-1.46 (m, 3H), 1.35 (m, 9H), 1.30-1.19 (m, 6H), 0.95-0.89 (m, 3H), 0.67-0.64 (m, 2H). MS Calcd.: 563; MS Found: 564 (M + 1). |
| 22/8 | 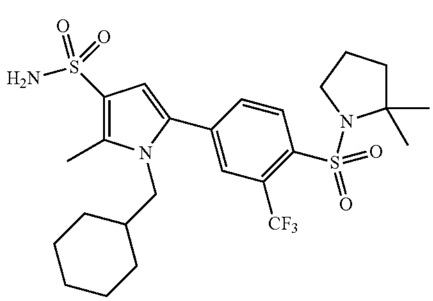 [SMILES: Cc1c(S(N)(=O)=O)cc(-c2ccc(S(=O)(=O)N3CCCC3(C)C)c(C(F)(F)F)c2)n1CC1CCCCC1] | ¹H NMR (400 MHz, DMSO-d₆) δ: 8.06 (d, 1H, J = 9.2 Hz), 7.89-7.88 (m, 2H), 7.04 (s, 1H), 6.58 (s, 1H), 3.89 (d, 2H, J = 6.4 Hz), 3.56-3.52 (m, 2H), 2.47 (m, 3H), 1.95-1.92 (m, 4H), 1.49-1.48 (m, 3H), 1.46 (m, 6H), 1.34-1.24 (m, 3H), 0.96-0.91 (m, 3H), 0.67-0.64 (m, 2H). MS Calcd.: 561; MS Found: 562 (M + 1). |

| # | Structure | Analytical data |
|---|---|---|
| 22/9 | 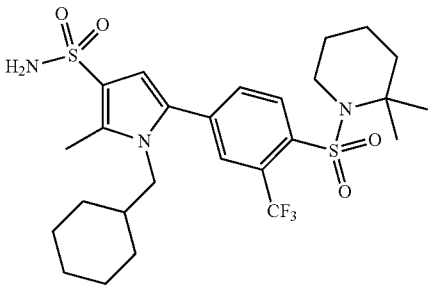 [SMILES: Cc1c(S(N)(=O)=O)cc(-c2ccc(S(=O)(=O)N3CCCCC3(C)C)c(C(F)(F)F)c2)n1CC1CCCCC1] | $^1$H-NMR (400 MHz, DMSO-d$_6$) δ: 8.21 (d, 1H, J = 8.0 Hz), 7.94-7.90 (m, 2H), 7.04 (s, 2H), 6.61 (s, 1H), 3.90 (d, 2H, J = 7.2 Hz), 3.51-3.50 (m, 2H), 2.47 (m, 3H), 1.61 (m, 3H), 1.47-1.46 (m, 5H), 1.23 (m, 9H), 0.95-0.87 (m, 3H), 0.67-0.64 (m, 2H). MS Calcd.: 575; MS Found: 576 (M + 1) |
| 22/10 | 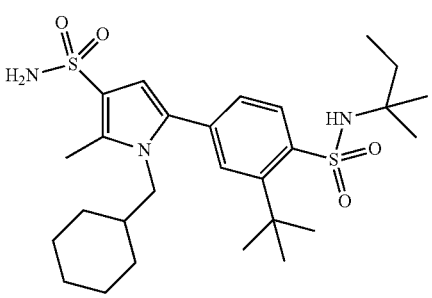 [SMILES: CCC(C)(C)NS(=O)(=O)c1ccc(-c2cc(S(N)(=O)=O)c(C)n2CC2CCCCC2)cc1C(C)(C)C] | $^1$H-NMR (400 MHz, DMSO-d$_6$) δ: 8.15 (d, J = 8.4 Hz, 1H), 7.64 (s, 1H), 7.50 (s, 1H), 7.44 (d, J = 8.4 Hz, 1H), 6.97 (s, 2H), 6.44 (s, 1H), 3.84 (d, J = 6.4 Hz, 2H), 2.44 (s, 3H), 1.60-1.51 (m, 11H), 1.48-1.41 (m, 3H), 1.30-1.18 (m, 3H), 1.08 (s, 6H), 0.92-0.81 (m, 6H), 0.70-0.52 (m, 2H). MS Calcd.: 537; MS Found: 538 (M + 1). |
| 22/11 | 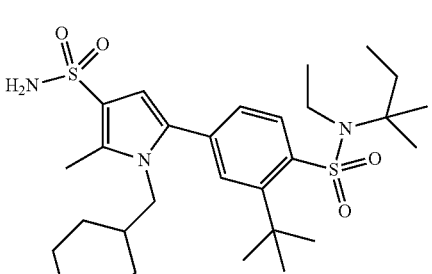 | $^1$H-NMR (400 MHz, DMSO-d$_6$) δ: 7.82 (d, J = 8.4 Hz, 1H), 7.56 (s, 1H), 7.41 (d, J = 8.4 Hz, 1H), 6.97 (s, 2H), 6.44 (s, 1H), 3.84 (d, J = 6.4 Hz, 2H), 3.63-3.58 (m, 2H), 2.47 (s, 3H), 1.59 (s, 9H), 1.50-1.41 (m, 3H), 1.39-1.26 (m, 12H), 1.24-1.18 (m, 3H), 0.95-0.82 (m, 3H), 0.68-0.58 (m, 2H). MS Calcd.: 551; MS Found: 552 (M + 1). |
| 22/12 | 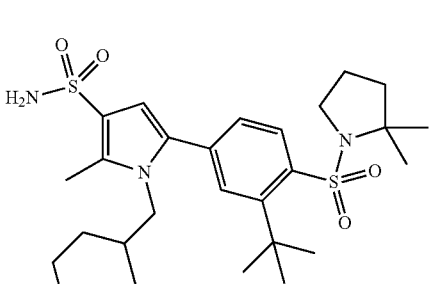 | $^1$H-NMR (500 MHz, CDCl$_3$) δ: 7.83 (d, J = 8.5 Hz, 1H), 7.57 (s, 1H), 7.23 (d, J = 8.5 Hz, 1H), 6.52 (s, 1H), 4.79 (s, 2H), 3.77 (d, J = 7.0 Hz, 2H), 3.54-3.56 (m, 2H), 2.55 (s, 3H), 1.95-2.01 (m, 4H), 1.61 (s, 12H), 1.50 (s, 6H), 1.31-1.34 (m, 3H), 0.68-1.03 (m, 5H). MS Calcd.: 549; MS Found: 550 (M + 1). |
| 22/13 | 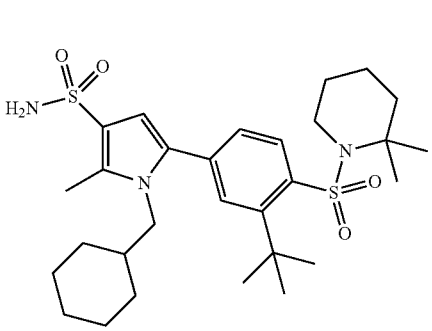 | $^1$H-NMR (400 MHz, MeOD) δ: 8.08 (d, J = 8.4 Hz, 1H), 7.63 (d, J = 1.6 Hz, 1H), 7.40 (dd, J = 8.4, 2.0 Hz, 1H), 6.52 (s, 1H), 4.79 (s, 2H), 3.90 (d, J = 6.8 Hz, 2H), 3.61 (d, J = 5.2 Hz, 2H), 2.53 (s, 3H), 1.80-1.70 (m, 4H), 1.62-1.58 (m, 2H), 1.60 (s, 9H), 1.58-1.52 (m, 3H), 1.37 (s, 6H), 1.36-1.28 (m, 3H), 1.06-0.95 (m, 3H), 0.75-0.62 (m, 2H). MS Calcd.: 563; MS Found: 564 (M + 1). |

-continued

| # | Structure | Analytical data |
|---|---|---|
| 22/14 | 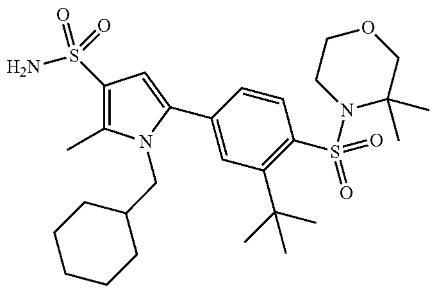 [SMILES: Cc1c(S(N)(=O)=O)cc(-c2ccc(S(=O)(=O)N3CCCCC3(C)C)c(C(C)(C)C)c2)n1CC1CCCCC1] | ¹H-NMR (400 MHz, MeOD) δ: 8.16 (d, J = 8.4 Hz, 1H), 7.66 (s, 1H), 7.43 (d, J = 8.4 Hz, 1H), 6.53 (s, 1H), 3.88-3.92 (m, 4H), 3.57 (t, J = 4.8 Hz, 2H), 3.43 (s, 2H), 2.54 (s, 3H), 1.61 (s, 9H), 1.54-1.60 (m, 3H), 1.36 (s, 6H), 1.31-1.35 (m, 3H), 0.66-1.03 (m, 5H). MS Calcd.: 565; MS Found: 566 (M + 1). |
| 22/15 | 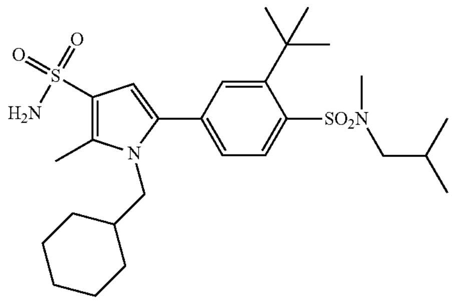 | ¹H-NMR (300 MHz, CDCl₃) δ: 7.61 (s, 1H), 7.46 (d, J = 8.3 Hz, 1H), 7.21 (d, J = 8.3 Hz, 1H), 6.51 (s, 1H), 4.68 (s, 2H), 3.77 (d, J = 6.9 Hz, 2H), 3.15 (d, J = 8.3 Hz, 2H), 2.95 (s, 3H), 2.56 (s, 3H), 2.05-1.96 (m, 1H) 1.63-1.55 (m, 2H), 1.60 (s, 9H), 1.40-1.25 (m, 4H), 1.02-0.99 (m, 3H), 0.95 (d, J = 10.5 Hz, 6H), 0.70-0.64 (m, 2H). MS Calcd.: 537; MS Found: 538 (M + 1). |
| 22/16 | 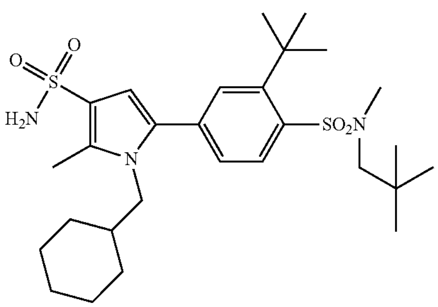 | ¹H-NMR (300 MHz, CDCl₃) δ: 7.62 (s, 1H), 7.38 (d, J = 8.1 Hz, 1H), 7.21 (d, J = 8.1 Hz, 1H), 6.51 (s, 1H), 4.67 (s, 2H), 3.77 (d, J = 7.2 Hz, 2H), 3.26 (s, 2H), 3.01 (s, 3H), 2.56 (s, 3H), 1.60 (s, 9H), 1.60-1.49 (m, 2H), 1.40-1.25 (m, 4H), 1.05 (s, 9H), 1.02-0.96 (m, 3H), 0.95 (d, J = 10.5 Hz, 6H), 0.69-0.60 (m, 2H). MS Calcd.: 551; MS Found: 552 (M + 1). |
| 22/17 | 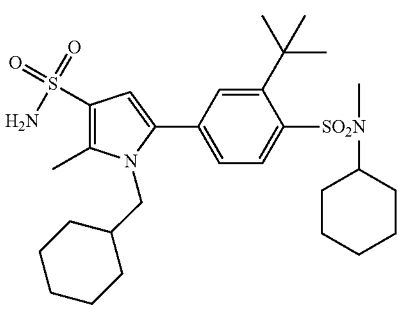 | ¹H-NMR (300 MHz, DMSO) δ: 7.83 (d, J = 8.4 Hz, 1H), 7.76 (s, 1H), 7.44 (d, J = 8.4 Hz, 1H), 6.98 (s, 2H), 6.44 (s, 1H), 3.86 (d, J = 6.0 Hz, 2H), 3.57-3.35 (m, 1H), 2.83 (s, 3H), 2.42 (s, 3H), 1.75-1.46 (m, 10H), 1.53 (s, 9H), 1.32-0.85 (m, 9H), 0.65-0.57 (m, 2H). MS Calcd.: 563; MS Found: 564 (M + 1). |
| 22/18 | 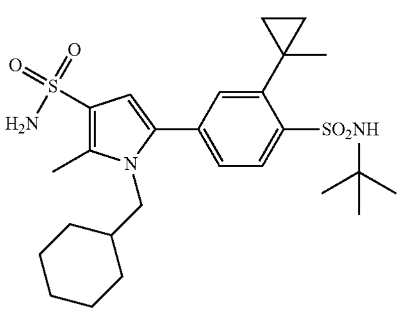 | ¹H-NMR (500 MHz, MeOD) δ: 7.90 (d, J = 8.0 Hz, 1H), 7.47 (s, 1H), 7.26 (d, J = 8.0 Hz, 1H,), 6.41 (s, 1H), 3.80-3.79 (m, 2H), 2.43 (s, 3H), 1.45-1.43 (m, 3H), 1.39 (s, 3H), 1.23-1.20 (m, 12H), 0.91-0.87 (m, 5H), 0.75 (m, 2H), 0.62-0.55 (m, 2H). MS Calcd.: 521; MS Found: 522 (M + 1). |

Example 24

Using a similar procedure as described in Scheme II above, the following compound can be obtained by using the appropriate building blocks.

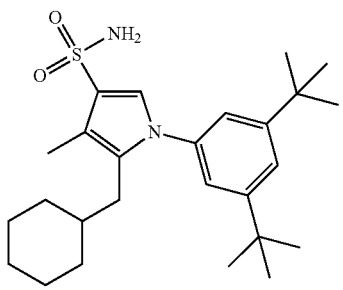

Example 25

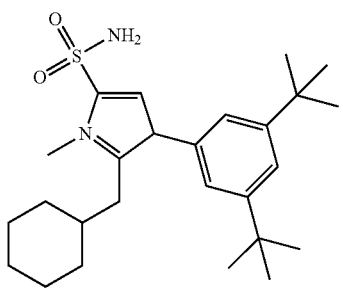

Step 1: Cyclohexyl(1H-pyrrol-2-yl)methanone (25a)

To a solution of MeMgBr (99.3 mL, 298 mmol) in Et$_2$O (500 mL) a solution of 1H-pyrrole (20 g, 298 mmol, dissolved in Et$_2$O) was added dropwise at rt under N$_2$. The mixture was heated to reflux for 30 min and cyclohexanecarbonyl chloride (43 g, 298 mmol) was added dropwise at −30° C. The reaction was refluxed for 30 min, quenched by slowly addition of sat. NH$_4$Cl, diluted with EA and water, washed with (3×) water and once with brine. The organic layer was dried over Na$_2$SO$_4$, concentrated and purified by CC to obtain compound 25a (10 g, 20%).

Step 2: Cyclohexyl(1-methyl-1H-pyrrol-2-yl)methanone (25b)

Compound 25a (2.0 g, 11.3 mmol dissolved dry DMF) was added portionwise to the mixture of NaH (60%; 0.904 g, 22.6 mmol) and dry DMF (200 mL) and the mixture was stirred for 30 min at rt, then MeI (1.9 g, 11.6 mmol) was added at 0° C. The stirred mixture was allowed to stand at rt for 2 h, poured slowly into ice-water and extracted with EA. The organic phase was dried (MgSO$_4$), evaporated and purified by CC to give compound 25b (1.73 g, 80%).

Step 3: 5-(Cyclohexanecarbonyl)-1-methyl-1H-pyrrole-2-sulfonyl chloride (25c)

To a solution of compound 25b (1.0 g, 5.2 mmol) was added portionwise chlorosulfonic acid (5 mL, 75 mmol) at 0° C., heated to 60° C. for 2 h, poured carefully into ice-water and extracted with CHCl$_3$. The organic phase was dried (MgSO$_4$), evaporated and purified by CC to give compound 25c (1.2 g, 80%).

Step 4: 5-(Cyclohexanecarbonyl)-1-methyl-1H-pyrrole-2-sulfonamide (25d)

Through a solution of compound 25c (1.7 g, 5.88 mmol) in DCM (120 mL) was bubbled NH$_3$ for 30 min at 0° C. with stirring and then was added HCl to adjusted pH to 4-5 and extracted with DCM. The combined organic layers were washed with brine, dried over Na$_2$SO$_4$, filtered and evaporated to give compound 25d (1.1 g, 69%) as a crude solid.

Step 5: 5-(Cyclohexylmethyl)-1-methyl-1H-pyrrole-2-sulfonamide (25e)

To a solution of compound 25d (1.1 g, 4.1 mmol) in diethylene glycol (50 mL) was added NH$_2$NH$_2$.H$_2$O (0.28 g, 4.5 mmol). The mixture was refluxed for 2 h and then the water and excess NH$_2$NH$_2$.H$_2$O was removed under vacuum. Then KOH (0.46 g, 8.2 mmol) was added and the mixture was refluxed for 4 h, cooled, diluted with water and extracted with EA. The combined organic layers were washed with brine, dried over Na$_2$SO$_4$, evaporated and purified by prep-TLC to give compound 25e (462 mg, 46%).

Step 6: 4-Bromo-5-(cyclohexylmethyl)-1-methyl-1H-pyrrole-2-sulfonamide (25f)

To a solution of NBS (68.7 mg, 386 µmol) was added a solution of compound 25e (104 mg, 410 µmol) in THF at −78° C. and stirred for 2 h at −78° C. Water (30 mL) was added and the reaction mixture was extracted with EA (150 mL). The organic layer was washed with brine, dried over Na$_2$SO$_4$, concentrated and purified by CC (hexane/EA=3/1) to give compound 25f (134 mg, 61%).

Step 7: 5-(Cyclohexylmethyl)-4-(3,5-di-tert-butylphenyl)-1-methyl-1H-pyrrole-2-sulfonamide (25)

A mixture of compound 25e (67.1 mg, 200 µmol), 2-(3,5-di-tert-butylphenyl)-4,4,5,5-tetramethyl-1,3,2-dioxaborolane (72.8 mg, 230 µmol), Cs$_2$CO$_3$ (326 mg, 1.0 mmol) and Pd(dppf)Cl$_2$ (22 mg) in dioxane and water was heated at 110° C. under microwave irradiation for 1 h. The solvent was removed and purified by prep-TLC to afford compound 25 (35 mg, 40%) as a white solid. $^1$H-NMR (300 MHz, CDCl$_3$) δ: 7.43 (t, J=1.5 Hz, 1H), 7.24 (s, 1H), 7.08 (d, J=1.5 Hz, 1H), 4.68 (s, 2H), 3.44 (s, 3H), 2.49 (d, J=7.8 Hz, 2H), 1.55-1.41 (m, 6H), 1.34 (s, 18H), 1.00-0.98 (m, 3H), 0.69-0.65 (m, 2H). MS Calcd.: 444.3; MS Found: 445.3 (M+1).

Example 26

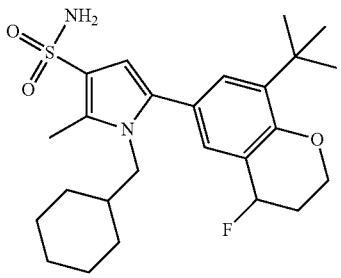

5-(8-(tert-Butyl)-4-fluorochroman-6-yl)-1-(cyclo-hexylmethyl)-2-methyl-1H-pyrrole-3-sulfonamide (26)

To a solution of alcohol 12/45 (180 mg, 0.39 mmol) in DCM (10 mL) was added DAST (126 mg, 0.78 mmol) in one portion at rt and the mixture was stirred for 1 h, poured into water and extracted with DCM. The organic layer was concentrated and purified by CC (PE/EA=4/1) to give compound 26 (111 mg, 62%) as a white solid. $^1$H-NMR (400 MHz, CDCl$_3$) δ: 7.20 (s, 1H), 7.15 (s, 1H), 6.41 (s, 1H), 5.43-5.56 (m, 1H), 4.64-4.66 (m, 2H), 4.40-4.45 (m, 1H), 4.21-4.27 (m, 1H), 3.63-3.73 (m, 2H), 2.53 (s, 3H), 2.17-2.32 (m, 2H), 1.53-1.56 (m, 3H), 1.33-1.43 (m, 12H), 1.02-1.06 (m, 3H), 0.65-0.71 (m, 2H). MS Calcd.: 462; MS Found: 463 (M+1)$^+$.

Example 27

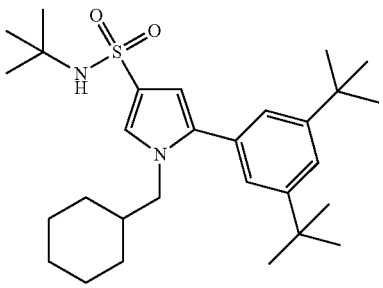

Step 1: 1-Tosyl-1H-pyrrole (27a)

To a stirred solution of 1H-pyrrole (5.0 g, 74.6 mmol) in dry THF (50 mL) was added n-BuLi (32.8 mL, 2.5 M) at −78° C. and stirred at this temperature for 30 min. Then a solution of TsCl (14.2 g, 74.6 mmol) in dry THF (100 mL) was added at −78° C. The mixture was stirred at rt overnight, quenched with water and extracted with EA twice. The combined organic layers were washed with brine and concentrated to give crude compound 27a (14.2 g, 86%) as a solid.

Step 2: 1-Tosyl-1H-pyrrole-3-sulfonyl chloride (27b)

To a stirred solution of compound 27a (5.0 g, 22.6 mmol) in ACN (50 mL) was carefully added ClSO$_3$H (15.8 g, 136 mmol) and the solution was stirred at rt overnight, poured on ice-water and extracted with CHCl$_3$ twice. The combined organic layers were washed with aq. NaHCO$_3$ and brine (3×), concentrated and purified by CC (PE/EA=50/1) to give compound 27b (1.45 g, 20%) as a solid.

Step 3: N-(tert-Butyl)-1-tosyl-1H-pyrrole-3-sulfonamide (27c)

To a solution of compound 27b (600 mg, 1.88 mmol) in dry CH$_2$Cl$_2$ (6 mL) was added tea-BuNH$_2$ (0.27 g, 3.76 mmol) and then the solution was stirred at rt overnight, quenched with 1N HCl and extracted with EA twice. The combined organic layers were washed with water (3×) and brine and concentrated to give crude compound 27c (660 mg, 99%) as a brown solid.

Step 4: N-(tert-Butyl)-1H-pyrrole-3-sulfonamide (27d)

To a solution of compound 27c (665 mg, 1.87 mmol) in a mixture of THF (12 mL), MeOH (12 mL) and water (3 mL) was added K$_2$CO$_3$ (3.1 g, 22 mmol) and then the solution was heated at 60° C. overnight, cooled, acidified to pH=5 with AcOH and extracted with EA twice. The combined organic layers were washed with water (3×) and brine, concentrated and purified by CC (PE/EA=2/1) to give compound 27d (260 mg, 69%) as a solid.

Step 5: N-(tert-Butyl)-1-(cyclohexylmethyl)-1H-pyrrole-3-sulfonamide (27e)

To a solution of compound 27d (29.4 g, 146 mmol), bromocyclohexylmethane (30.9 g, 175 mmol), K$_2$CO$_3$ (40.2 g, 291 mmol) in dry DMF (300 mL) was heated at 85° C. overnight, quenched with water and extracted with EA twice. The combined organic layers were washed with water (3×) and brine, concentrated and purified by CC (PE/EA=2/1) to give compound 27e (17.8 g, 41%) as a solid.

Step 6: 5-Bromo-N-(tert-butyl)-1-(cyclohexylmethyl)-1H-pyrrole-3-sulfonamide (27f)

To a stirred mixture of compound 27e (280 mg, 0.94 mmol) in dry THF (3 mL) was added NBS (200 mg, 1.13 mmol) at −78° C. and the solution was stirred at this temperature for 30 min, quenched with water and extracted with EA twice. The combined organic layers were washed with water (3×) and brine, concentrated and purified by CC (PE/EA=5/1) to give compound 27f (300 mg, 85%) as an oil.

Step 7: N-(tert-Butyl)-1-(cyclohexylmethyl)-5-(3,5-di-tert-butylphenyl)-1H-pyrrole-3-sulfonamide 27)

A mixture of compound 27f (200 mg, 532 μmol), (3,5-di-tert-butylphenyl)boronic acid (150 mg, 638 μmol), K$_2$CO$_3$ (110 mg, 798 μmol) and Pd(dppf)Cl$_2$ (20 mg) in dry DMF (3 mL) was heated at 120° C. overnight under N$_2$. The mixture was concentrated and purified by prep-HPLC to give compound 27 (88 mg, 34%) as a white solid. $^1$H-NMR (CDCl$_3$, 400 MHz) δ: 0.70-0.76 (2H, m), 1.07-1.09 (3H, m), 1.31-1.34 (27H, m), 1.47-1.61 (6H, m), 3.69 (2H, d, J=7.2 Hz), 4.29

(1H, s), 6.42 (1H, d), 7.17-7.19 (3H, m), 7.43 (1H, t). MS Calcd.: 486.3; MS Found: 487.3 (M+1).

Example 28

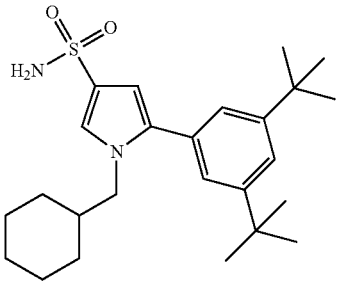

28

1-(Cyclohexylmethyl)-5-(3,5-di-tert-butylphenyl)-1H-pyrrole-3-sulfonamide (28)

To a solution of compound 27 (400 mg, 823 μmol) in dry DCM (4 mL) was added TFA (9 mL) at 0° C. and then the solution was stirred at rt overnight, quenched with water and extracted with EA twice. The combined organic layers were washed with water and brine consecutively, concentrated and purified by prep-HPLC to give compound 28 (100 mg, 28%) as a white solid. $^1$H-NMR (CD$_3$OD, 400 MHz) δ: 0.83-0.85 (2H, m), 1.08-1.13 (3H, m), 1.38 (18H, m), 1.45-1.65 (6H, m), 3.81 (2H, d, J=7.2 Hz), 6.44 (1H, d), 7.22 (2H, d), 7.31 (1H, d), 7.51 (1H, d). MS Calcd.: 430.3; MS Found: 431.3 (M+1).

Example 29 and Example 30

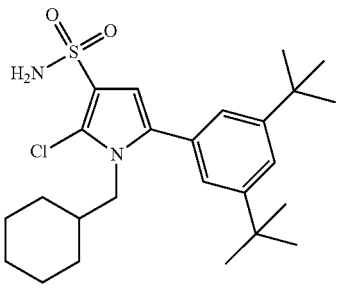

29

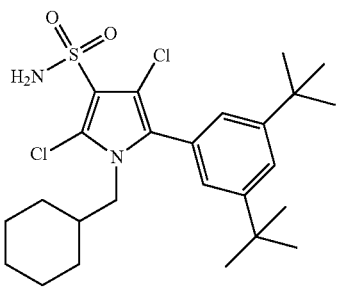

30

2-Chloro-1-(cyclohexylmethyl)-5-(3,5-di-tert-butylphenyl)-1H-pyrrole-3-sulfonamide (29) and 2,4-Dichloro-1-(cyclohexylmethyl)-5-(3,5-di-tert-butylphenyl)-1H-pyrrole-3-sulfonamide (30)

To a solution of compound 28 (150 mg, 394 μmol) in dry THF (2 mL) was added NCS (93 mg, 349 μmol) and then the mixture was stirred overnight at rt, quenched with water and extracted with EA twice. The combined organic layers were washed with water and brine consecutively, concentrated and purified by prep-HPLC to give compound 29 (35 mg, 22%) and compound 30 (12 mg, 6%) as white solids. 29: $^1$H-NMR (CDCl$_3$, 400 MHz) δ: 0.70 (2H, m), 1.01 (3H, m), 1.31-1.37 (18H, m), 1.49-1.58 (6H, m), 3.81 (2H, d, J=7.2 Hz), 4.87 (2H, s), 6.56 (1H, s), 7.13-7.14 (2H, m), 7.44 (1H, s). MS Calcd.: 464.2; MS Found: 465.4 (M+1). 29: $^1$H-NMR (CDCl$_3$, 400 MHz) δ: 0.70 (2H, m), 1.01 (3H, m), 1.31-1.37 (18H, m), 1.54-1.58 (6H, m), 3.76 (2H, d, J=7.2 Hz), 5.05 (2H, s), 7.13 (2H, d), 7.48 (1H, s). MS Calcd.: 498.2; MS Found: 499.3 (M+1).

Example 31 and Example 32

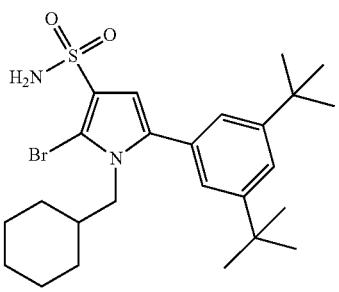

31

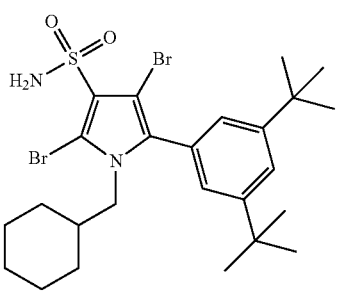

32

2-Bromo-1-(cyclohexylmethyl)-5-(3,5-di-tert-butylphenyl)-1H-pyrrole-3-sulfonamide (31) and 2,4-Dibromo-1-(cyclohexylmethyl)-5-(3,5-di-tert-butylphenyl)-1H-pyrrole-3-sulfonamide (32)

To a solution of compound 28 (200 mg, 465 μmol) in dry THF (2 mL) was added NBS (99 mg, 558 μmol) at 0° C. and then the mixture was stirred for 2 h at rt, quenched with water and extracted with EA twice. The combined organic layers were washed with water and brine consecutively, concentrated and purified by prep-TLC to give compound 31 (42 mg, 18%) and compound 32 (45 mg, 17%) as white solids. 31: $^1$H-NMR (CDCl$_3$, 400 MHz) δ: 0.66-0.69 (2H, m), 1.00 (3H, m), 1.34 (18H, m), 1.48-1.56 (6H, m), 3.85 (2H, d, J=7.6 Hz), 4.86 (2H, s), 6.64 (1H, s), 7.13 (2H, d), 7.44 (1H, t). MS Calcd.: 508.2; MS Found: 509.1/511.1 (M+1). 32: $^1$H-NMR (CDCl$_3$, 400 MHz) δ: 0.66-0.69 (2H, m), 1.00 (3H, m), 1.30-1.34 (18H, m), 1.53-1.55 (6H, m), 3.81 (2H, d, J=7.2 Hz), 5.06 (2H, s), 7.12 (2H, d), 7.48 (1H, t). MS Calcd.: 586.1; MS Found: 587.0/589.1/591.0 (M+1).

Example 33

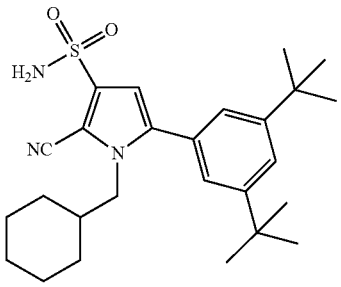

2-Cyano-1-(cyclohexylmethyl)-5-(3,5-di-tert-butylphenyl)-1H-pyrrole-3-sulfonamide (33)

A mixture of compound 31 (80 mg, 157 μmol), Zn(CN)$_2$ (37 mg, 317 μmol) and Pd(PPh$_3$)$_4$ (20 mg) in dry DMF (2 mL) under N$_2$ was heated at 160° C. for 30 min under microwave irradiation, concentrated and purified by prep-TLC to give compound 33 (40 mg, 56%) as a white solid. $^1$H-NMR (CDCl$_3$, 400 MHz) δ: 0.78-0.80 (2H, m), 1.05 (3H, m), 1.31-1.37 (18H, m), 1.56-1.58 (6H, m), 3.93 (2H, d, J=7.2 Hz), 5.04 (2H, s), 6.62 (1H, s), 7.15 (2H, d), 7.51 (1H, t). MS Calcd.: 455.3; MS Found: 473.3 (M+18).

Example 34

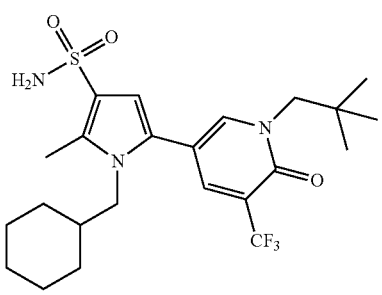

Step 1: 1-(Cyclohexylmethyl)-2-methyl-5-(4,4,5,5-tetramethyl-1,3,2-dioxaborolan-2-yl)-1H-pyrrole-3-sulfonamide (34a)

A mixture of compound 1d (5.00 g, 15.0 mmol), (PinB)$_2$ (5.70 g, 22.5 mmol), K$_2$CO$_3$ (8.30 g, 60.0 mmol) and PdCl$_2$(dppf) (0.60 g) in DMF (200 mL) was stirred at 90° C. under N$_2$ overnight, cooled to rt, diluted with water and extracted with Et$_2$O (3×100 mL). The combined organic phases were dried over Na$_2$SO$_4$, filtered, concentrated and purified by CC (PE/EA=2/1) to give compound 34a (3.0 g, 59%) as a white solid. $^1$H-NMR (CDCl$_3$, 300 MHz) δ: 0.92-1.04 (2H, m), 1.15-1.28 (3H, m), 1.35 (12H, s), 1.55-1.72 (6H, m), 2.48 (3H, s), 3.93 (2H, d, J=6.6 Hz), 4.66 (2H, s), 7.13 (1H, s).

Step 2: 1-(Cyclohexylmethyl)-2-methyl-5-(1-neopentyl-6-oxo-5-(trifluoromethyl)-1,6-dihydropyridin-3-yl)-1H-pyrrole-3-sulfonamide (34)

A solution of compound P45 (250 mg, 0.80 mmol), compound 34a (367 mg, 0.96 mmol), K$_2$CO$_3$ (332 mg, 2.40 mmol) and Pd(dppf)Cl$_2$ (25 mg) in DMF (5 mL) was stirred at 120° C. under N$_2$ for 2 h. Water was added and the resulting solution was extracted with EA (3×). The combined organic layers were washed with water (3×) and brine consecutively and dried over Na$_2$SO$_4$, filtered, concentrated and purified by prep-TLC to give compound 34 (106 mg, 27%) as a white solid. $^1$H-NMR (400 MHz, DMSO-d$_6$) δ: 0.71-0.78 (2H, m), 0.81-1.02 (12H, m), 1.32-1.41 (3H, m), 1.55-1.57 (3H, m), 2.38 (3H, s), 3.71 (2H, d, J=6.8 Hz), 3.94 (2H, s), 6.33 (1H, s), 6.93 (2H, s), 7.93 (1H, s), 8.01 (1H, s). MS Calcd.: 487; MS Found: 488 (M+1).

Example 34/1 to Example 34/5

Similar to Example 34 the following compounds were obtained using the pyrrole boronic ester intermediate.

| # | Structure | Analytical data |
|---|-----------|-----------------|
| 34/1 | ![structure] | $^1$H-NMR (CDCl$_3$, 400 MHz) δ: 0.63-0.66 (m, 2H), 0.76-0.77 (m, 2H), 0.86-0.89 (m, 2H), 0.98-0.99 (m, 3H), 1.33-1.41 (m, 3H), 1.42 (s, 3H), 1.54-1.58 (m, 9H), 1.71 (s, 1H), 2.53 (s, 3H), 3.72-3.74 (d, 2H, J = 8.0 Hz), 4.64 (s, 2H), 6.45 (s, 1H), 7.07 (s, 1H), 7.20 (s, 1H), 7.42 (s, 1H). MS Calcd.: 444; MS Found: 445 (M + 1). |

| # | Structure | Analytical data |
|---|---|---|
| 34/2 | 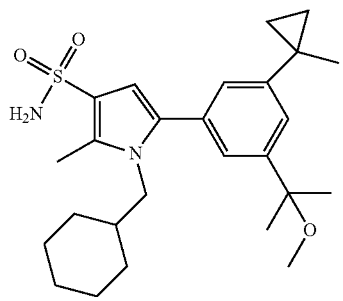 [SMILES: COC(C)(C)c1cc(-c2cc(S(N)(=O)=O)c(C)n2CC2CCCCC2)cc(C2(C)CC2)c1] | ¹H-NMR (CDCl₃, 400 MHz) δ: 0.63-0.66 (m, 2H), 0.76-0.77 (m, 2H), 0.86-0.89 (m, 2H), 0.97-0.98 (m, 3H), 1.33-1.42 (m, 3H), 1.52 (s, 3H), 1.55 (m, 9H), 2.53 (s, 3H), 3.07 (s, 3H) 3.73-3.74 (d, 2H, J = 8.0 Hz), 4.65 (s, 2H), 6.46 (s, 1H), 7.07 (s, 1H), 7.15 (s, 1H), 7.28 (s, 1H). MS Calcd.: 458; MS Found: 459 (M + 1). |
| 34/3 | 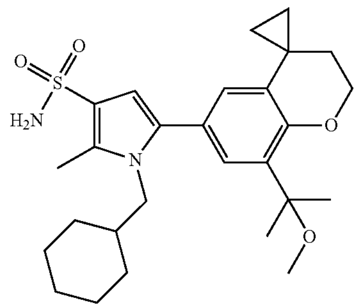 [SMILES: COC(C)(C)c1cc(-c2cc(S(N)(=O)=O)c(C)n2CC2CCCCC2)cc2c1OCCC21CC1] | ¹H-NMR (CDCl₃, 400 MHz) δ: 0.67-0.72 (2H, m), 0.87-0.89 (2H, m), 1.00-1.03 (5H, m), 1.35-1.38 (3H, m), 1.60 (9H, m), 1.88-1.91 (2H, t, J = 10 Hz), 2.52 (3H, s), 3.19 (3H, s), 3.67-3.39 (2H, d, J = 7.2 Hz), 4.32-4.34 (2H, t, J = 10 Hz), 4.64 (2H, s), 6.36 (1H, s), 6.48 (1H, s), 7.12 (1H, s). MS Calcd.: 486; MS Found: 487 (M + 1)⁺. |
| 34/4 | 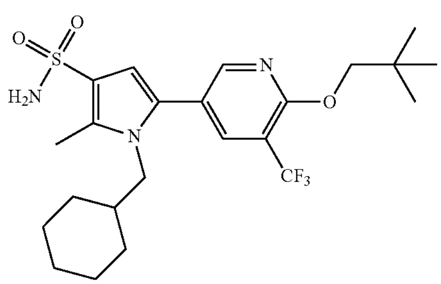 [SMILES: Cc1c(S(N)(=O)=O)cc(-c2cnc(OCC(C)(C)C)c(C(F)(F)F)c2)n1CC1CCCCC1] | ¹H-NMR (DMSO-d₆, 400 MHz) δ: 0.67-0.69 (2H, m), 0.86-1.02 (12H, m), 1.29-1.36 (3H, m), 1.51-1.53 (3H, m), 2.45 (3H, s), 3.76 (2H, d, J = 6.8 Hz), 4.12 (2H, s), 6.42 (1H, s), 6.97 (2H, s), 8.08 (1H, d, J = 2.0 Hz), 8.42 (1H, d, J = 2.0 Hz). MS Calcd.: 487; MS Found: 488 (M + 1). |
| 34/5 | 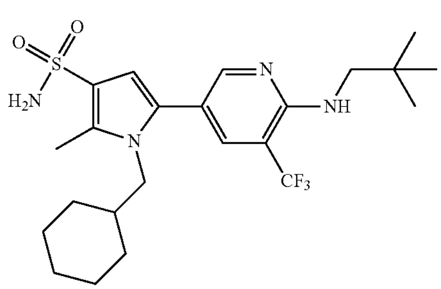 [SMILES: Cc1c(S(N)(=O)=O)cc(-c2cnc(NCC(C)(C)C)c(C(F)(F)F)c2)n1CC1CCCCC1] | ¹H-NMR (CDCl₃, 400 MHz) δ: 0.69-0.75 (2H, m), 1.01 (9H, s), 1.04-1.09 (3H, m), 1.39-1.46 (3H, m), 1.57-1.61 (3H, m), 2.53 (3H, s), 3.41 (2H, d, J = 5.6 Hz), 3.65 (2H, d, J = 8.8 Hz), 4.64 (1H, s), 5.06 (1H, s), 6.43 (1H, s), 7.57 (1H, d, J = 1.6 Hz), 8.18 (1H, d, J = 2.0 Hz). MS Calcd.: 486; MS Found: 487 (M + 1)⁺ |

Preparative Example 35 to Example 37

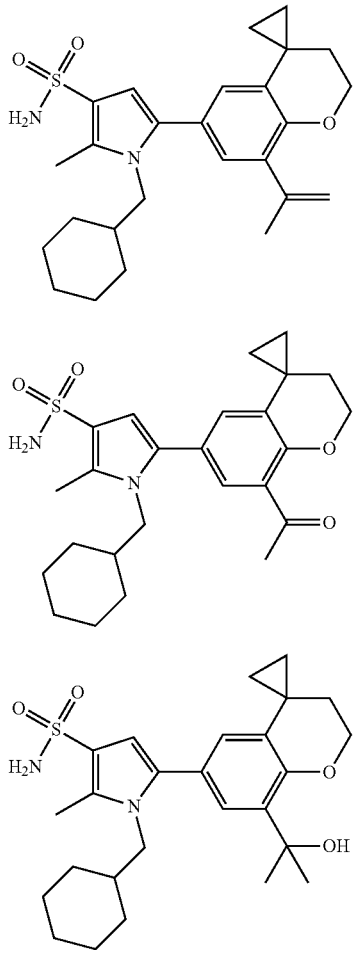

Step 1: 1-(Cyclohexylmethyl)-2-methyl-5-(8-(oroo-1-en-2-yl)spiro[chroman-4,1'-cyclopropan]-6-yl)-1H-pyrrole-3-sulfonamide (35)

A solution of compound P39 (80 mg, 0.271 mmol), compound 34a (155 mg, 0.406 mmol), Pd(dppf)Cl$_2$ (10 mg) and K$_2$CO$_3$ (112 mg, 813 µmol) in DMF (2 mL) under N$_2$ was stirred at 115° C. for 4 h, concentrated and purified by CC (PE/EE=5/1) to give compound 35 (111 mg, 90%) as a white solid.

Step 2: 5-(8-Acetylspiro[chroman-4,1'-cyclopropan]-6-yl)-1-(cyclohexylmethyl)-2-methyl-1H-pyrrole-3-sulfonamide (36)

To a stirred mixture of compound 35 (111 mg, 0.24 mmol) and OsO$_4$ (5 mg) in dioxane (12 mL) was added a solution of NaIO$_4$ (210 mg, 0.98 mmol) in water (4 mL). Then the mixture was stirred at 30° C. for 2 h, quenched with water and extracted with EA twice. The combined organic layers were washed with brine, concentrated and purified by CC (PE/EE=5/1) to give compound 36 (86 mg, 77%) as a white solid.

Step 3: 1-(Cyclohexylmethyl)-5-(8-(2-hydroxypropan-2-yl)spiro[chroman-4,1'-cyclopropan]-6-yl)-2-methyl-1H-pyrrole-3-sulfonamide (37)

To a stirred solution of compound 36 (86 mg, 0.19 mmol) in dry THF (2 mL) was added CH$_3$MgBr (3M, 70 µL, 0.21 mmol) and the mixture was stirred at rt for 2 h, quenched with aq. NH$_4$Cl at 0° C. and extracted with EA. The organic layer was concentrated and purified by CC (PE/EE=4/1) to give compound 37 (21 mg, 24%) as a colorless solid. $^1$H-NMR (CDCl$_3$+D$_2$O, 400 MHz) δ: 0.67-0.72 (2H, m), 0.88-0.91 (2H, m), 1.01-1.05 (5H, m), 1.36-1.44 (3H, m), 1.60 (9H, m), 1.93-1.95 (2H, t, J=10.4 Hz), 2.52 (3H, s), 3.63-3.65 (2H, d, J=7.2 Hz), 4.43-4.45 (2H, t, J=10.4 Hz), 6.35 (1H, s), 6.49 (1H, s), 6.98 (1H, s). MS Calcd.: 472; MS Found: 473 (M+1)$^+$.

Example 38 to Example 41

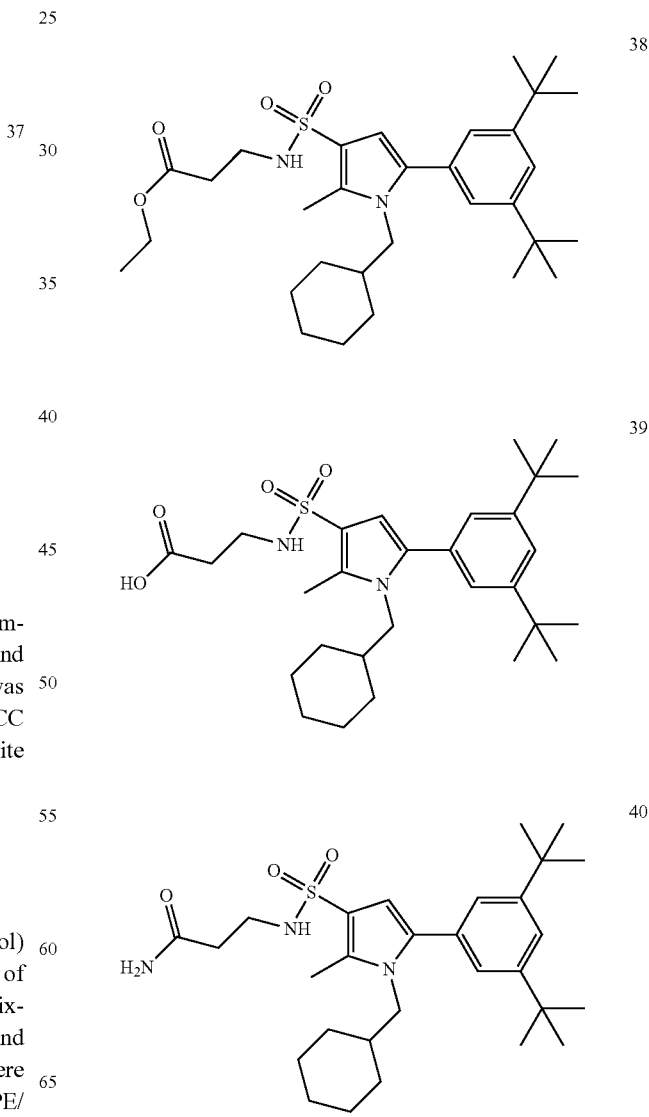

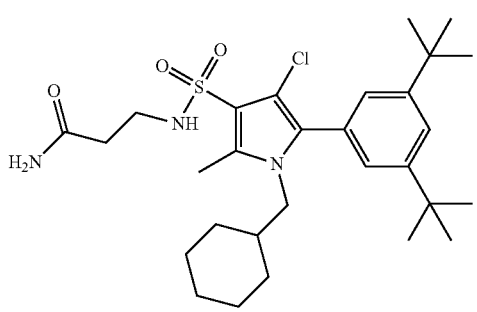

41

Step 1: Methyl 3-(1-(cyclohexylmethyl)-5-(3,5-di-tert-butylphenyl)-2-methyl-1H-pyrrole-3-sulfonamido)propanoate (38)

To a solution of compound 1 (1.0 g, 2.25 mmol) in dry DMF (10 mL) was added NaH (60%, 92 mg, 2.3 mmol) at 0° C. and the mixture was stirred for 10 min, ethyl 3-bromopropanoate (410 mg, 2.25 mmol) was added and stirred at rt for 5 h. Water was added and the solution was extracted with EA. The organic layer was washed with brine twice, concentrated and purified by CC (PE/EA=5/1) to give compound 38 (400 mg, 34%) as a white solid.

Step 2: 3-(1-(Cyclohexylmethyl)-5-(3,5-di-tert-butylphenyl)-2-methyl-1H-pyrrole-3-sulfonamido)propanoic acid (39)

To a solution of compound 38 (400 mg, 0.75 mmol) in a mixture of MeOH (10 mL) and water (3 mL) was added LiOH.H$_2$O (200 mg, 4.60 mmol) and then this mixture was stirred at 60° C. for 4 h, evaporated and acidified to pH~5 with 3N HCl. The aq. layer was extracted with EA (3×). The combined organic layers were concentrated and purified by CC (PE/EA=2/1) to give compound 39 (345 mg, 79%) as a colorless oil. $^1$H-NMR (CDCl$_3$, 300 MHz) δ: 0.60-0.66 (2H, m), 0.93-1.02 (3H, m), 1.23-1.38 (3H, m), 1.34 (18H, s), 1.51-1.55 (3H, m), 2.51 (3H, s), 2.64 (2H, t, J=5.4 Hz), 3.23-3.29 (2H, m), 3.70 (2H, d, J=7.2 Hz), 5.45 (1H, m), 6.42 (1H, s), 7.14 (2H, s), 7.40 (1H, s). MS Calcd.: 516; MS Found: 517 (M+1).

Step 3: 3-(1-(cyclohexylmethyl)-5-(3,5-di-tert-butylphenyl)-2-methyl-1H-pyrrole-3-sulfonamido)propanamide (40) and 3-(4-chloro-1-(cyclohexylmethyl)-5-(3,5-di-tert-butylphenyl)-2-methyl-1H-pyrrole-3-sulfonamido)propanamide (41)

To a solution of compound 39 (240 mg, 0.46 mmol) in dry DCM (5 mL) was added (COCl)$_2$ (126 mg, 0.5 mmol) and one drop DMF at 0° C. under N$_2$ and the mixture was stirred at rt for 30 min, concentrated and the residue was treated with 6N NH$_3$/THF (20 mL) and stirred for additional 30 min. The resulting solution was concentrated and water was added. After phase separation, the aq. layer was extracted with EA twice. The combined organic layers were concentrated and purified by CC (PE/EA=2/1) to give compound 40 (50 mg, 21%) as a white oil and compound 41 (110 mg, 43%) as colorless oil. 40: $^1$H-NMR (CDCl$_3$, 300 MHz) δ: 0.60-0.66 (2H, m), 0.93-1.02 (3H, m), 1.23-1.38 (3H, m), 1.34 (18H, s), 1.51-1.55 (3H, m), 2.51 (3H, s), 2.51-2.55 (2H, m), 3.26 (2H, m), 3.71 (2H, d, J=7.2 Hz), 5.13 (1H, t, J=6.9 Hz), 5.40 (1H, br s), 5.61 (1H, s), 6.42 (1H, br s), 7.14 (2H, d, J=1.8 Hz), 7.40 (1H, t, J=1.8 Hz). MS Calcd.: 515; MS Found: 516 (M+1). 41: $^1$H-NMR (CDCl$_3$, 300 MHz) δ: 0.60-0.64 (2H, m), 0.93-1.02 (3H, m), 1.23-1.38 (3H, m), 1.34 (18H, s), 1.51-1.55 (3H, m), 2.54 (5H, m), 3.27 (2H, m), 3.64 (2H, d, J=6.9 Hz), 5.35 (1H, t, J=6.6 Hz), 5.43 (1H, br s), 5.68 (1H, br s), 7.13 (2H, d, J=1.8 Hz), 7.43 (1H, t, J=1.8 Hz). MS Calcd.: 549; MS Found: 550 (M+1).

Example 42 and Example 43

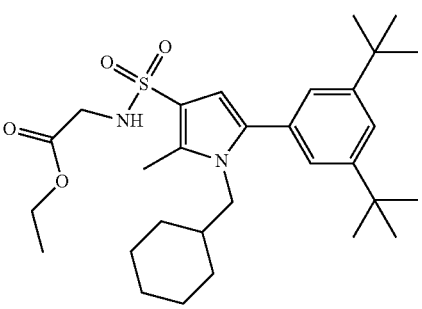

42

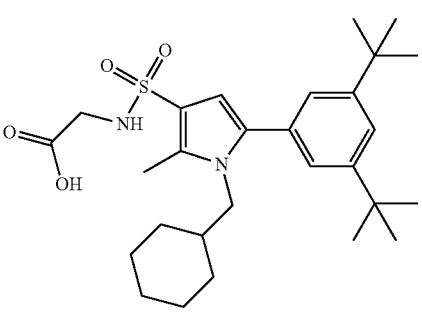

43

Step 1: Ethyl 2(1-(cyclohexylmethyl)-5(3,5-di-tert-butylphenyl)-2-methyl-1H-pyrrole-3-sulfonamido)acetate (42)

To a solution of compound 1 (600 mg, 1.36 mmol) in dry DMF (10 mL) was added NaH (60%, 60 mg, 1.50 mmol) at 0° C. and the mixture was stirred at 0° C. for 10 min. Ethyl 2-bromoacetate (225 mg, 1.36 mmol) was added and then this mixture was stirred at rt for 5 h. Water was added for quench and the solution was extracted with EA. The organic layer was washed with brine twice, concentrated and purified by CC (PE/EA=5/1) to give compound 42 (150 mg, 21%) as a white solid.

Step 2: 2(1-(Cyclohexylmethyl)-5(3,5-di-tert-butylphenyl)-2-methyl-1H-pyrrole-3-sulfonamido)acetic acid (43)

Similar to Example 39 compound 43 was obtained in 50% yield. $^1$H-NMR (CDCl$_3$, 300 MHz) δ: 0.60-0.66 (2H, m), 0.93-1.00 (3H, m), 1.23-1.38 (3H, m), 1.33 (18H, s), 1.51-1.55 (3H, m), 2.50 (3H, s), 3.70 (2H, d, J=7.2 Hz), 3.81 (2H, s), 5.20 (1H, s), 6.41 (1H, s), 7.13 (2H, d, J=1.8 Hz), 7.40 (1H, t, J=1.8 Hz). MS Calcd.: 502; MS Found: 503 (M+1).

Example 44

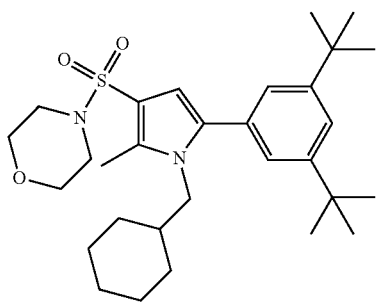

44

4-((1-(Cyclohexylmethyl)-5-(3,5-di-tert-butylphenyl)-2-methyl-1H-pyrrol-3-yl)sulfonyl)morpholine (44)

To a solution of compound 1 (300 mg, 0.68 mmol) in dry DMF (5 mL) was added NaH (60%, 60 mg, 1.50 mmol) at 0° C. and the mixture was stirred at 0° C. for 10 min. 2-chloro-1-(2-chloroethoxy)ethane (97 mg, 0.68 mmol) and KI (113 mg, 0.68 mmol) was added and then this mixture was stirred overnight at rt, quenched with water and extracted with EA. The organic layer was washed with brine twice, concentrated and purified by CC (PE/EA=4/1) to give compound 44 (70 mg, 21%) as a white solid. $^1$H-NMR (CDCl$_3$, 300 MHz) δ: 0.60-0.70 (2H, m), 0.95-1.03 (3H, m), 1.23-1.40 (3H, m), 1.36 (18H, s), 1.49-1.52 (3H, m), 2.52 (3H, s), 3.02-3.05 (4H, m), 3.73-3.78 (6H, m), 6.35 (1H, s), 7.15 (2H, d, J=1.8 Hz), 7.41 (1H, t, J=1.8 Hz). MS Calcd.: 514; MS Found: 515 (M+1).

Examples 45 to Example 50

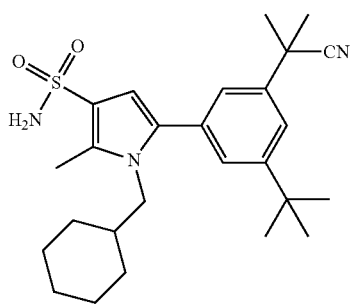

45

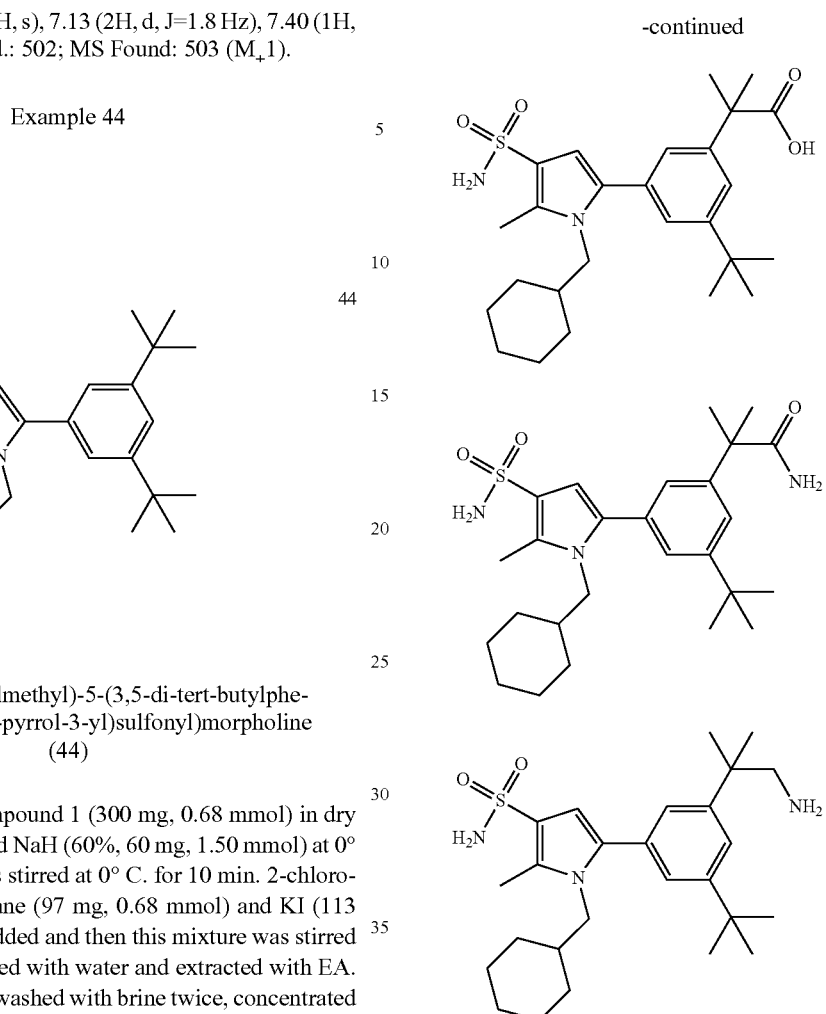

Step 1: 2-(3-(tert-Butyl)-5-(4,4,5,5-tetramethyl-1,3, 2-dioxaborolan-2-yl)phenyl)-2-methylpropanenitrile (P45a)

A solution of 2-(3-bromo-5-(tert-butyl)phenyl)-2-methylpropanenitrile (4.0 g, 14.3 mmol), $Pin_2B_2$ (5.4 g, 21.4 mmol), AcOK (2.1 g, 21.4 mmol) and $Pd(dppf)Cl_2$ (500 mg) in dry DMF (100 mL) was stirred and heated at 90° C. overnight under $N_2$, diluted with water and extracted with EA twice. The combined organic layers were washed with water (3×) and brine consecutively, concentrated and purified by CC (PE/EA=50/1) to afford compound P45a (2.1 g, 45%) as a white solid.

Step 2: 5-(3-(tert-Butyl)-5-(2-cyanopropan-2-yl)phenyl)-1-(cyclohexylmethyl)-2-methyl-1H-pyrrole-3-sulfonamide (45)

To a solution of compound P45a (2.1 g, 6.40 mmol), compound 1d (2.1 g, 6.40 mmol), $K_2CO_3$ (2.2 g, 16.0 mmol) and tetrabutylammonium bromide (300 mg, 0.96 mmol) in a mixture of dioxane (30 mL) and water (15 mL) was added $Pd(dppf)Cl_2$ (450 mg) under $N_2$. Under microwave conditions (120W), the solution was heated to 100° C. for 1 h, cooled to rt and poured into a water/EA. The aq. phase was extracted with EA twice. The combined organic layers were washed with water (3×) and brine consecutively, concentrated and purified CC (PE/EA=2/1) to give compound 45 (2.0 g, 68%) as a white solid. $^1$H-NMR (DMSO-$d_6$, 400 MHz) δ: 0.61-0.69 (2H, m), 0.85-0.94 (3H, m), 1.13-1.19 (3H, m), 1.33 (9H, s), 1.46 (3H, m), 1.72 (6H, s), 2.40 (3H, s), 3.79 (2H, d, J=6.8 Hz), 6.35 (1H, s), 6.94 (2H, s), 7.30 (2H, m), 7.50 (1H, m). MS Calcd.: 455; MS Found: 456 (M+1).

Step 3: 2-(3-(tert-Butyl)-5-(1-(cyclohexylmethyl)-5-methyl-4-sulfamoyl-1H-pyrrol-2-yl)phenyl)-2-methylpropanoic acid (46)

A solution of compound 45 (720 mg, 1.58 mmol) and NaOH (5.0 g, 127 mmol) in a mixture of EtOH (15 mL) and $H_2O$ (10 mL) was stirred at reflux for 3 d, cooled to rt, concentrated and redissolved in $H_2O$ (30 mL) and acidified with 1N HCl solution to pH=6. The formed solid was collected by filtration, washed with EA and dried in vacuum to give the title compound 46 (750 mg, 100%) as a white solid. $^1$H-NMR (DMSO-$d_6$, 400 MHz) δ: 0.63-0.65 (2H, m), 0.90-0.95 (3H, m), 1.22-1.25 (3H, m), 1.30 (9H, s), 1.45 (3H, m), 1.49 (6H, s), 2.43 (3H, s), 3.76 (2H, d, J=6.8 Hz), 6.29 (1H, s), 6.92 (2H, s), 7.08 (1H, s), 7.23 (1H, s), 7.34 (1H, s), 12.38 (1H, s). MS Calcd.: 474; MS Found: 475 (M+1).

Step 4: 2-(3-(tert-Butyl)-5-(1-(cyclohexylmethyl)-5-methyl-4-sulfamoyl-1H-pyrrol-2-yl)phenyl)-2-methylpropanamide (47)

A solution of compound 45 (455 mg, 1.0 mmol) and NaOH (3.2 g, 80 mmol) in EtOH (10 mL) and water (10 mL) was stirred at reflux overnight, cooled to rt, concentrated and redissolved in $H_2O$ (30 mL), acidified with 1N HCl solution to pH=6. The formed solid was collected by filtration, washed with water and dried under vacuum. The residue was purified by CC (DCM/MeOH=50/1) to give compound 47 (400 mg, 85%) of as a white solid.

Step 5: 5-(3-(1-Amino-2-methylpropan-2-yl)-5-(tert-butyl)phenyl)-1-(cyclohexyl-methyl)-2-methyl-1H-pyrrole-3-sulfonamide (48)

To a solution of compound 47 (330 mg, 0.70 mol) in dry THF (5 mL) was added a solution of $BH_3$ in THF (1M, 7 mL, 7 mmol) dropwise under cooling with an ice-bath. After the addition, the mixture was stirred at rt overnight, slowly diluted MeOH (5 mL), concentrated and purified by CC (DCM/MeOH=10/1) to give compound 48 (280 mg, 87%) as a white solid. $^1$H-NMR (DMSO-$d_6$, 400 MHz) δ: 0.64-0.67 (2H, m), 0.89-0.96 (3H, m), 1.21-1.35 (20H, m), 1.46 (3H, d, J=8.0 Hz), 2.44 (3H, s), 3.03 (2H, s), 3.78 (3H, d, J=6.8 Hz), 6.31 (1H, s), 6.93 (2H, s), 7.18 (1H, s), 7.24 (1H, s), 7.37 (1H, s). MS Calcd.: 459; MS Found: 460, (M+1).

Step 6: N-(2-(3-(tert-Butyl)-5-(1-(cyclohexylmethyl)-5-methyl-4-sulfamoyl-1H-pyrrol-2-yl)phenyl)-2-methylpropyl)acetamide (49)

To a solution of compound 48 (100 mg, 0.22 mmol) in dry DCM (5 mL) was added $Ac_2O$ (25 mg, 0.24 mmol) at 0° C. and then the solution was stirred overnight at rt, concentrated and purified by prep-TLC to afford compound 49 (60 mg, 54%) as a white solid. $^1$H-NMR (DMSO-$d_6$, 400 MHz) δ: 0.64-0.67 (2H, m), 0.93-0.95 (3H, m), 1.26-1.30 (20H, m), 1.46 (3H, d, J=6.8 Hz), 1.77 (3H, s), 2.43 (3H, s), 3.28 (2H, d, J=5.6 Hz), 3.76 (3H, d, J=7.2 Hz), 6.28 (1H, s), 6.91 (2H, s), 7.09 (1H, s), 7.16 (1H, s), 7.35 (1H, s), 7.67 (1H, m). MS Calcd.: 501; MS Found: 502 (M+1).

Step 7: 5434 tert-Butyl)-5-(1-hydroxy-2-methylpropan-2-yl)phenyl)-1-(cyclohexyl-methyl)-2-methyl-1H-pyrrole-3-sulfonamide (50)

To a solution of compound 46 (150 mg, 0.32 mmol) in dry THF (10 mL) was added a solution of $BH_3$ in THF (1 M, 1 mL, 1.00 mmol) dropwise under cooling with an ice-bath. After addition, the mixture was stirred at rt overnight, slowly diluted with MeOH (1 mL), concentrated and purified by prep-TLC (PE/EA=1/1) to afford compound 50 (29 mg, 20%) as a white solid. $^1$H-NMR (DMSO-$d_6$, 400 MHz) δ: 0.62-0.65 (2H, m), 0.99-1.01 (3H, m), 1.18 (3H, m), 1.34 (9H, s), 1.36 (7H, m), 1.54 (3H, m), 2.54 (3H, s), 3.63 (2H, s), 3.71 (2H, d, J=6.8 Hz), 4.68 (2H, s), 6.47 (1H, s), 7.14 (1H, s), 7.20 (1H, s), 7.40 (1H, s). MS Calcd.: 460; MS Found: 461 (M+1).

Example 49/1 to Example 49/2

Similar to Example 49 the following compounds were prepared.

| # | Structure | Analytical data |
|---|---|---|
| 49/1 | 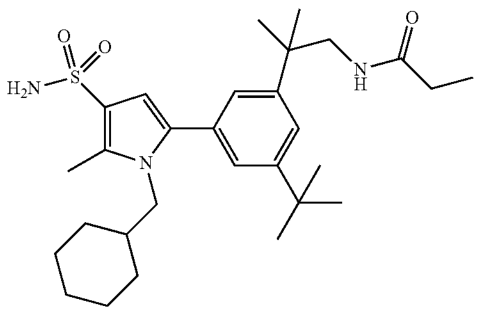 [SMILES: CCC(=O)NCC(C)(C)c1cc(-c2cc(S(N)(=O)=O)c(C)n2CC2CCCCC2)cc(C(C)(C)C)c1] | $^1$H-NMR (DMSO-$d_6$, 400 MHz) δ: 0.63-0.67 (2H, m), 0.89-1.01 (6H, m), 1.26 (9H, s), 1.30 (9H, s), 1.46 (3H, d, J = 8.0 Hz), 2.03 (2H, m), 2.43 (3H, s), 3.30 (2H, m), 3.76 (2H, d, J = 6.8 Hz), 6.27 (1H, s), 6.90 (2H, s), 7.09 (1H, s), 7.15 (1H, s), 7.34 (1H, s), 7.55 (1H, t, J = 6.0 Hz). MS Calcd.: 515; MS Found: 516 (M + 1). |
| 49/2 | 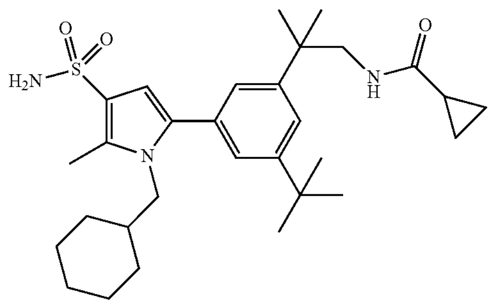 [SMILES: Cc1c(S(N)(=O)=O)cc(-c2cc(C(C)(C)C)cc(C(C)(C)CNC(=O)C3CC3)c2)n1CC1CCCCC1] | $^1$H-NMR (DMSO-$d_6$, 400 MHz) δ: 0.56-0.60 (4H, m), 0.64-0.67 (2H, m), 0.91-0.96 (3H, m), 1.27 (9H, m), 1.30 (9H, s), 1.46 (3H, d, J = 7.2 Hz), 1.62 (1H, m), 2.43 (3H, s), 3.32 (2H, m), 3.76 (2H, d, J = 6.8 Hz), 6.28 (1H, s), 6.90 (2H, s), 7.10 (1H, s), 7.16 (1H, s), 7.36 (1H, s), 7.87 (1H, m). MS Calcd.: 527; MS Found: 528 (M + 1). |

Examples 51 to Example 53

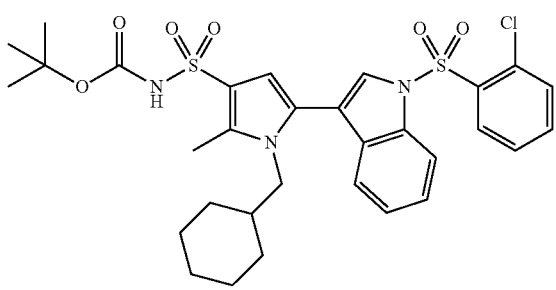

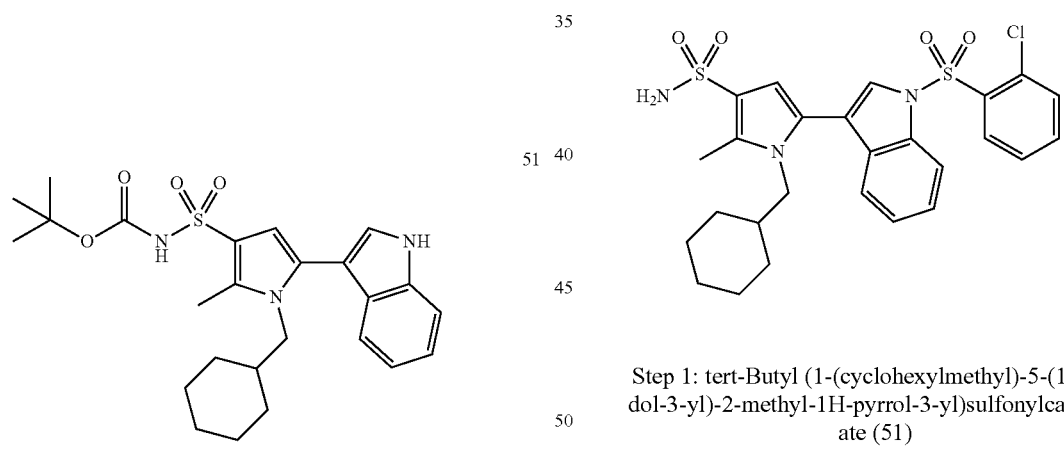

Step 1: tert-Butyl (1-(cyclohexylmethyl)-5-(1H-indol-3-yl)-2-methyl-1H-pyrrol-3-yl)sulfonylcarbamate (51)

To a solution of compound 1/43 (5.8 g, 9.5 mmol) in EtOH was added KOH (2.1 g, 38 mmol). The mixture was stirred at reflux overnight, cooled to rt, diluted with water and 2N HCl (50 mL) and extracted with EA. The combined organic layers were washed with brine and dried over Na$_2$SO$_4$, filtered, concentrated and purified by CC (hexane/EA=1/1) to afford compound 51 (3.8 g, 85%).

Step 2: tea-Butyl (5-(1-((2-chlorophenyl)sulfonyl)-1H-indol-3-yl)-1-(cyclohexylmethyl)-2-methyl-1H-pyrrol-3-yl)sulfonylcarbamate (52)

To a suspension of NaH (60% in mineral oil, 80 mg, 2 mmol) in DMF was added compound 51 (471 mg, 1 mmol, dissolved in DMF) dropwise at 0° C. under N$_2$. The mixture was stirred for 30 minutes at 0° C. and 2-chlorobenzene-1-sulfonyl chloride (1.5 mmol) was added dropwise. The reaction was stirred at rt for 16 h, quenched with sat. aq. NH₄Cl, diluted with DCM and water and extracted with DCM (3×). The combined organic layers were washed with brine, dried over Na₂SO₄ and concentrated to afford the crude compound 52 (320 mg, 50%).

Step 3: 5-(1-((2-Chlorophenyl)sulfonyl)-1H-indol-3-yl)-1-(cyclohexylmethyl)-2-methyl-1H-pyrrole-3-sulfonamide (53)

Crude intermediate 52 (0.50 mmol) was dissolved in dry MeOH/HCl under N₂. The mixture was stirred overnight at rt, concentrated, treated with 3% aq. K₂CO₃, extracted with DCM, dried over Na₂SO₄, filtered, concentrated and purified by prep-HPLC to afford compound 53 (95 mg, 35%). ¹H-NMR (DMSO-d₆, 400 MHz) δ: 0.50-0.62 (2H, m), 0.83-0.95 (3H, m), 1.13-1.39 (3H, m), 1.41-1.50 (3H, m), 2.47 (3H, s), 3.81 (2H, d, J=5.6 Hz), 6.47 (1H, s), 7.00 (2H, s), 7.30-7.39 (2H, m), 7.50-7.54 (1H, m), 7.68-7.80 (4H, m), 8.00 (1H, s), 8.38-8.42 (1H, m). MS Calcd.: 545; MS Found: 546 (M+1).

Example 53/1 to Example 53/2

Similar to Example 52/53 the following compounds were prepared:

Additional Examples

If one were to use similar procedures as described above, the following compounds can be prepared:

| Structure |
| --- |

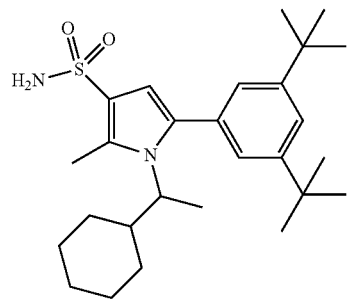

| # | Structure | Analytical data |
| --- | --- | --- |
| 53/1 | 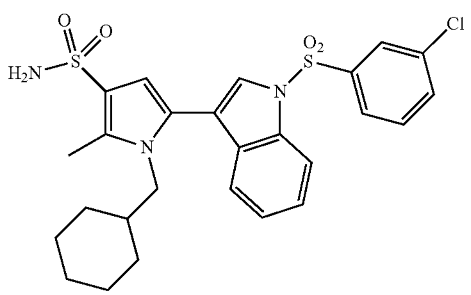 [SMILES: Cc1c(S(N)(=O)=O)cc(-c2cn(S(=O)(=O)c3cccc(Cl)c3)c3ccccc23)n1CC1CCCCC1] | ¹H-NMR (DMSO-d₆, 400 MHz) δ: 0.38-0.46 (2H, m), 0.69-0.82 (3H, m), 1.10-1.18 (3H, m), 1.32-1.40 (3H, m), 2.45 (3H, s), 3.79 (2H, d, J = 5.6 Hz), 6.45 (1H, s), 6.99 (2H, s), 7.33-7.39 (1H, m), 7.42-7.50 (2H, m), 7.62-7.67 (1H, m), 7.80-7.85 (1H, m), 8.02-8.07 (2H, m), 8.10-8.16 (1H, m), 8.18-8.20 (1H, m). MS Calcd.: 545; MS Found: 546 (M + 1). |
| 53/2 | 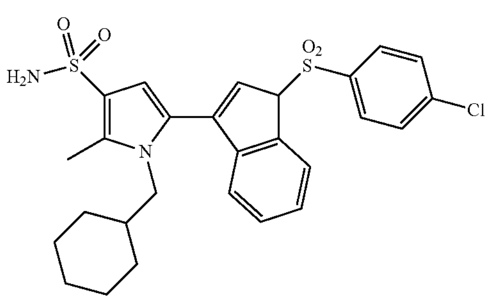 [SMILES: Cc1c(S(N)(=O)=O)cc(C2=CC(S(=O)(=O)c3ccc(Cl)cc3)c3ccccc32)n1CC1CCCCC1] | ¹H-NMR (DMSO-d₆, 400 MHz) δ: 0.32-0.43 (2H, m), 0.70-0.82 (3H, m), 1.08-1.15 (3H, m), 1.32-1.42 (3H, m), 2.50 (3H, s), 3.76 (2H, d, J = 5.6 Hz), 6.44 (1H, s), 6.98 (2H, s), 7.34-7.40 (1H, m), 7.42-7.48 (2H, m), 7.68-7.70 (2H, m), 7.98 (1H, s), 8.05-8.12 (3H, m). MS Calcd.: 545; MS Found: 546 (M + 1). |

| 199 -continued | 200 -continued |
|---|---|
| Structure | Structure |
| 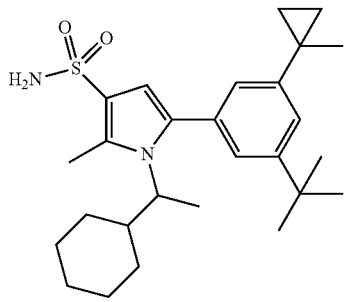 [SMILES: Cc1c(S(N)(=O)=O)cc(-c2cc(C(C)(C)C)cc(C3(C)CC3)c2)n1C(C)C1CCCCC1] | 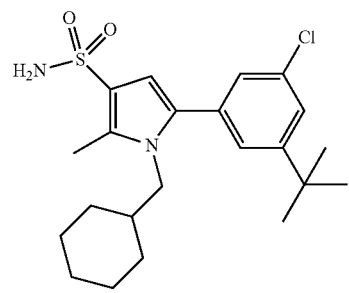 |
| 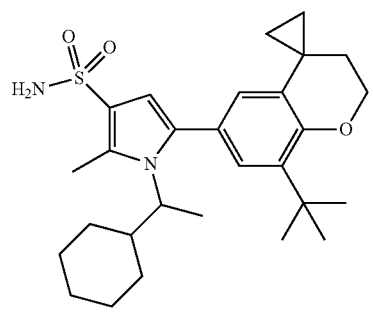 [SMILES: Cc1c(S(N)(=O)=O)cc(-c2cc(C(C)(C)C)c3c(c2)C2(CCO3)CC2)n1C(C)C1CCCCC1] | 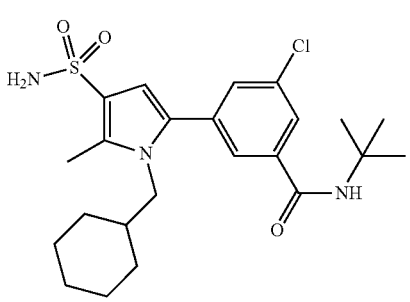 |
| 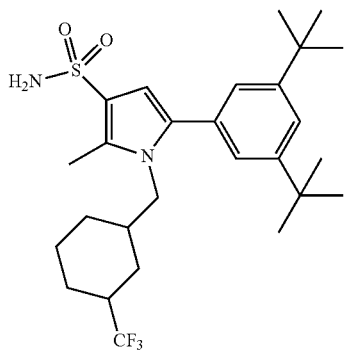 [SMILES: Cc1c(S(N)(=O)=O)cc(-c2cc(C(C)(C)C)cc(C(C)(C)C)c2)n1CC1CCCC(C(F)(F)F)C1] | 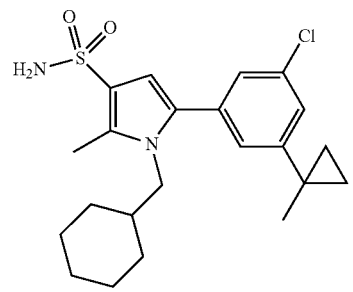 |
| 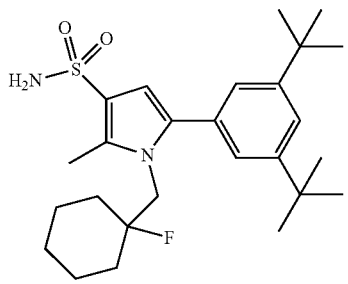 [SMILES: Cc1c(S(N)(=O)=O)cc(-c2cc(C(C)(C)C)cc(C(C)(C)C)c2)n1CC1(F)CCCCC1] | 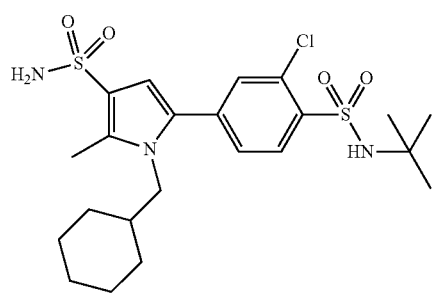 |
| 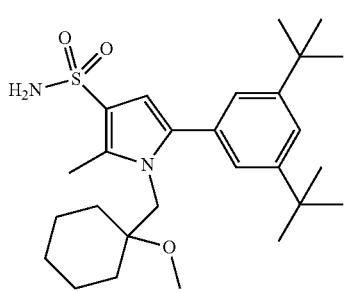 [SMILES: COC1(Cn2c(-c3cc(C(C)(C)C)cc(C(C)(C)C)c3)cc(S(N)(=O)=O)c2C)CCCCC1] | 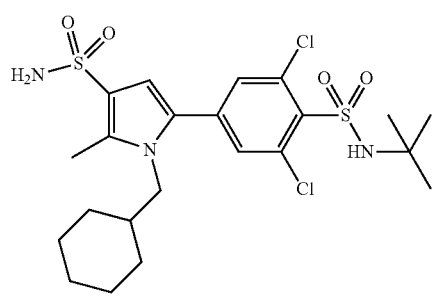 |

| 201 -continued | 202 -continued |
|---|---|
| Structure | Structure |
| 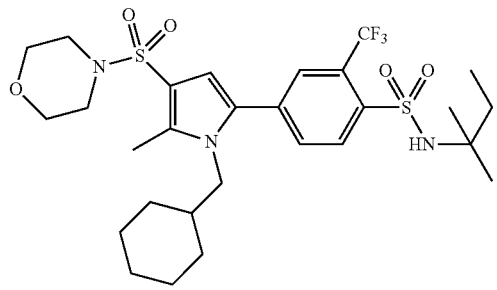 [SMILES: CCC(C)(C)NS(=O)(=O)c1ccc(-c2cc(S(=O)(=O)N3CCOCC3)c(C)n2CC2CCCCC2)cc1C(F)(F)F] | 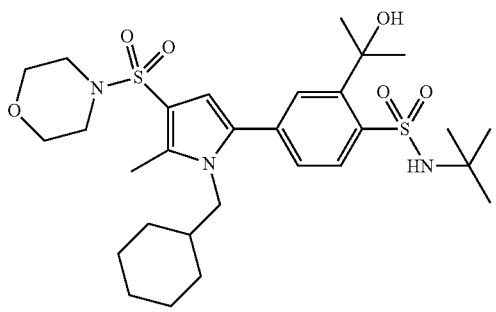 |
| 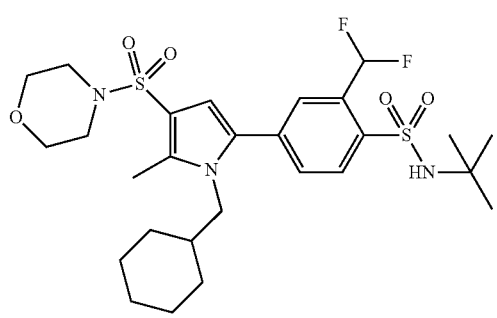 [SMILES: Cc1c(S(=O)(=O)N2CCOCC2)cc(-c2ccc(S(=O)(=O)NC(C)(C)C)c(C(F)F)c2)n1CC1CCCCC1] | 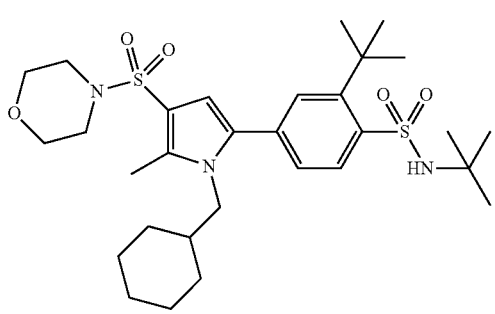 |
| 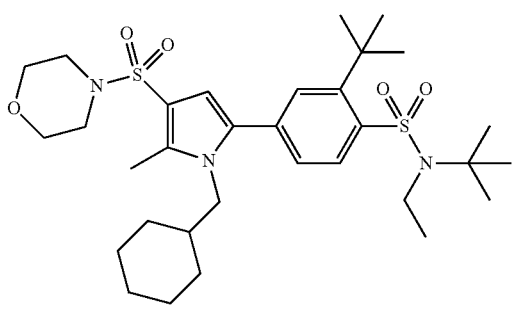 [SMILES: CCN(C(C)(C)C)S(=O)(=O)c1ccc(-c2cc(S(=O)(=O)N3CCOCC3)c(C)n2CC2CCCCC2)cc1C(C)(C)C] | 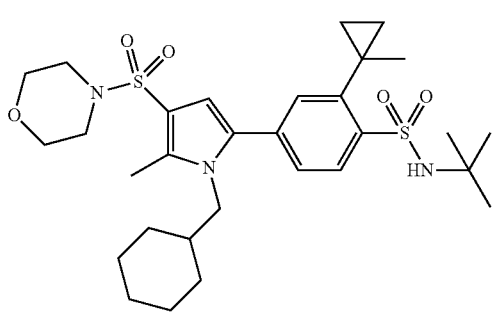 |
| 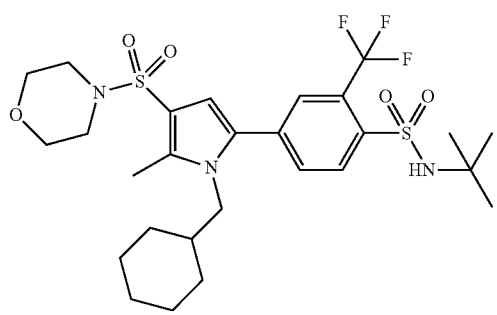 [SMILES: Cc1c(S(=O)(=O)N2CCOCC2)cc(-c2ccc(S(=O)(=O)NC(C)(C)C)c(C(F)(F)F)c2)n1CC1CCCCC1] | 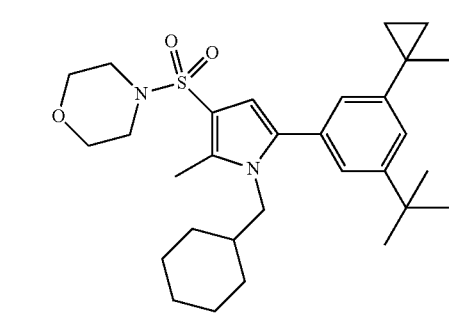 |
| 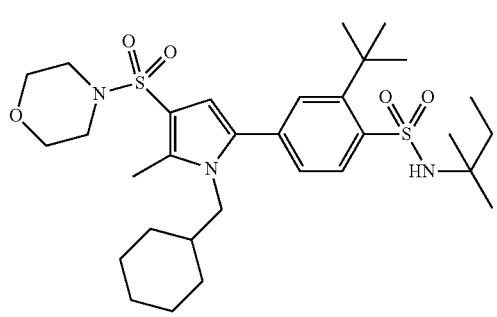 [SMILES: CCC(C)(C)NS(=O)(=O)c1ccc(-c2cc(S(=O)(=O)N3CCOCC3)c(C)n2CC2CCCCC2)cc1C(C)(C)C] | 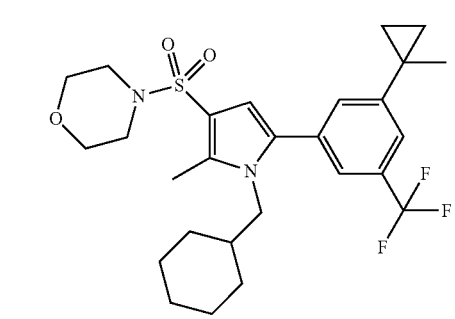 [SMILES: Cc1c(S(=O)(=O)N2CCOCC2)cc(-c2cc(C(F)(F)F)cc(C3(C)CC3)c2)n1CC1CCCCC1] |

| 203 -continued | 204 -continued |
|---|---|
| Structure | Structure |
| 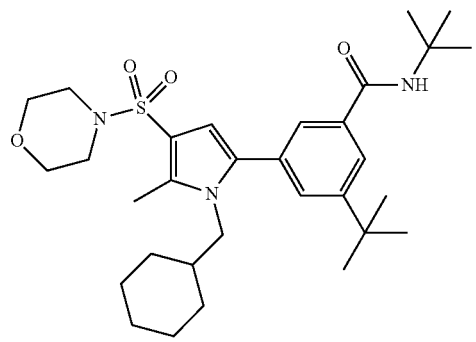 [SMILES: Cc1c(S(=O)(=O)N2CCOCC2)cc(-c2cc(C(=O)NC(C)(C)C)cc(C(C)(C)C)c2)n1CC1CCCCC1] | 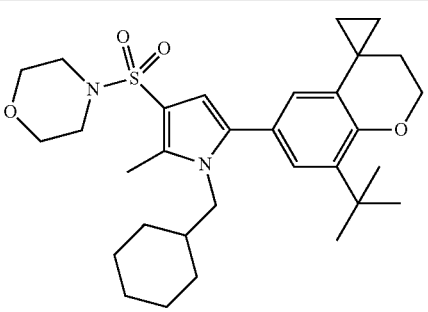 |
| 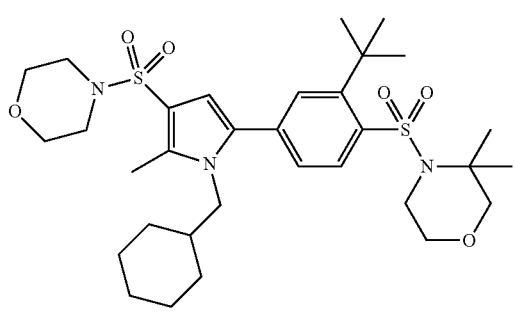 [SMILES: Cc1c(S(=O)(=O)N2CCOCC2)cc(-c2ccc(S(=O)(=O)N3CCOCC3(C)C)c(C(C)(C)C)c2)n1CC1CCCCC1] | 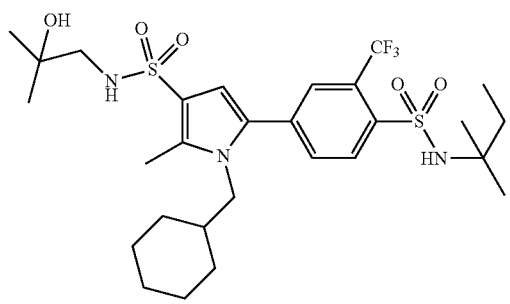 |
| 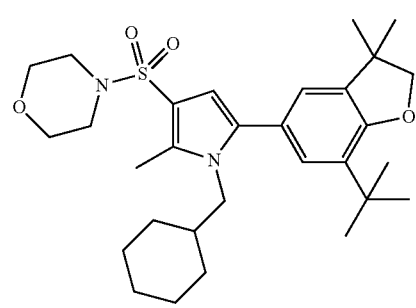 [SMILES: Cc1c(S(=O)(=O)N2CCOCC2)cc(-c2cc(C(C)(C)C)c3c(c2)C(C)(C)CO3)n1CC1CCCCC1] | 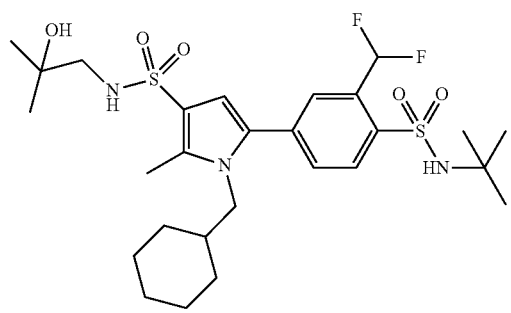 |
| 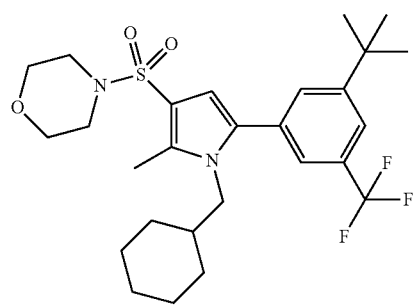 [SMILES: Cc1c(S(=O)(=O)N2CCOCC2)cc(-c2cc(C(C)(C)C)cc(C(F)(F)F)c2)n1CC1CCCCC1] | 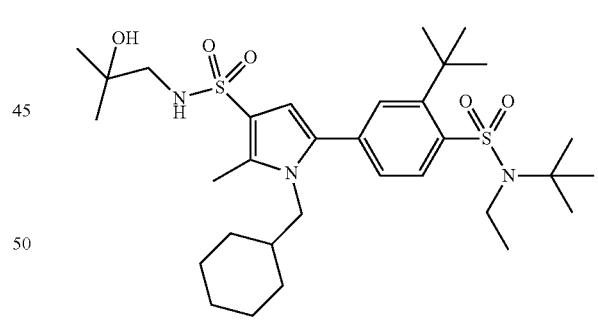 |
| 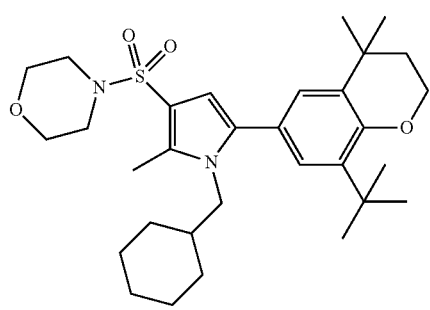 [SMILES: Cc1c(S(=O)(=O)N2CCOCC2)cc(-c2cc(C(C)(C)C)c3c(c2)C(C)(C)CCO3)n1CC1CCCCC1] | 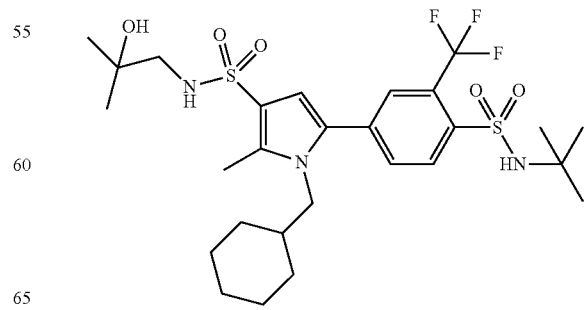 |

| 205 -continued | 206 -continued |
|---|---|
| Structure | Structure |
| 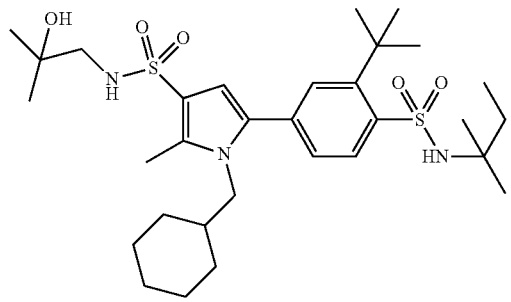 [SMILES: CCC(C)(C)NS(=O)(=O)c1ccc(-c2cc(S(=O)(=O)NCC(C)(C)O)c(C)n2CC2CCCCC2)cc1C(C)(C)C] | 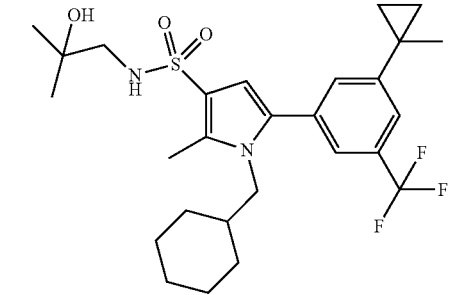 |
| 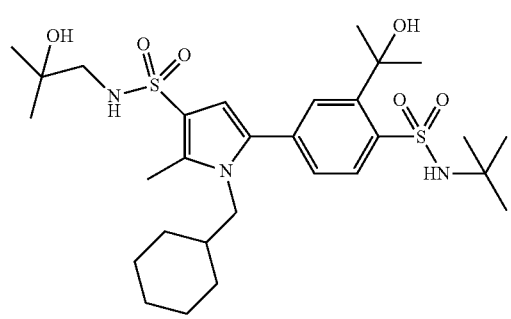 [SMILES: Cc1c(S(=O)(=O)NCC(C)(C)O)cc(-c2ccc(S(=O)(=O)NC(C)(C)C)c(C(C)(C)O)c2)n1CC1CCCCC1] | 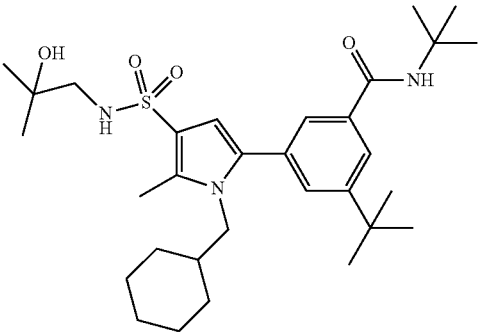 |
| 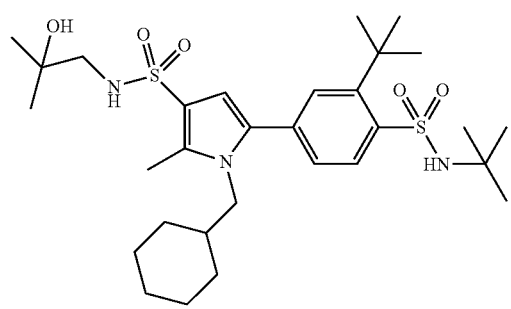 [SMILES: Cc1c(S(=O)(=O)NCC(C)(C)O)cc(-c2ccc(S(=O)(=O)NC(C)(C)C)c(C(C)(C)C)c2)n1CC1CCCCC1] | 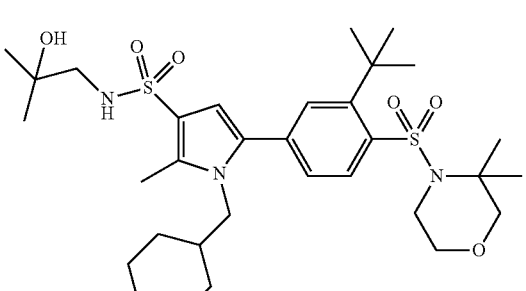 |
| 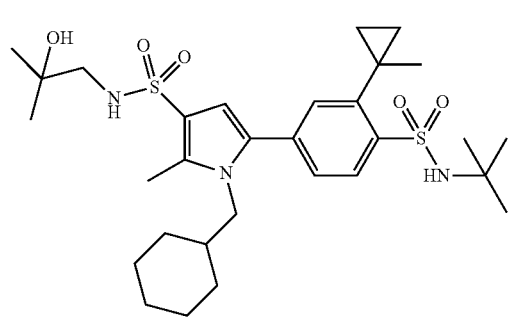 [SMILES: Cc1c(S(=O)(=O)NCC(C)(C)O)cc(-c2ccc(S(=O)(=O)NC(C)(C)C)c(C3(C)CC3)c2)n1CC1CCCCC1] | 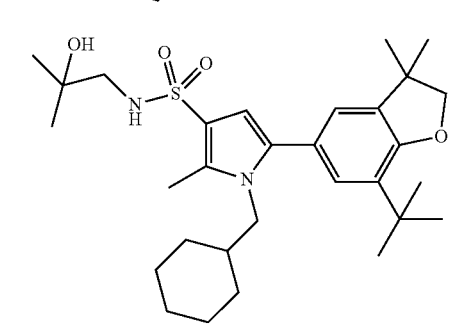 |
| 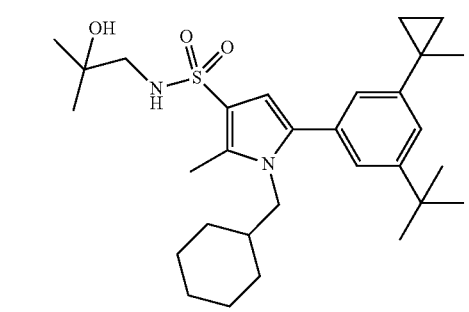 [SMILES: Cc1c(S(=O)(=O)NCC(C)(C)O)cc(-c2cc(C(C)(C)C)cc(C3(C)CC3)c2)n1CC1CCCCC1] | 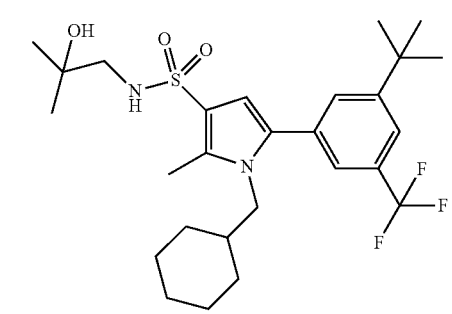 [SMILES: Cc1c(S(=O)(=O)NCC(C)(C)O)cc(-c2cc(C(C)(C)C)cc(C(F)(F)F)c2)n1CC1CCCCC1] |

| 207 -continued | | 208 -continued |
|---|---|---|
| Structure | | Structure |
| 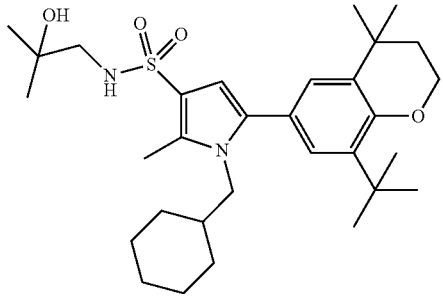 [SMILES: Cc1c(S(=O)(=O)NCC(C)(C)O)cc(-c2cc(C(C)(C)C)c3c(c2)C(C)(C)CCO3)n1CC1CCCCC1] | | 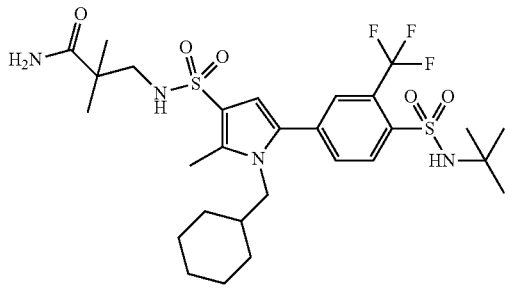 |
| 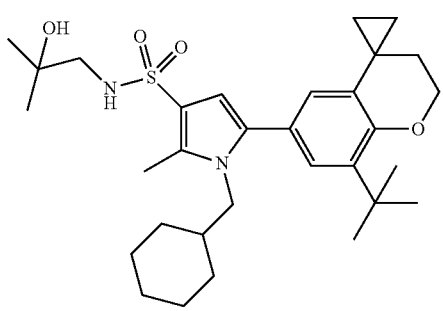 [SMILES: Cc1c(S(=O)(=O)NCC(C)(C)O)cc(-c2cc(C(C)(C)C)c3c(c2)C2(CCO3)CC2)n1CC1CCCCC1] | | 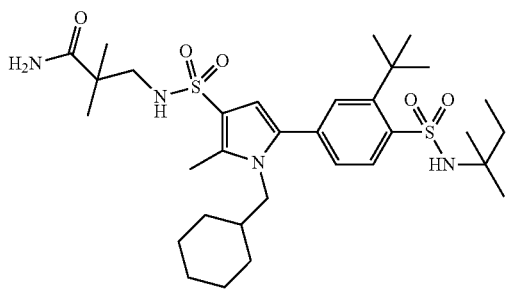 |
| 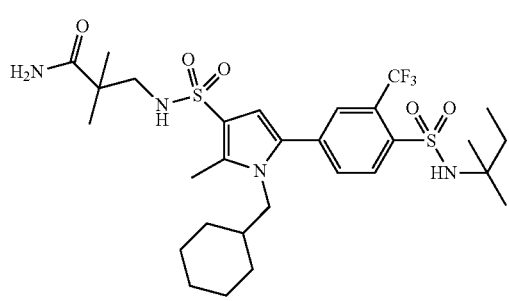 [SMILES: CCC(C)(C)NS(=O)(=O)c1ccc(-c2cc(S(=O)(=O)NCC(C)(C)C(N)=O)c(C)n2CC2CCCCC2)cc1C(F)(F)F] | | 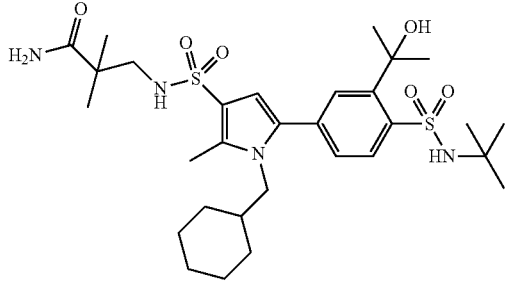 [SMILES: CCC(C)(C)NS(=O)(=O)c1ccc(-c2cc(S(=O)(=O)NCC(C)(C)C(N)=O)c(C)n2CC2CCCCC2)cc1C(C)(C)C] |
| 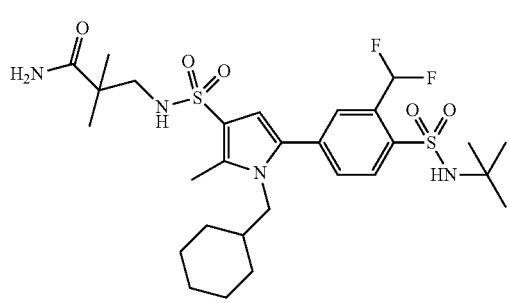 | | 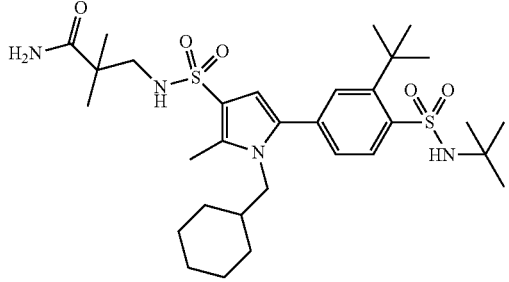 [SMILES: Cc1c(S(=O)(=O)NCC(C)(C)C(N)=O)cc(-c2ccc(S(=O)(=O)NC(C)(C)C)c(C(C)(C)C)c2)n1CC1CCCCC1] |
| 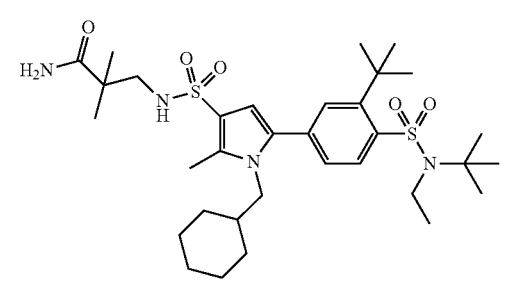 | | 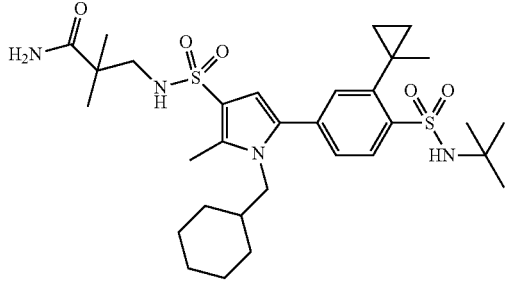 [SMILES: Cc1c(S(=O)(=O)NCC(C)(C)C(N)=O)cc(-c2ccc(S(=O)(=O)NC(C)(C)C)c(C3(C)CC3)c2)n1CC1CCCCC1] |

| 209 -continued | 210 -continued |
|---|---|
| Structure | Structure |
| 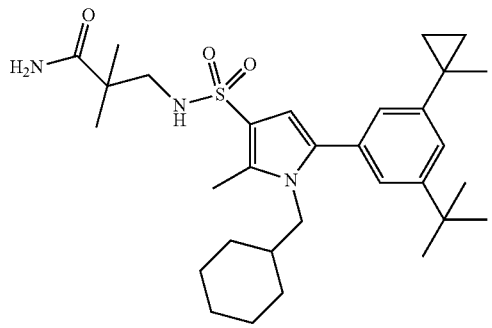 [SMILES: Cc1c(S(=O)(=O)NCC(C)(C)C(N)=O)cc(-c2cc(C(C)(C)C)cc(C3(C)CC3)c2)n1CC1CCCCC1] | 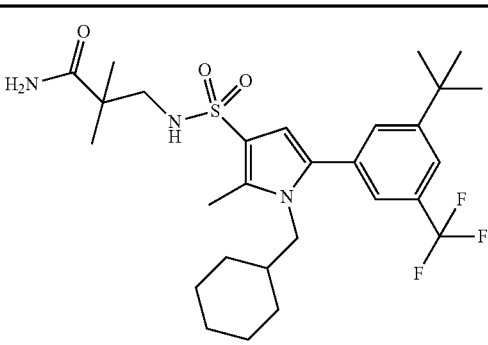 |
| 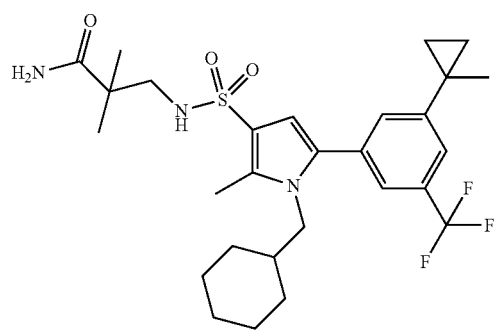 [SMILES: Cc1c(S(=O)(=O)NCC(C)(C)C(N)=O)cc(-c2cc(C(F)(F)F)cc(C3(C)CC3)c2)n1CC1CCCCC1] | 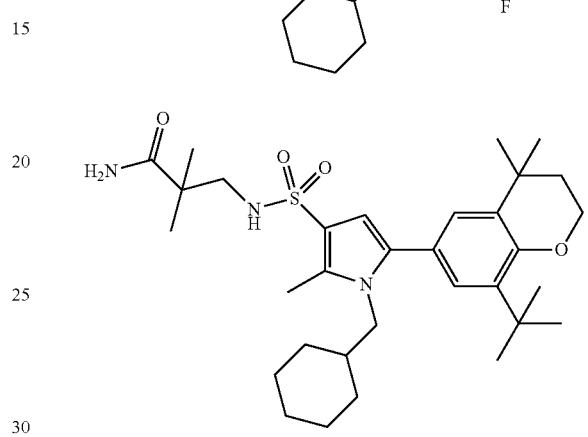 |
| 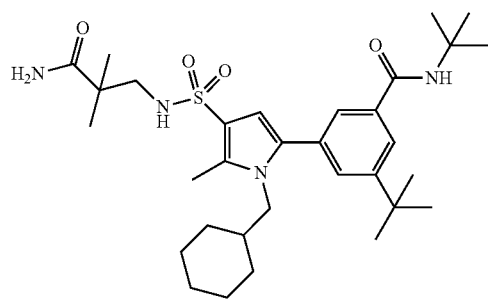 [SMILES: Cc1c(S(=O)(=O)NCC(C)(C)C(N)=O)cc(-c2cc(C(=O)NC(C)(C)C)cc(C(C)(C)C)c2)n1CC1CCCCC1] | 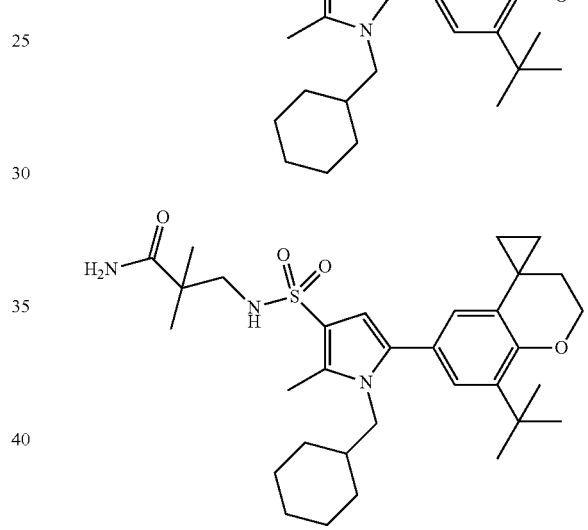 |
| 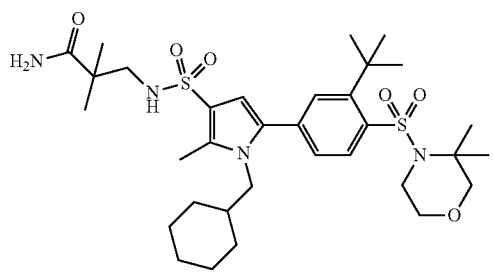 [SMILES: Cc1c(S(=O)(=O)NCC(C)(C)C(N)=O)cc(-c2ccc(S(=O)(=O)N3CCOCC3(C)C)c(C(C)(C)C)c2)n1CC1CCCCC1] | 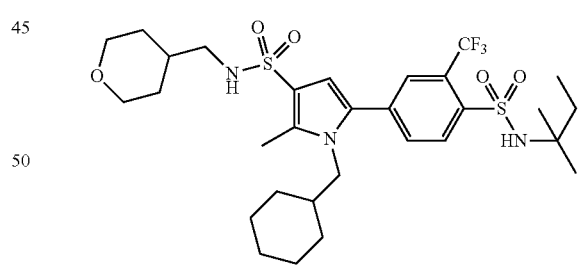 |
| 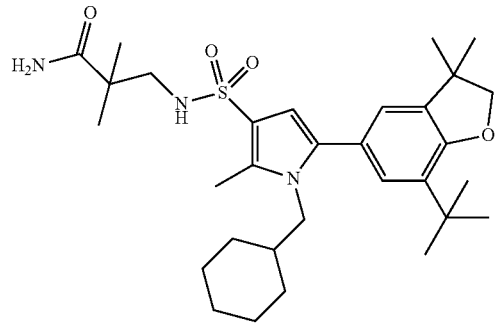 [SMILES: Cc1c(S(=O)(=O)NCC(C)(C)C(N)=O)cc(-c2cc(C(C)(C)C)c3c(c2)C(C)(C)CO3)n1CC1CCCCC1] | 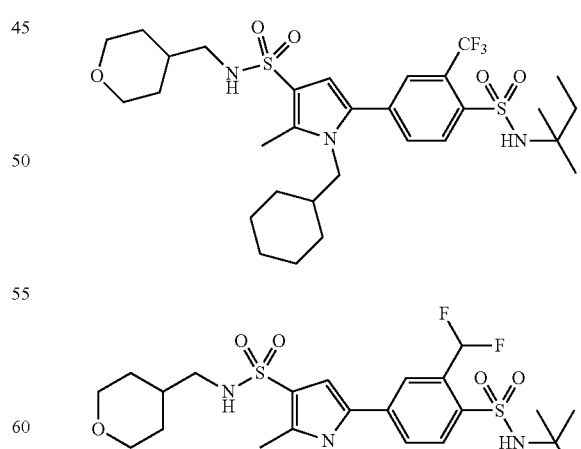 |
|  | 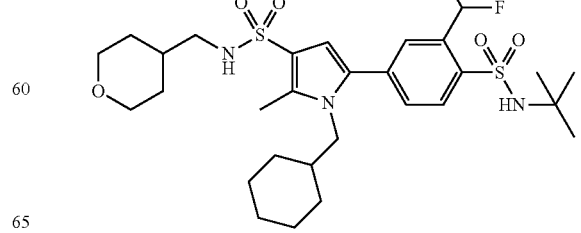 |

| 211 -continued | 212 -continued |
|---|---|
| Structure | Structure |
| 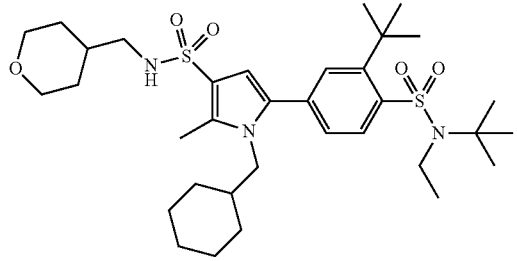 [SMILES: CCN(C(C)(C)C)S(=O)(=O)c1ccc(-c2cc(S(=O)(=O)NCC3CCOCC3)c(C)n2CC2CCCCC2)cc1C(C)(C)C] | 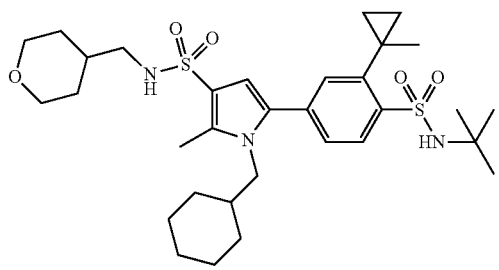 |
| 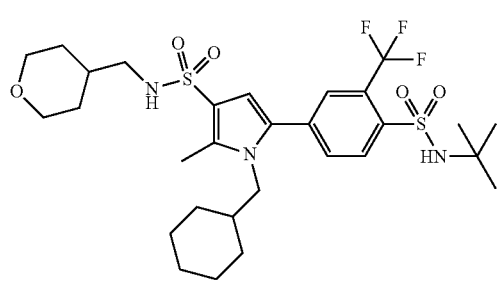 [SMILES: Cc1c(S(=O)(=O)NCC2CCOCC2)cc(-c2ccc(S(=O)(=O)NC(C)(C)C)c(C(F)(F)F)c2)n1CC1CCCCC1] | 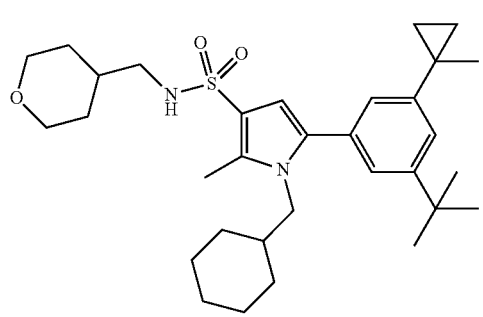 |
| 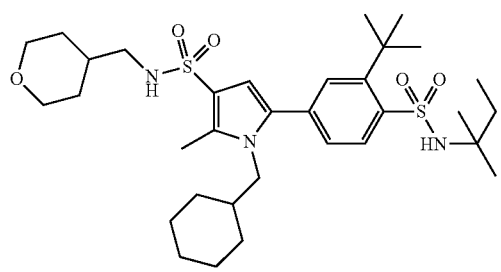 [SMILES: CCC(C)(C)NS(=O)(=O)c1ccc(-c2cc(S(=O)(=O)NCC3CCOCC3)c(C)n2CC2CCCCC2)cc1C(C)(C)C] | 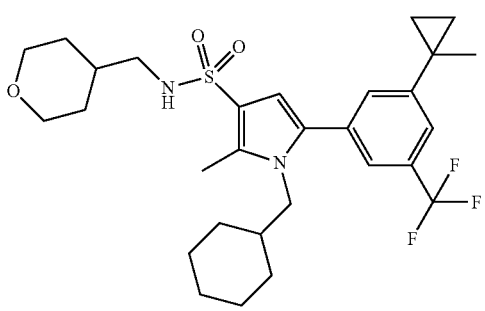 |
| 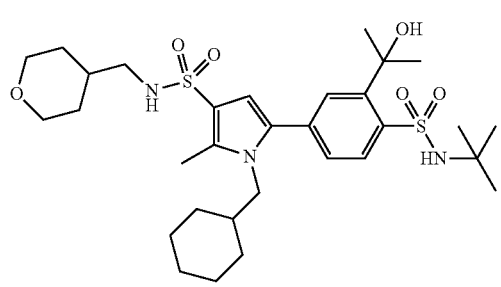 [SMILES: Cc1c(S(=O)(=O)NCC2CCOCC2)cc(-c2ccc(S(=O)(=O)NC(C)(C)C)c(C(C)(C)O)c2)n1CC1CCCCC1] | 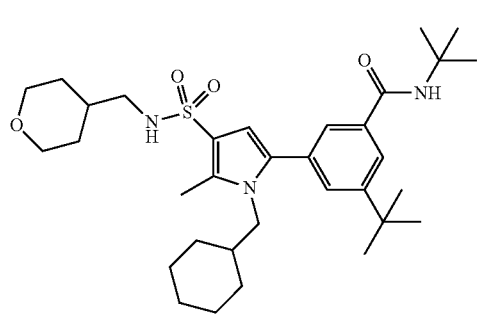 [SMILES: Cc1c(S(=O)(=O)NCC2CCOCC2)cc(-c2cc(C(=O)NC(C)(C)C)cc(C(C)(C)C)c2)n1CC1CCCCC1] |
| 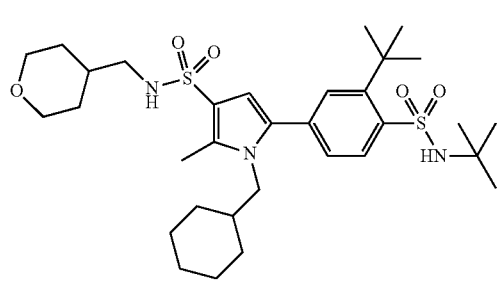 | 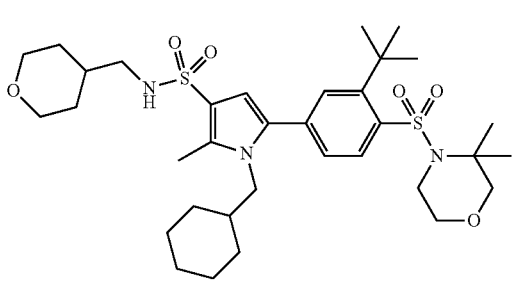 [SMILES: Cc1c(S(=O)(=O)NCC2CCOCC2)cc(-c2ccc(S(=O)(=O)N3CCOCC3(C)C)c(C(C)(C)C)c2)n1CC1CCCCC1] |

| 213 -continued | 214 -continued |
|---|---|
| Structure | Structure |
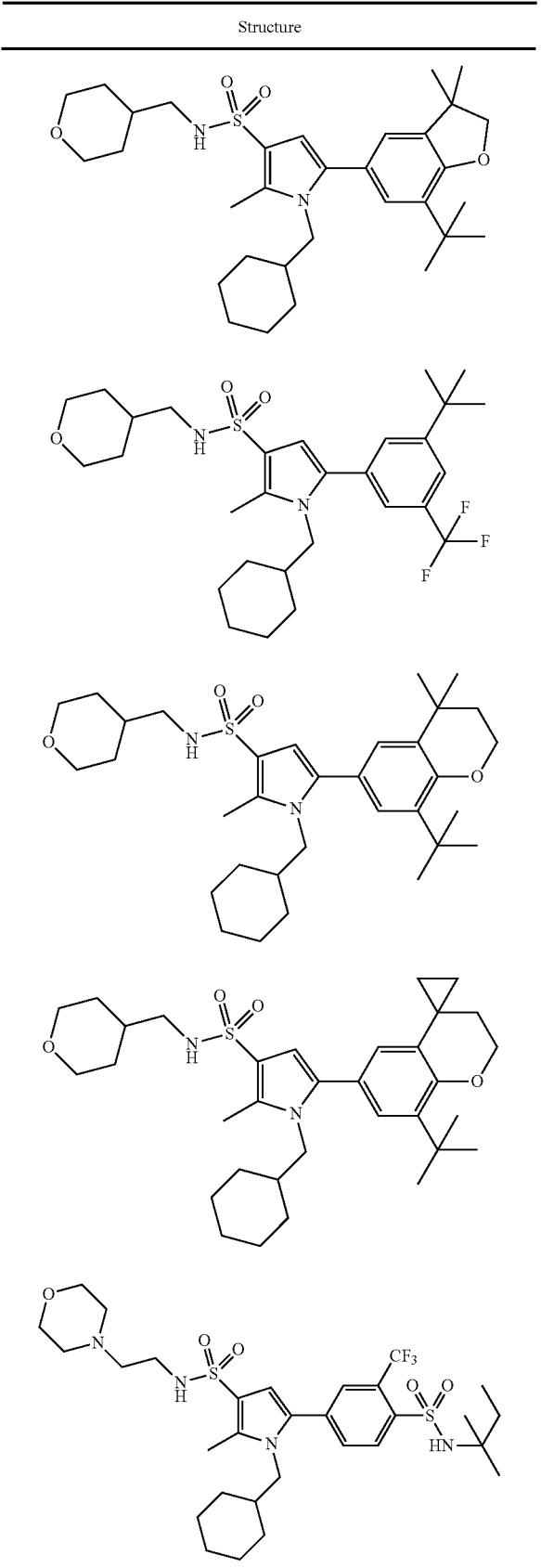
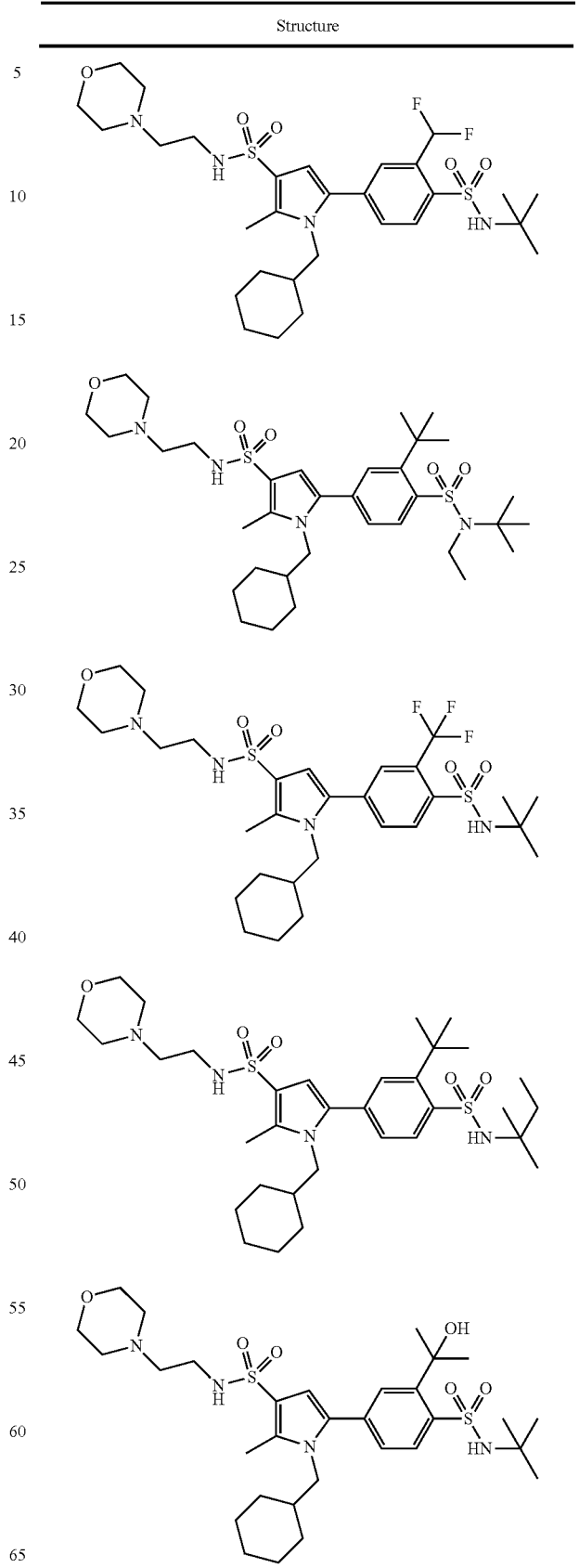

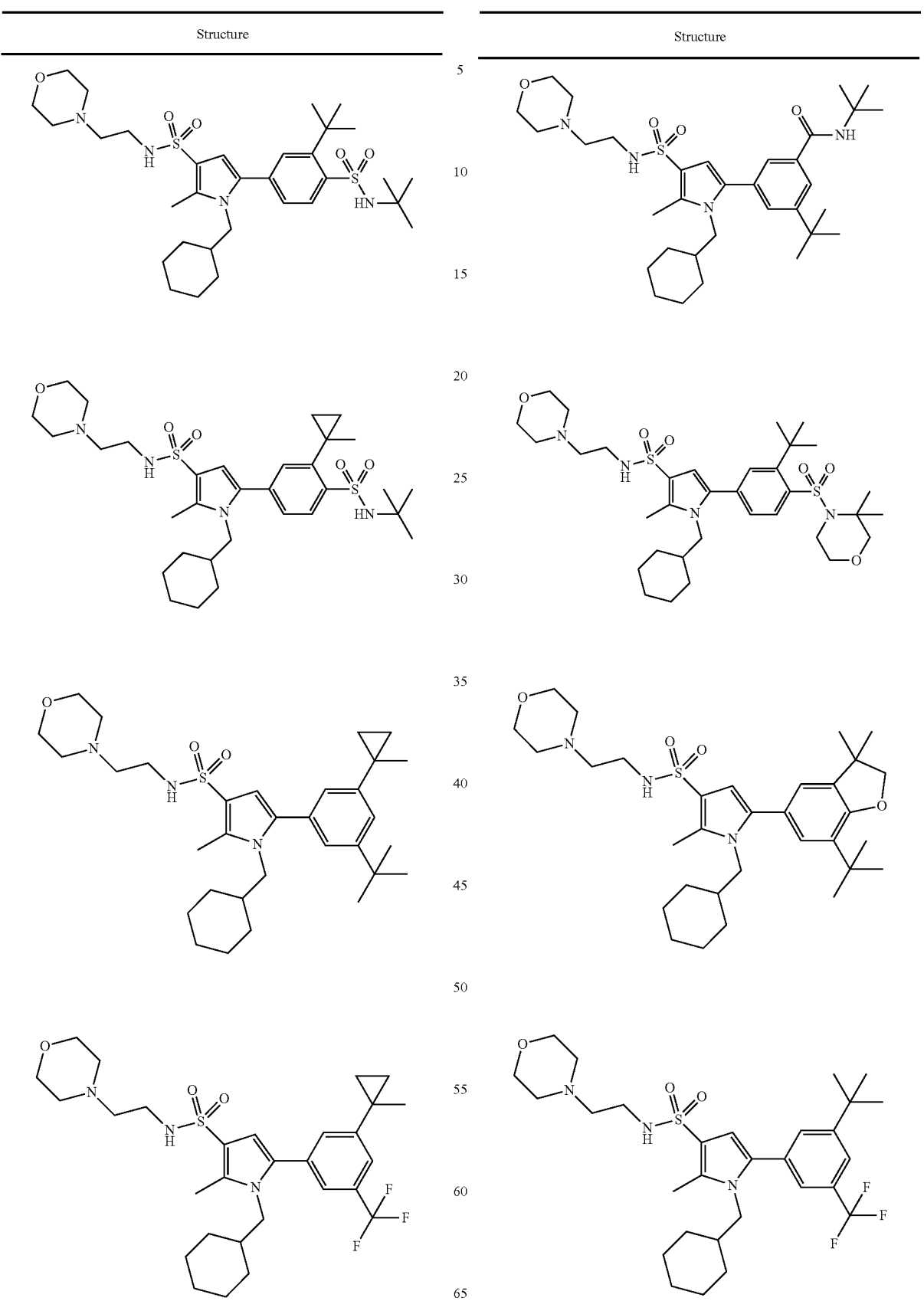

| 217 -continued | 218 -continued |
|---|---|
| Structure | Structure |
| 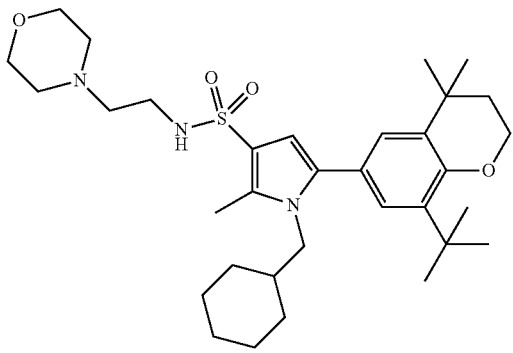 [SMILES: Cc1c(S(=O)(=O)NCCN2CCOCC2)cc(-c2cc(C(C)(C)C)c3c(c2)C(C)(C)CCO3)n1CC1CCCCC1] | 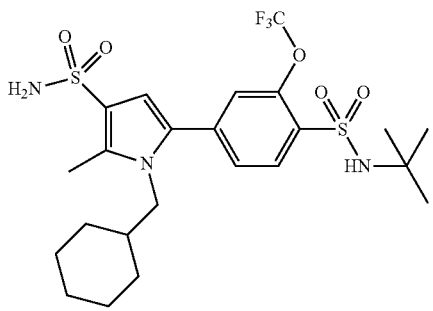 |
| 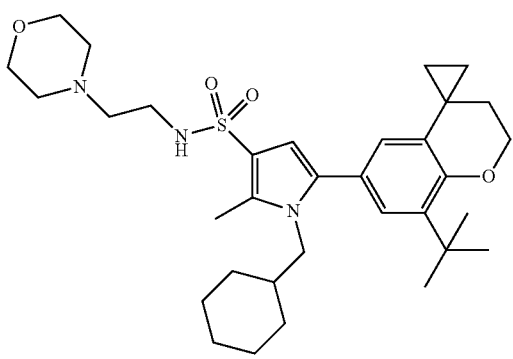 [SMILES: Cc1c(S(=O)(=O)NCCN2CCOCC2)cc(-c2cc(C(C)(C)C)c3c(c2)C2(CCO3)CC2)n1CC1CCCCC1] | 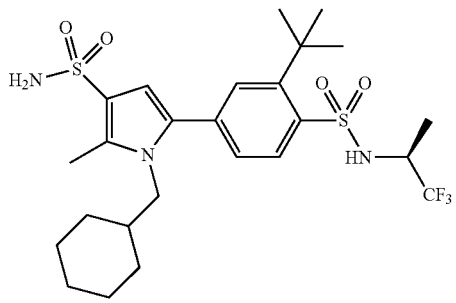 |
| 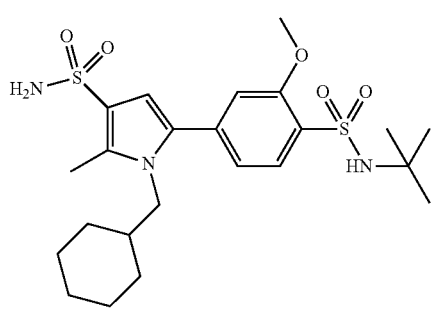 [SMILES: COc1cc(-c2cc(S(N)(=O)=O)c(C)n2CC2CCCCC2)ccc1S(=O)(=O)NC(C)(C)C] | 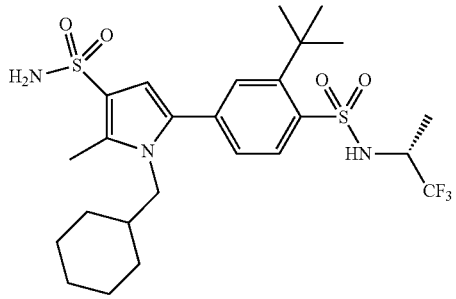 |
| 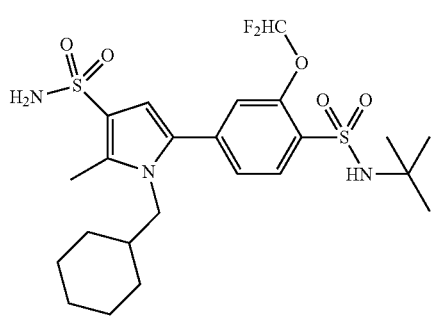 [SMILES: Cc1c(S(N)(=O)=O)cc(-c2ccc(S(=O)(=O)NC(C)(C)C)c(OC(F)F)c2)n1CC1CCCCC1] | 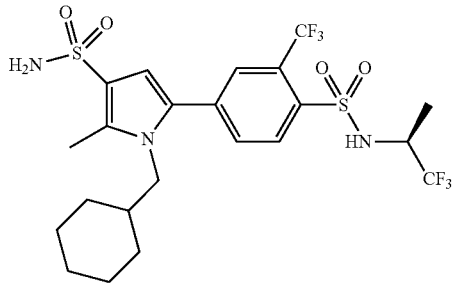 [SMILES: Cc1c(S(N)(=O)=O)cc(-c2ccc(S(=O)(=O)N[C@@H](C)C(F)(F)F)c(C(F)(F)F)c2)n1CC1CCCCC1] |
| | 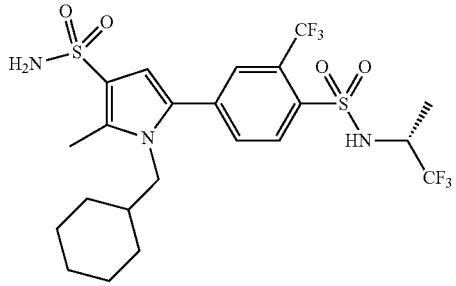 [SMILES: Cc1c(S(N)(=O)=O)cc(-c2ccc(S(=O)(=O)N[C@H](C)C(F)(F)F)c(C(F)(F)F)c2)n1CC1CCCCC1] |

| 219 -continued | 220 -continued |
|---|---|
| Structure | Structure |
| 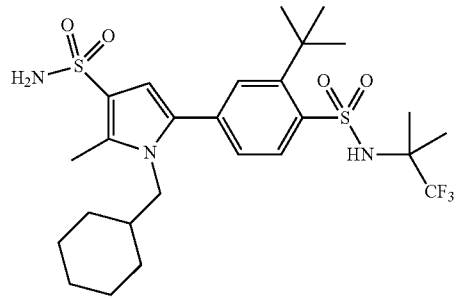 [SMILES: Cc1c(S(N)(=O)=O)cc(-c2ccc(S(=O)(=O)NC(C)(C)C(F)(F)F)c(C(C)(C)C)c2)n1CC1CCCCC1] | 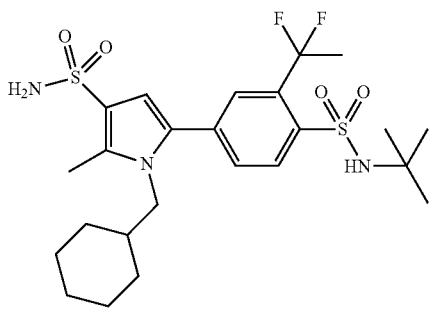 |
| 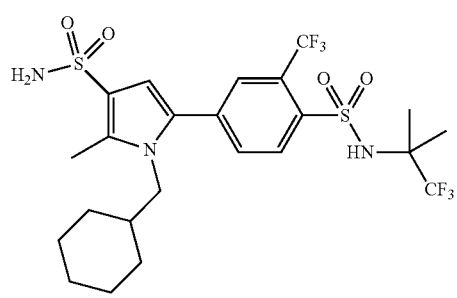 [SMILES: Cc1c(S(N)(=O)=O)cc(-c2ccc(S(=O)(=O)NC(C)(C)C(F)(F)F)c(C(F)(F)F)c2)n1CC1CCCCC1] | 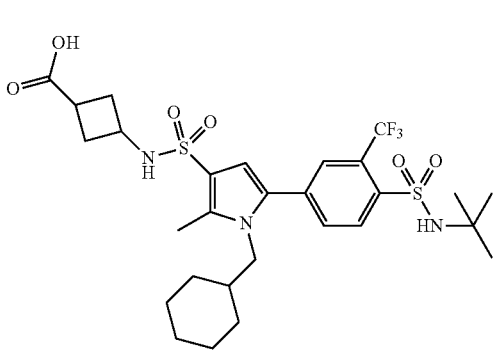 |
| 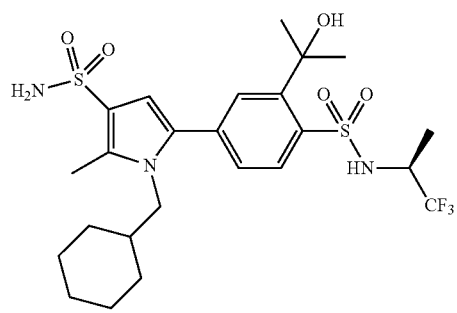 [SMILES: Cc1c(S(N)(=O)=O)cc(-c2ccc(S(=O)(=O)N[C@@H](C)C(F)(F)F)c(C(C)(C)O)c2)n1CC1CCCCC1] | 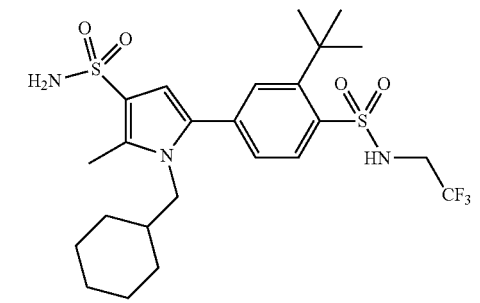 |
| 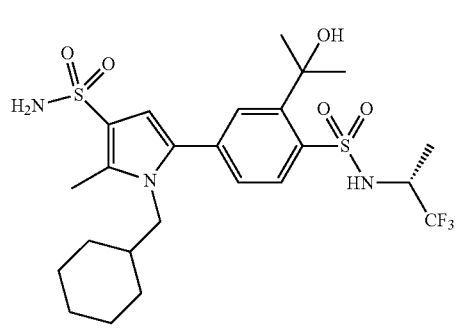 [SMILES: Cc1c(S(N)(=O)=O)cc(-c2ccc(S(=O)(=O)N[C@H](C)C(F)(F)F)c(C(C)(C)O)c2)n1CC1CCCCC1] | 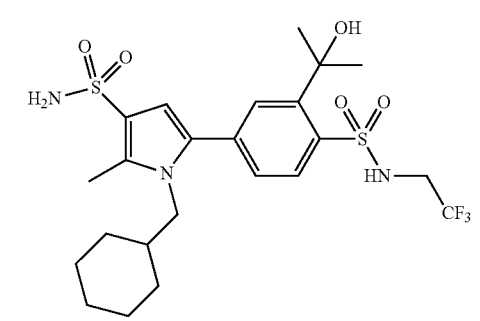 |
| 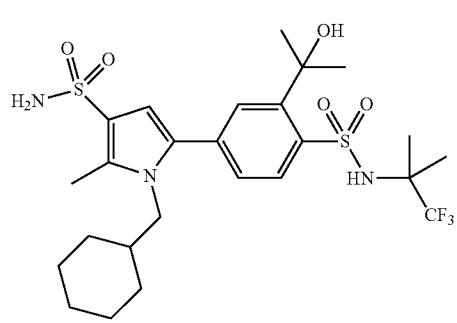 [SMILES: Cc1c(S(N)(=O)=O)cc(-c2ccc(S(=O)(=O)NC(C)(C)C(F)(F)F)c(C(C)(C)O)c2)n1CC1CCCCC1] | 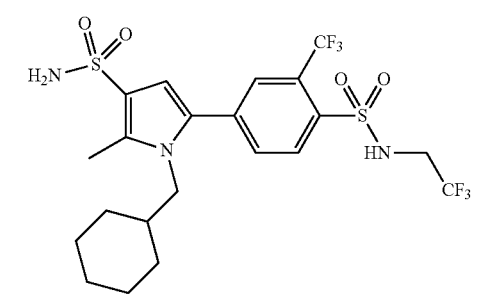 [SMILES: Cc1c(S(N)(=O)=O)cc(-c2ccc(S(=O)(=O)NCC(F)(F)F)c(C(F)(F)F)c2)n1CC1CCCCC1] |

| 221 -continued | 222 -continued |
|---|---|
| Structure | Structure |
| 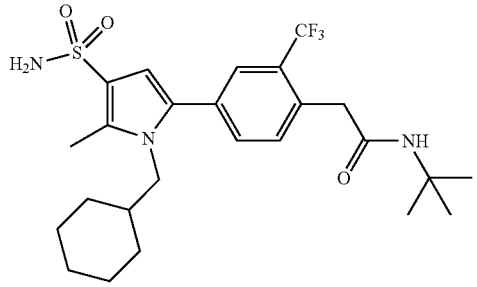 [SMILES: Cc1c(S(N)(=O)=O)cc(-c2ccc(CC(=O)NC(C)(C)C)c(C(F)(F)F)c2)n1CC1CCCCC1] | 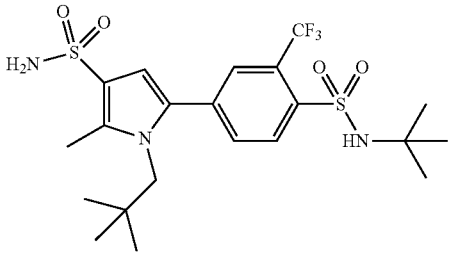 |
| 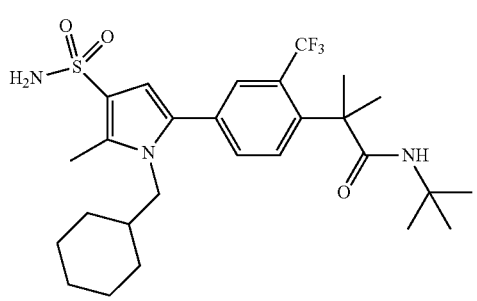 [SMILES: Cc1c(S(N)(=O)=O)cc(-c2ccc(C(C)(C)C(=O)NC(C)(C)C)c(C(F)(F)F)c2)n1CC1CCCCC1] | 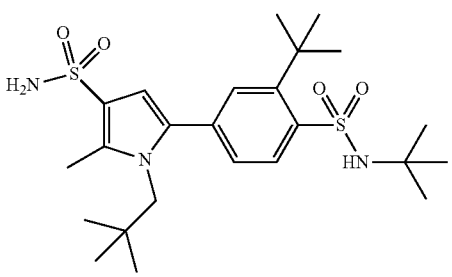 |
| 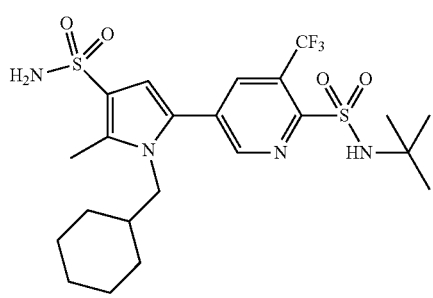 [SMILES: Cc1c(S(N)(=O)=O)cc(-c2cnc(S(=O)(=O)NC(C)(C)C)c(C(F)(F)F)c2)n1CC1CCCCC1] | 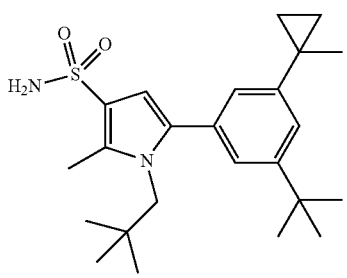 |
| 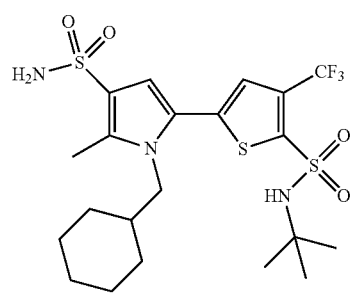 [SMILES: Cc1c(S(N)(=O)=O)cc(-c2cc(C(F)(F)F)c(S(=O)(=O)NC(C)(C)C)s2)n1CC1CCCCC1] | 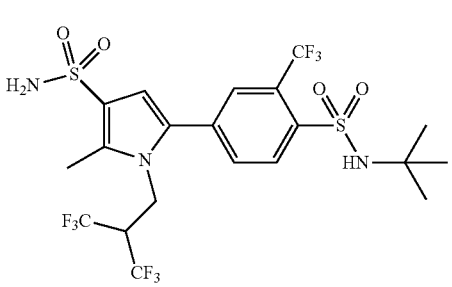 |
| 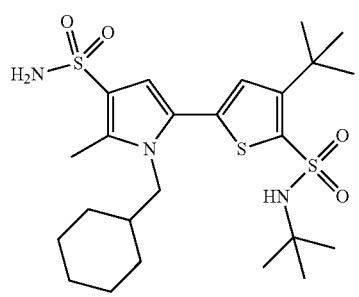 [SMILES: Cc1c(S(N)(=O)=O)cc(-c2cc(C(C)(C)C)c(S(=O)(=O)NC(C)(C)C)s2)n1CC1CCCCC1] | 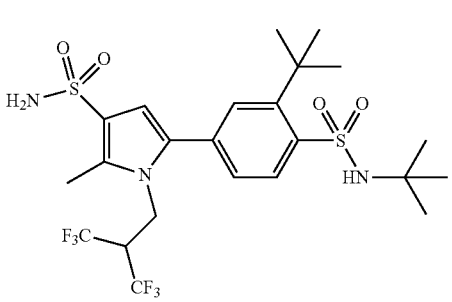 [SMILES: Cc1c(S(N)(=O)=O)cc(-c2ccc(S(=O)(=O)NC(C)(C)C)c(C(C)(C)C)c2)n1CC(C(F)(F)F)C(F)(F)F] |

| 223 -continued | 224 -continued |
|---|---|
| Structure | Structure |
| 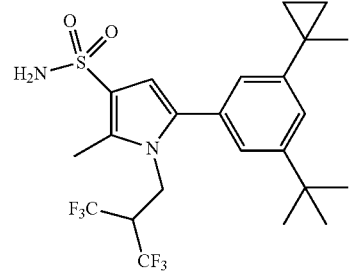 [SMILES: Cc1c(S(N)(=O)=O)cc(-c2cc(C(C)(C)C)cc(C3(C)CC3)c2)n1CC(C(F)(F)F)C(F)(F)F] | 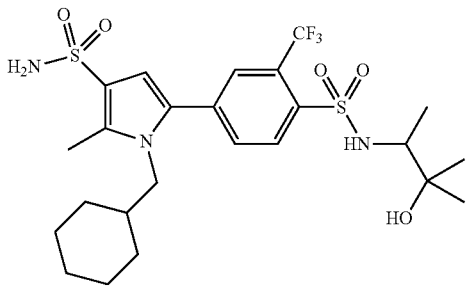 |
| 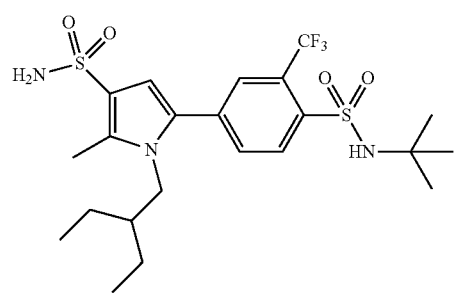 [SMILES: CCC(CC)Cn1c(-c2ccc(S(=O)(=O)NC(C)(C)C)c(C(F)(F)F)c2)cc(S(N)(=O)=O)c1C] | 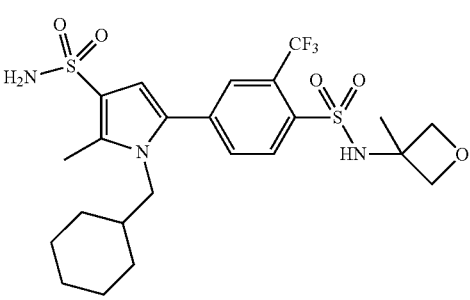 |
| 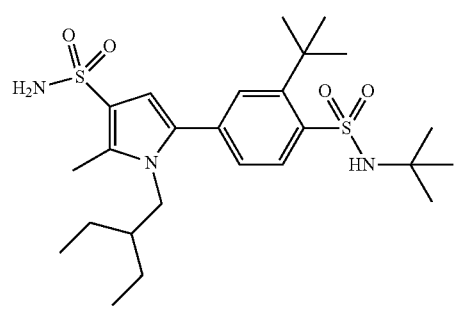 [SMILES: CCC(CC)Cn1c(-c2ccc(S(=O)(=O)NC(C)(C)C)c(C(C)(C)C)c2)cc(S(N)(=O)=O)c1C] | 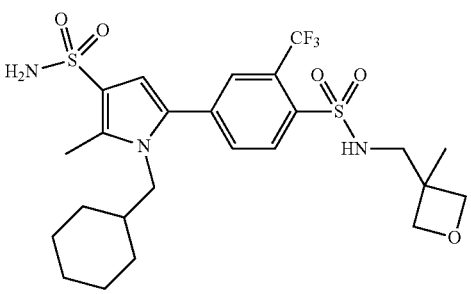 |
| 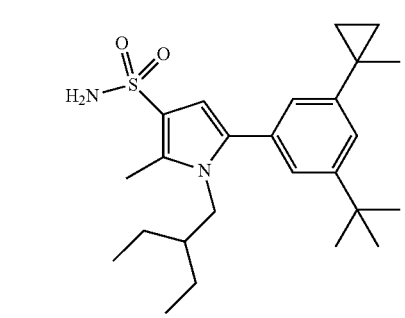 [SMILES: CCC(CC)Cn1c(-c2cc(C(C)(C)C)cc(C3(C)CC3)c2)cc(S(N)(=O)=O)c1C] | 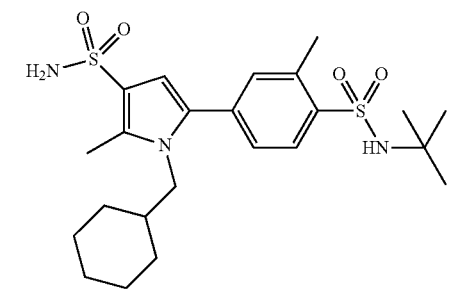 |
| 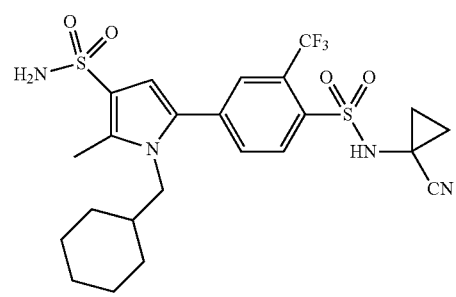 [SMILES: Cc1c(S(N)(=O)=O)cc(-c2ccc(S(=O)(=O)NC3(C#N)CC3)c(C(F)(F)F)c2)n1CC1CCCCC1] | 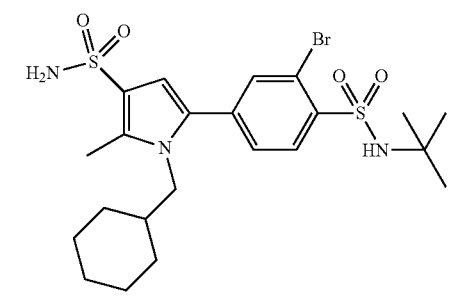 |

| 225 -continued | 226 -continued |
|---|---|
| Structure | Structure |
| 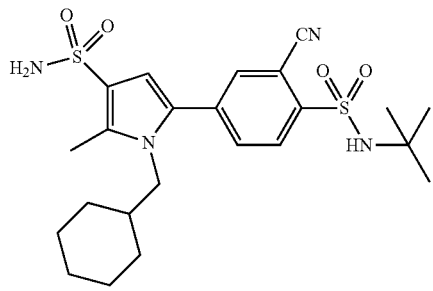 [SMILES: Cc1c(S(N)(=O)=O)cc(-c2ccc(S(=O)(=O)NC(C)(C)C)c(C#N)c2)n1CC1CCCCC1] | 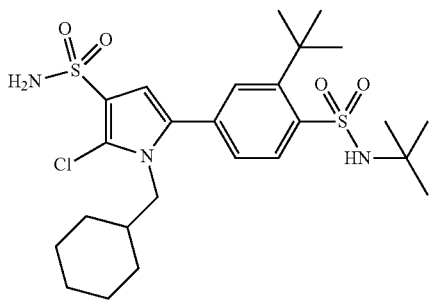 |
| 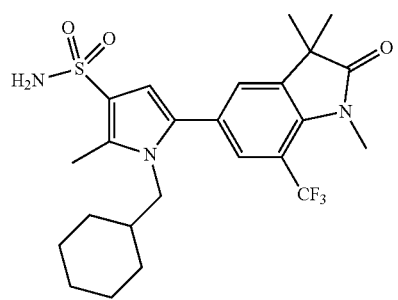 [SMILES: Cc1c(S(N)(=O)=O)cc(-c2cc(C(F)(F)F)c3c(c2)C(C)(C)C(=O)N3C)n1CC1CCCCC1] | 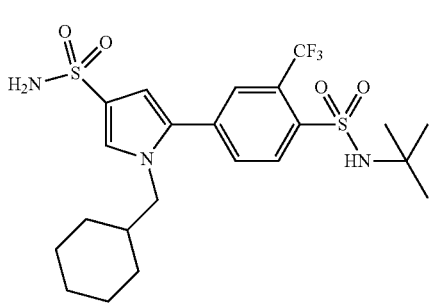 |
| 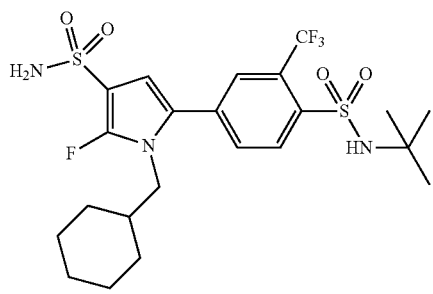 [SMILES: CC(C)(C)NS(=O)(=O)c1ccc(-c2cc(S(N)(=O)=O)c(F)n2CC2CCCCC2)cc1C(F)(F)F] | 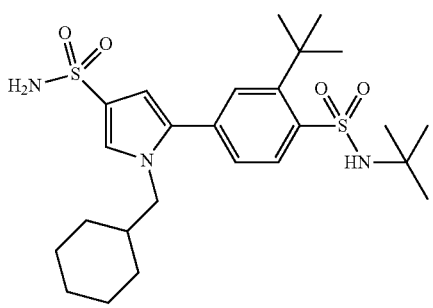 |
| 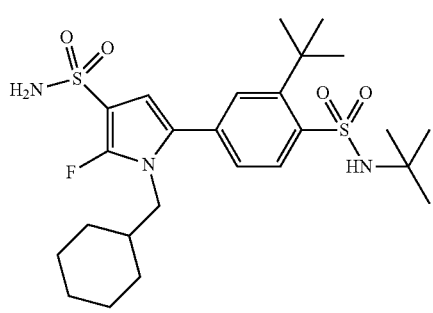 [SMILES: CC(C)(C)NS(=O)(=O)c1ccc(-c2cc(S(N)(=O)=O)c(F)n2CC2CCCCC2)cc1C(C)(C)C] | 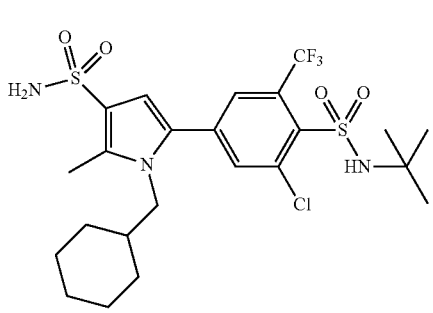 |
| 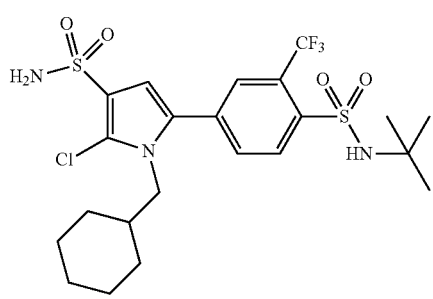 [SMILES: CC(C)(C)NS(=O)(=O)c1ccc(-c2cc(S(N)(=O)=O)c(Cl)n2CC2CCCCC2)cc1C(F)(F)F] | 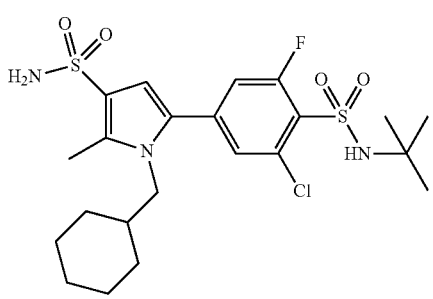 |

| 227 -continued | 228 -continued |
|---|---|
| Structure | Structure |

| 229 -continued | 230 -continued |
|---|---|
| Structure | Structure |
| 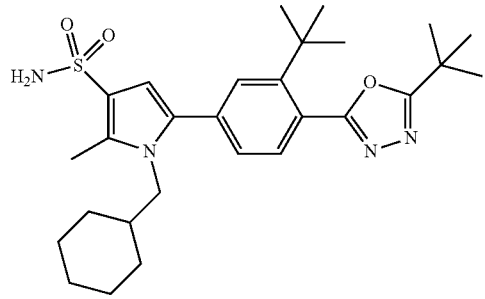 [SMILES: Cc1c(S(N)(=O)=O)cc(-c2ccc(-c3nnc(C(C)(C)C)o3)c(C(C)(C)C)c2)n1CC1CCCCC1] | 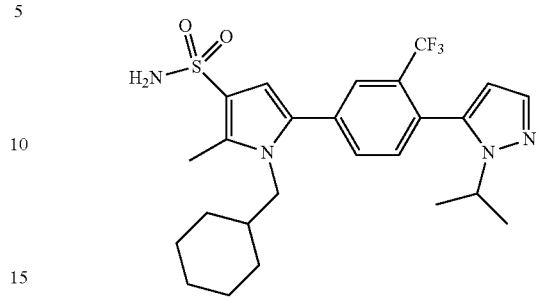 |
| 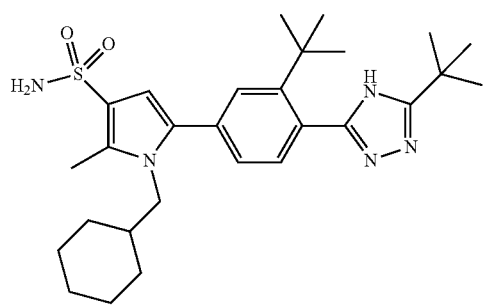 [SMILES: Cc1c(S(N)(=O)=O)cc(-c2ccc(-c3nnc(C(C)(C)C)[nH]3)c(C(C)(C)C)c2)n1CC1CCCCC1] | 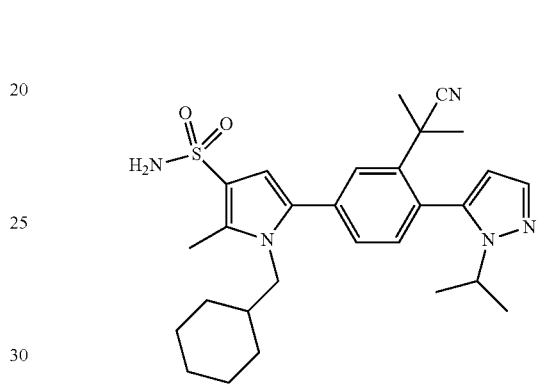 |
| 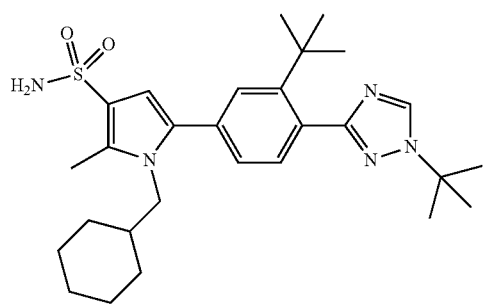 [SMILES: Cc1c(S(N)(=O)=O)cc(-c2ccc(-c3ncn(C(C)(C)C)n3)c(C(C)(C)C)c2)n1CC1CCCCC1] | 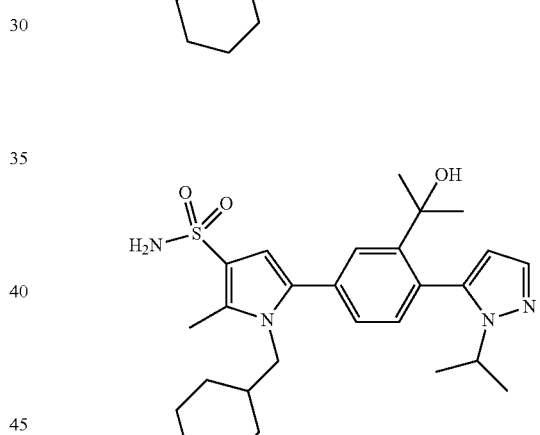 |
| 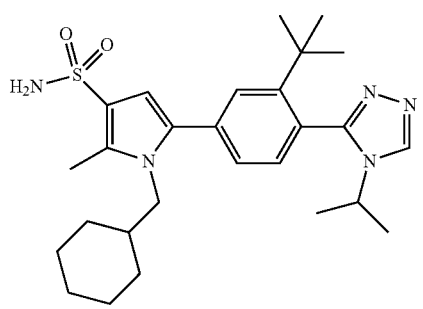 [SMILES: Cc1c(S(N)(=O)=O)cc(-c2ccc(-c3nncn3C(C)C)c(C(C)(C)C)c2)n1CC1CCCCC1] | |
| 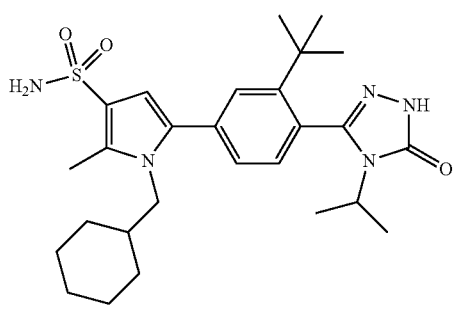 [SMILES: Cc1c(S(N)(=O)=O)cc(-c2ccc(-c3n[nH]c(=O)n3C(C)C)c(C(C)(C)C)c2)n1CC1CCCCC1] | |

Protein Expression and Purification

Protein expression and purification was done as described in WO2010/049144.

TR-FRET Activity Assay

This method measures the ability of putative ligands to modulate the interaction between the purified bacterial expressed RORγ ligand binding domain (LBD) and synthetic N-terminally biotinylated peptides which are derived from nuclear receptor coactivator proteins such as but not limited to SRC1 (NcoA1), SRC2 (NcoA2, TIF2), SRC3 (NcoA3), PGC1α, PGC1β, CBP, GRIP1, TRAP220, RIP140. The peptides used are listed in Table 1 below:

TABLE 1

| Peptide Name (aa range) | DB entry Protein | DB entry DNA | Sequence |
|---|---|---|---|
| SRC1(676-700) | NP_003734 | NM_003743.4 | NH2-CPSSHSSLTERHKILHRLLQEGSPS-COOH |
| TRAP220(631-655) | NP_004765 | NM_004774.3 | NH2-PVSSMAGNTKNHPMLMNLLKDNPAQ-COOH |
| TIF2(628-651) | NP_006531 | NM_006540.2 | NH2-GQSRLHDSKGQTKLLQLLTTKSDQ-COOH |

The ligand-binding domain (LBD) of RORγ was expressed as fusion protein with GST in BL-21 (BL3) cells using the vector pDEST15. Cells were lysed by lysozyme-treatment and sonication, and the fusion proteins purified over glutathione sepharose (Pharmacia) according to the manufacturers instructions. For screening of compounds for their influence on the RORγ-peptide interaction, the LANCE technology (Perkin Elmer) was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection assays were done in a final volume of 25 μL in a 384 well plate, in a Tris-based buffer system (20 mM Tris-HCl pH6.8; 60 mM KCl, 1 mM DTT; 5 mM MgCl$_2$; 35 ng/μL BSA), containing 20-60 ng/well recombinantly expressed RORγ-LBD fused to GST, 200-600 nM N-terminally biotinylated peptide, 200 ng/well Streptavidin-xIAPC conjugate (Prozyme) and 6-10 ng/well Eu W1024-antiGST (Perkin Elmer). DMSO content of the samples was kept at 1%.

After generation of the Tris-based buffer system, the potentially RORγ modulating ligands were diluted. After his step, protein, peptide and fluorescent acceptor and donor solutions were mixed in the Tris-based buffer system and have been added to the compound dilutions, after this addition of 'detection mix', the assay was equilibrated for one hour in the dark at rt in FIA-plates black 384 well (Corning). The LANCE signal was detected by a Perkin Elmer EnVision™ Multilabel Counter. The results were visualized by plotting the ratio between the emitted light at 665 nm and 615 nm. A basal level of RORγ-peptide formation is observed in the absence of added ligand. Ligands that promote the complex formation induce a concentration-dependent increase in time-resolved fluorescent signal. Compounds which bind equally well to both monomeric RORγ and to the RORγ-peptide complex would be expected to give no change in signal, whereas ligands, which bind preferentially to the monomeric receptor would be expected to induce a concentration-dependent decrease in the observed signal.

To assess the antagonistic potential of the compounds, $IC_{50}$ values were determined using a Ligand Sensing Assay based on Time-resolved Fluorescence Energy Transfer (TR-FRET) as described above. The normalised TR-FRET assay values, using the following equation: 1000*665 nm measurement value/615 nm measurement value, were transferred to the program GraphPad Prism to generate graphs and dose response curves using the following equation:

Equation: Sigmoidal Dose-Response (Variable Slope)

$$Y = \text{Bottom} + (\text{Top} - \text{Bottom})/(1 + 10^{((\text{LogEC50} - X)*\text{HillSlope})})$$

X is the logarithm of the concentration. Y is the response. Y starts at Bottom and goes to Top with a sigmoidal shape.

This is identical to the "four parameter logistic equation". The $IC_{50}$ values are calculated using this equation. Preparative examples listed below do reduce the signal in the TR-FRET assay in a dose dependent manner. The Preparative Examples of the present invention usually have an inhibition activity ($IC_{50}$ FRET) ranging from below 100 nM to about 20 μM, and, typically, from about 100 nM to about 2 μM. The RORγ modulating compounds of the invention desirably have an inhibition in the TR-FRET Activity Assay ranging from below 100 nM to about 1 μM. Table 2 lists typical examples of compounds of the invention that have an RORγ activity in the TR-FRET Activity Assay lower than 500 nM (Group A), from about 500 nM to 2 μM (Group B) and above 2 μM (Group C).

TABLE 2

| Group | Example # |
|---|---|
| A | 1, 1/22, 1/24, 1/25, 1/27, 1/31, 1/35, 1/37, 2, 2/1, 2/2, 2/5, 2/6, 3, 5, 5/1-5/4, 5/6-5/10, 7, 9, 12/1-12/4, 12/12, 12/23-12/25, 12/29, 12/33, 12/39, 12/40, 12/42-12/44, 17, 18, 22/2, 22/5, 22/6, 22/10-22/14, 22/18, 27-29, 31, 33, 40, 41, 44 |
| B | 1/19, 1/21, 1/23, 1/26, 1/28-1/30, 1/33, 1/34, 1/38, 1/39, 2/3, 2/4, 5/5, 5/11, 6, 12/8, 12/10, 12/13-12/16, 12/19-12/22, 12/28, 12/31, 12/32, 12/34, 12/36-12/38, 12/41, 13, 13/6-13/8, 13/13, 16/2, 16/3, 16/8, 16/11, 17/2, 17/4, 20, 22/1, 22/4, 22/9, 22/15-22/17, 30, 32, 34/1-34/3, 34/5, 39, 45, 53, 53/2 |
| C | 1/1-1/11, 1/14, 1/16, 1/17, 1/20, 1/32, 1/36, 1/41-1/43, 6/1, 8, 11, 11/1, 11/2, 12/5-12/7, 12/9, 12/17, 12/18, 12/26, 12/27, 12/35, 12/45, 13/1-13/5, 13/9-13/12, 13/14, 14, 16, 16/1, 16/4-16/6, 16/9, 16/10, 17/1, 17/3, 20/1-20/3, 22/3, 25, 34, 34/4, 37, 43, 46, 48, 49, 49/1, 49/2, 50, 53/1 |

RORγ Gal4 Reporter Gene Assay

Determination of a ligand mediated Gal4 promoter driven transactivation to quantify ligand binding to RORγ was performed as follows: DNA encoding three different RORγ protein fragments was cloned into vector pCMV-BD (Stratagene). Expression was under control of a CMV promoter and as fusion to the DNA-binding domain of the yeast protein GAL4. The amino acid boundaries of the three proteins and the respective database entries are listed in Table 3. Other vectors used were pFR-Luc (Stratagene) as regulated reporter plasmid. pFR-Luc contains a synthetic promoter with five tandem repeats of the yeast GAL4 binding sites that control expression of the *Photinus pyralis* (American firefly) luciferase gene. In order to improve experimental accuracy the plasmid pRL-CMV was cotransfected. pRL-CMV contains the constitutive CMV promoter, controlling the expression of the Renilla reniformis luciferase.

TABLE 3

| construct name | aa borders (RefSeq) | Ref sequence ID |
|---|---|---|
| hRORg-LBD | aa259-518 | NP_005051.2 |
| hRORgt | aa1-497 | NP_001001523 (RORg, t isoform, 497aa) |
| mRORg-LBD | aa264-516 | NP_035411 |

All Gal4 reporter gene assays were done in 293T cells (DSMZ (German Collection of Microorganisms and Cell Cultures), Braunschweig, Germany, ACC635) grown in Minimum Essential Medium (MEM) with Phenol Red. The medium is supplemented with 10% fetal bovine serum, 0.1 mM nonessential amino acids, 1 mM sodium pyruvate, 1% Glutamax and 100 units Penicilin/Streptavidin per mL at 37° C. in 5% $CO_2$.

For the assay, $5 \times 10^5$ cells were plated per well in 96 well plates in 100 µL per well, incubated over night at 37° C. in 5% $CO_2$. The following day, medium was discarded and the cells were transiently transfected using 20 µL per well of a Opti-MEM—PEI-based transfection-reagent (Sigma-Aldrich, 408727) including the three plasmids described above. About 4 h after addition of the transfection solution, fresh Minimal Essential Medium (MEM, same composition as used for plating cells, but without serum) was added. Then compound stocks, prediluted in MEM (same composition as used for plating cells) were added (final vehicle concentration not exceeding 0.1%).

Cells were incubated for additional 16 h before firefly (FF) and renilla (REN) luciferase activities were measured sequentially in the same cell extract using a Dual-Light-Luciferase-Assay system (Dyer et al., Anal. Biochem. 2000, 282:158). All experiments were done at least in triplicates.

Applying the Gal4 reporter gene assay as described above, the Preparative Examples of the present invention usually have an inhibition activity ($IC_{50}$ FF resp. $IC_{50}$ RENnorm) ranging from below 25 nM to about 20 µM, and typically, from about 100 nM to about 1 µM. The RORγ modulating compounds of the invention desirably have an inhibition in the Gal4 reporter gene assay ranging from below 25 nM to about 1 µM. Table 4 and 5 list typical examples of compounds of the invention that have an RORγ activity in the Gal4 reporter gene assay lower than 500 nM (Group A), from about 500 nM to 2 µM (Group B) and above 2 µM (Group C) for firefly (FF, Table 4) and renilla normalised (RENnorm, Table 5) luciferase measurements.

TABLE 4

| Group | Example # |
|---|---|
| A | 1, 1/24-1/27, 1/30-1/35, 1/37, 2, 2/2, 2/3, 2/5, 2/6, 5, 5/1-5/3, 5/5-5/11, 6, 7, 9, 11, 11/1, 11/2, 12/1-12/4, 12/13-12/16, 12/20-12/22, 12/24, 12/26, 12/29, 12/33, 12/37-12/44, 13/6-13/8, 13/12-13/14, 16/2, 16/8, 17, 17/2, 17/4, 22/1-22/14, 22/16, 22/18, 27-29, 31, 34/2, 34/3, 34/5, 37, 39-41, 44, 45, 53, 53/2 |
| B | 1/2, 1/7, 1/14, 1/16, 1/19, 1/20-1/23, 1/28, 1/29, 1/36, 1/38, 1/39, 1/41, 1/42, 2/1, 2/4, 3, 5/4, 6/1, 12/6, 12/9, 12/10, 12/12, 12/17-12/19, 12/23, 12/25, 12/27, 12/28, 12/31, 12/32, 12/34, 12/36, 13, 13/2, 13/5, 13/10, 14, 16/1, 16/3, 16/4, 16/7, 16/9-16/11, 17/1, 17/3, 18, 20, 20/1-20/3, 22/15, 22/17, 33, 34, 34/1, 34/4, 49, 49/1, 49/2, 50, 53/1 |
| C | 1/12, 1/13, 1/15, 1/17, 1/18, 16, 16/6 |

TABLE 5

| Group | Example # |
|---|---|
| A | 1, 1/24-1/27, 1/30-1/35, 1/37, 1/38, 1/41, 2, 2/1-2/3, 2/5, 2/6, 5, 5/1-5/11, 6, 7, 9, 11, 11/1, 11/2, 12/1-12/4, 12/14-12/16, 12/19, 12/20, 12/22, 12/24-12/26, 12/29, 12/33, 12/37, 12/38, 12/40-12/44, 13/6-13/8, 13/12-13/14, 16/2, 16/8, 17, 17/2, 22/1-22/14, 22/18, 27, 29, 31, 33, 34/2, 34/3, 34/5, 37, 39-41, 44, 45, 53, 53/2 |
| B | 1/7, 1/19, 1/20-1/23, 1/28, 1/29, 1/36, 1/39, 1/42, 2/4, 3, 6/1, 12/6, 12/9, 12/10, 12/12, 12/13, 12/17, 12/18, 12/21, 12/23, 12/27, 12/28, 12/31, 12/32, 12/34, 12/36, 12/39, 13, 13/2, 13/5, 13/10, 14, 16/1, 16/3, 16/7, 16/10, 16/11, 17/1, 17/3, 17/4, 18, 20, 20/1-20/3, 22/15-22/17, 28, 34/1, 34/4, 49, 49/1, 49/2, 50, 53/1 |
| C | 1/2, 1/12-1/18, 4, 16, 16/4, 16/6, 16/9, 34 |

The invention claimed is:
1. A compound represented by formula (1):

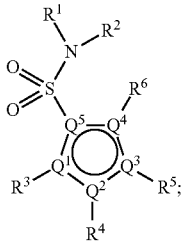

(1)

enantiomers, diastereomers and tautomers thereof and pharmaceutically acceptable salts thereof,
wherein:
one of $Q^1$ to $Q^5$ is a nitrogen atom and the remaining radicals are carbon atoms;
$R^1$ is selected from the group consisting of H, $C_{1-10}$ alkyl, $C_{1-10}$ alkenyl, $C_{1-10}$ alkynyl, $C_{0-6}$ alkylene-$C_{3-10}$ cycloalkyl, $C_{0-6}$ alkylene-$C_{3-10}$ heterocycloalkyl, and $C_{0-6}$ alkylene-5-membered heteroaromatic ring system containing 1, 2, or 3 heteroatoms independently selected from the group consisting of N, O and S,
wherein alkyl, alkylene, alkenyl, alkynyl, cycloalkyl, heterocycloalkyl and the 5-membered heteroaromatic ring system are unsubstituted or substituted with 1 to 6 substituents independently selected from the group consisting of OH, oxo, CN, O—$C_{1-6}$ alkyl, O-halo-$C_{1-6}$ alkyl, $C_{1-6}$ alkyl, halo-$C_{1-6}$ alkyl, halogen, COOR$^{10}$, CON(R$^{10}$)$_2$, SO$_2$R$^{10}$, SO$_2$N(R$^{10}$)$_2$, NR$^{10}$COR$^{10}$, NR$^{10}$SO$_2$R$^{10}$ and N(R$^{10}$)$_2$;
$R^2$ is selected from the group consisting of H, $C_{1-6}$ alkyl and halo-$C_{1-6}$ alkyl,
or $R^1$ and $R^2$ when taken together with the nitrogen to which they are attached complete a 3- to 8-membered ring containing carbon atoms and optionally containing an additional heteroatom selected from O, S, SO, SO$_2$ or NR$^{10}$, wherein the ring is unsubstituted or substituted with one to four substitutents independently selected from halogen, oxo or $C_{1-6}$-alkyl;
$R^3$ is H, $C_{1-6}$ alkyl, halo-$C_{1-6}$ alkyl, CN or halogen,
wherein alkyl is unsubstituted or substituted with 1 to 3 substituents independently selected from the group consisting of O—$C_{1-6}$ alkyl, O-halo-$C_{1-6}$ alkyl, oxo and OH;
$R^4$ is SO$_2$—(CR$^8$R$^8$)$_y$R$^7$ or (CR$^8$R$^8$)$_x$—R$^{11}$;
$R^5$ is pyridinone, a 6-10 membered mono- or bicyclic aryl or a 5-14 membered mono-, bi- or tricyclic heteroaryl containing 1 to 4 heteroatoms independently selected from the group consisting of N, O and S,
wherein pyridinone, aryl and heteroaryl are unsubstituted or substituted with 1 to 5 substituents independently selected from halogen, CN, $C_{1-6}$ alkyl, $C_{1-6}$ alkenyl, $C_{1-6}$ alkynyl, halo-$C_{1-6}$ alkyl, OH, O—$C_{1-6}$ alkyl, O-halo-$C_{1-6}$ alkyl, $C_{3-10}$ cycloalkyl, O—$C_{3-10}$ cycloalkyl, COOR$^9$, C(O)R$^9$, C(O)N(R$^9$)$_2$, SO$_2$—N(R$^9$)$_2$, SO$_2$—R$^9$, $C_{3-10}$ heterocycloalkyl, phenyl, or 5-6 membered heteroaryl containing 1 to 4 heteroatoms independently selected from N, O and S,
wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, =N—OH, =N—O—($C_{1-6}$ alkyl), N(R$^9$)$_2$, O—$C_{1-6}$ alkyl, COOH, CON(R$^9$)$_2$, CN, NR$^9$—COR$^{10}$, $C_{3-10}$ cycloalkyl, $C_{3-10}$ heterocycloalkyl, and 6-10 membered mono- or bicyclic aryl, or wherein two adjacent substituents may complete a 3- to 8-membered saturated or partially unsaturated ring containing carbon atoms and optionally containing 1 to 3 heteroatoms selected from O, S, SO, SO$_2$ or NR$^{10}$, wherein the ring is unsubstituted or substituted with one to four substituents independently selected from halogen, oxo, =N—OH, =N—O—($C_{1-6}$ alkyl), OH, O—$C_{1-6}$-alkyl, O-halo-$C_{1-6}$-alkyl, $C_{1-6}$-alkyl, $C_{3-6}$-cycloalkyl or halo-$C_{1-6}$-alkyl;
$R^6$ is H, $C_{1-6}$ alkyl, halo-$C_{1-6}$ alkyl or halogen;
$R^7$ is $C_{1-10}$ alkyl, $C_{3-10}$ cycloalkyl, $C_{3-10}$ heterocycloalkyl, 6-10 membered mono- or bicyclic aryl or
5-10 membered mono- or bicyclic heteroaryl,
wherein cycloalkyl, heterocycloalkyl, aryl and heteroaryl are unsubstituted or substituted with 1 to 3 substituents independently selected from the group consisting of halogen, OH, O—$C_{1-6}$ alkyl, O-halo-$C_{1-6}$ alkyl, $C_{1-6}$ alkyl, halo-$C_{1-6}$ alkyl and NH$_2$,
and wherein alkyl is unsubstituted or substituted with 1 to 3 substituents independently selected from the group consisting of halogen, OH, O—$C_{1-6}$ alkyl, O-halo-$C_{1-6}$ alkyl and NH$_2$;
$R^8$ is independently H, $C_{1-4}$ alkyl, O—$C_{1-4}$ alkyl, halo-$C_{1-4}$ alkyl or halogen;
$R^9$ is independently selected from H, $C_{1-6}$ alkyl, $C_{3-10}$ cycloalkyl, $C_{3-10}$ heterocycloalkyl, phenyl,
5-6 membered heteroaryl containing 1 to 4 heteroatoms independently selected from N, O or S,
wherein alkyl, cycloalkyl and heterocycloalkyl is unsubstituted or substituted with 1 to 3 substituents selected from the group consisting of OH, O-$C_{1-6}$ alkyl, O-halo-$C_{1-6}$ alkyl, phenyl, heteroaryl, halogen, NH$_2$, NH($C_{1-6}$ alkyl), N($C_{1-6}$ alkyl)$_2$, $C_{3-10}$ heterocycloalkyl and $C_{3-10}$ cycloalkyl,
wherein cycloalkyl and heterocycloalkyl is unsubstituted or substituted with 1 to 3 substituents independently selected from the group consisting of $C_{1-6}$ alkyl, halo-$C_{1-6}$ alkyl, OH, O—$C_{1-6}$ alkyl, O-halo-$C_{1-6}$ alkyl, phenyl, heteroaryl, halogen, NH$_2$, NH($C_{1-6}$ alkyl), N($C_{1-6}$ alkyl)$_2$ and $C_{3-10}$ cycloalkyl,
and wherein phenyl and heteroaryl are unsubstituted or substituted with 1 to 3 substituents independently selected from the group consisting of OH, O—$C_{1-6}$ alkyl, O-halo-$C_{1-6}$ alkyl, halogen, $C_{1-6}$ alkyl, halo-$C_{1-6}$ alkyl, NH$_2$, NH($C_{1-6}$ alkyl), N($C_{1-6}$ alkyl)$_2$ and $C_{3-10}$ cycloalkyl;
$R^{10}$ is independently selected from H, $C_{1-6}$ alkyl, halo-$C_{1-6}$ alkyl or $C_{3-10}$ cycloalkyl;
$R^{11}$ is $C_{2-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl,
wherein alkyl, cycloalkyl, heterocycloalkyl, aryl and heteroaryl is unsubstituted or substituted with 1 to 3 substituents independently selected from the group consisting of halogen, OH, oxo, O—$C_{1-6}$ alkyl, O-halo-$C_{1-6}$ alkyl, $C_{1-6}$ alkyl, halo-$C_{1-6}$ alkyl and NH$_2$;
x is 1, 2 or 3; and
y is 0, 1, or 2;
with the proviso that for $R^5$ the 5-14 membered mono-, bi- or tricyclic heteroaryl containing ring is not

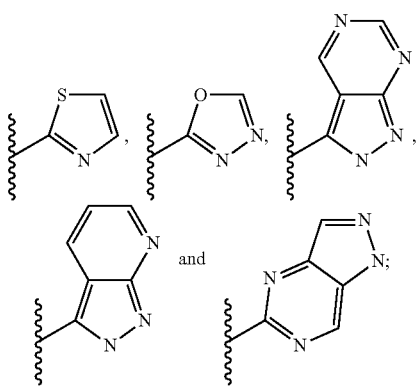

and with the proviso that $(CR^8R^8)_x—R^{11}$ is not

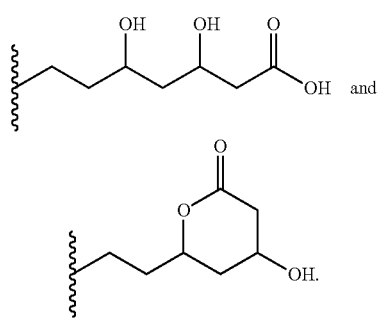

2. A compound represented by formula (1):

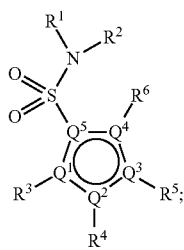

(1)

enantiomers, diastereomers and tautomers thereof and pharmaceutically acceptable salts thereof,
wherein:
one of $Q^1$ to $Q^5$ is a nitrogen atom and the remaining radicals are carbon atoms;
$R^1$ is selected from the group consisting of H, $C_{1-10}$ alkyl, $C_{1-10}$ alkenyl, $C_{1-10}$ alkynyl, $C_{0-6}$ alkylene-$C_{3-10}$ cycloalkyl, $C_{0-6}$ alkylene-$C_{3-10}$ heterocycloalkyl, and $C_{0-6}$ alkylene-5-membered heteroaromatic ring system containing 1, 2, or 3 heteroatoms independently selected from the group consisting of N, O and S,
wherein alkyl, alkylene, alkenyl, alkynyl, cycloalkyl, heterocycloalkyl and the 5-membered heteroaromatic ring system are unsubstituted or substituted with 1 to 6 substituents independently selected from the group consisting of OH, oxo, CN, O—$C_{1-6}$ alkyl, O-halo-$C_{1-6}$ alkyl, $C_{1-6}$ alkyl, halogen, $COOR^{10}$, $CON(R^{10})_2$, $SO_2R^{10}$, $SO_2N(R^{10})_2$, $NR^{10}COR^{10}$, $NR^{10}SO_2R^{10}$ and $N(R^{10})_2$;

$R^2$ is selected from the group consisting of H, $C_{1-6}$ alkyl and halo-$C_{1-6}$ alkyl,
or $R^1$ and $R^2$ when taken together with the nitrogen to which they are attached complete a 3- to 8-membered ring containing carbon atoms and optionally containing an additional heteroatom selected from O, S, SO, $SO_2$ or $NR^{10}$, wherein the ring is unsubstituted or substituted with one to four substituents independently selected from halogen, oxo or $C_{1-6}$-alkyl;
$R^3$ is H, $C_{1-6}$ alkyl, halo-$C_{1-6}$ alkyl or halogen,
wherein alkyl is unsubstituted or substituted with 1 to 3 substituents independently selected from the group consisting of O—$C_{1-6}$ alkyl, O-halo-$C_{1-6}$ alkyl and OH;
$R^4$ is $SO_2—(CR^8R^8)_y R^7$ or $(CR^8R^8)_x—R^{11}$;
$R^5$ is a 6-10 membered mono- or bicyclic aryl or a 5-14 membered mono-, bi- or tricyclic heteroaryl containing 1 to 4 heteroatoms independently selected from the group consisting of N, O and S,
wherein aryl and heteroaryl are unsubstituted or substituted with 1 to 5 substituents independently selected from halogen, CN, $C_{1-6}$ alkyl, $C_{1-6}$ alkenyl, $C_{1-6}$ alkynyl, halo-$C_{1-6}$ alkyl, OH, O—$C_{1-6}$ alkyl, O-halo-$C_{1-6}$ alkyl, O—$C_{3-10}$ cycloalkyl, $COOR^9$, $C(O)R^9$, $C(O)N(R^9)_2$, $SO_2—N(R^9)_2$, $SO_2—R^9$, $C_{3-10}$ heterocycloalkyl, phenyl, or 5-6 membered heteroaryl containing 1 to 4 heteroatoms independently selected from N, O and S,
wherein alkyl, alkenyl, alkynyl, cycloalkyl, heterocycloalkyl, phenyl and heteroaryl are unsubstituted or substituted by 1 to 3 substituents independently selected from the group consisting of halogen, OH, oxo, $N(R^9)_2$, O—$C_{1-6}$ alkyl; COOH, $CON(R^9)_2$, CN, $NR^9—COR^{10}$, 3-10 membered cycloalkyl, 3-10 membered mono- or bicyclic heterocycloalkyl, and 6-10 membered mono- or bicyclic aryl, or wherein two substituents may complete a 3- to 8-membered saturated or partially unsaturated ring containing carbon atoms and optionally containing 1 to 3 heteroatoms selected from 0, S, SO, $SO_2$ or $NR^{10}$, wherein the ring is unsubstituted or substituted with one to four substituents independently selected from halogen, oxo, OH, O—$C_{1-6}$-alkyl, O-halo-$C_{1-6}$-alkyl, $C_{3-6}$-cycloalkyl and halo-$C_{1-6}$-alkyl;
$R^6$ is H, $C_{1-6}$ alkyl, halo-$C_{1-6}$ alkyl or halogen;
$R^7$ is $C_{1-10}$ alkyl, $C_{3-10}$ cycloalkyl, $C_{3-10}$ heterocycloalkyl, 6-10 membered mono- or bicyclic aryl or 5-10 membered mono- or bicyclic heteroaryl,
wherein cycloalkyl, heterocycloalkyl, aryl and heteroaryl are unsubstituted or substituted with 1 to 3 substituents independently selected from the group consisting of halogen, OH, O—$C_{1-6}$ alkyl, O-halo-$C_{1-6}$ alkyl, $C_{1-6}$ alkyl, halo-$C_{1-6}$ alkyl and $NH_2$,
and wherein alkyl is unsubstituted or substituted with 1 to 3 substituents independently selected from the group consisting of halogen, OH, O—$C_{1-6}$ alkyl, O-halo-$C_{1-6}$ alkyl and $NH_2$;
$R^8$ is independently H, $C_{1-4}$ alkyl, halo-$C_{1-4}$ alkyl or halogen;
$R^9$ is independently selected from H, $C_{1-6}$ alkyl, $C_{3-10}$ cycloalkyl, $C_{3-10}$ heterocycloalkyl, phenyl, 5-6 membered heteroaryl containing 1 to 4 heteroatoms independently selected from N, O and S,
wherein alkyl, cycloalkyl and heterocycloalkyl is unsubstituted or substituted with 1 to 3 substituents independently selected from the group consisting of OH, O—C$_{1-6}$ alkyl, O-halo-C$_{1-6}$ alkyl, phenyl, halogen, NH$_2$, NH(C$_{1-6}$ alkyl), N(C$_{1-6}$ alkyl)$_2$, and C$_{3-10}$ cycloalkyl, and wherein phenyl and heteroaryl are unsubstituted or substituted with 1 to 3 substituents independently selected from the group consisting of OH, O—C$_{1-6}$ alkyl, O-halo-C$_{1-6}$ alkyl, halogen, C$_{1-6}$ alkyl, halo-C$_{1-6}$ alkyl, NH$_2$, NH(C$_{1-6}$ alkyl), N(C$_{1-6}$ alkyl)$_2$ and C$_{3-10}$ cycloalkyl;

R$^{10}$ is independently selected from H, C$_{1-6}$ alkyl, halo-C$_{1-6}$ alkyl and C$_{3-10}$ cycloalkyl;

R$^{11}$ is C$_{2-10}$ alkyl, C$_{3-10}$ cycloalkyl, C$_{3-10}$ heterocycloalkyl, 6-10 membered mono- or bicyclic aryl or 5-10 membered mono- or bicyclic heteroaryl, wherein alkyl, cycloalkyl, heterocycloalkyl, aryl and heteroaryl is unsubstituted or substituted with 1 to 3 substituents independently selected from the group consisting of halogen, OH, oxo, O—C$_{1-6}$ alkyl, O-halo-C$_{1-6}$ alkyl, C$_{1-6}$ alkyl, halo-C$_{1-6}$ alkyl and NH$_2$;

x is 1, 2 or 3; and
y is 0, 1, or 2;
with the proviso that for R$^5$ the 5-14 membered mono-, bi- or tricyclic heteroaryl containing ring is not

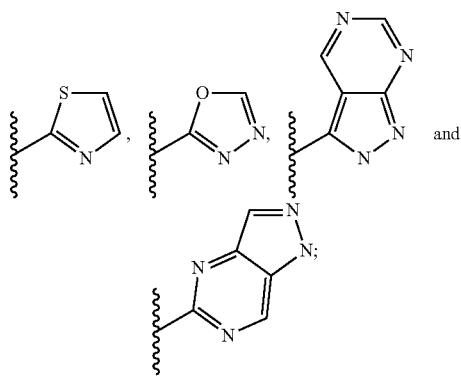

and with the proviso that (CR$^8$R$^8$)$_x$—R$^{11}$ is not

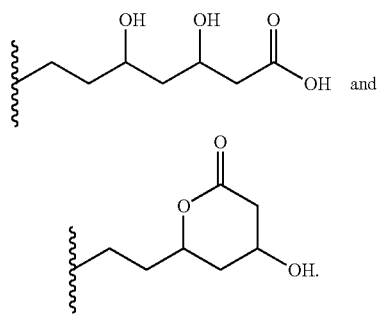

3. The compound of claim 1 or claim 2 wherein:
Q$^2$ is the nitrogen atom.
4. The compound of claim 1 or claim 2 wherein:
R$^1$ is selected from the group consisting of H, C$_{1-10}$ alkyl, C$_{3-10}$ cycloalkyl and C$_{3-10}$ heterocycloalkyl, wherein alkyl, cycloalkyl and heterocycloalkyl are unsubstituted or substituted with 1 to 3 substituents independently selected from the group consisting of OH, oxo, CN, O—C$_{1-6}$ alkyl, O-halo-C$_{1-6}$ alkyl, C$_{1-6}$ alkyl, halogen, COOR$^{10}$, CON(R$^{10}$)$_2$, SO$_2$R$^{10}$, SO$_2$N(R$^{10}$)$_2$, NR$^{10}$COR$^{10}$, NR$^{10}$SO$_2$R$^{10}$ and N(R$^{10}$)$_2$;

R$^2$ is selected from the group consisting of H, C$_{1-6}$ alkyl and halo-C$_{1-6}$ alkyl, or R$^1$ and R$^2$ when taken together with the nitrogen to which they are attached complete a 3- to 8-membered ring containing carbon atoms and optionally containing an additional heteroatom selected from O, S, SO, SO$_2$ or NR$^{10}$, wherein the ring is unsubstituted or substituted with one to four substituents independently selected from halogen, oxo or C$_{1-6}$-alkyl.

5. The compound of claim 1 or claim 2 wherein R$^1$ and R$^2$ are hydrogen.

6. The compound of claim 1 or claim 2 wherein
R$^4$ is CH$_2$—R$^{11}$; and
R$^{11}$ is C$_{4-8}$ cycloalkyl,
wherein cycloalkyl is unsubstituted or substituted with 1 to 3 substituents independently selected from the group consisting of halogen, OH, oxo, O—C$_{1-6}$ alkyl, O-halo-C$_{1-6}$ alkyl, C$_{1-6}$ alkyl, and halo-C$_{1-6}$ alkyl.

7. The compound of claim 1 or claim 2 wherein
R$^5$ is a 6-10 membered mono- or bicyclic aryl or a 5-10 membered mono- or bicyclic heteroaryl containing 1 to 4 heteroatoms independently selected from the group consisting of N, O and S, wherein aryl and heteroaryl is unsubstituted or substituted with 1 to 5 substituents independently selected from halogen, CN, C$_{1-6}$ alkyl, C$_{1-6}$ alkenyl, alkynyl, halo-C$_{1-6}$ alkyl, OH, O—C$_{1-6}$ alkyl, O-halo-C$_{1-6}$ alkyl, C$_{3-10}$ cycloalkyl, O—C$_{3-10}$ cycloalkyl, COOR$^9$, C(O)R$^9$, C(O)N(R$^9$)$_2$, SO$_2$—N(R$^9$)$_2$, SO$_2$—R$^9$, C$_{3-10}$ heterocycloalkyl, phenyl, or 5-6 membered heteroaryl containing 1 to 4 heteroatoms independently selected from N, O and S, wherein alkyl, alkeny, alkynyl, cycloalkyl, heterocycloalkyl, phenyl and heteroaryl are unsubstituted or substituted by 1 to 3 substituents independently selected from the group consisting of halogen, OH, oxo, N(R$^9$)$_2$, O—C$_{1-6}$ alkyl; COOH, CON(R$^9$)$_2$, CN, NR$^9$—COR$^{10}$, C$_{3-10}$ cycloalkyl, C$_{3-10}$ heterocycloalkyl, and 6-10 membered mono- or bicyclic aryl, and wherein two adjacent substituents complete a 3- to 8-membered saturated or partially saturated ring containing carbon atoms and optionally containing 1 to 3 heteroatoms selected from O, S, SO, SO$_2$ or NR$^{10}$, wherein the ring is unsubstituted or substituted with one to four substitutents independently selected from halogen, oxo, OH, O—C$_{1-6}$-alkyl, O-halo-C$_{1-6}$-alkyl, C$_{3-6}$-cycloalkyl and halo-C$_{1-6}$-alkyl.

8. The compound of claim 1 or claim 2 wherein R$^5$ is selected from:

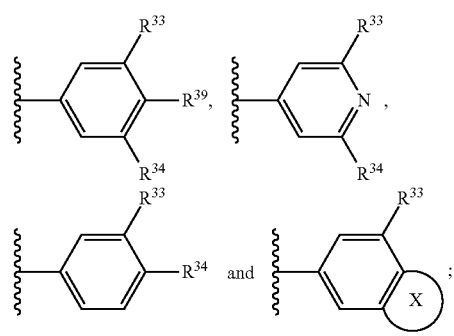

wherein

R$^{33}$ is selected from C$_{1-6}$-alkyl, fluoro-C$_{1-6}$-alkyl, C$_{1-4}$-alkylene-OH, C$_{1-4}$-alkylene-O-fluoro-C$_{1-3}$-alkyl, O-fluoro-C$_{1-6}$-alkyl, C$_{3-10}$-cycloalkyl, C(O)N(R$^{37}$)$_2$, wherein alkylene is unsubstituted or substituted with 1 to 3 substituents selected from F, and cycloalkyl is unsubstituted or substituted with 1 to 3 substituents independently selected from F, C$_{1-3}$-alkyl or fluoro-C$_{1-3}$-alkyl;

R$^{34}$ is selected from C$_{1-4}$-alkylene-OH, C$_{1-4}$-alkylene-O—C$_{1-3}$-alkyl, C$_{1-4}$-alkylene-O-fluoro-C$_{1-3}$-alkyl, C$_{3-10}$-cycloalkyl, C(O)N(R$^{37}$)$_2$, or S(O$_2$)N(R$^{37}$)$_2$, wherein alkylene is unsubstituted or substituted with 1 to 3 substituents selected from F, and cycloalkyl is unsubstituted or substituted with 1 to 3 substituents independently selected from F, C$_{1-3}$-alkyl or fluoro-C$_{1-3}$-alkyl;

R$^{37}$ is independently selected from H, C$_{1-6}$-alkyl, halo-C$_{1-6}$-alkyl, or C$_{1-6}$-cycloalkyl, wherein cycloalkyl is unsubstituted or substituted with 1 to 3 substituents independently selected from F, C$_{1-3}$-alkyl or fluoro-C$_{1-3}$-alkyl, and wherein two R$^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, oxo, C$_{1-4}$-alkyl or halo-C$_{1-4}$-alkyl;

R$^{38}$ is selected from H, C$_{1-3}$-alkyl or fluoro-C$_{1-3}$-alkyl;

R$^{39}$ is independently selected from H, F, OH, C$_{1-6}$-alkyl, halo-C$_{1-6}$-alkyl, O—C$_{1-6}$-alkyl or C$_{1-6}$-cycloalkyl;

X is an annelated saturated heterocycle selected from the group consisting of:

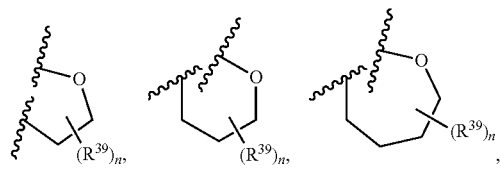

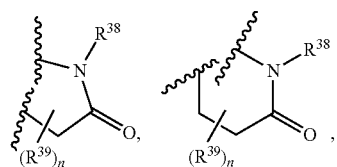

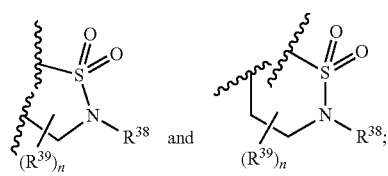

and n is selected from 1 to 4.

9. The compound of claim 1 or claim 2 wherein R$^5$ is selected from:

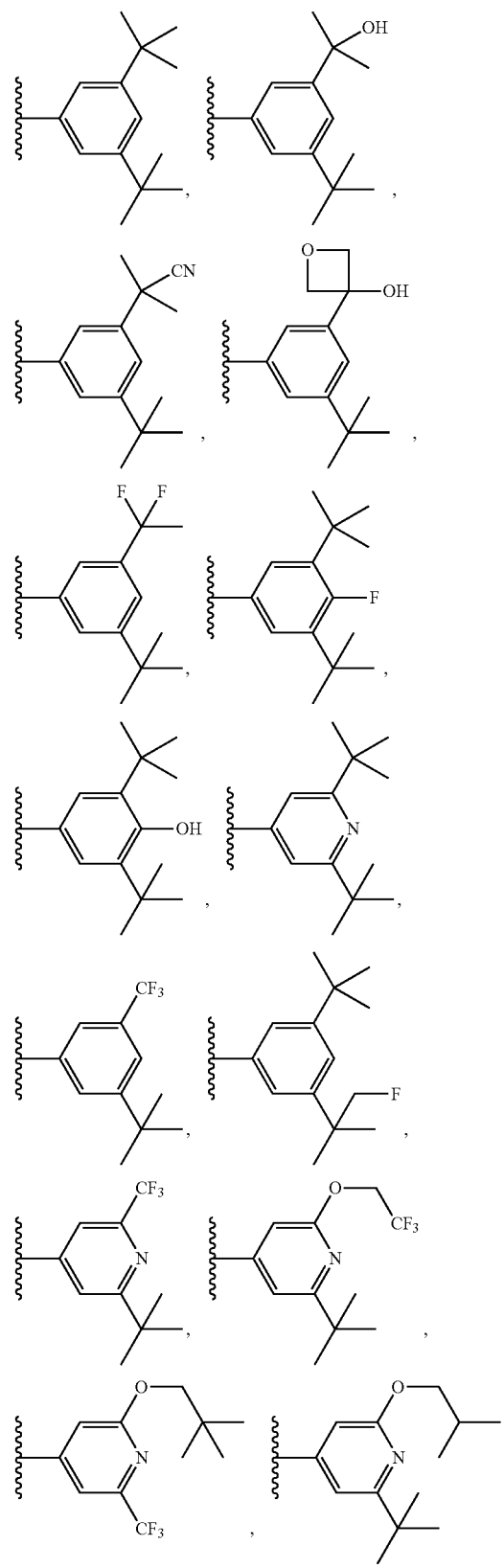

243
-continued
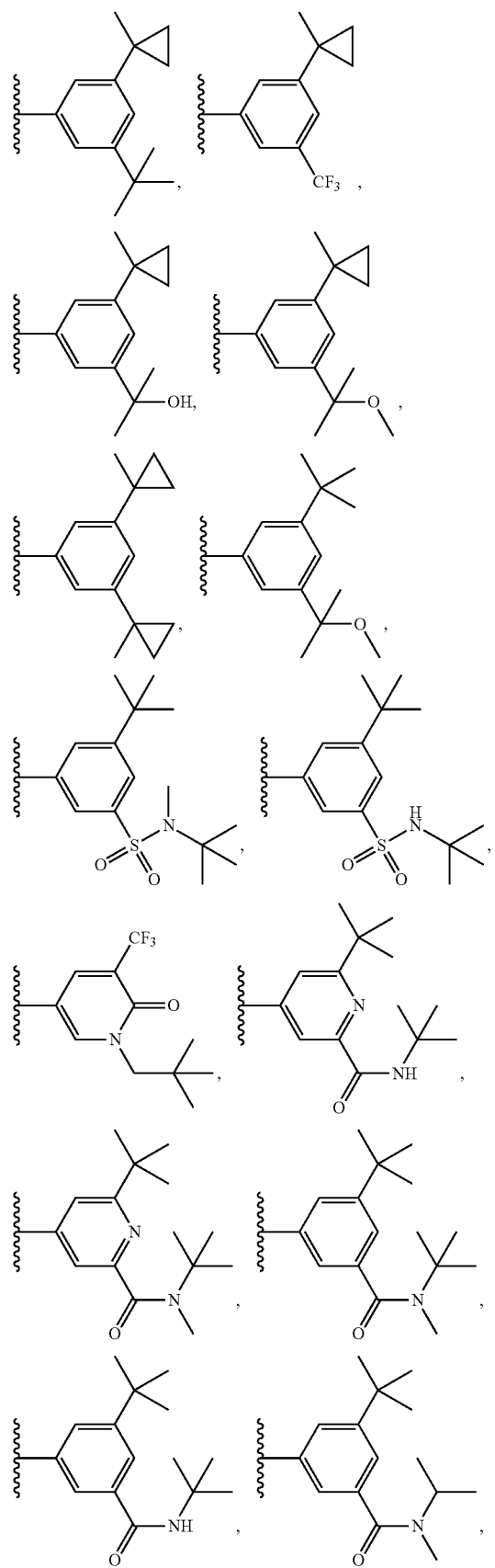
244
-continued
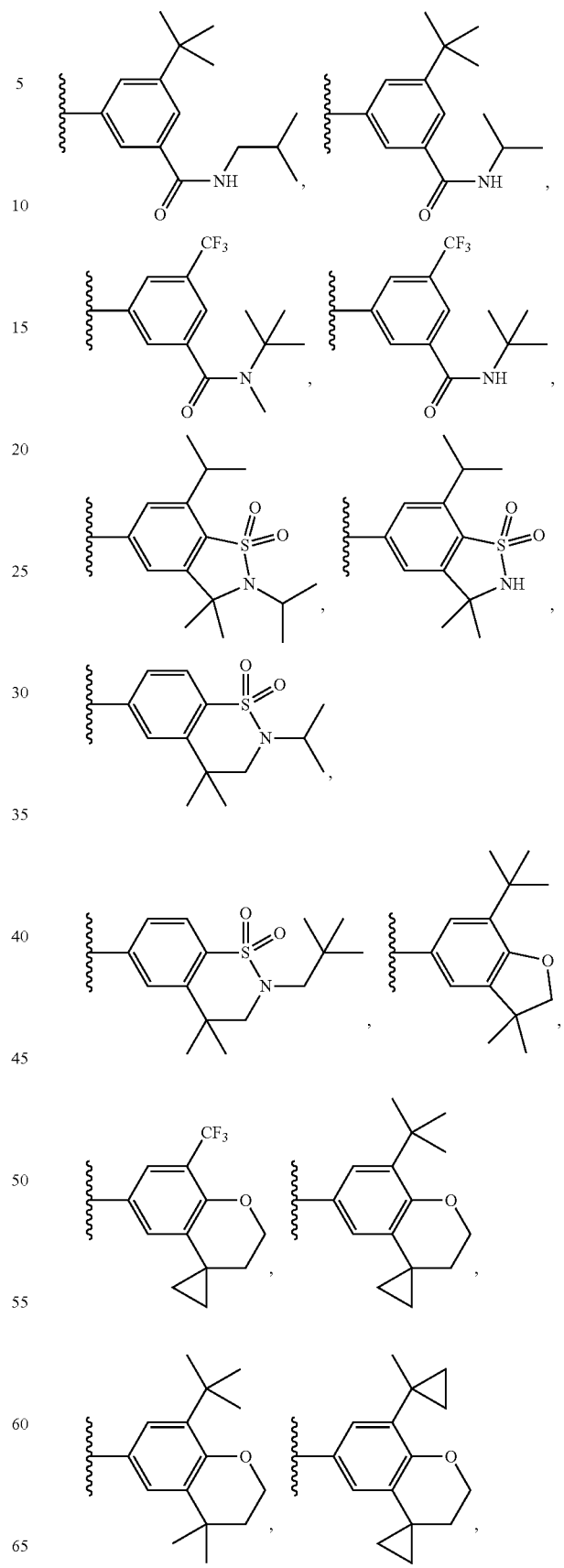

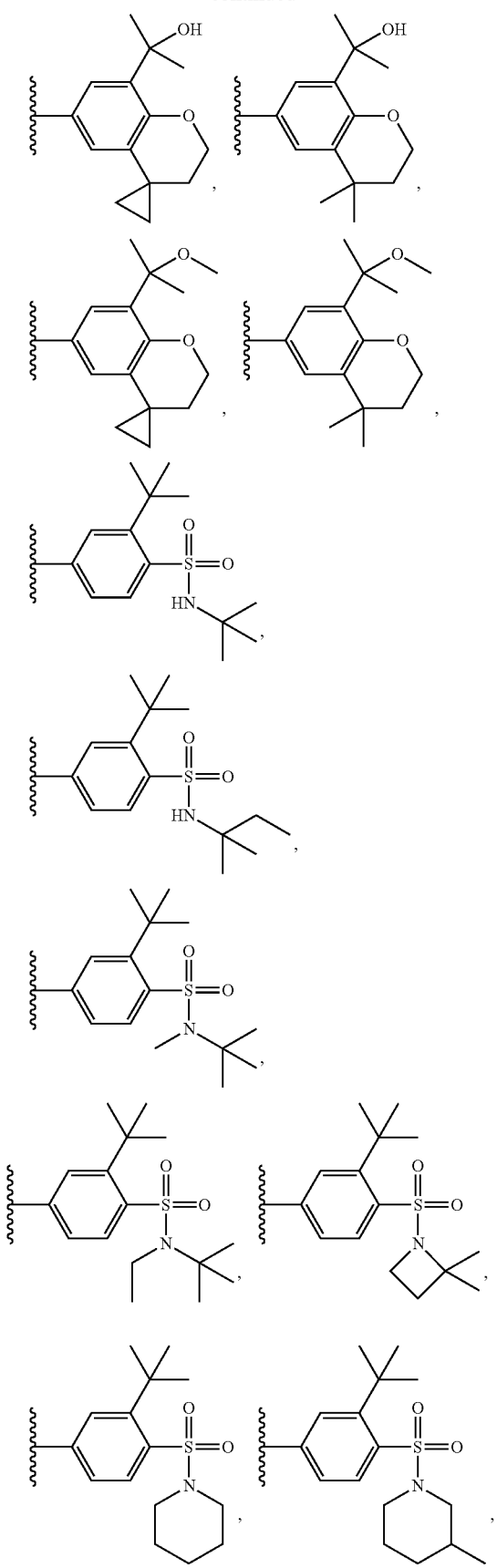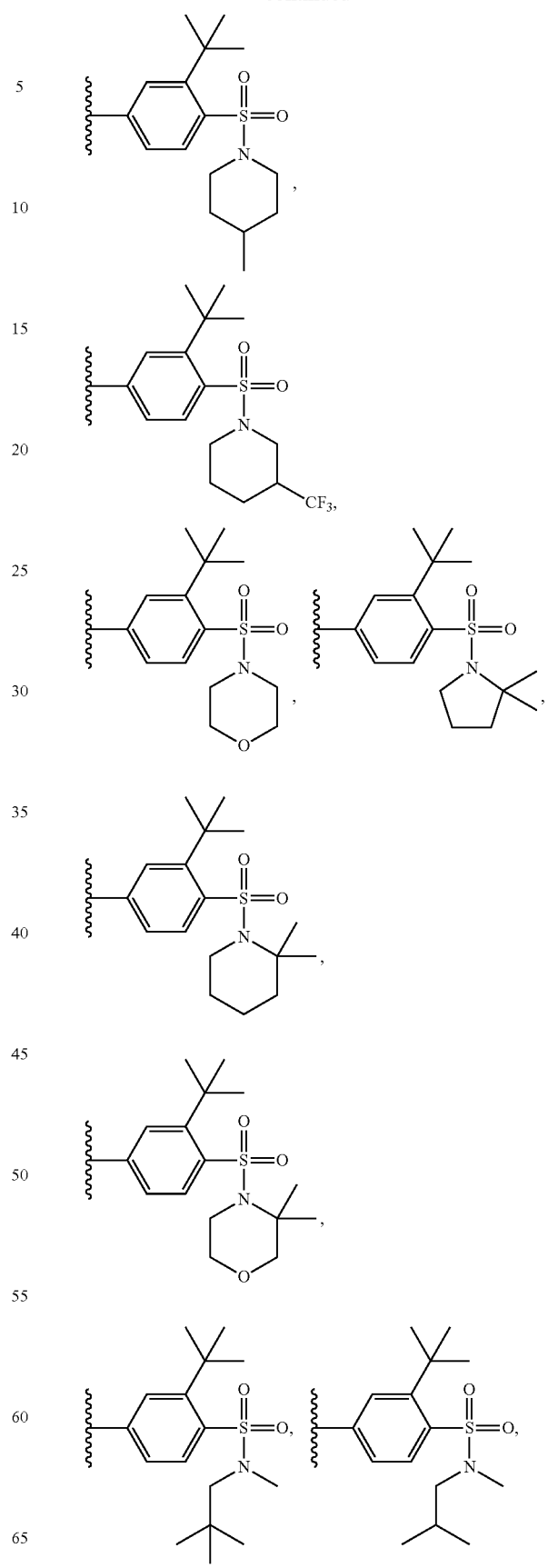

247
-continued
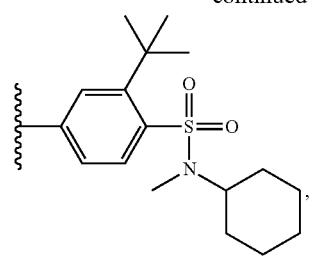
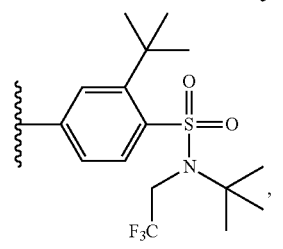
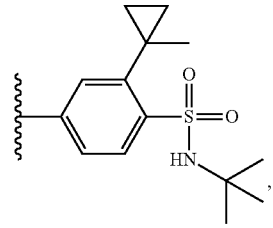
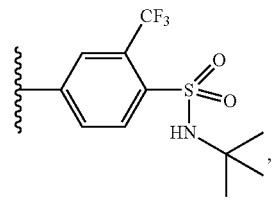
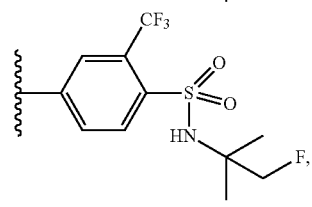
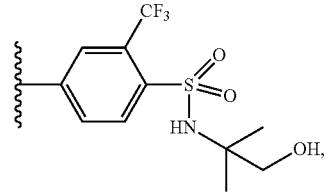
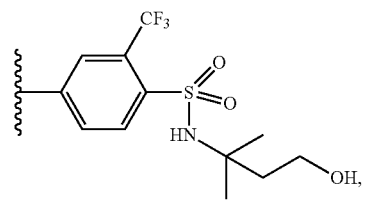
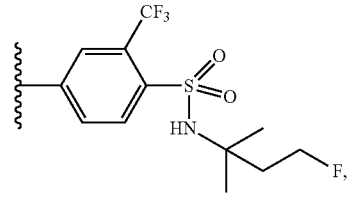
248
-continued
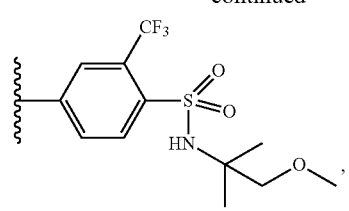
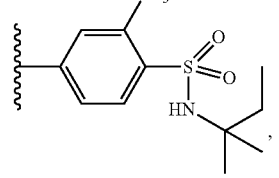
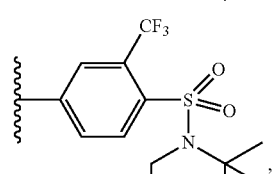
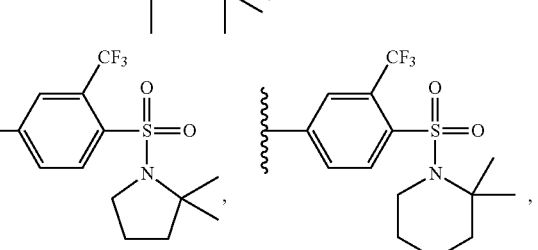
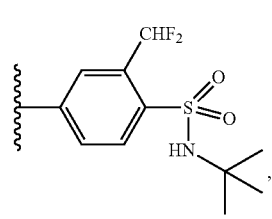
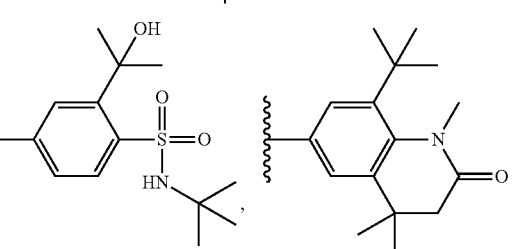
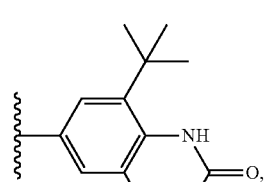
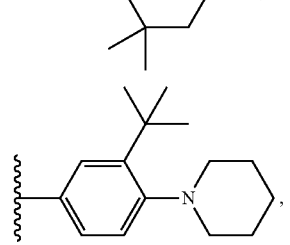

-continued
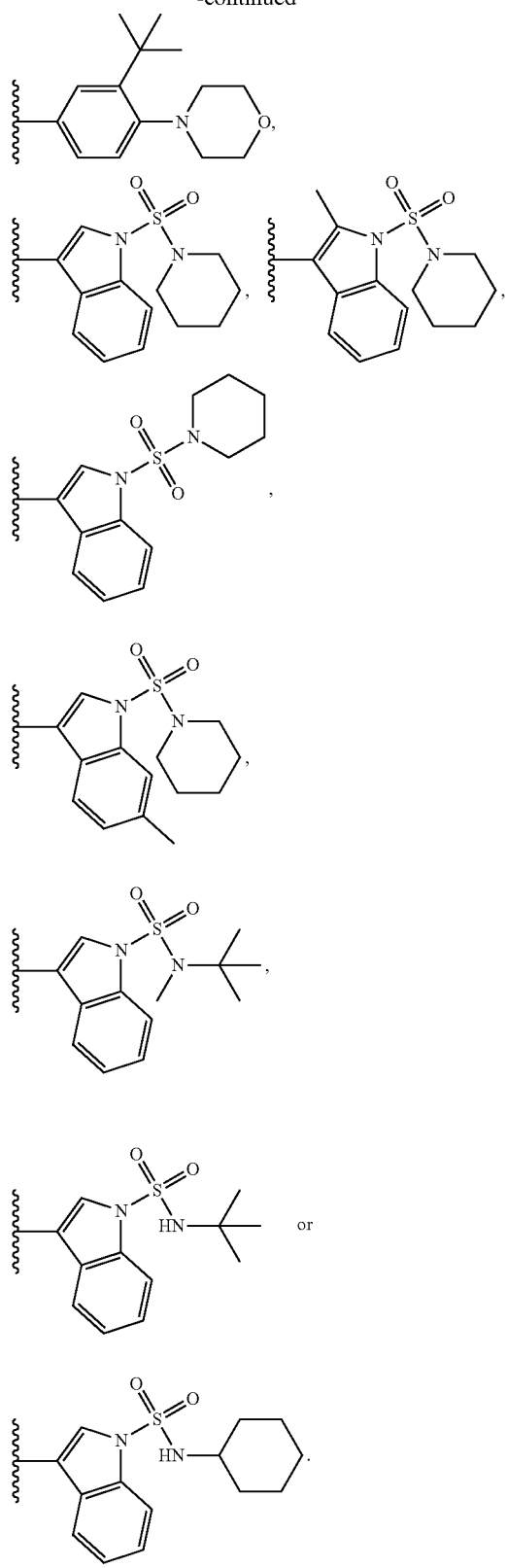
10. The compound of claim 1 or claim 2 wherein:
R³ is methyl; and
R⁶ is H.
11. The compound of claim 1 or claim 2 selected from:
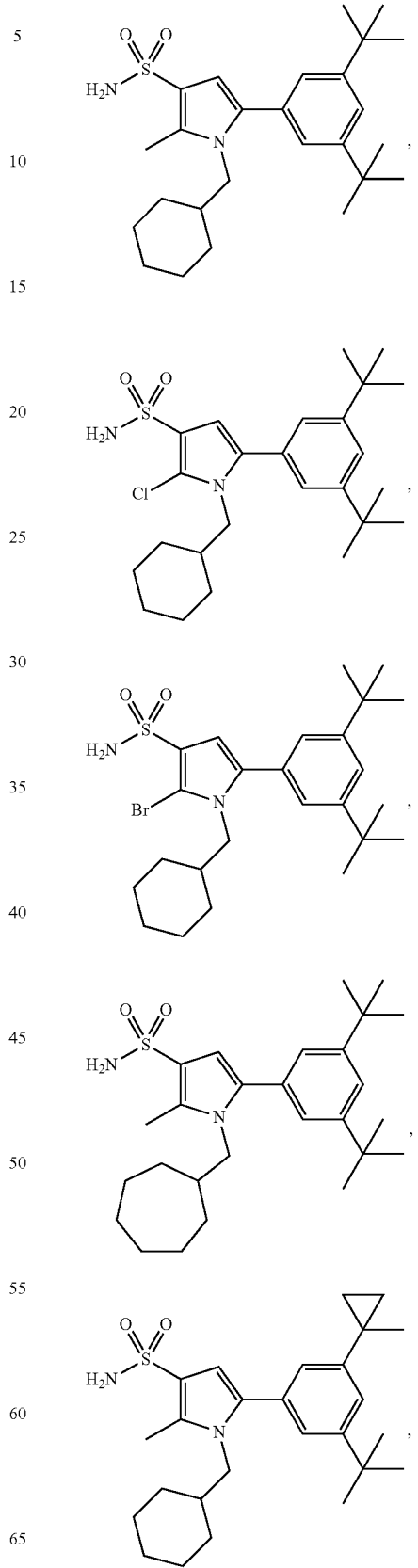

251
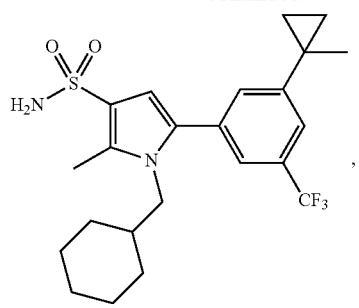
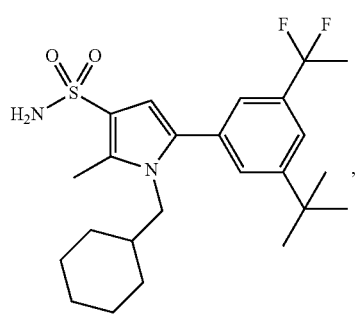
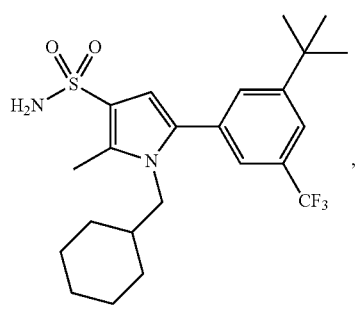
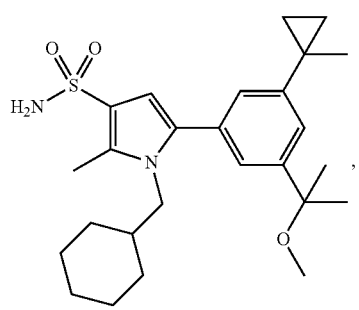
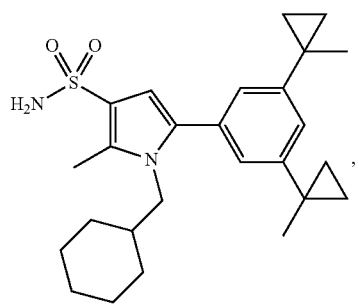
252
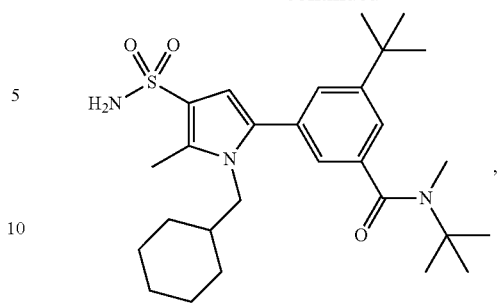
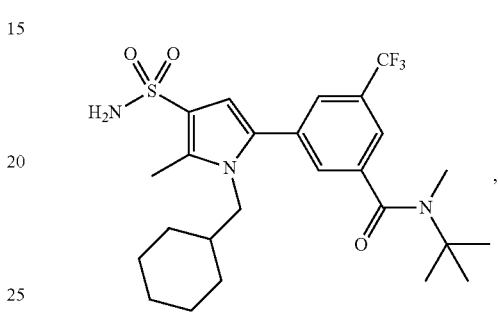
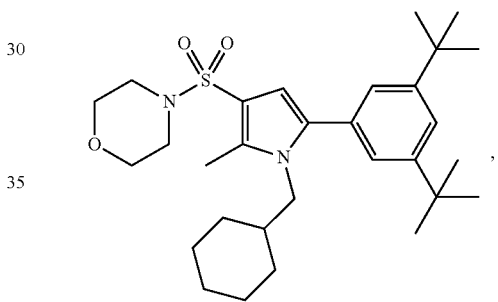
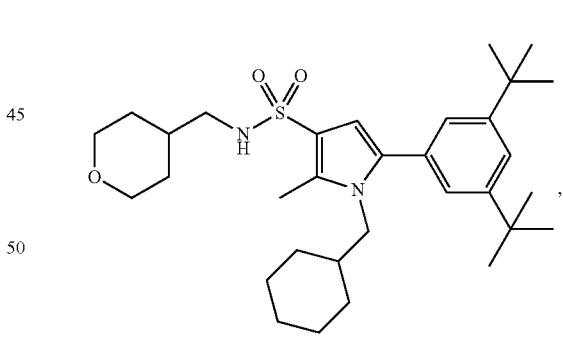
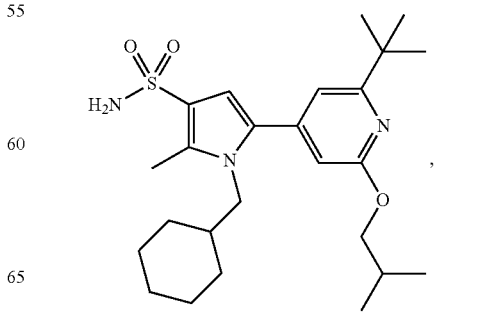

253
-continued
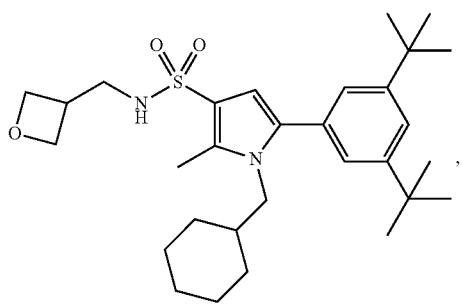
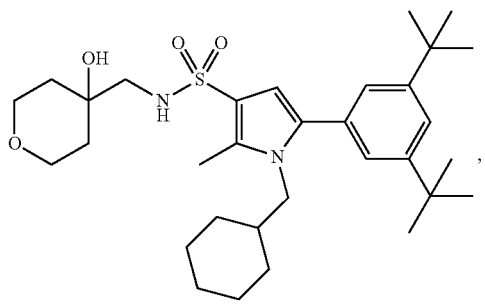
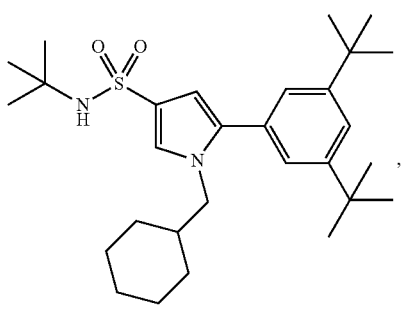
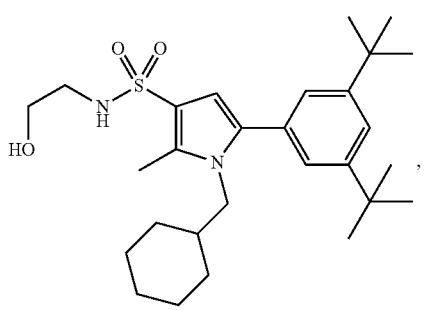
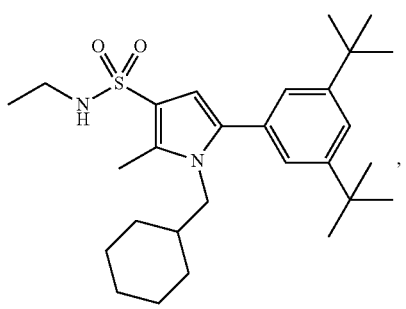
254
-continued
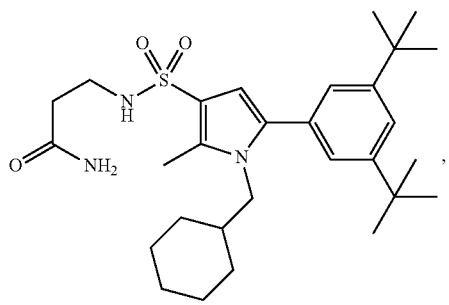
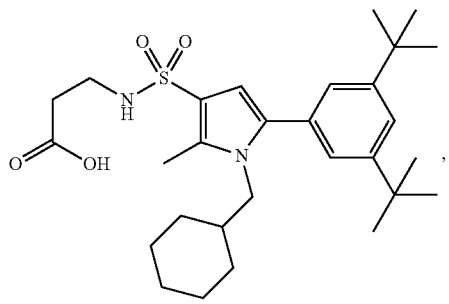
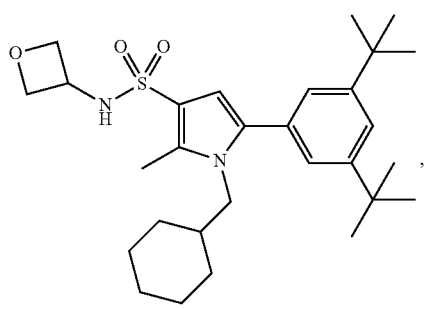
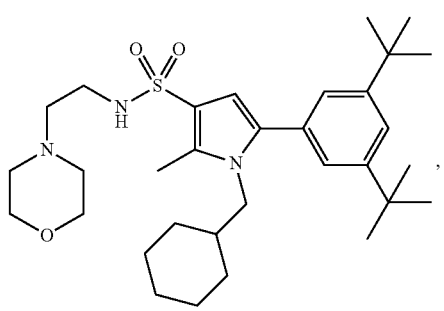
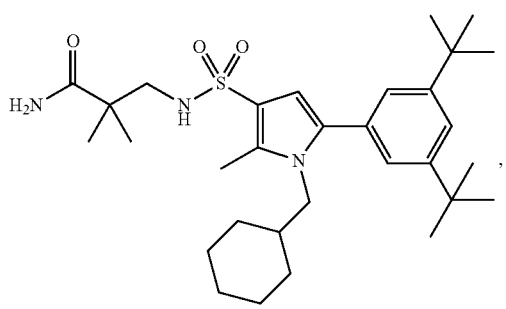

255
-continued
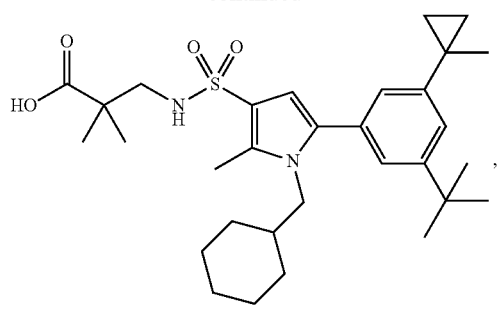
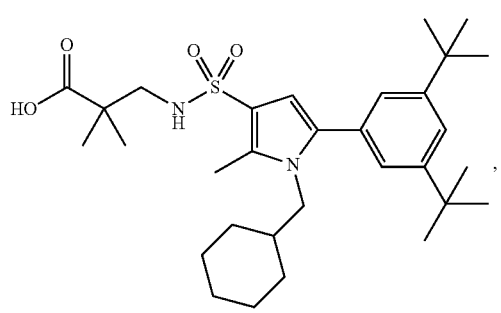
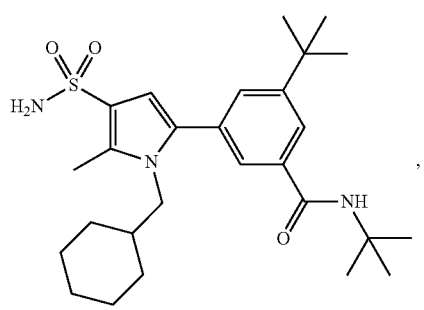
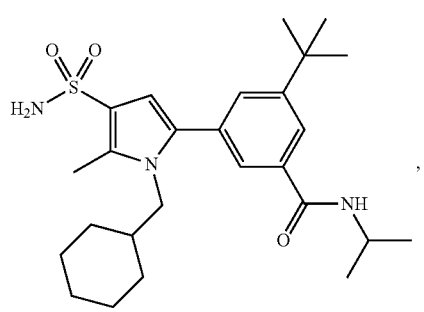
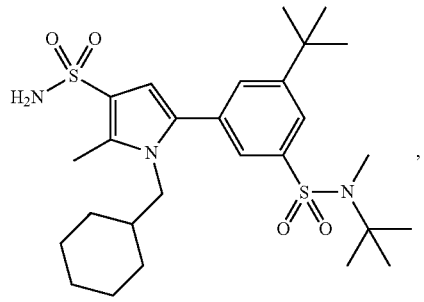
256
-continued
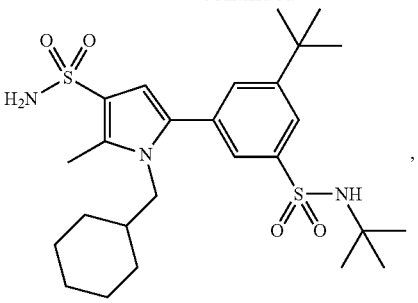
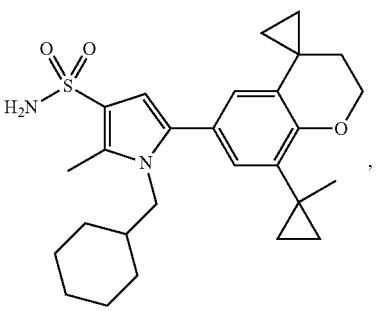
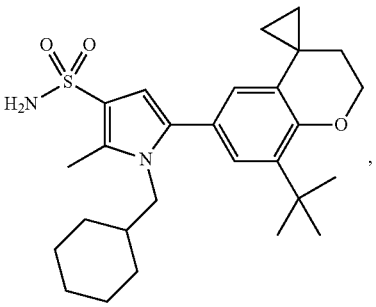
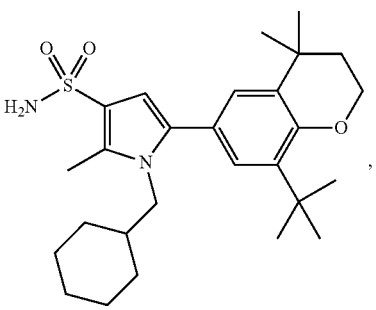
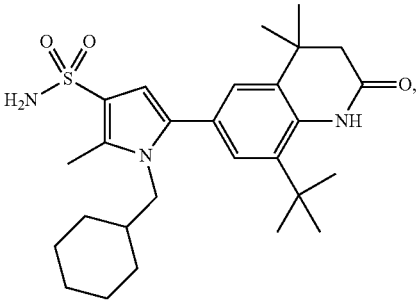

257
-continued
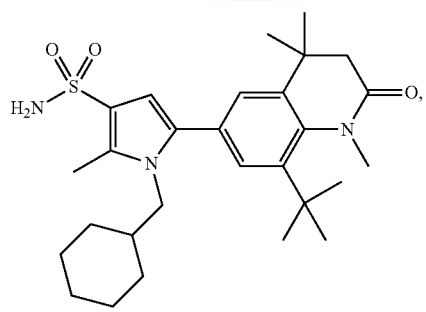
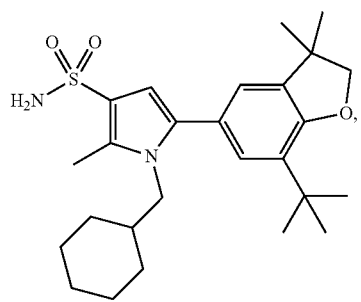
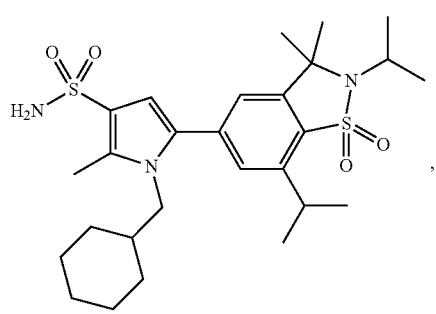
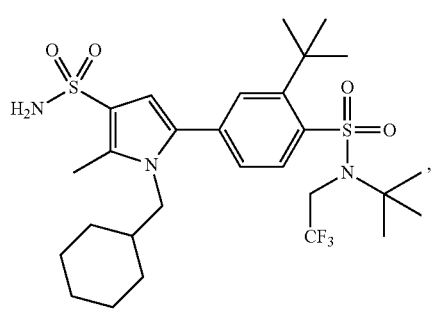
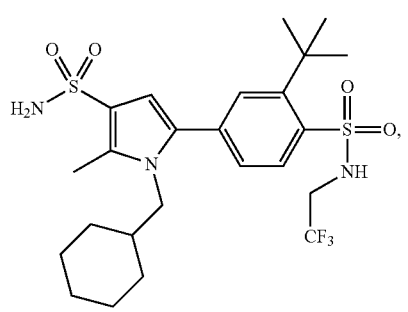
258
-continued
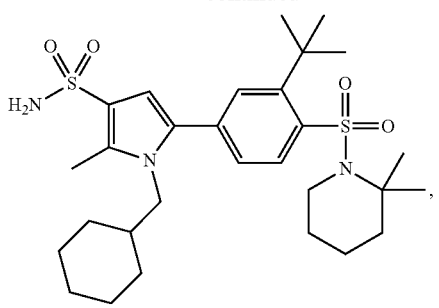
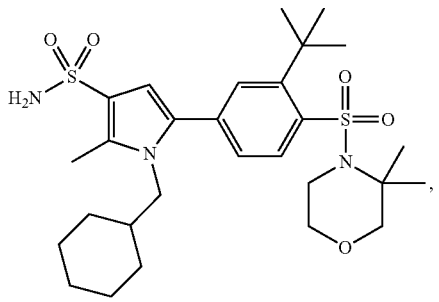
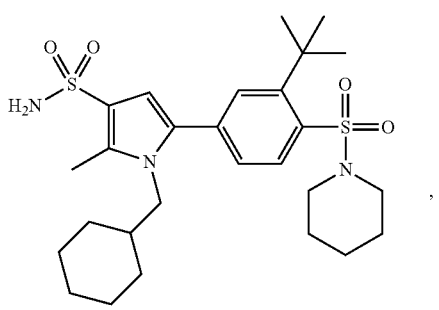
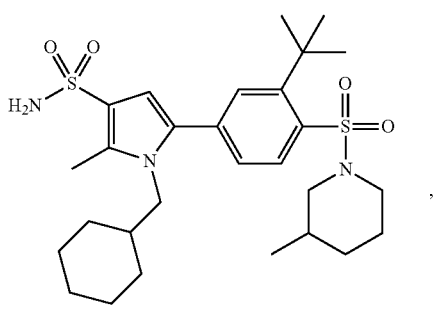
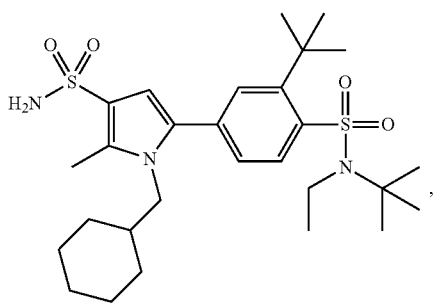

259
-continued
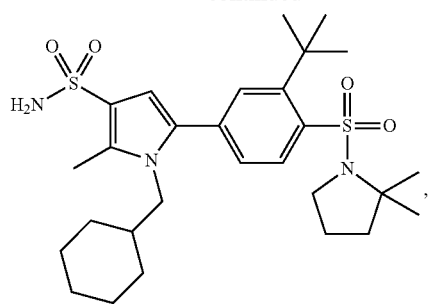
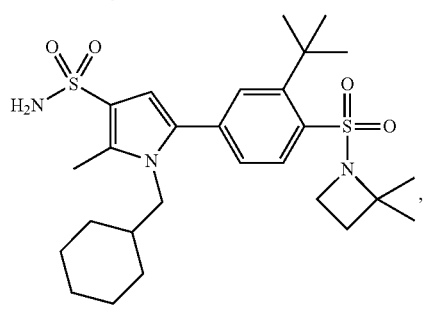
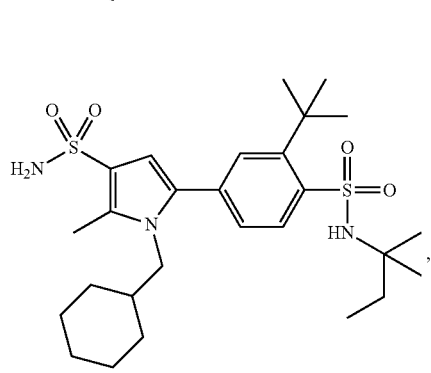
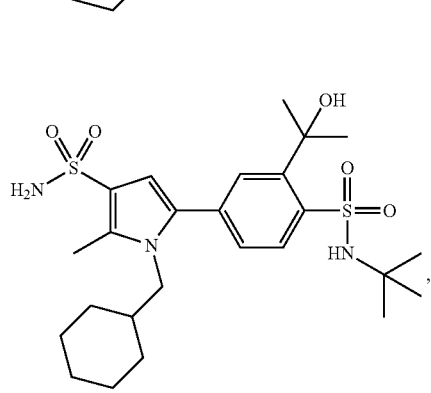
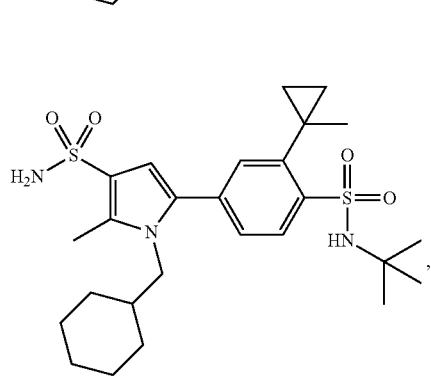
260
-continued
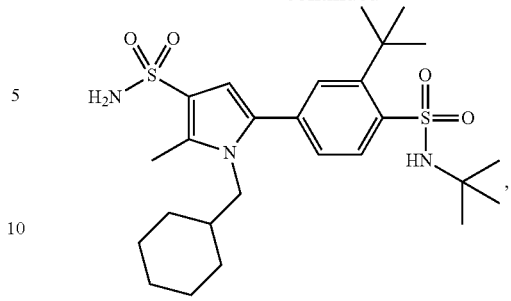
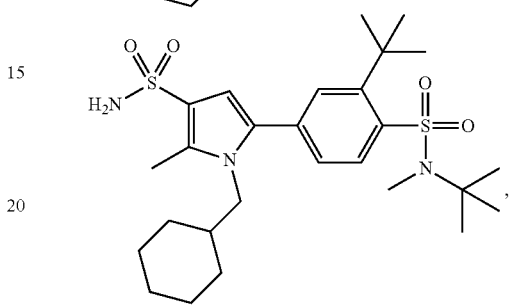
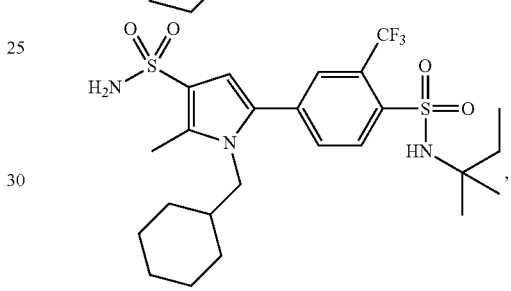
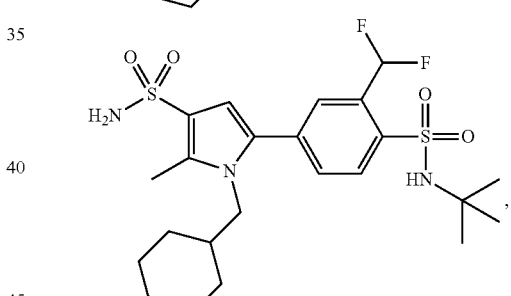
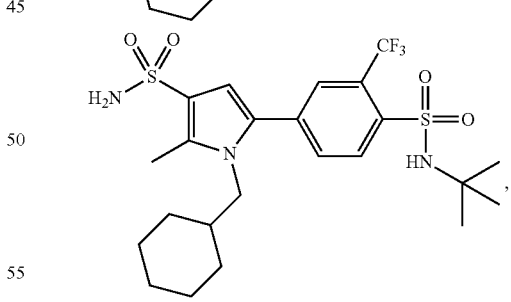
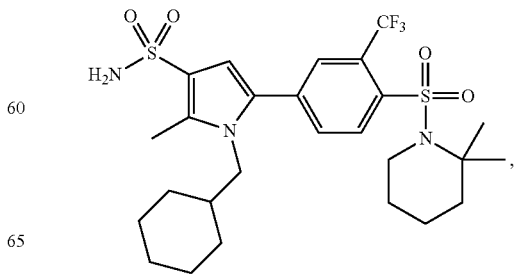

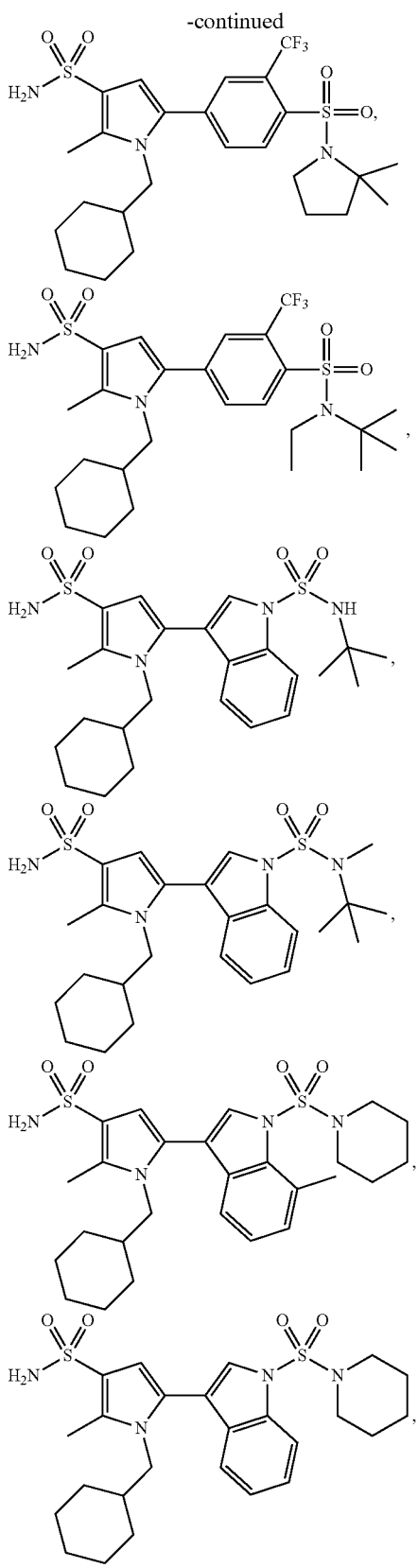
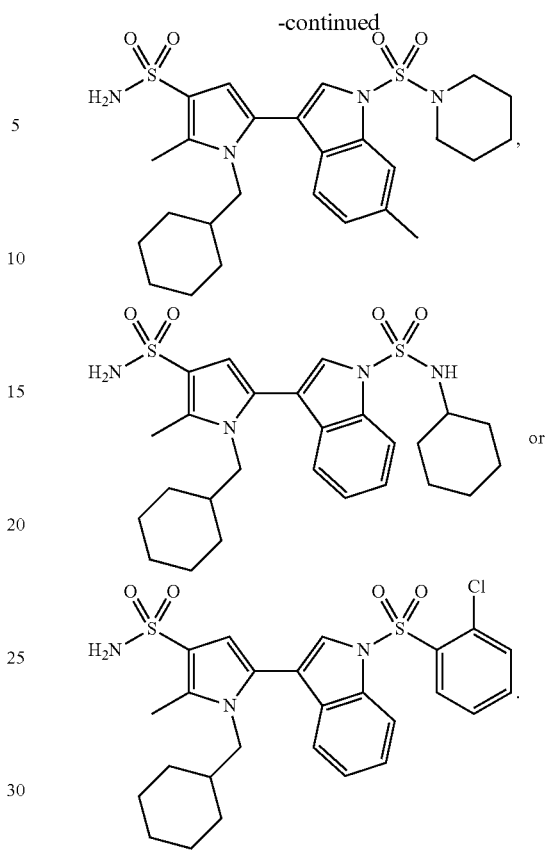

12. A method for treating a RORγ mediated disease or disorder in a mammal, wherein the method comprises administering to a mammal in need thereof an effective amount of a compound of claim 1 or claim 2, enantiomers, diastereomers and tautomers thereof and pharmaceutically acceptable salts thereof.

13. The method of claim 12 wherein the disease or disorder is TH17 mediated tissue inflammation, of autoimmune etiology or a skin disease with associated symptoms selected from pain, itching or excoriations.

14. The method of claim 12 wherein the disease or disorder is selected from rheumatoid arthritis, ankylosing spondylitis, lupus erythematosus, psoriasis, atopic eczema, inflammatory bowel diseases, Crohn's disease, ulcerative colitis, asthma, multiple sclerosis, type 1 diabetes or amyotrophic lateral sclerosis.

15. A method for treatment of a disease or disorder in a mammal associated with the inhibition or activation of the RORγ receptor, wherein the method comprises administering to the mammal in need thereof an effective amount of a compound of claim 1 or claim 2, enantiomers, diastereomers and tautomers thereof and pharmaceutically acceptable salts thereof.

16. A pharmaceutical composition comprising a compound of claim 1 or claim 2, enantiomers, diastereomers and tautomers thereof and pharmaceutically acceptable salts thereof, and a pharmaceutically acceptable carrier.

\* \* \* \* \*